United States Patent
Yukimasa

(10) Patent No.: US 9,340,500 B2
(45) Date of Patent: May 17, 2016

(54) AROMATIC HETEROCYCLIC DERIVATIVE HAVING TRPV4-INHIBITING ACTIVITY

(75) Inventor: Akira Yukimasa, Toyonaka (JP)

(73) Assignee: SHIONOGI & CO., LTD., Osaka (JP)

( * ) Notice: Subject to any disclaimer, the term of this patent is extended or adjusted under 35 U.S.C. 154(b) by 90 days.

(21) Appl. No.: 14/009,400

(22) PCT Filed: Apr. 18, 2012

(86) PCT No.: PCT/JP2012/061621
§ 371 (c)(1),
(2), (4) Date: Oct. 2, 2013

(87) PCT Pub. No.: WO2012/144661
PCT Pub. Date: Oct. 26, 2012

(65) Prior Publication Data
US 2014/0024647 A1    Jan. 23, 2014

Related U.S. Application Data

(60) Provisional application No. 61/485,943, filed on May 13, 2011.

(30) Foreign Application Priority Data

Apr. 20, 2011    (JP) .................................. 2011-093633

(51) Int. Cl.
| | | |
|---|---|---|
| C07D 403/12 | (2006.01) | |
| C07D 403/04 | (2006.01) | |
| C07D 401/04 | (2006.01) | |
| C07D 409/12 | (2006.01) | |
| C07D 405/12 | (2006.01) | |
| C07D 413/04 | (2006.01) | |
| C07D 417/12 | (2006.01) | |
| C07D 417/14 | (2006.01) | |
| C07D 207/34 | (2006.01) | |
| C07D 213/82 | (2006.01) | |
| C07D 231/14 | (2006.01) | |
| C07D 233/90 | (2006.01) | |
| C07D 401/12 | (2006.01) | |
| C07D 209/08 | (2006.01) | |

(52) U.S. Cl.
CPC ............ *C07D 207/34* (2013.01); *C07D 209/08* (2013.01); *C07D 213/82* (2013.01); *C07D 231/14* (2013.01); *C07D 233/90* (2013.01); *C07D 401/04* (2013.01); *C07D 401/12* (2013.01); *C07D 403/04* (2013.01); *C07D 403/12* (2013.01); *C07D 405/12* (2013.01); *C07D 409/12* (2013.01); *C07D 413/04* (2013.01); *C07D 417/12* (2013.01); *C07D 417/14* (2013.01)

(58) Field of Classification Search
CPC .. C07D 403/12; C07D 401/04; C07D 401/12; C07D 403/04; C07D 409/12; C07D 405/12; C07D 413/04; C07D 417/12; C07D 417/14
See application file for complete search history.

(56) References Cited

U.S. PATENT DOCUMENTS

| | | | |
|---|---|---|---|
| 6,806,286 B2 * | 10/2004 | Walter et al. ................... | 514/423 |
| 2010/0075957 A1 | 3/2010 | Tamura et al. | |

FOREIGN PATENT DOCUMENTS

| | | |
|---|---|---|
| JP | 2003-519697 | 6/2003 |
| JP | 2004-502642 | 1/2004 |
| JP | 2004-315511 | 11/2004 |
| JP | 2006-124387 | 5/2006 |
| JP | 2008-308504 | 12/2008 |
| JP | 2009-502948 | 1/2009 |
| JP | 2009-508968 | 3/2009 |
| JP | 2009-84209 | 4/2009 |
| JP | 2009-102423 | 5/2009 |

(Continued)

OTHER PUBLICATIONS

International Search Report and Written Opinion issued Aug. 14, 2012 in International (PCT) Application No. PCT/JP2012/061621.

(Continued)

*Primary Examiner* — Rebecca Anderson
(74) *Attorney, Agent, or Firm* — Wenderoth, Lind & Ponack, L.L.P.

(57) ABSTRACT

A compound having TRPV4 inhibitory activity or a pharmaceutically acceptable salt thereof is provided. The present invention is related to a compound represented by the formula (I), wherein $R^{1a}$ is substituted or unsubstituted alkyl or the like; $R^{1b}$ is hydrogen or substituted or unsubstituted alkyl; $R^{1c}$ is hydrogen, halogen, substituted or unsubstituted alkyl, substituted or unsubstituted cycloalkyl, substituted or unsubstituted nonaromatic heterocyclic group or the like; -L- is —C(=O)—NR$^{2-}$ or the like; X is substituted or unsubstituted aryl, substituted or unsubstituted heteroaryl or the like, or a pharmaceutically acceptable salt thereof.

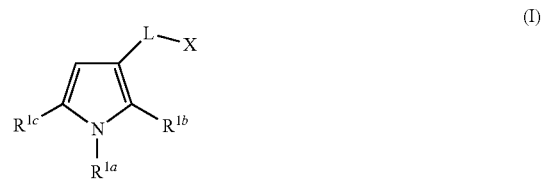

(I)

9 Claims, No Drawings

(56) References Cited

FOREIGN PATENT DOCUMENTS

| | | |
|---|---|---|
| WO | 01/51487 | 7/2001 |
| WO | 01/53257 | 7/2001 |
| WO | 01/58869 | 8/2001 |
| WO | 03/009841 | 2/2003 |
| WO | 03/068738 | 8/2003 |
| WO | 2005/014543 | 2/2005 |
| WO | 2006/038070 | 4/2006 |
| WO | 2007/014290 | 2/2007 |
| WO | 2007/038215 | 4/2007 |
| WO | 2007/059608 | 5/2007 |
| WO | 2007/071055 | 6/2007 |
| WO | 2007/115403 | 10/2007 |
| WO | 2007/115408 | 10/2007 |
| WO | 2007/115409 | 10/2007 |
| WO | 2007/115410 | 10/2007 |
| WO | 2008/133274 | 11/2008 |
| WO | 2008/144931 A1 | 12/2008 |
| WO | 2008/144931 A8 | 12/2008 |
| WO | 2009/049421 | 4/2009 |
| WO | 2009/111680 | 9/2009 |
| WO | 2009/141386 | 11/2009 |
| WO | 2009/146177 | 12/2009 |
| WO | 2009/146182 | 12/2009 |
| WO | 2010/011912 | 1/2010 |
| WO | 2010/011914 | 1/2010 |
| WO | 2010/137350 | 12/2010 |

OTHER PUBLICATIONS

W. Everaerts et al., "The Vanilloid Transient Receptor Potential Channel TRPV4: From Structure to Disease", Progress in Biophysics and Molecular Biology, vol. 103, pp. 2-17, 2010.

C. D. Benham et al., "TRPV Channels as Temperature Sensors", Cell Calcium, vol. 33, pp. 479-487, 2003.

T. Numata et al., Seikagaku, vol. 81, No. 11, pp. 962-998, 2009 (in Japanese).

M. Tominaga, "TRP Channels and Nociception", Folia Pharmacologica Japonica, No. 127, pp. 128-132, 2006 (in Japanese).

M. Suzuki, "TRPV4 as a Mechano-Sensing Channel", Seibutsu Bursuri, vol. 45, No. 5, pp. 268-271, 2005 (in Japanese).

M. N. Phan et al., "Functional Characterization of TRPV4 as an Osmotically Sensitive Ion Channel in Porcine Articular Chondrocytes", Arthritis & Rheumatism, vol. 60, No. 10, pp. 3028-3037, Oct. 2009.

F. Vincent et al., "Identification and Characterization of Novel TRPV4 Modulators", Biochemical and Biophysical Research Communications, vol. 389, pp. 490-494, 2009.

W. Everaerts et al., "Inhibition of the Cation Channel TRPV4 Improves Bladder Function in Mice and Rats with Cyclophosphamide-Induced Cystitis", Proceedings of the National Academy of Sciences, vol. 107, No. 44, pp. 19084-19089, Nov. 2, 2010.

S. Materazzi et al., "TRPA1 and TRPV4 Mediate Paclitaxel-Induced Peripheral Neuropathy in Mice Via a Glutathione-Sensitive Mechanism", Pflugers Arch—Eur. J. Physiol., vol. 463, pp. 561-569, 2012.

E. Martin et al., "Involvement of TRPV1 and TRPV4 Channels in Migration of Rat Pulmonary Arterial Smooth Muscle Cells", Pflugers Arch—Eur. J. Physiol., vol. 464, pp. 261-272, 2012.

F. Vincent et al., "TRPV4 Agonists and Antagonists", Current Topics in Medicinal Chemistry, vol. 11, pp. 2216-2226, 2011.

Kohei Fuchibe et al., "Synthesis of pyrroles: reaction of chromium N-alkylaminocarbene complexes with α,β-unsaturated aldehydes", Chemical Communications, Cambridge, United Kingdom, 2006, No. 21, pp. 2271-2273.

Alan R. Katritzky et al., "General and Efficient Approaches to Fused [1,2-a]Pyrroles and [1,2-a]Indoles", J. Org. Chem., 1997, vol. 62, No. 12, pp. 4148-4154.

Alan R. Katritzky et al., "1,4-Disubstituted and 1,4,5-Trisubstituted 2-[(Benzotriazol-1-yl)methyl]pyrroles as Versatile Synthetic Intermediates", J. Org. Chem., 1996, vol. 61, No. 5, pp. 1624-1628.

Japanese Office Action mailed Mar. 11, 2016 in corresponding Japanese Application No. 2013-540560.

* cited by examiner

AROMATIC HETEROCYCLIC DERIVATIVE HAVING TRPV4-INHIBITING ACTIVITY

The application is a national stage application filed under 35 U.S.C. 371 of international application no. PCT/JP2012/061621, filed Apr. 18, 2012, which claims priority to Japan Patent Application No. 2011-093633, filed Apr. 20, 2011 and claims the benefit of U.S. Provisional Application No. 61/485,943, filed May 13, 2011.

TECHNICAL FIELD

The present invention is related to a compound that has a TRPV4 inhibitory activity and is useful in the treatment and/or prevention of a TRPV4 receptor-mediated disorder, or a pharmaceutically acceptable salt thereof, and a pharmaceutical composition containing thereof.

BACKGROUND ART

TRPV4 is one of a cation channel of the TRP (Transient Receptor Potential) superfamily. It was discovered as an osmotic-sensitivity receptor activated by hypotonic stimulus. Then, it was shown that TRPV4 had a temperature-sensitive property, that is, TRPV4 was activated at the body temperature rage, and TRPV4 is activated by heat and low pH. It is reported that the gene and protein of TRPV4 is expressed in brain, spinal code, peripheral nerve fiber, skin, kidney, trachea, cochlea and bone, etc. Moreover, it is also reported that TRPV4 is activated by the compounds, such as arachidonic acid, arachidonate metabolite, endocannabinoids, and phorbol ester. The increase of activation of the C-fiber by hypotonic stimulation under the inflammatory environment induced by inflammatory mediators, is known, and it is also reported that TRPV4 relates to this activation. Furthermore, it is also reported that TRPV4 is activated by fluid pressure and mechanical stimuli, and TRPV4 relates to hyperalgesia caused by mechanical stimuli. In addition, it is also reported that TRPV4 relates to paclitaxel-induced pain (Non-patent document 1-5). Therefore, it is expected that TRPV4 participates in many physiological roles. The compound which exhibits high affinity to TRPV4 has a high potential as useful medicine in the therapy and/or prevention of TRPV4 receptor-mediated disorder. The compounds having TRPV4 inhibitory activity are disclosed in patent-documents 1 to 5, 14, and non-patent documents 6 to 13. However, the compounds of this present invention are not disclosed in any documents.

PRIOR ART REFERENCES

Patent Document

[Patent Document 1] International Publication No. 2009/111680 pamphlet
[Patent Document 2] International Publication No. 2009/146177 pamphlet
[Patent Document 3] International Publication No. 2009/146182 pamphlet
[Patent Document 4] International Publication No. 2010/011912 pamphlet
[Patent Document 5] International Publication No. 2010/011914 pamphlet
[Patent Document 6] International Publication No. 2006/038070 pamphlet
[Patent Document 7] International Publication No. 2007/059608 pamphlet
[Patent Document 8] International Publication No. 2007/071055 pamphlet
[Patent Document 9] International Publication No. 2007/115403 pamphlet
[Patent Document 10] International Publication No. 2007/115408 pamphlet
[Patent Document 11] International Publication No. 2007/115409 pamphlet
[Patent Document 12] International Publication No. 2007/115410 pamphlet
[Patent Document 13] International Publication No. 2008/144931 pamphlet
[Patent Document 14] JP-A No. 2009-084209

Non-Patent Document

[Non-patent document 1] Progress in Biophysics and Molecular Biology, 2010, 103, pp. 2-17
[Non-patent document 2] Cell Calcium, 2003, 33, pp. 79-487
[Non-patent document 3] Seikagaku, 2009, 81(11), pp. 962-98,
[Non-patent document 4] Folia Pharmacologica Japonica, 2006, 127, pp. 128-132
[Non-patent document 5] Seibutsu Butsuri, 2005, 45(5), pp. 268-271
[Non-patent document 6] ARTHRITIS & RHEUMATISM, 2009, 60, pp. 3028-3037
[Non-patent document 7] Biochemical and Biophysical Research Communications, 2009, 389, pp. 490-494
[Non-patent document 8] Proceedings of the National Academy of Sciences, 2010, 107, pp. 19084-19089

SUMMARY OF THE INVENTION

Problems to be Solved by the Invention

The purpose of the present invention is to provide a compound that has a TRPV4 inhibitory activity or a pharmaceutically acceptable salt thereof, or a pharmaceutical composition containing thereof that has a TRPV4 inhibitory activity.

Means for Solving Problem

The present inventors have eagerly made progress in their studies, resulting in finding that a compound that has a TRPV4 inhibitory activity and is useful in the treatment and/or prevention of a TRPV4 receptor-mediated disorder, or a pharmaceutically acceptable salt thereof, and have accomplished the following invention.

(1) A compound represented by the formula (I):

[Formula 1]

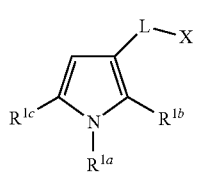

(I)

wherein $R^{1a}$ is substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;

$R^{1b}$ is hydrogen or substituted or unsubstituted alkyl;

$R^{1c}$ is hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted cycloalkyloxy, substituted or unsubstituted cycloalkenyloxy, substituted or unsubstituted non-aromatic heterocyclic group-oxy, substituted or unsubstituted aryloxy, substituted or unsubstituted heteroaryloxy, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclic group-oxycarbonyl, substituted or unsubstituted aryloxycarbonyl, substituted or unsubstituted heteroaryloxycarbonyl, substituted or unsubstituted sulfamoyl, substituted sulfinyl, substituted sulfonyl, substituted or unsubstituted alkylsulfonyloxy, substituted or unsubstituted arylsulfonyloxy, substituted or unsubstituted amino, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;

-L- is —C(=O)—N($R^2$)—, —N($R^2$)—C(=O)—, —N($R^2$)—C(=O)—, —N($R^3$)—, —N($R^2$)—$SO_2$, —C(=O)—O—(C$R^4R^5$)m-, —$SO_2$—N($R^2$)—(C$R^4R^4$)m-, or a single bond;

$R^2$ to $R^5$ are each independently hydrogen or substituted or unsubstituted alkyl;

m is 0 or 1;

X is substituted or unsubstituted aryl, substituted or unsubstituted heteroaryl, substituted or unsubstituted cycloalkyl, substituted or unsubstituted cycloalkenyl, or a substituted or unsubstituted non-aromatic heterocyclic group, provided that the following compounds are excluded:

[Formula 2]

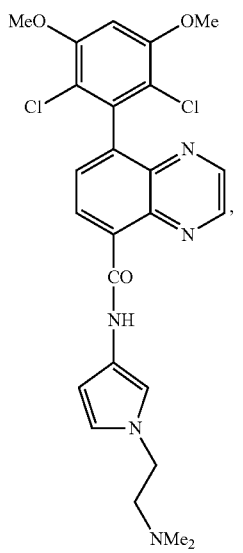
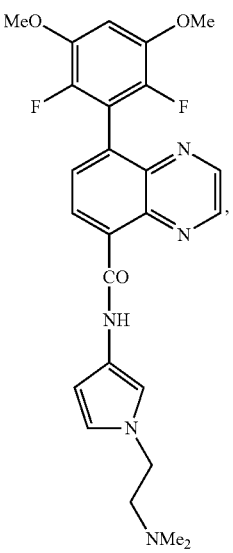

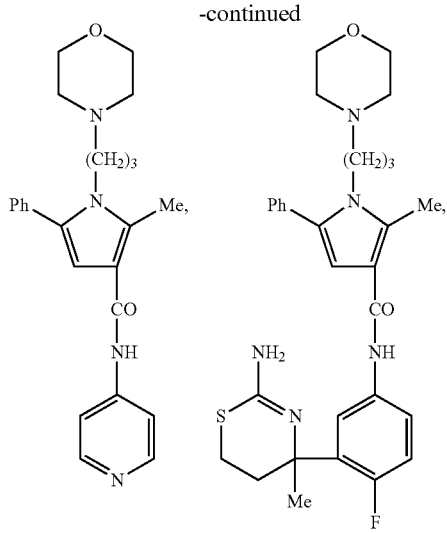

-continued

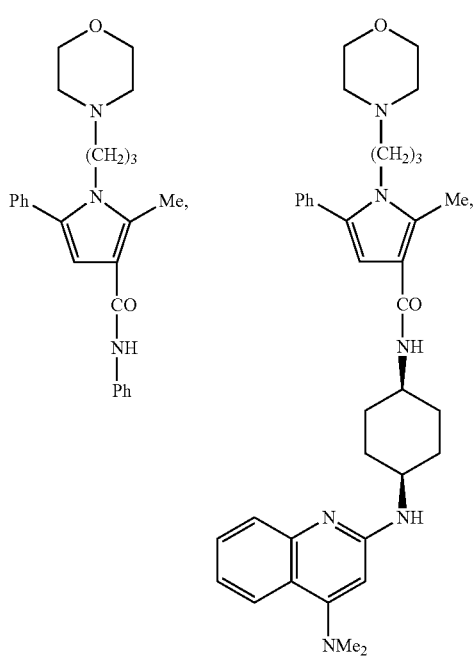

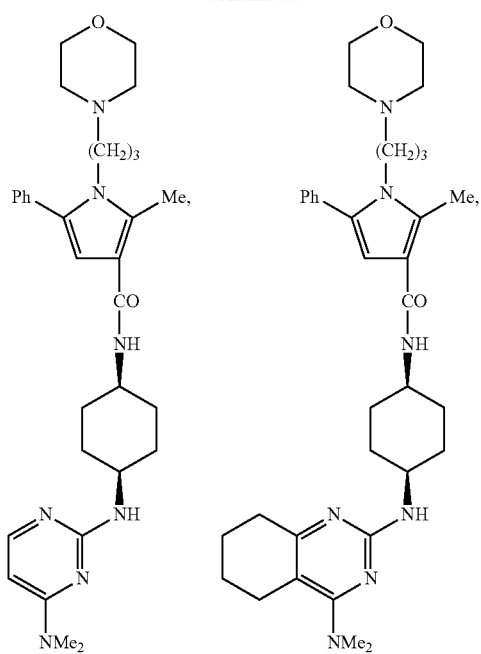
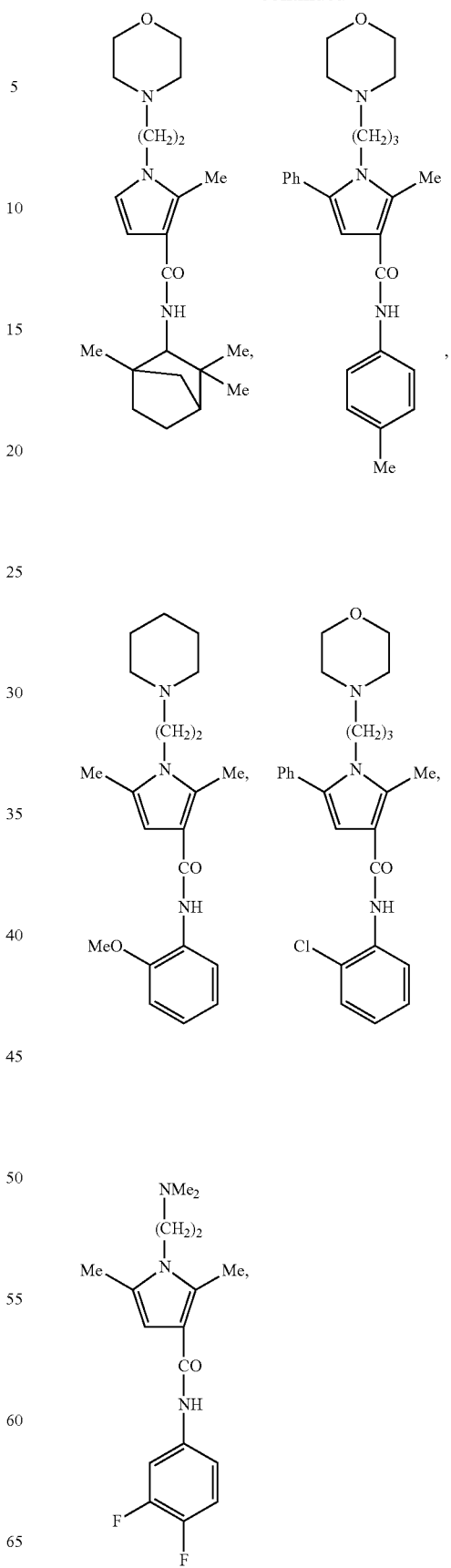

-continued
[Formula 3]
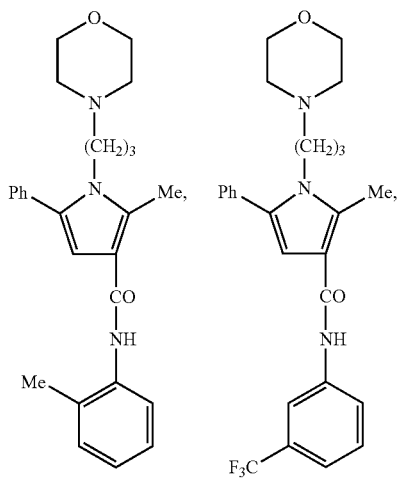
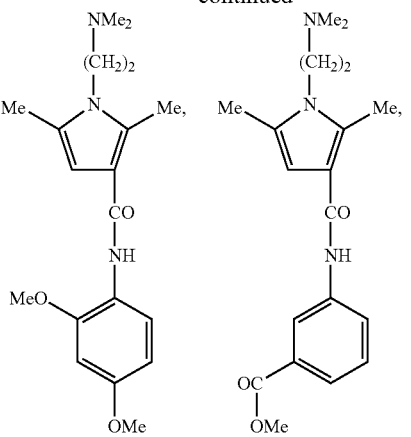
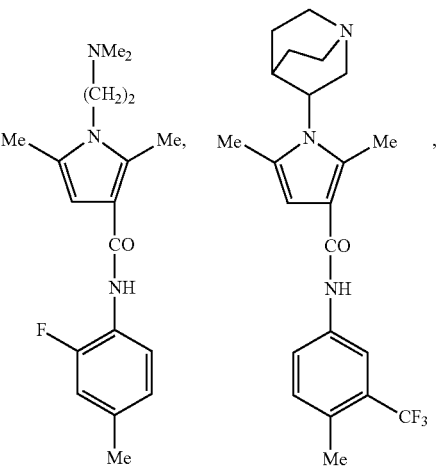
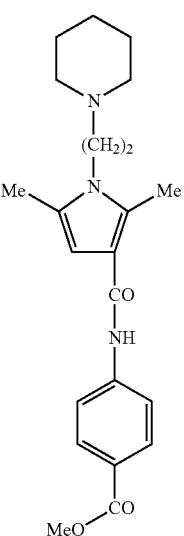
and

-continued

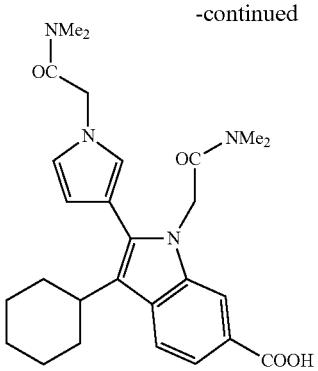

wherein Me is methyl and Ph is phenyl,
or a pharmaceutically acceptable salt thereof.

(2) The compound according to (1),
wherein —$R^{1a}$ is —$(CR^7R^8)$n-Y;
$R^7$ is each independently hydrogen, halogen, or substituted or unsubstituted alkyl; $R^8$ is each independently hydrogen, halogen, or substituted or unsubstituted alkyl; or $R^7$ and $R^8$ taken together form oxo;
n is an integer from 1 to 3;
—Y is —$(SO_2)$p-$N(R^9)(R^{10})$;
$R^9$ and $R^{10}$ are each independently hydrogen, substituted or unsubstituted alkyl, substituted or unsubstituted alkenyl, substituted or unsubstituted alkynyl, substituted or unsubstituted acyl, substituted or unsubstituted alkyloxycarbonyl, substituted or unsubstituted alkenyloxycarbonyl, substituted or unsubstituted alkynyloxycarbonyl, substituted sulfinyl, substituted sulfonyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl; or $R^9$ and $R^{10}$ taken together with the adjacent nitrogen atom may form a ring in which oxygen atom, sulfur atom, or nitrogen atom may intervene;
p is 0 or 1;
$R^{1c}$ is cyano, substituted or unsubstituted alkyl of which carbon number is 2 or more, substituted or unsubstituted alkenyl, substituted or unsubstituted alkynyl, substituted or unsubstituted cycloalkyl, substituted or unsubstituted cycloalkenyl, a substituted, or unsubstituted non-aromatic heterocyclic group, or substituted or unsubstituted heteroaryl;
-L- is —C(=O)—N($R^2$)—, —N($R^2$)—C(=O)—, —N($R^2$)—$SO_2$—, or —$SO_2$—N($R^2$)—$(CR^4R^5)$m-;
$R^2$ is the same as (1),
or a pharmaceutically acceptable salt thereof.

(2') The compound according to (1),
wherein —$R^{1a}$ is —$(CR^7R^8)$n-Y;
$R^7$ is each independently hydrogen, halogen, or substituted or unsubstituted alkyl; $R^8$ is each independently hydrogen, halogen, or substituted or unsubstituted alkyl; or $R^7$ and $R^8$ taken together form oxo;
n is an integer from 1 to 3;
—Y is —$(SO_2)$p-$N(R^9)(R^{10})$, or substituted or unsubstituted alkyloxy;
$R^9$ and $R^{10}$ are each independently hydrogen, substituted or unsubstituted alkyl, substituted or unsubstituted alkenyl, substituted or unsubstituted alkynyl, substituted or unsubstituted acyl, substituted or unsubstituted alkyloxycarbonyl, substituted or unsubstituted alkenyloxycarbonyl, substituted or unsubstituted alkynyloxycarbonyl, substituted sulfinyl, substituted sulfonyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl; or $R^9$ and $R^{10}$ taken together with the adjacent nitrogen atom may form a ring in which oxygen atom, sulfur atom, or nitrogen atom may intervene;
p is 0 or 1; and
$R^{1c}$ is cyano, substituted or unsubstituted alkyl of which carbon number is 2 or more, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, or substituted or unsubstituted heteroaryl;
-L- is —C(=O)—N($R^2$)—, —N($R^2$)—C(=O)—, —N($R^2$)—$SO_2$—, or —$SO_2$—N($R^2$)—$(CR^4R^5)$m-;
$R^2$, $R^4$, $R^5$ and m are the same, as (1),
or a pharmaceutically acceptable salt thereof.

(3) The compound according to (1),
wherein $R^{1a}$ is a substituted or unsubstituted nitrogen containing saturated heterocyclic group, or cycloalkyl substituted with substituted or unsubstituted amino;
-L- is —C(=O)—N($R^2$)—, —N($R^2$)—C(=O)—, —N($R^2$)—C(=O)—N($R^3$)—, N($R^2$)—$SO_2$—, —C(=O)—O—$(CR^4R^5)$m-, or —$SO_2$—N($R^2$)—$(CR^4R^5)$m-;
$R^2$ to $R^5$ and m are the same as (1); and
$R^{1c}$ is substituted or unsubstituted alkyl of which carbon number is 2 or more, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl,
or a pharmaceutically acceptable salt thereof.

(4) The compound according to (1),
wherein —$R^{1a}$ is —$(CR^7R^8)$n-Y;
$R^7$, $R^8$, n and —Y are the same as the above (2);
$R^{1c}$ is substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
-L- is a single bond; and
—X is a group represented by the following formula:

[Formula 4]

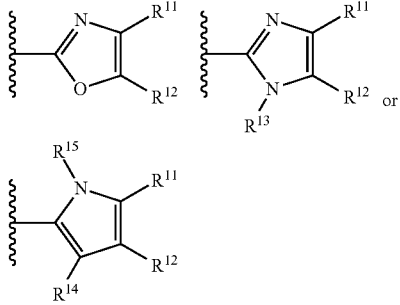

wherein $R^{11}$ and $R^{12}$ are each independently hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl; or $R^{11}$ and $R^{12}$ taken together with the adjacent carbon atoms may form a ring in which nitrogen atom may intervene;

$R^{13}$ to $R^{15}$ are each independently hydrogen, substituted or unsubstituted alkyl, substituted or unsubstituted acyl, substituted or unsubstituted aryl, or substituted or unsubstituted heteroaryl, or a pharmaceutically acceptable salt thereof.

(5) A pharmaceutical composition for inhibiting TRPV4 receptor which contains a compound of the formula (I):

[Formula 5]

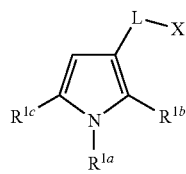

(I)

wherein $R^{1a}$ is substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;

$R^{1b}$ is hydrogen or substituted or unsubstituted alkyl;

$R^{1c}$ is hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted cycloalkyloxy, substituted or unsubstituted cycloalkenyloxy, substituted or unsubstituted non-aromatic heterocyclic group-oxy, substituted or unsubstituted aryloxy, substituted or unsubstituted heteroaryloxy, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclic group-oxycarbonyl, substituted or unsubstituted aryloxycarbonyl, substituted or unsubstituted heteroaryloxycarbonyl, substituted or unsubstituted sulfamoyl, substituted sulfinyl, substituted sulfonyl, substituted or unsubstituted alkylsulfonyloxy, substituted or unsubstituted arylsulfonyloxy, substituted or unsubstituted amino, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;

-L- is —C(=O)—N($R^2$)—, —N($R^2$)—C(=O)—, —N($R^2$)—C(=O)—N($R^3$)—, —N($R^2$)—SO$_2$—, —C(=O)—O—(CR$^4$R$^5$)m-, —SO$_2$—N($R^2$)—(CR$^4$R$^5$)m-, or a single bond;

$R^2$ to $R^5$ are each independently hydrogen or substituted or unsubstituted alkyl;

m is 0 or 1;

X is substituted or unsubstituted aryl, substituted or unsubstituted heteroaryl, substituted or unsubstituted cycloalkyl, substituted or unsubstituted cycloalkenyl, or a substituted or unsubstituted non-aromatic heterocyclic group, or a pharmaceutically acceptable salt thereof.

(5') A method for treating a TRPV4 receptor-mediated disorder, which comprises administering to a subject in need of such treatment a therapeutically effective amount of the compound or a pharmaceutically acceptable salt thereof according to the above (5).

(6) The pharmaceutical composition for inhibiting TRPV4 receptor according to (5), wherein —$R^{1a}$ is —(CR$^7$R$^8$)n-Y;

$R^7$ is each independently hydrogen, halogen, or substituted or unsubstituted alkyl; $R^8$ is each independently hydrogen, halogen, or substituted or unsubstituted alkyl; or $R^7$ and $R^8$ taken together form oxo;

n is an integer from 1 to 3;

—Y is —(SO$_2$)p-N($R^9$)($R^{10}$);

$R^9$ and $R^{10}$ are each independently hydrogen, substituted or unsubstituted alkyl, substituted or unsubstituted alkenyl, substituted or unsubstituted alkynyl, substituted or unsubstituted acyl, substituted or unsubstituted alkyloxycarbonyl, substituted or unsubstituted alkenyloxycarbonyl, substituted or unsubstituted alkynyloxycarbonyl, substituted sulfinyl, substituted sulfonyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl; or $R^9$ and $R^{10}$ taken together with the adjacent nitrogen atom may form a ring in which oxygen atom, sulfur atom, or nitrogen atom may intervene;

p is 0 or 1;

$R^{1c}$ is hydrogen, cyano, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

-L- is —C(=O)—N($R^2$)—, —N($R^2$)—C(=O)—, or —N($R^2$)—SO$_2$—; and $R^2$ is the same as the above (5), or a pharmaceutically acceptable salt thereof.

(6') A method for treating a TRPV4 receptor-mediated disorder, which comprises administering to a subject in need of such treatment a therapeutically effective amount of the compound or a pharmaceutically acceptable salt thereof according to the above (6).

(6") The pharmaceutical composition for inhibiting TRPV4 receptor according to claim 5, wherein —$R^{1a}$ is —(CR$^7$R$^8$)n-Y;

$R^7$ is each independently hydrogen, halogen, or substituted or unsubstituted alkyl; $R^8$ is each independently hydrogen, halogen, or substituted or unsubstituted alkyl; or $R^7$ and $R^8$ taken together form oxo;

n is an integer from 1 to 3;

—Y is —(SO$_2$)p-N($R^9$)($R^{10}$), or substituted or unsubstituted alkyloxy;

$R^9$ and $R^{10}$ are each independently hydrogen, substituted or unsubstituted alkyl, substituted or unsubstituted alkenyl, substituted or unsubstituted alkynyl, substituted or unsubstituted acyl, substituted or unsubstituted alkyloxycarbonyl, substituted or unsubstituted alkenyloxycarbonyl, substituted or unsubstituted alkynyloxycarbonyl, substituted sulfinyl, substituted sulfonyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl; or $R^9$ and $R^{10}$ taken together with the adjacent nitrogen atom may form a ring in which oxygen atom, sulfur atom, or nitrogen atom may intervene;

p is 0 or 1;

$R^{1c}$ is hydrogen, cyano, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

-L- is —C(=O)—N($R^2$)—, —N($R^2$)—C(=O)—, N($R^2$)—SO$_2$—, or —SO$_2$—N($R^2$)—(CR$^4$R$^5$)m-;

$R^2$, $R^4$, $R^5$ and m are the same as the above (5), or a pharmaceutically acceptable salt thereof.

(7) A pharmaceutical composition for inhibiting TRPV4 receptor which contains a compound of the formula (II):

[Formula 6]

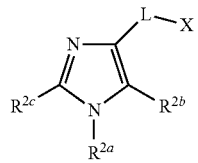

(II)

wherein $R^{2a}$ is substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;

$R^{2b}$ is hydrogen or substituted or unsubstituted alkyl;

$R^{2c}$ is hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted cycloalkyloxy, substituted or unsubstituted cycloalkenyloxy, substituted or unsubstituted non-aromatic heterocyclic group-oxy, substituted or unsubstituted aryloxy, substituted or unsubstituted heteroaryloxy, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or, unsubstituted cycloalkenyloxycarbonyl, substituted or unsubstituted non-aromatic heterocyclic group-oxycarbonyl, substituted or unsubstituted aryloxycarbonyl, substituted or unsubstituted heteroaryloxycarbonyl, substituted or unsubstituted sulfamoyl, substituted sulfinyl, substituted sulfonyl, substituted or unsubstituted alkylsulfonyloxy, substituted or unsubstituted arylsulfonyloxy, substituted or unsubstituted amino, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;

-L- is —C(=O)—N($R^2$)—, —N($R^2$)—C(=O)—, —N($R^2$)—C(=O)—N($R^3$)—, —N($R^2$)—SO$_2$—, —C(=O)—O—(C$R^4R^5$)m-, —SO$_2$—N($R^2$)—(C$R^4R^5$)m-, or a single bond;

$R^2$ to $R^5$ are each independently hydrogen or substituted or unsubstituted alkyl;

m is 0 or 1;

X is substituted or unsubstituted aryl, substituted or unsubstituted heteroaryl, substituted or unsubstituted cycloalkyl, substituted or unsubstituted cycloalkenyl, or a substituted or unsubstituted non-aromatic heterocyclic group;

provide that X is not a group represented by the formula:

[Formula 7]

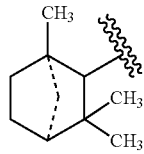

or a pharmaceutically acceptable salt thereof.

(7') A method for treating a TRPV4 receptor-mediated disorder, which comprises administering to a subject in need of such treatment a therapeutically effective amount of the compound or a pharmaceutically acceptable salt thereof according to the above (7)

(8) A compound represented by the formula (II):

[Formula 8]

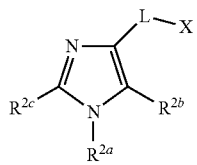

(II)

wherein $R^{2a}$ is substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;

$R^{2b}$ is hydrogen or substituted or unsubstituted alkyl;

$R^{2c}$ is hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted cycloalkyloxy, substituted or unsubstituted cycloalkenyloxy, substituted or unsubstituted non-aromatic heterocyclic group-oxy, substituted or unsubstituted aryloxy, substituted or unsubstituted heteroaryloxy, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclic group-oxycarbonyl, substituted or unsubstituted aryloxycarbonyl, substituted or unsubstituted heteroaryloxycarbonyl, substituted or unsubstituted sulfamoyl, substituted sulfinyl, substituted sulfonyl, substituted or unsubstituted alkylsulfonyloxy, substituted or unsubstituted arylsulfonyloxy, substituted or unsubstituted amino, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;

-L- is —C(=O)—N($R^2$)—, —N($R^2$)—C(=O)—, —N($R^2$)—C(=O)—N($R^3$)—, —N($R^2$)—SO$_2$—C(=O)—O—(C$R^4R^5$)m-, —SO$_2$—N($R^2$)—(C$R^4R^5$)m-, or a single bond;

$R^2$ to $R^5$ are each independently hydrogen or substituted or unsubstituted alkyl;

m is 0 or 1;

X is substituted or unsubstituted aryl, substituted or unsubstituted heteroaryl, substituted or unsubstituted cycloalkyl, substituted or unsubstituted cycloalkenyl; or a substituted or unsubstituted non-aromatic heterocyclic group;

provided that X is not aryl substituted with sulfo, or is not a group represented by the formula:

[Formula 9]

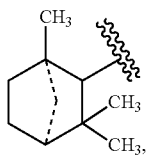

and
R$^{2a}$ is not alkyl substituted with pyrrolidinyl, wherein the pyrrolidinyl is substituted with a group selected from the substituent group A (substituent group A: substituted or unsubstituted aryloxy, substituted or unsubstituted with heteroaryloxy or substituted and unsubstituted non-aromatic heterocyclic group-oxy) and with carboxy; or
R$^{2a}$ is not alkyl substituted with pyrrolidinyl, wherein the pyrrolidinyl is substituted with a group selected from the substituent group A and with alkyloxycarbonyl, and the following compounds are excluded:

[Formula 10]

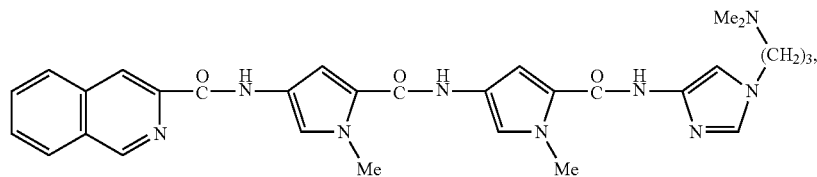

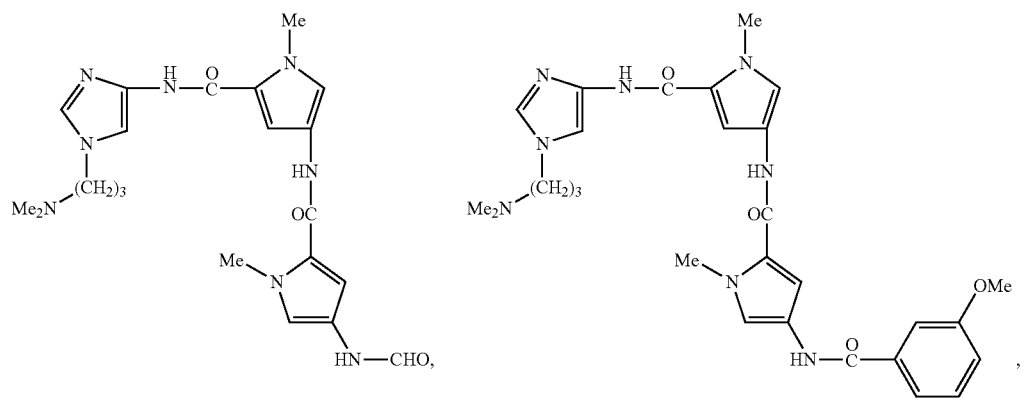

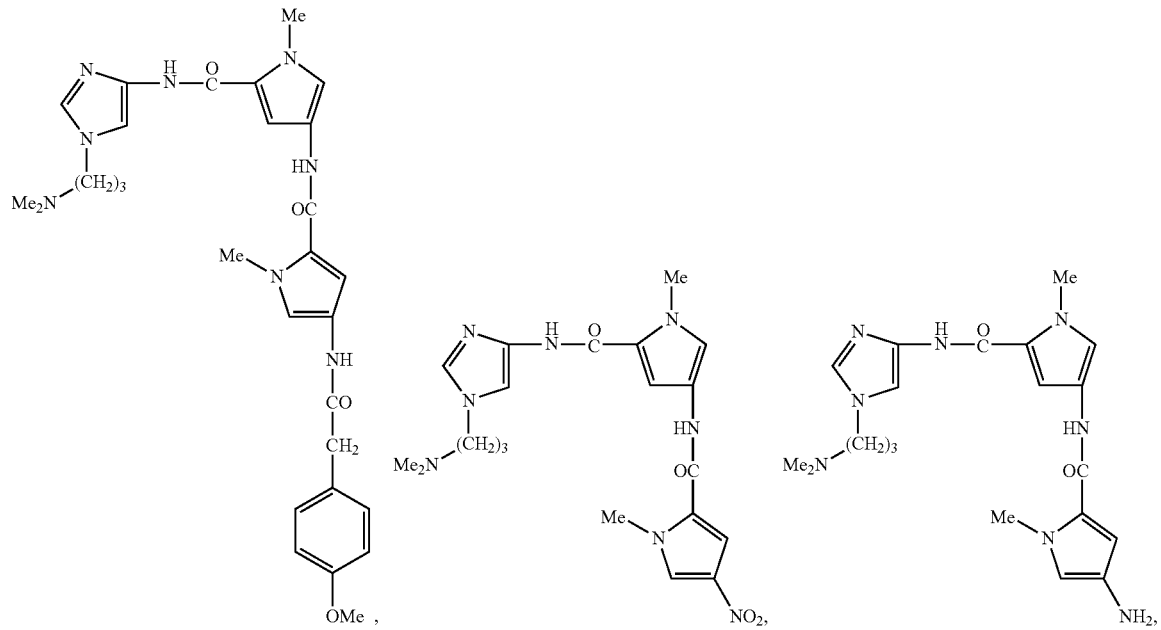

-continued

[Formula 11]

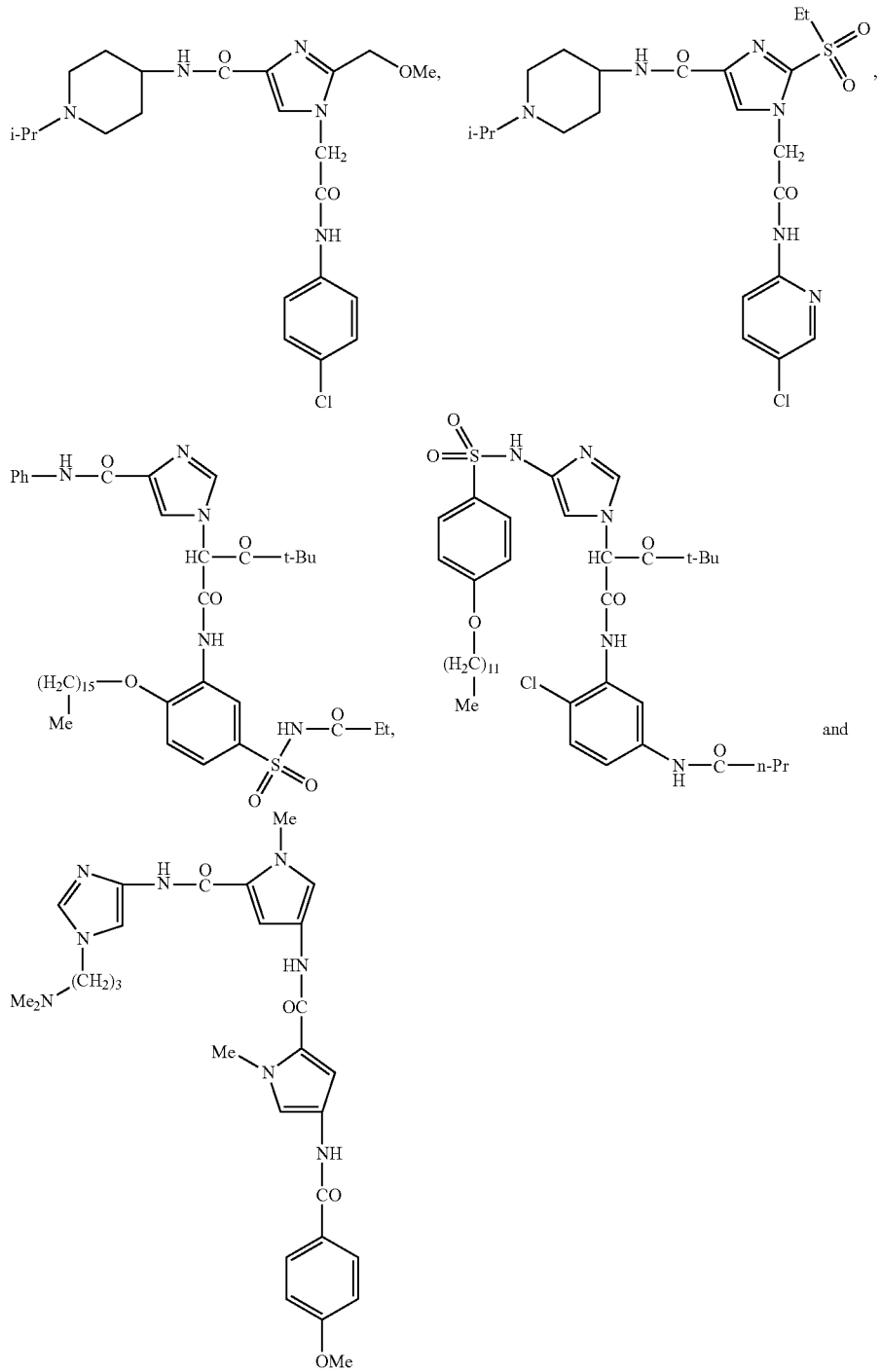

wherein, Me is methyl, Et is ethyl, n-Pr is normal propyl, i-Pr is iso-propyl, t-Bu is tert-buthyl, and Ph is phenyl, or a pharmaceutically acceptable salt thereof.

(9) The compound according to (8),
wherein —$R^{2a}$ is —$(CR^7R^8)n$-Y;
$R^7$ is each independently hydrogen, halogen, or substituted or unsubstituted alkyl; $R^8$ is each independently hydrogen, halogen, or substituted or unsubstituted alkyl; or $R^7$ and $R^8$ taken together form oxo;

n is an integer from 1 to 3;
—Y is —$(SO_2)p$-$N(R^9)(R^{10})$;
$R^9$ and $R^{10}$ are each independently hydrogen, substituted or unsubstituted alkyl, substituted or unsubstituted alkenyl, substituted or unsubstituted alkynyl, substituted or unsubstituted acyl, substituted or unsubstituted alkyloxycarbonyl, substituted or unsubstituted alkenyloxycarbonyl, substituted or unsubstituted alkynyloxycarbonyl, substituted sulfinyl, substituted sulfonyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl; or $R^9$ and $R^{10}$ taken together with the adjacent nitrogen atom may form a ring in which oxygen atom, sulfur atom, or nitrogen atom may intervene;

p is 0 or 1;

$R^{2c}$ is substituted or unsubstituted alkyl of which carbon number is 2 or more, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

-L- is —C(=O)—N($R^2$)—, —N($R^2$)—C(=O)—, or —N($R^2$)—SO$_2$—;

$R^2$ is hydrogen or substituted or unsubstituted alkyl, or a pharmaceutically acceptable salt thereof.

(10) A pharmaceutical composition for inhibiting TRPV4 receptor which contains a compound of the formula (III):

[Formula 12]

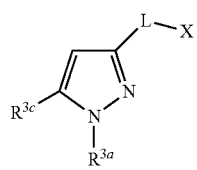

(III)

wherein —$R^{3a}$ is —(CR$^7$R$^8$)n-Y;

$R^7$ is each independently hydrogen, halogen, or substituted or unsubstituted alkyl; $R^8$ is each independently hydrogen, halogen, or substituted or unsubstituted alkyl; or $R^7$ and $R^8$ taken together form oxo;

n is an integer from 1 to 3;

—Y is —(SO$_2$)p-N($R^9$)($R^{10}$);

$R^9$ and $R^{10}$ are each independently hydrogen, substituted or unsubstituted alkyl, substituted or unsubstituted alkenyl, substituted or unsubstituted alkynyl, substituted or unsubstituted acyl, substituted or unsubstituted alkyloxycarbonyl, substituted or unsubstituted alkenyloxycarbonyl, substituted or unsubstituted alkynyloxycarbonyl, substituted sulfinyl, substituted sulfonyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl; or $R^9$ and $R^{10}$ taken together with the adjacent nitrogen atom may form a ring in which oxygen atom, sulfur atom, or nitrogen atom may intervene;

p is 0 or 1;

$R^{3c}$ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;

-L- is —C(=O)—N($R^2$)—, —N($R^2$)—C(=O)—, or —N($R^2$)—SO$_2$—;

$R^2$ is hydrogen or substituted or unsubstituted alkyl;

X is substituted or unsubstituted aryl, substituted or unsubstituted heteroaryl, substituted or unsubstituted cycloalkyl, substituted or unsubstituted cycloalkenyl, or a substituted or unsubstituted non-aromatic heterocyclic group, or a pharmaceutically acceptable salt thereof.

(10') A method for treating a TRPV4 receptor-mediated disorder, which comprises administering to a subject in need of such treatment a therapeutically effective amount of the compound or a pharmaceutically acceptable salt thereof according to the above (10).

(11) A compound represented by the formula (III);

[Formula 13]

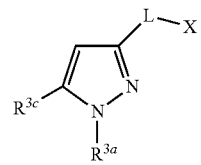

(III)

wherein —$R^{3a}$ is —(CR$^7$R$^8$)n-Y;

$R^7$ is each independently hydrogen, halogen, or substituted or unsubstituted alkyl; $R^8$ is each independently hydrogen, halogen, or substituted or unsubstituted alkyl; or $R^7$ and $R^8$ taken together form oxo;

n is an integer from 1 to 3;

—Y is —(SO$_2$)p-N($R^9$)($R^{10}$);

$R^9$ and $R^{10}$ are each independently hydrogen, substituted or unsubstituted alkyl, substituted or unsubstituted alkenyl, substituted or unsubstituted alkynyl, substituted or unsubstituted acyl, substituted or unsubstituted alkyloxycarbonyl, substituted or unsubstituted alkenyloxycarbonyl, substituted or unsubstituted alkynyloxycarbonyl, substituted sulfinyl, substituted sulfonyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl; or $R^9$ and $R^{10}$ taken together with the adjacent nitrogen atom may form a ring in which oxygen atom, sulfur atom, or nitrogen atom may intervene;

p is 0 or 1;

$R^{3c}$ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;

-L- is —C(=O)—N($R^2$)—, —N($R^2$)—C(=O)—, or —N($R^2$)—SO$_2$—;

$R^2$ is hydrogen or substituted or unsubstituted alkyl;

X is substituted or unsubstituted aryl, substituted or unsubstituted heteroaryl, substituted or unsubstituted cycloalkyl, substituted or unsubstituted cycloalkenyl, or a substituted or unsubstituted non-aromatic heterocyclic group, provided that the following compound is excluded:

[Formula 14]

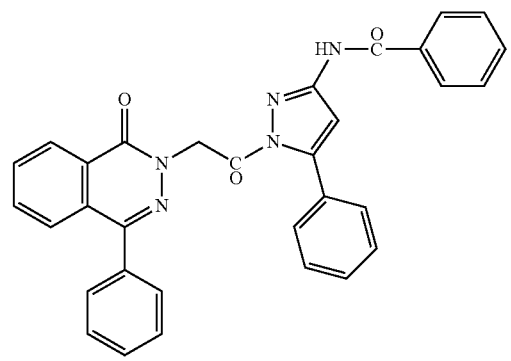

or a pharmaceutically acceptable salt thereof.

(12) A pharmaceutical composition for inhibiting TRPV4 receptor which contains a compound of the formula (IV):

[Formula 15]

$$\text{(IV)}$$

wherein —$R^{4a}$ is —$(CR^7R^8)n$-Y;
$R^7$ is each independently hydrogen, halogen, or substituted or unsubstituted alkyl; $R^8$ is each independently hydrogen, halogen, or substituted or unsubstituted alkyl; or $R^7$ and $R^8$ taken together form oxo;
n is an integer from 1 to 3;
—Y is —$(SO_2)p$-$N(R^9)(R^{10})$;
$R^9$ and $R^{10}$ are each independently hydrogen, substituted or unsubstituted alkyl, substituted or unsubstituted alkenyl, substituted or unsubstituted alkynyl, substituted or unsubstituted acyl, substituted or unsubstituted alkyloxycarbonyl, substituted or unsubstituted alkenyloxycarbonyl, substituted or unsubstituted alkynyloxycarbonyl, substituted sulfinyl, substituted sulfonyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl; or $R^9$ and $R^{10}$ taken together with the adjacent nitrogen atom may form a ring in which oxygen atom, sulfur atom, or nitrogen atom may intervene;
p is 0 or 1;
$R^{4c}$ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
-L- is —C(=O)—N($R^2$)—, —N($R^2$)—C(=O)—, or —N($R^2$)—$SO_2$—;
$R^2$ is hydrogen or substituted or unsubstituted alkyl;
X is substituted or unsubstituted aryl, substituted or unsubstituted heteroaryl, substituted or unsubstituted cycloalkyl, substituted or unsubstituted cycloalkenyl, or a substituted or unsubstituted non-aromatic heterocyclic group,
or a pharmaceutically acceptable salt thereof.
(12') A method for treating a TRPV4 receptor-mediated disorder, which comprises administering to a subject in need of such treatment a therapeutically effective amount of the compound or a pharmaceutically acceptable salt thereof according to the above (12).
(13) A compound represented by the formula (IV):

[Formula 16]

$$\text{(IV)}$$

wherein —$R^{4a}$ is —$(CR^7R^8)n$-Y;
$R^7$ is each independently hydrogen, halogen, or substituted or unsubstituted alkyl; $R^8$ is each independently hydrogen, halogen, or substituted or unsubstituted alkyl; or $R^7$ and $R^8$ taken together form oxo;
n is an integer from 1 to 3;
—Y is —$(SO_2)p$-$N(R^9)(R^{10})$;
$R^9$ and $R^{10}$ are each independently hydrogen, substituted or unsubstituted alkyl, substituted or unsubstituted alkenyl, substituted or unsubstituted alkynyl, substituted or unsubstituted acyl, substituted or unsubstituted alkyloxycarbonyl, substituted or unsubstituted alkenyloxycarbonyl, substituted or unsubstituted alkynyloxycarbonyl, substituted sulfinyl, substituted sulfonyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl; or $R^9$ and $R^{10}$ taken together with the adjacent nitrogen atom may form a ring in which oxygen atom, sulfur atom, or nitrogen atom may intervene;
p is 0 or 1;
$R^{4c}$ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
-L- is —C(=O)—N($R^2$)—, —N($R^2$)—C(=O)—, or —N($R^2$)—$SO_2$—;
$R^2$ is hydrogen or substituted or unsubstituted alkyl;
X is substituted or unsubstituted aryl, substituted or unsubstituted heteroaryl, substituted or unsubstituted cycloalkyl, substituted or unsubstituted cycloalkenyl, or a substituted or unsubstituted non-aromatic heterocyclic group:
provided that X is not cycloalkyl substituted with methyl and with propyl, and
the following compounds are excluded:

[Formula 17]

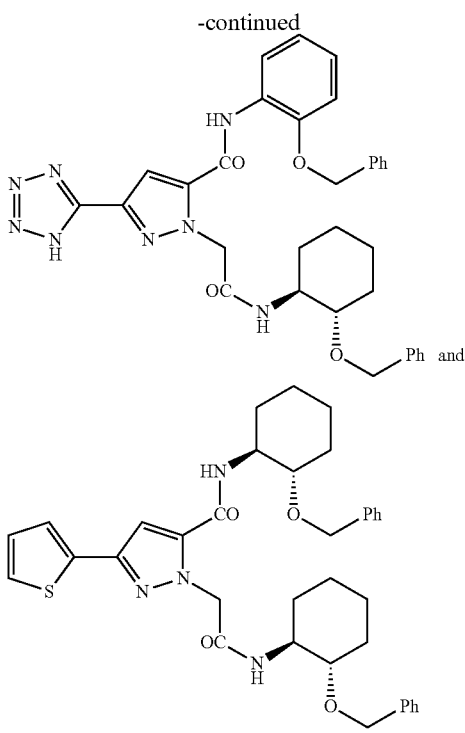

wherein Ph is phenyl,
or a pharmaceutically acceptable salt thereof.
(14) The compound according to (13),
$R^{4c}$ is substituted or unsubstituted cycloalkyl, substituted or unsubstituted cycloalkenyl, a substituted or unsubstituted non-aromatic heterocyclic group, or substituted or unsubstituted aryl; and
X is substituted or unsubstituted aryl, substituted or unsubstituted heteroaryl, or a substituted or unsubstituted non-aromatic heterocyclic group,
or a pharmaceutically acceptable salt thereof.
(15) A compound represented by the formula (V):

[Formula 18]

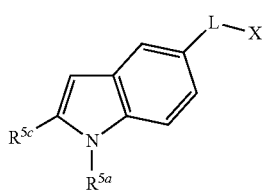

(V)

wherein —$R^{5a}$ is —$(CR^7R^8)n$-Y;
$R^7$ is each independently hydrogen, halogen, or substituted or unsubstituted alkyl; $R^8$ is each independently hydrogen, halogen, or substituted or unsubstituted alkyl; or $R^7$ and $R^8$ taken together form oxo;
n is an integer from 1 to 3;
—Y is —$(SO_2)p$-$N(R^9)(R^{10})$;
$R^9$ and $R^{10}$ are each independently hydrogen, substituted or unsubstituted alkyl, substituted or unsubstituted alkenyl, substituted or unsubstituted alkynyl, substituted or unsubstituted acyl, substituted or unsubstituted alkyloxycarbonyl, substituted or unsubstituted alkenyloxycarbonyl, substituted or unsubstituted alkynyloxycarbonyl, substituted sulfinyl, substituted sulfonyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
or $R^9$ and $R^{10}$ taken together with the adjacent nitrogen atom may form a ring in which oxygen atom, sulfur atom, or nitrogen atom may intervene;
p is 0 or 1;
-L- is —C(=O)—$N(R^2)$—, —$N(R^2)$—C(=O)—, —$N(R^2)$— or —$N(R^2)$—$SO_2$—;
$R^2$ is hydrogen or substituted or unsubstituted alkyl;
$R^{5c}$ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
X is substituted or unsubstituted aryl, substituted or unsubstituted heteroaryl, substituted or unsubstituted cycloalkyl, substituted or unsubstituted cycloalkenyl, or a substituted or unsubstituted non-aromatic heterocyclic group:
provided that -L- is not —NH—C(=O)—, when both of $R^9$ and $R^{10}$ are hydrogen or methyl and $R^{5c}$ is substituted or unsubstituted phenyl,
or a pharmaceutically acceptable salt thereof.
(16) The compound according to (15),
wherein -L- is —C(=O)—$N(R^2)$—, —$N(R^2)$— or —$N(R^2)$—$SO_2$—; and
$R^2$ is the same as (15),
or a pharmaceutically acceptable salt thereof.
(17) A compound represented by the formula (VI):

[Formula 19]

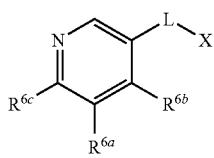

(VI)

wherein —$R^{6a}$ is —$(CR^7R^8)n$-Y;
$R^7$ is each independently hydrogen, halogen, or substituted or unsubstituted alkyl; $R^8$ is each independently hydrogen, halogen, or substituted or unsubstituted alkyl; or $R^7$ and $R^8$ taken together form oxo;
n is an integer from 1 to 3;
—Y is —$(SO_2)p$-$N(R^9)(R^{10})$;
$R^9$ and $R^{10}$ are each independently hydrogen, substituted or unsubstituted alkyl, substituted or unsubstituted alkenyl, substituted or unsubstituted alkynyl, substituted or unsubstituted acyl, substituted or unsubstituted alkyloxycarbonyl, substituted or unsubstituted alkenyloxycarbonyl, substituted or unsubstituted alkynyloxycarbonyl, substituted sulfinyl, substituted sulfonyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
or $R^9$ and $R^{10}$ taken together with the adjacent nitrogen atom may form a ring in which oxygen atom, sulfur atom, or nitrogen atom may intervene;
p is 0 or 1;
$R^{6b}$ is hydrogen or substituted or unsubstituted alkyl:
$R^{6c}$ is hydrogen, halogen, hydroxy, cyano, nitro, substituted or unsubstituted, alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted cycloalkyloxy, substituted or unsubstituted cycloalkenyloxy, substituted or unsubstituted non-aromatic heterocyclic group-oxy, substituted or unsubstituted aryloxy, substituted or unsubstituted heteroaryloxy, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclic group-oxycarbonyl, substituted or unsubstituted aryloxycarbonyl, substituted or unsubstituted heteroaryloxycarbonyl, substituted or unsubstituted sulfamoyl, substituted sulfinyl, substituted sulfonyl, substituted or unsubstituted alkylsulfonyloxy, substituted or unsubstituted arylsulfonyloxy, substituted or unsubstituted amino, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;

-L- is —C(=O)—N($R^2$)—, —N($R^2$)—C(=O)—, —N($R^2$)—C(=O)—N($R^3$)—, —N($R^2$)—SO$_2$—, —C(=O)—O—(CR$^4$R$^5$)m-, or —SO$_2$—N($R^2$)—(CR$^4$R$^5$)m-;

$R^2$ to $R^5$ are each independently hydrogen or substituted or unsubstituted alkyl;

X is substituted or unsubstituted aryl, substituted or unsubstituted heteroaryl, substituted or unsubstituted cycloalkyl, substituted or unsubstituted cycloalkenyl, or a substituted or unsubstituted non-aromatic heterocyclic group, or a pharmaceutically acceptable salt thereof.

(18) A pharmaceutical composition, containing the compound according to any of (1) to (4), (8), (9), (11), and (13) to (17), or a pharmaceutically acceptable salt thereof.

(19) The pharmaceutical composition according to claim 18 for inhibiting a TRPV4 receptor.

(20) Method for treating and/or preventing a TRPV4 receptor-mediated disorder characterized by administration of the compound according to any of (1) to (4), (8), (9), (11), and (13) to (17), or a pharmaceutically acceptable salt thereof.

(20') A method for treating a TRPV4 receptor-mediated disorder, which comprises administering to a subject in need of such treatment a therapeutically effective amount of the compound or a pharmaceutically acceptable salt thereof according to any of (1) to (4), (8), (9), (11), and (13) to (17), or a pharmaceutically acceptable salt thereof.

(21) Use of the compound of any one of (1) to (4), (8), (9), (11), and (13) to (17), or its pharmaceutically acceptable salt in the manufacturing of an agent for treating a TRPV4 receptor-mediated disorder.

(22) The compound of any one of (1) to (4), (8), (9), (11), and (13) to (17), or its pharmaceutically acceptable salt for use in a method for treating a TRPV4 receptor-mediated disorder.

Effect of the Invention

The present invention provides a compound is useful in the treatment and/or prevention of a TRPV4 receptor-mediated disorder, or a pharmaceutically acceptable salt thereof. The compound of the present invention shows an excellent TRPV4 inhibitory activity as described in test examples below. Thus, a pharmaceutical composition of the present invention is available for therapeutic agent and/or prophylactic agent for inflammatory pain (bladder inflammatory pain, pain after tooth extraction, postoperative pain, pain in the low back, periarthritis scapulohumeralis, cervico-omo-brachial syndrome, inflammation of a tendon or a tendon sheath, osteoarthritis, chronic articular rheumatism), neuropathic pain (sciatica, postherpetic neuralgia, diabetic neuropathy), pain related to cancer (cancer pain, bone metastasis pain, pain with the administration of anticancer agent), IBS, inflammatory bowel disease, osteoporosis, articular cartilage degeneration, cerebral stroke, incontinence, overactive bladder, urinary disturbance by bladder inflammation, asthma, dry skin, atopic dermatitis, metastasis and invasion of cancer, corneal ulcer, obesity, insulin resistance, diabetes, or the like.

The compound of the present invention is a compound having utility as a medicament. Here, utility as a medicament includes the following points: the compound has good metabolic stability; the induction of a drug-metabolizing enzyme is low; the inhibition of a drug-metabolizing enzyme which metabolizes another drug is low; the compound has high oral absorbency; the inhibition of hERG is low; the clearance is low; the half-life is sufficiently long to express the efficacy; or the like.

MODE FOR CARRYING OUT THE INVENTION

Hereinafter, the present invention is described with reference to embodiments. It should be understood that, throughout the present specification, the expression of a singular form includes the concept of its plural form unless specified otherwise. Accordingly, it should be understood that an article in singular form (for example, in the English language, "a," "an," "the," and the like) includes the concept of its plural form unless specified otherwise. Furthermore, it should be understood that the terms used herein are used in a meaning normally used in the art unless specified otherwise. Thus, unless defined otherwise, all technical and scientific terms used herein have the same meaning as those generally understood by those skilled in the art in the field to which the present invention pertains. If there is a contradiction, the present specification (including definitions) precedes.

Each meaning of terms used herein is described below. In the present specification, each term is used in an unequivocal meaning. Both when used alone and in combination with another word, each term is used in the same meaning.

As used herein, the term "halogen" means fluorine, chlorine, bromine, and iodine. Examples thereof include fluorine, chlorine, and bromine.

As used herein, the term "alkyl" encompasses a linear or branched monovalent hydrocarbon group having 1 to 8 carbon atoms. Examples thereof include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl, and the like. An example is C1-C6 alkyl. Another example is C1-C4 alkyl. When the carbon number is specified in particular, an "alkyl" having carbon in a range of the number is meant.

As used herein, the term "alkenyl" encompasses a linear or branched monovalent hydrocarbon group having 2 to 8 carbon atoms and one or more double bonds. Examples thereof include vinyl, allyl, 1-propenyl, 2-butenyl, 2-pentenyl, 2-hexenyl, 2-heptenyl, 2-octenyl, and the like. An example is C2-C6 alkenyl. Another example is C2-C4 alkenyl.

As used herein, the term "alkynyl" encompasses a linear or branched monovalent hydrocarbon group having 2 to 8 carbon atoms and one or more triple bonds. Examples thereof include ethynyl, 1-propynyl, 2-propynyl, 2-butynyl, 2-pentynyl, 2-hexynyl, 2-heptynyl, 2-octynyl, and the like. An example is C2-C6 alkynyl. Another example is C2-C4 alkynyl.

As used herein, the term "cycloalkyl" encompasses cycloalkyl having 3 to 8 carbon atoms. Examples thereof include cyclopropyl, cyclobutyl, cyclopentyl, cyclohexyl, cycloheptyl, and cyclooctyl. An example is C3-C6 cycloalkyl.

As used herein, the term "cycloalkenyl" encompasses cycloalkenyl having 3 to 8 carbon atoms. Examples thereof include cyclopropenyl, cyclobutenyl, cyclopentenyl, cyclohexenyl, and cycloheptenyl. An example is C3-C6 cycloalkenyl.

The alkyl portion of "alkyloxy" means the aforementioned "alkyl". Examples thereof include methyloxy, ethyloxy, propyloxy, isopropyloxy, butyloxy, isobutyloxy, sec-butyloxy, tert-butyloxy, pentyloxy, isopentyloxy, neopentyloxy, hexyloxy, and the like. An example is C1-C6 alkyloxy. Another example is C1-C4 alkyloxy. When the carbon number is specified in particular, an "alkyloxy" having carbon in a range thereof is meant.

As used herein, the term "alkylsulfonyl" includes methylsulfonyl, ethylsulfonyl, n-propylsulfonyl, isopropylsulfonyl, n-butylsulfonyl, isobutylsulfonyl, sec-butylsulfonyl, tert-butylsulfonyl, n-pentylsulfonyl, isopentylsulfonyl, 2-pentylsulfonyl, 3-pentylsulfonyl, n-hexylsulfonyl, isohexylsulfonyl, 2-hexylsulfonyl, 3-hexylsulfonyl, n-heptylsulfonyl, n-octylsulfonyl, and the like. An example is C1-C6 alkylsulfonyl. Another example is C1-C4 alkylsulfonyl.

The alkylsulfonyl portion of "alkylsulfonyloxy" means the aforementioned "alkylsulfonyloxy". Examples thereof include methylsulfonyloxy, ethylsulfonyloxy, n-propylsulfonyloxy, isopropylsulfonyloxy, n-butylsulfonyloxy, tert-butylsulfonyloxy, n-pentylsulfonyloxy, and the like.

The alkyloxy portion of "alkyloxycarbonyl" means the aforementioned "alkyloxy". Examples thereof include methyloxycarbonyl, ethyloxycarbonyl, n-propyloxycarbonyl, isopropyloxycarbonyl, n-butyloxycarbonyl, tert-butyloxycarbonyl, n-pentyloxycarbonyl, and the like. An example is C1-C6 alkyloxy. Another example is C1-C4 alkyloxycarbonyl. Another example is C1-C2 alkyloxycarbonyl.

As used herein, the term "acyl" encompasses formyl, alkylcarbonyl, alkenylcarbonyl, cycloalkylcarbonyl, cycloalkenylcarbonyl, arylcarbonyl, heteroarylcarbonyl, non-aromatic heterocyclic group carbonyl. Examples thereof include acetyl, propionyl, butyloyl, benzoyl, and the like.

As used herein, the term "aryl" includes a monovalent group derived from aromatic carbocycle which is monocyclic or fused-cyclic. Both in the cases where aryl is monocyclic and fused-cyclic, it may be bound at any possible position. Examples thereof include phenyl, 1-naphthyl, 2-naphthyl, anthryl, and the like. Examples include phenyl, 1-naphthyl, and 2-naphthyl. An example is phenyl.

As used herein, the term "aromatic carbocycle" includes an aromatic carbocycle which is monocyclic or fused-cyclic consisting only of carbon atom in the ring. For example, benzene ring, naphthalene ring, anthracene ring, etc. are exemplified. Examples include benzene ring and naphthalene ring.

As used herein, the term "heteroaryl" includes a monovalent group derived from a 5 to 7-membered aromatic heterocycle containing one or more optionally-selected oxygen atoms, sulfur atoms, and/or nitrogen atoms in the ring. This may be fused with the aforementioned "aryl" and/or another heteroaryl at any possible position. Both in the cases that heteroaryl is monocyclic and fused-cyclic, it may be bound at any possible position. Examples thereof include pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), imidazolyl (e.g., 2-imidazolyl, 4-imidazolyl), pyrazolyl (e.g., 1-pyrazolyl, 3-pyrazolyl, 4-pyrazolyl), isothiazolyl (e.g., 3-isothiazolyl), isoxazolyl (e.g., 3-isoxazolyl), oxazolyl (e.g., 2-oxazolyl, 4-oxazolyl, 5-oxazolyl), thiazolyl (e.g., 2-thiazolyl, 4-thiazolyl, 5-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1H-tetrazolyl), oxadiazolyl (e.g., 1,3,4-oxadiazolyl), thiadiazolyl (e.g., 1,3,4-thiadiazolyl), indolizinyl (e.g., 2-indolizinyl, isoindolyl (e.g., 2-isoindolyl), indolyl (e.g., 1-indolyl, 2-indolyl, indazolyl (e.g., 3-indazolyl), purinyl (e.g., 8-purinyl), quinolizinyl (e.g., 2-quinolizinyl), isoquinolyl (e.g., 3-isoquinolyl), quinolyl (e.g., 2-quinolyl, 5-quinolyl), phthalazinyl (e.g., 1-phthalazinyl), naphthyridinyl (e.g., 2-naphthyridinyl), quinazolinyl (e.g., 2-quinazolinyl), cinnolinyl (e.g., 3-cinnolinyl); pteridinyl (e.g., 2-pteridinyl), carbazolyl (e.g., 2-carbazolyl, 4-carbazolyl), phenanthridinyl (e.g., 2-phenanthridinyl, 3-phenanthridinyl), acridinyl (e.g., 1-acridinyl, 2-acridinyl), dibenzofuranyl (e.g., 1-dibenzofuranyl, 2-dibenzofuranyl), benzimidazolyl (e.g., 2-benzimidazolyl), benzisoxazolyl (e.g., 3-benzisoxazolyl), benzoxazolyl (e.g., 2-benzoxazolyl), benzoxadiazolyl (e.g., 4-benzoxadiazolyl), benzisothiazolyl (e.g., 3-benzisothiazolyl), benzothiazolyl (e.g., 2-benzothiazolyl), benzofuryl (e.g., 3-benzofuryl), benzothienyl (e.g., 2-benzothienyl), dibenzothienyl (e.g., 2-dibenzothienyl), and the like.

As used herein, the term "non-aromatic heterocyclic group" includes a monovalent group derived from a 3 to 8-membered non-aromatic heterocycle containing one or more optionally-selected oxygen atoms, sulfur atoms, and/or nitrogen atoms in the ring. The aforementioned non-aromatic heterocycle may be substituted at any possible position. Such non-aromatic heterocycle may be further crosslinked via C1-C4 alkyl chain. Additionally, such non-aromatic heterocycle may be fused with the aforementioned "cycloalkyl," (example include 3 to 6-membered cycloalkyl), the aforementioned "cycloalkenyl," (example include 3 to 6-membered cycloalkenyl), the aforementioned "aryl," the aforementioned "heteroaryl", and/or another non-aromatic heterocyclic group at any possible position. As long as fused ring is non-aromatic ring as a ring, it may have being unsaturated in one of rings. Examples thereof include pyrrolinyl (e.g., 1-pyrrolinyl, 2-pyrrolinyl, 3-pyrrolinyl), pyrrolidinyl (e.g., 1-pyrrolidinyl, 2-pyrrolidinyl, 3-pyrrolidinyl), pyrrolidinone, imidazolinyl (e.g., 1-imidazolinyl, 2-imidazolinyl, imidazolidinyl (e.g., 1-imidazolidinyl, 2-imidazolidinyl, imidazolidinone, pyrazolinyl (e.g., 1-pyrazolinyl, 3-pyrazolinyl, 4-pyrazolinyl), pyrazolidinyl (e.g., 1-pyrazolidinyl, 3-pyrazolidinyl, 4-pyrazolidinyl), piperidinone, piperidino, piperidinyl (e.g., 2-piperidinyl, 3-piperidinyl, 4-piperidinyl), piperazinyl (e.g., 1-piperazinyl, 2-piperazinyl), morpholinyl (e.g., 2-morpholinyl, 3-morpholinyl), morpholino, tetrahydropyranyl (e.g., 2-tetrahydropyranyl, 3-tetrahydropyranyl, 4-tetrahydropyranyl), tetrahydrofuranyl (2-tetrahydrofuranyl, 3-tetrahydrofuranyl), and the like.

As used herein, the term "nitrogen-containing saturated heterocyclic group" includes non-aromatic heterocyclic group which is saturated as a ring and includes one and more nitrogen atoms in the ring. Examples thereof include piperidinyl (e.g., 2-piperidinyl, 3-piperidinyl, 4-piperidinyl), piperazinyl (e.g., 1-piperazinyl, 2-piperazinyl), morpholinyl (e.g., 2-morpholinyl, 3-morpholinyl), morpholino, and the like.

As used herein, the term "aromatic heterocycle" includes a 5 to 7-membered aromatic heterocycle containing one or more optionally-selected oxygen atoms, sulfur atoms, and/or nitrogen atoms in the ring or a fusedring consisting of two or more said 5 to 7-membered aromatic heterocycle. This may be fused with the aforementioned "aromatic carbocycle". Examples thereof include pyrrole, furan, thiophene, imidazole, pyrazole, isothiazole, isoxazole, oxazole, thiazole, pyridine, pyrazine, pyrimidine, pyridazine, tetrazole, oxadiazole, thiadiazole, indolizine, isoindole, indole, indazole, purine, quinolizine, isoquinoline, quinoline, phthalazine, naphthyridine, quinazoline, cinnoline, pteridine, carbazole, phenanthridine, acridine, dibenzofuran, benzimidazole, benzisoxazole, benzoxazole, benzisothiazole, benzothiazole, benzofuran, benzothiophene, dibenzothiophene, and the like. Examples include thiophene, pyridine, furan, thiazole, oxazole and pyrimidine.

As used herein, the term "non-aromatic heterocycle" includes a 3 to 8-membered non-aromatic heterocycle containing one or more optionally-selected oxygen atoms, sulfur atoms, and/or nitrogen atoms in the ring or a fusedring consisting of two or more said 3 to 8-membered non-aromatic heterocycle. Such non-aromatic heterocycle may be further crosslinked via C1-C4 alkyl chain. Additionally, such non-aromatic heterocycle may be fused with the aforementioned "aromatic carbocycle" (example includes 6-membered aromatic carbocycle), the aforementioned "non-aromatic carbocycle" (example includes 3 to 6-membered non-aromatic carbocycle), the aforementioned "aromatic heterocycle", and/or another non-aromatic heterocycle. As long as fused ring is non-aromatic ring as a ring, it may have being unsaturated in one of rings. Examples thereof include pyrroline, pyrrolidine, pyrrolidinone, imidazoline, imidazolidine, pyrazoline, pyrazolidine, piperidinone, piperidine, piperazine, morpholine, tetrahydropyran, tetrahydrofuran, dihydropyran, dihydrofuran, benzodioxole, and the like. Examples include dihydropyran, tetrahydropyran, dihydrofuran, tetrahydrofuran.

As used herein, the alkyl portion of "alkylthio" and "alkylcarbonyl" means the aforementioned "alkyl".

As used herein, the alkenyl portion of "alkenylthio", "alkenyloxy" and "alkenylcarbonyl" means the aforementioned "alkenyl".

As used herein, the alkynyl portion of "alkynyloxy" and "alkynylthio" means the aforementioned "alkynyl".

As used herein, the cycloalkyl portion of "cycloalkyloxy", "cycloalkylcarbonyl" and "cycloalkylsulfonyl" means the aforementioned "cycloalkyl".

As used herein, the cycloalkenyl portion of "cycloalkenyloxy", "cycloalkenylcarbonyl" and "cycloalkenyloxycarbonyl" means the aforementioned "cycloalkenyl".

As used herein, the aryl portion of "aryloxy", "arylcarbonyl", "aryloxycarbonyl", "arylsulfonyloxy" and "arylsulfonyl" means the aforementioned "aryl".

As used herein, the heteroaryl portion of "heteroaryloxy", "heteroarylcarbonyl", "heteroaryloxycarbonyl" and "heteroarylsulfonyl" means the aforementioned "heteroaryl".

As used herein, the non-aromatic heterocyclic group portion of "non-aromatic heterocyclic group-oxy", "non-aromatic heterocyclic group-carbonyl", "non-aromatic heterocyclic group-sulfonyl" and "non-aromatic heterocyclic group-oxycarbonyl" means the aforementioned "non-aromatic heterocyclic group".

As used herein, substituents of "substituted or unsubstituted alkyl" "substituted or unsubstituted alkenyl", "substituted or, unsubstituted alkynyl", "substituted or unsubstituted aryl", "substituted or unsubstituted cycloalkyl", "substituted or unsubstituted cycloalkenyl", "substituted or unsubstituted heteroaryl", "substituted or unsubstituted non-aromatic heterocyclic group", "substituted or unsubstituted nitrogen-containing saturated heterocyclic group", "substituted or unsubstituted acyl", "substituted or unsubstituted alkyloxycarbonyl", "substituted or unsubstituted carbamoyl", "substituted or unsubstituted alkyloxy", "substituted or unsubstituted alkenyloxy", "substituted or unsubstituted alkynyloxy", "substituted or unsubstituted non-aromatic heterocyclic group-oxy", "substituted or unsubstituted aryloxy", "substituted or unsubstituted heteroaryloxy", "substituted or unsubstituted alkylthio" "substituted or unsubstituted alkenylthio", "substituted or unsubstituted alkynylthio", "substituted or unsubstituted cycloalkyloxycarbonyl", "substituted or unsubstituted cycloalkenyloxycarbonyl", "substituted or unsubstituted non-aromatic heterocyclic group-oxycarbonyl", "substituted or unsubstituted aryloxycarbonyl", "substituted or unsubstituted heteroaryloxycarbonyl", "substituted or unsubstituted alkylsulfonyloxy", "substituted or unsubstituted arylsulfonyloxy" and "substituted or unsubstituted alkylsulfonyl" are selected from the group consisting of, for example, hydroxy, carboxy, halogen, halogenated alkyl (e.g., $CF_3$, $CH_2CF_3$, $CH_2CCl_3$), nitro, nitroso, cyano, alkyl (e.g., methyl, ethyl, isopropyl, tert-butyl), hydroxyalkyl (e.g., hydroxyethyl), alkenyl (e.g., vinyl), alkynyl (e.g., ethynyl), cycloalkyl (e.g., cyclopropyl, adamantyl), cycloalkylalkyl (e.g., cyclohexylmethyl, adamantylmethyl), cycloalkenyl (e.g., cyclopropenyl), aryl (e.g., phenyl, naphthyl), arylalkyl (e.g., benzyl, phenethyl), heteroaryl (e.g., pyridyl, furyl), heteroarylalkyl (e.g., pyridylmethyl), non-aromatic heterocyclic group (e.g., piperidyl), non-aromatic heterocyclic group-alkyl (e.g., morpholylmethyl), alkyloxy (e.g., methoxy, ethoxy, propoxy, butoxy), halogenated alkyloxy(e.g., $OCF_3$), alkenyloxy(e.g., vinyloxy, allyloxy), aryloxy(e.g., phenyloxy), alkyloxycarbonyl (e.g., methoxycarbonyl, ethoxycarbonyl, tert-butoxycarbonyl), arylalkyloxy (e.g., benzyloxy), aryloxyalkyloxycarbonyl (e.g., benzyloxycarbonyl), unsubstituted amino, substituted amino [(e.g., alkylamino (e.g., methylamino, ethylamino, dimethylamino), acylamino (e.g., acetylamino, benzoylamino), arylalkylamino (e.g., benzylamino, tritylamino), hydroxyamino], alkylaminoalkyl (e.g., diethylaminomethyl), alkylaminocarbonyl (e.g., N-methylaminoarbonyl, N-ethylaminocarbonyl, N-n-propylaminocarbonyl, N-isopropylaminocarbonyl), alkylcarbonyl (e.g., formyl, acetyl, propionyl), alkylsulfonyl (methylsulfonyl, ethylsulfonyl), non-aromatic heterocyclic group-sulfonyl (e.g., piperidinylsulfonyl), sulfamoyl, oxo, and the like. Substitution may occur with 1 to 4 of such substituents.

As used herein, the term "substituted or unsubstituted amino" encompasses amino that may be substituted with the aforementioned "alkyl," the aforementioned "cycloalkyl" the aforementioned "aryl", the aforementioned "heteroaryl", the aforementioned "non-aromatic heterocyclic group", the aforementioned "acyl", the aforementioned "alkyloxycarbonyl," the aforementioned "alkylsulfonyl," the aforementioned "arylsulfonyl," the aforementioned "heteroarylsulfonyl," the aforementioned "non-aromatic heterocyclic group-sulfonyl" at 1 or 2 positions. The said substituent may be substituted with the following substitutents; alkyl, hydroroxyalkyl, alkenyl, aryl, alkyloxyaryl, heteroaryl, alkylcarbonyl, arylcarbonyl, arylalkyloxy, heteroarylcarbonyl, non-aromatic heterocyclic group-carbonyl, alkyloxyalkyloxy, alkyloxycarbonyl, aryloxycarbonyl, heteroaryloxycarbonyl, non-aromatic heterocyclkic group-oxycarbonyl, sulfamoyl, alkylsulfonyl, carbamoyl, cycloalkylsulfonyl, arylsulfonyl, heteroarylsulfonyl, non-aromatic heterocyclic group-sulfonyl, hydroxy, sulfonyl, sulfinyl, unsubstituted amino, alkylamino, alkylcarbonylamino, halogen, cyano, alkyloxy, carboxy, oxo, or the like. As to "substituted or unsubstituted amino", examples include amino, methylamino, dimethylamino, ethylamino, diethylamino, ethylmethylamino, cyclohexylamino, benzylamino, acetylamino, benzoylamino, methoxycarbonylamino, methylsulfonylamino, tetrahydropyranylamino, tetrahydrofuranylamino, morpholinoamino, morpholinylamino, piperidinylamino, piperadinylamino, and the like.

As used herein, the term "substituted or unsubstituted carbamoyl" encompasses substituted or unsubstituted aminocarbonyl in which the substituted or unsubstituted amino portion is the aforementioned "substituted or unsubstituted amino." Examples thereof include carbamoyl, N-methylcarbamoyl, N,N-dimethylcarbamoyl; N-ethyl-N-methylcarbamoyl, N,N-diethylcarbamoyl, N-n-propylaminocarbamoyl, N-isopropylcarbamoyl, N-morpholinocarbamoyl, N-tetrahydrofuranylcarbamoyl, N-piperidylcarbamoyl, N-tetrahydropyranylcarbamoyl, N-benzylcarbamoyl, N-acetylcarbamoyl, N-methylsulfonylcarbamoyl, N-(2,2,2-trifluoroethyl)carbamoyl, N-(2-hydroxy-1-methylethyl)carbamoyl, and the like. Implies include carbamoyl, N-methylcarbamoyl, N,N-dimethylcarbamoyl, N-n-propylaminocarbamoyl, N-isopropylcarbamoyl, N-morpholinocarbamoyl, N-tetrahydrofuranylcarbamoyl, N-piperidylcarbamoyl, N-tetrahydropyranylcarbamoyl, N-methylsulfonylcarbamoyl, N-(2,2,2-trifluoroethyl)carbamoyl, N-(2-hydroxy-1-methylethyl)carbamoyl, and the like.

As used herein, the term "substituted or unsubstituted sulfamoyl" encompasses substituted or unsubstituted aminosulfonyl in which the substituted or unsubstituted amino portion is the aforementioned "substituted or unsubstituted amino." As to "substituted or unsubstituted sulfamoyl", examples include sulfamoyl, N-methylsulfamoyl, N,N-dimethylsulfamoyl, N-ethyl-N-methylsulfamoyl, N,N-diethylsulfamoyl, N-n-propylamiosulfamoyl, N-isopropylsulfamoyl, N-morpholinosulfamoyl, N-tetrahydrofuranylsulfamoyl, N-piperidylsulfamoyl, N-tetrahydropyranylsulfamoyl, N-benzylsulfamoyl, N-acetylsulfamoyl, N-methylsulfonylsulfamoyl, and the like. Examples includes sulfamoyl, N-methylsulfamoyl, N,N-dimethylsulfamoyl, N-n-propylamiosulfamoyl, N-isopropylsulfamoyl, N-morpholinosulfamoyl, N-tetrahydrofuranylsulfamoyl, N-piperidylsulfamoyl, N-tetrahydropyranylsulfamoyl, N-methylsulfonylsulfamoyl, and the like.

As used herein, the term "substituted sulfinyl" encompasses a group represented by —S(=O)—R, wherein R is the aforementioned "alkyl", "alkenyl", "aryl", "heteroaryl", "cycloalkyl", "cycloalkenyl" or "non-aromatic heterocyclic group". These may be independently substituted with hydroxy, carboxy, the aforementioned "alkyl", "alkenyl", "alkynyl", "halogen", "alkyloxy", "alkenyloxy", "alkynyloxy", "alkylthio", "carbamoyl", "alkyloxycarbonyl", "aryloxycarbonyl", or the like.

As used herein, a group defined as "-L-" of the formulas (I) to (VI) have bonds on the left and right sides, respectively. The right bond is to bind to a group defined as "X" of the formulas (I) to (VI), and the left bond is to bind to carbon atom of aromatic heterocycle. For example, the left bond of a group defined as "-L-" of the formula (I) is to bind to carbon atom of pyrrole.

Moreover, one or more hydrogen, carbon, or other atoms in the compound of formulas (I) to (VI) may be replaced with isotopes of hydrogen, carbon, or other atoms respectively. The compound of formulas (I) to (VI) encompasses all of radiolabeled compounds of the compound of formulas (I) to (VI). Such "radiolabeling," "a radiolabeled compound," and the like of the compound of formulas (I) to (VI) are each encompassed by the present invention, and are useful for studies on metabolized drug pharmacokinetics and studies on binding assay, and/or a diagnostic tool. Furthermore, they are also useful as medicines. Examples of isotopes that may be incorporated in the compound of formulas (I) to (VI) include hydrogen, carbon, nitrogen, oxygen, phosphorus, sulfur, fluorine, and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$ respectively. A radiolabeled compound of the present invention can be prepared using a well-known method in the relevant technical field. For example, a tritium-labeled compound of formulas (I) to (VI) can be prepared by introducing a tritium to a certain compound of formulas (I) to (VI), for example, through a catalytic dehalogenation reaction using a tritium. This method may comprise reacting with an appropriately-halogenated precursor of the compound of formulas (I) to (VI) with tritium gas in the presence of an appropriate catalyst, such as Pd/C, and in the presence or absent of a base. For another appropriate method of preparing a tritium-labeled compound, the document: Isotopes in the Physical and Biomedical Sciences, Vol. 1, Labeled Compounds (Part A), Chapter 6 (1987) can be referred to. A $^{14}C$-labeled compound can be prepared by using a raw material having $^{14}C$.

In the compound of the present invention, the preferable embodiments are as follows.

In the formula (I-A);

[Formula 20]

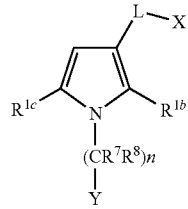

(I-A)

1) $R^7$ is each independently hydrogen, halogen, or substituted or unsubstituted alkyl; $R^8$ is each independently hydrogen, halogen, or substituted or unsubstituted alkyl; or $R^7$ and $R^8$ taken together form oxo (hereafter, $R^7$, $R^8$ being a1), 2) $R^7$ is each independently hydrogen, halogen, or substituted or unsubstituted alkyl or $R^8$ is each independently hydrogen, halogen, or substituted or unsubstituted alkyl (hereafter, $R^7$, $R^8$ being a2), 3) $R^7$ and $R^8$ are hydrogen (hereafter, $R^7$, $R^8$ being a3), 4) n is an integer from 1 to 3 (hereafter, n being n1), 5) n is 2 or 3 (hereafter, n being n2), 6) n is 3 (hereafter n being n3), 7) —Y is —N($R^9$)($R^{10}$), wherein $R^9$ and $R^{10}$ are each independently hydrogen, substituted or unsubstituted alkyl, substituted or unsubstituted acyl, substituted or unsubstituted alkyloxycarbonyl, substituted sulfonyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl; or $R^9$ and $R^{10}$ taken together with the adjacent nitrogen atom may form a ring in which oxygen atom, sulfur atom, or nitrogen atom (hereafter Y being y1), 8) —Y is —N($R^9$)($R^{10}$), wherein $R^9$ and $R^{10}$ are each independently hydrogen, unsubstituted alkyl, substituted alkyl (substituent is hydroxy, substituted or unsubstituted amino, substituted or unsubstituted non-aromatic heterocyclic group or substituted or unsubstituted cycloalkyl); or $R^9$ and $R^{10}$ taken together with the adjacent nitrogen atom may form a ring in which nitrogen atom may intervene (hereafter Y being y2), 9) —Y is a group represented by the following group (hereafter Y is y3),

[Formula 21]

10) —Y is a group represented by the following group (hereafter Y is y4),

[Formula 22]

11) —Y is —N(R$^9$)(R$^{10}$), wherein R$^9$ and R$^{10}$ are independently hydrogen, substituted or unsubstituted alkyl or substituted sulfonyl (hereafter Y being y5), 12) R$^{1b}$ is hydrogen or substituted or unsubstituted alkyl (hereafter R$^{1b}$ being b1), 13) R$^{1b}$ is substituted or unsubstituted alkyl (hereafter R$^{1b}$ being b2), 14) R$^{1c}$ is substituted or unsubstituted aryl (hereafter R$^{1c}$ being c1), 15) R$^{1c}$ is cyano, substituted or unsubstituted alkyl which the carbon number is 2 or more, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, or substituted or unsubstituted heteroaryl (hereafter R$^{1c}$ being c2), 16) R$^{1c}$ is substituted or unsubstituted cycloalkyl (hereafter R$^{1c}$ being c3), 17) R$^{1c}$ is substituted or unsubstituted C4-C6 alkyl (e.g., substituted or unsubstituted tert-butyl), substituted or unsubstituted heteroaryl (e.g., substituted or unsubstituted pyridinyl) or a substituted or unsubstituted non-aromatic heterocyclic group (e.g., substituted or unsubstituted pyperidinyl) (hereafter R$^{1c}$ being c4), 18) -L- is —C(=O)—N(R$^2$)—, —N(R$^2$)—C(=O)—, or —N(R$^2$)—SO$_2$—, wherein R$^2$ is hydrogen or substituted or unsubstituted alkyl (hereafter L being l1), 19) -L- is —C(=O)—NH— (hereafter L being l2), 20) -L- is —NH—C(=O)— (hereafter L being l3), 21) -L- is —NH—SO$_2$ (hereafter L being l4), 22) -L- is a single bond (hereafter L being l5), 23) X is substituted or unsubstituted aryl, substituted or unsubstituted heteroaryl, substituted or unsubstituted cycloalkyl, substituted or unsubstituted cycloalkenyl, or a substituted or unsubstituted non-aromatic heterocyclic group (hereafter X being x1)

24) X is substituted or unsubstituted heteroaryl which is monocyclic (e.g., substituted or unsubstituted pyridyl, substituted or unsubstituted pyrazinyl) (hereafter X being x2), 25) X is unsubstituted phenyl of substituted phenyl having a substitutent at ortho position. (hereafter X being x3), 26) —X is a group represented by the formula:

[Formula 23]

wherein R$^{11}$ and R$^{12}$ are each independently hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl; or R$^{11}$ and R$^{12}$ taken together with the adjacent carbon atoms may form a ring in which nitrogen atom may intervene;
R$^{13}$ to R$^{15}$ are each independently hydrogen, substituted or unsubstituted alkyl, substituted or unsubstituted acyl, substituted or unsubstituted aryl or substituted or unsubstituted heteroaryl (hereafter X being x4).

The compounds represented by the formula (I) encompass compounds shown on the basis of all possible combinations of all alternatives of respective substituents exemplified in the formula (I-A) above, wherein the compounds shown in the combinations of the following substituents are excluded:
((R$^7$,R$^8$),n,Y,R$^{1b}$,R$^{1c}$,L,X)=(a1,n1,y1,b1,c1,l1,x1),(a1,n1,y1,b1,c1,l1,x2),(a1,n1,y1,b1,c1,l1,x3),(a1,n1,y1,b1,c1,l2,x1),(a1,n1,y1,b1,c1,l2,x2),(a1,n1,y1,b1,c1,l2,x3),(a1,n1,y1,b1,c1,l3,x1),(a1,n1,y1,b1,c1,l3,x2),(a1,n1,y1,b1,c1,l3,x3),(a1,n1,y1,b2,c1,l1,x1),(a1,n1,y1,b2,c1,l1,x2),(a1,n1,y1,b2,c1,l1,x3),(a1,n1,y1,b2,c1,l2,x1),(a1,n1,y1,b2,c1,l2,x2),(a1,n1,y1,b2,c1,l2,x3),(a1,n1,y1,b2,c1,l3,x1),(a1,n1,y1,b2,c1, l3,x2),(a1,n1,y1,b2,c1,l3,x3),(a1,n2,y1,b1,c1,l1,x1),(a1,n2, y1,b1,c1,l1,x2),(a1,n2,y1,b1,c1,l1,x3),(a1,n2,y1,b1,c1,l2, x1),(a1,n2,y1,b1,c1,l2,x2),(a1,n2,y1,b1,c1,l2,x3),(a1,n2,y1, b1,c1,l3,x1),(a1,n2,y1,b1,c1,l3,x2),(a1,n2,y1,b1,c1,l3,x3), (a1,n2,y1,b2,c1,l1,x1),(a 1,n2,y1,b2,c1,l1,x2),(a1,n2,y1,b2, c1,l1,x3),(a1,n2,y1,b2,c1,l2,x1),(a1,n2,y1,b2,c1,l2,x2),(a1, n2,y1,b2,c1,l2,x3),(a1,n2,y1,b2,c1,l3,x1),(a1,n2,y1,b2,c1, l3,x2),(a1,n2,y1,b2,c1,l3,x3),(a1,n3,y1,b1,c1,l1,x1),(a1,n3, y1,b1,c1,l1,x2),(a1,n3,y1,b1,c1,l1,x3),(a1,n3,y1,b1,c1,l2, x1),(a1,n3,y1,b1,c1,l2,x2),(a1,n3,y1,b1,c1,l2,x3),(a1,n3,y1, b1,c1,l3,x1),(a1,n3,y1,b1,c1,l3,x2),(a1,n3,y1,b1,c1,l3,x3), (a1,n3,y1,b2,c1,l1,x1),(a1,n3,y1,b2,c1,l1,x2),(a 1,n3,y1,b2, c1,l1,x3),(a1,n3,y1,b2,c1,l2,x1), (a1,n3,y1,b2,c1,l2,x2), (a1, n3,y1,b2,c1,l2,x3),(a1,n3,y1,b2,c1,l3,x1),(a1,n3,y1,b2,c1, l3,x2),(a1,n3,y1,b2,c1,l3,x3),(a2,n1,y1,b1,c1,l1,x1),(a2,n1, y1,b1,c1,l1,x2),(a2,n1,y1,b1,c1,l1,x3),(a2,n1,y1,b1,c1,l2, x1),(a2,n1,y1,b1,c1,l2,x2),(a2,n1,y1,b1,c1,l2,x3),(a2,n1,y1, b1,c1,l3,x1),(a2,n1,y1,b1,c1,l3,x2),(a2,n1,y1,b1,c1,l3,x3), (a2,n1,y1,b2,c1,l1,x1),(a2,n1,y1,b2,c1,l1,x2),(a2,n1,y1,b2, c1,l1,x3),(a2,n1,y1, b2,c1,l2,x1),(a2,n1,y1,b2,c1,l2,x2),(a2, n1,y1,b2,c1,l2,x3),(a2,n1,y1,b2,c1,l3,x1),(a2,n1,y1,b2,c1, l3,x2),(a2,n1,y1,b2,c1,l3,x3),(a2,n2,y1,b1,c1,l1,x1),(a2,n2, y1,b1,c1,l1,x2),(a2,n2,y1,b1,c1,l1,x3),(a2,n2,y1,b1,c1,l2, x1),(a2,n2,y1,b1,c1,l2,x2),(a2,n2,y1,b1,c1,l2,x3),(a2,n2,y1, b1,c1,l3,x1),(a2,n2,y1,b1,c1,l3,x2),(a2,n2,y1,b1,c1,l3,x3), (a2,n2,y1,b2,c1,l1,x1),(a2,n2,y1,b2,c1,l1,x2),(a2,n2,y1,b2, c1,l1,x3),(a2,n2,y1,b2,c1,l2,x1),(a2,n2,y1,b2,c1,l2,x2),(a2, n2,y1,b2,c1,l2,x3),(a2,n2,y1,b2,c1,l3,x1),(a2,n2,y1,b2,c1, l3,x2),(a2,n2,y1,b2,c1,l3,x3),(a2,n3,y1,b1,c1,l1,x1),(a2,n3, y1,b1,c1,l1,x2),(a2,n3,y1,b1,c1,l1,x3),(a2,n3,y1,b1,c1,l2, x1),(a2,n3,y1,b1,c1,l2,x2),(a2,n3,y1,b1,c1,l2,x3),(a2,n3,y1, b1,c1,l3,x1),(a2,n3,y1,b1,c1,l3,x2),(a2,n3,y1,b1,c1,l3,x3), (a2,n3,y1,b2,c1,l1,x1),(a2,n3,y1,b2,c1,l1,x2),(a2,n3,y1,b2, c1,l1,x3),(a2,n3,y1,b2,c1,l2,x1),(a2,n3,y1,b2,c1,l2,x2),(a2, n3,y1,b2,c1,l2,x3),(a2,n3,y1,b2,c1,l3,x1),(a2,n3,y1,b2,c1, l3,x2),(a2,n3,y1,b2,c1,l3,x3),(a3,n1,y1,b1,c1,l1,x1),(a3,n1, y1,b1,c1,l1,x2),(a3,n1,y1,b1,c1,l1,x3),(a3,n1,y1,b1,c1,l2, x1),(a3,n1,y1,b1,c1,l2,x2),(a3,n1,y1,b1,c1,l2,x3),(a3,n1,y1, b1,c1,l3,x1),(a3,n1,y1,b1,c1,l3,x2),(a3,n1,y1,b1,c1,l3,x3), (a3,n1,y1,b2,c1,l1,x1),(a3,n1,y1,b2,c1,l1,x2),(a3,n1,y1,b2, c1,l1,x3),(a3,n1,y1,b2,c1,l2,x1),(a3,n1,y1,b2,c1,l2,x2),(a3, n1,y1,b2,c1,l2,x3),(a3,n1,y1,b2,c1,l3,x1),(a3,n1,y1,b2,c1, l3,x2),(a3,n1,y1,b2,c1,l3,x3),(a3,n2,y1,b1,c1,l1,x1),(a3,n2, y1,l3,c1,l1,x2),(a3,n2,y1,b1,c1,l1,x3),(a3,n2,y1,b1,c1,l2, x1),(a3,n2,y1,b1,c1,l2,x2),(a3,n2,y1,b1,c1,l2,x3),(a3,n2,y1, b1,c1,l3,x1),(a3,n2,y1,b1,c1,l3,x2),(a3,n2,y1,b1,c1,l3,x3), (a3,n2,y1,b2,c1,l1,x1),(a3,n2,y1,b2,c1,l1,x2),(a3,n2,y1,b2, c1,l1,x3),(a3,n2,y1,b2,c1,l2,x1),(a3,n2,y1,b2,c1,l2,x2),(a3, n2,y1,b2,c1,l2,x3),(a3,n2,y1,b2,c1,l3,x1),(a3,n2,y1,b2,c1, l3,x2),(a3,n2,y1,b2,c1,l3,x3),(a3,n3,y1,b1,c1,l1,x1),(a3,n3, y1,b1,c1,l1,x2),(a3,n3,y1,b1,c1,l1,x3),(a3,n3,y1,b1,c1,l2, x1),(a3,n3,y1,b1,c1,l2,x2),(a3,n3,y1,b1,c1,l2,x3),(a3,n3,y1, b1,c1,l3,x1),(a3,n3,y1,b1,c1,l3,x2),(a3,n3,y1,b1,c1,l3,x3), (a3,n3,y1,b2,c1,l1,x1),(a3,n3,y1,b2,c1,l1,x2),(a3,n3,y1,b2, c1,l1,x3),(a3,n3,y1,b2,c1,l2,x1),(a3,n3,y1,b2,c1,l2,x2),(a3, n3,y1,b2,c1,l2,x3),(a3,n3,y1,b2,c1,l3,x1),(a3,n3,y1,b2,c1, l3,x2),(a3,n3,y1,b2,c1,l3,x3)

The compounds represented by the formula (I) encompass compounds shown on the basis of all possible combinations of all alternatives of respective substituents exemplified in the formula (I-B) below.

In the formula (I-B);

[Formula 24]

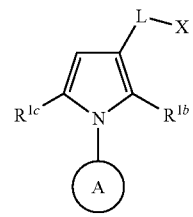

(I-B)

1α) ring A is cycloalkane substituted with substituted or unsubstituted amino or substituted or unsubstituted nitrogen containing saturated heterocycle, 2α) ring A is cycloalkane substituted with substituted or unsubstituted amino, 3α) ring A is substituted or unsubstituted nitrogen containing saturated heterocycle, 4α) $R^{1b}$ is hydrogen or substituted or unsubstituted alkyl, 5α) $R^{1b}$ is substituted or unsubstituted alkyl, 6α) $R^{1c}$ is substituted or unsubstituted alkyl which the carbon number is 2 or more, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, or substituted or unsubstituted heteroaryl, 7α) $R^{1c}$ is substituted or unsubstituted alkyl, 8α) -L- is —C(=O)—N($R^2$)—, —N($R^2$)—C(=O)—, or —N($R^2$)—SO$_2$—, wherein $R^2$ is hydrogen or substituted or unsubstituted alkyl, 9α) -L- is —C(=O)—NH—, 10α) X is substituted or unsubstituted aryl, substituted or unsubstituted heteroaryl, substituted or unsubstituted cycloalkyl, substituted or unsubstituted cycloalkenyl, or a substituted or unsubstituted non-aromatic heterocyclic group, 11α) X is substituted or unsubstituted aryl.

The compounds represented by the formula (II) encompass compounds shown on the basis of all possible combinations of all alternatives of respective substituents exemplified in the formula (II-A) below.

In the formula (II-A);

[Formula 25]

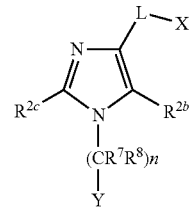

(II-A)

1β) $R^7$ is each independently hydrogen, halogen, or substituted or unsubstituted alkyl; $R^8$ is each independently hydrogen, halogen, or substituted or unsubstituted alkyl; or $R^7$ and $R^8$ taken together form oxo, 2β) $R^7$ is each independently hydrogen, halogen, or substituted or unsubstituted alkyl, or $R^8$ is each independently hydrogen, halogen, or substituted or unsubstituted alkyl, 3β) $R^7$ and $R^8$ are hydrogen,
4β) n is an integer from 1 to 3,
5β) n is 2 or 3,
6β) n is 3,
7β) —Y is —N($R^9$)($R^{10}$), wherein $R^9$ and $R^{10}$ are each independently hydrogen, substituted or unsubstituted alkyl, substituted or unsubstituted acyl, substituted or unsubstituted alkyloxycarbonyl, substituted sulfonyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl; or $R^9$ and $R^{10}$ taken together with the adjacent nitrogen atom may form a ring in which oxygen atom, sulfur atom, or nitrogen atom may intervene,
8β) —Y is —N($R^9$)($R^{10}$), wherein $R^9$ and $R^{10}$ are each independently hydrogen, unsubstituted alkyl, substituted alkyl (substituent is hydroxy, substituted or unsubstituted amino, substituted or unsubstituted non-aromatic heterocyclic group or substituted or unsubstituted cycloalkyl); or $R^9$ and $R^{10}$ taken together with the adjacent nitrogen atom may form a ring in which nitrogen atom may intervene,
9β) —Y is a group represented by the following group,

[Formula 26]

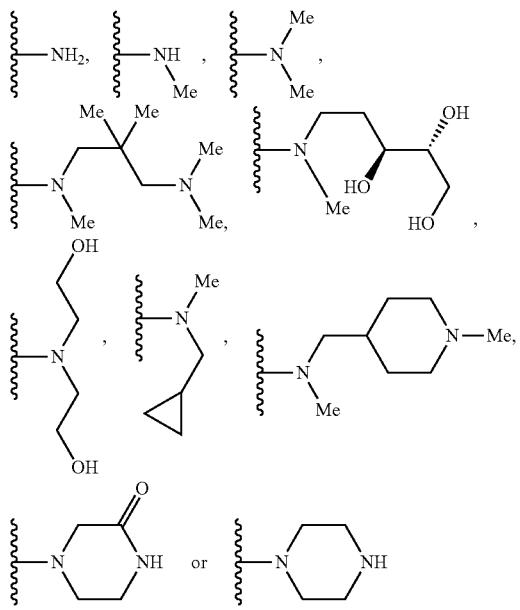

10β) —Y is a group represented by the following group,

[Formula 27]

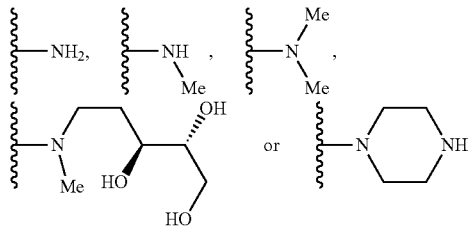

11β) —Y is —N($R^9$)($R^{10}$), wherein $R^9$ and $R^{10}$ are each independently hydrogen, substituted or unsubstituted alkyl or substituted sulfonyl, 12β) Y is a substituted or unsubstituted non-aromatic heterocyclic group,
13β) $R^{2b}$ is hydrogen or substituted or unsubstituted alkyl,
14β) $R^{2b}$ is substituted or unsubstituted alkyl,
15β) $R^{2c}$ is substituted or unsubstituted alkyl which the carbon number is 2 or more, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, or substituted or unsubstituted heteroaryl,
16β) $R^{2c}$ is substituted or unsubstituted cycloalkyl,
17β) $R^{2c}$ is substituted or unsubstituted C4-C6 alkyl, substituted or unsubstituted heteroaryl or a substituted or unsubstituted non-aromatic heterocyclic group,
18β) $R^{2c}$ is substituted or unsubstituted aryl,
19β) -L- is —C(=O)—N($R^2$)—, —N($R^2$)—C(=O)—, or —N($R^2$)—SO$_2$—, wherein $R^2$ is hydrogen or substituted or unsubstituted alkyl,
20β) -L- is —C(=O)—NH—,
21β) -L- is —NH—C(=O)—,
22β) -L- is —NH—SO$_2$—
23β) -L- is a single bond,
24β) X is substituted or unsubstituted aryl, substituted or unsubstituted heteroaryl, substituted or unsubstituted cycloalkyl, substituted or unsubstituted cycloalkenyl, or a substituted or unsubstituted non-aromatic heterocyclic group,
25β) X is substituted or unsubstituted heteroaryl,
26β) X is substituted or unsubstituted aryl,
27β) —X is a group represented by the formula:

[Formula 28]

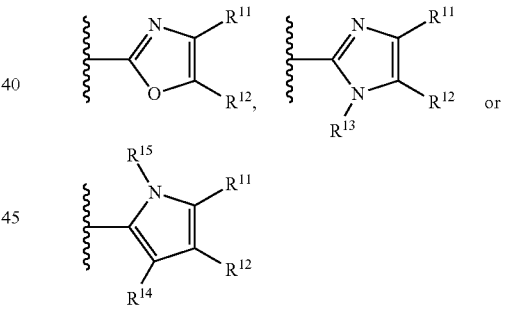

wherein $R^{11}$ and $R^{12}$ are each independently hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl; or $R^{11}$ and $R^{12}$ taken together with the adjacent carbon atoms may form a ring in which nitrogen atom may intervene;
$R^{13}$ to $R^{15}$ are each independently hydrogen, substituted or unsubstituted alkyl, substituted or unsubstituted acyl, substituted or unsubstituted aryl or substituted or unsubstituted heteroaryl, The compounds represented by the formula (III) encompass compounds shown on the basis of all possible combinations of all alternatives of respective substituents exemplified in the formula (III-A) below.

In the formula (III-A);

[Formula 29]

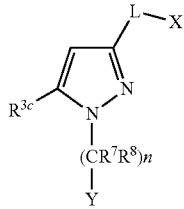

(III-A)

1γ) R$^7$ is each independently hydrogen, halogen, or substituted or unsubstituted alkyl; R$^8$ is each independently hydrogen, halogen, or substituted or unsubstituted alkyl; or R$^7$ and R$^8$ taken together form oxo,
2γ) R$^7$ is each independently hydrogen, halogen, or substituted or unsubstituted alkyl; or R$^8$ is each independently hydrogen, halogen, or substituted or unsubstituted alkyl,
3γ) R$^7$ and R$^8$ are hydrogen,
4γ) n is an integer from 1 to 3,
5γ) n is 2 or 3,
6γ) n is 3,
7γ) —Y is —N(R$^9$)(R$^{10}$), wherein R$^9$ and R$^{10}$ are each independently hydrogen, substituted or unsubstituted alkyl, substituted or unsubstituted acyl, substituted or unsubstituted alkyloxycarbonyl, substituted sulfonyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl; or R$^9$ and R$^{10}$ taken together with the adjacent nitrogen atom may form a ring in which oxygen atom, sulfur atom, or nitrogen atom may intervene,
8γ) —Y is —N(R$^9$)(R$^{10}$), wherein R$^9$ and R$^{10}$ are each independently hydrogen, unsubstituted alkyl, substituted alkyl (substituent is hydroxy, substituted or unsubstituted amino, substituted or unsubstituted non-aromatic heterocyclic group or substituted or unsubstituted cycloalkyl); or R$^9$ and R$^{10}$ taken together with the adjacent nitrogen atom may form a ring in which nitrogen atom may intervene,
9γ) —Y is a group represented by the following group,

[Formula 30]

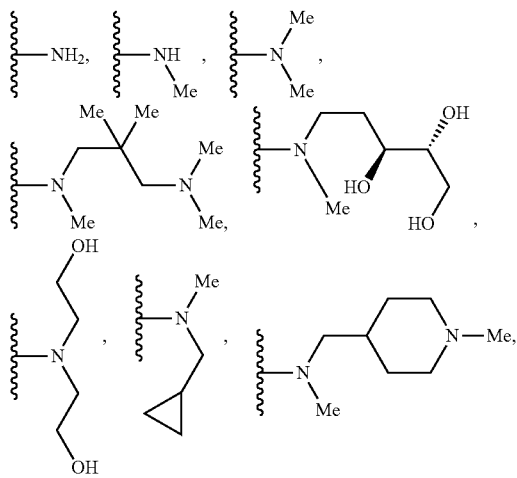

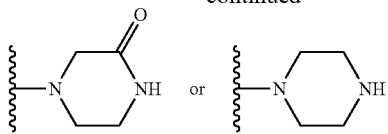

10γ) —Y is a group represented by the following group,

[Formula 31]

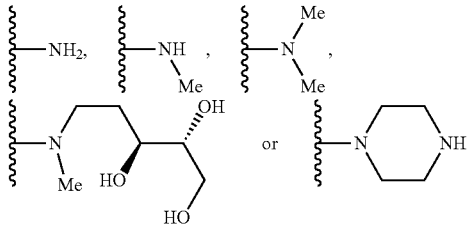

11γ) —Y is —N(R$^9$)(R$^{10}$), wherein R$^9$ and R$^{10}$ are each independently hydrogen, substituted or unsubstituted alkyl or substituted sulfonyl,
12γ) Y is a substituted or unsubstituted non-aromatic heterocyclic group,
13γ) R$^{3c}$ is substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl,
14γ) R$^{3c}$ is substituted or unsubstituted cycloalkyl,
15γ) R$^{3c}$ is substituted or unsubstituted heteroaryl or a substituted or unsubstituted non-aromatic heterocyclic group,
16γ) R$^{3c}$ is substituted or unsubstituted aryl,
17γ) -L- is —C(=O)—N(R$^2$)—, —N(R$^2$)—C(=O)—, or —N(R$^2$)—SO$_2$—, wherein R$^2$ is hydrogen or substituted or unsubstituted alkyl,
18γ) -L- is —C(=O)—NH—,
19γ) -L- is —NH—C(=O)—,
20γ) -L- is —NH—SO$_2$—,
21γ) -L- is a single bond,
22γ) X is substituted or unsubstituted aryl, substituted or unsubstituted heteroaryl, substituted or unsubstituted cycloalkyl, substituted or unsubstituted cycloalkenyl, or a substituted or unsubstituted non-aromatic heterocyclic group,
23γ) X is substituted or unsubstituted heteroaryl,
24γ) X is substituted or unsubstituted aryl,
25γ) —X is a group represented by the formula:

[Formula 32]

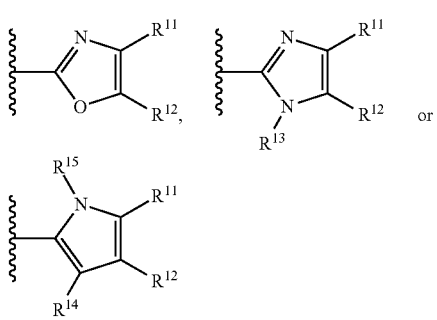

wherein $R^{11}$ and $R^{12}$ are each independently hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or, unsubstituted heteroaryl; or $R^{11}$ and $R^{12}$ taken together with the adjacent carbon atoms may form a ring in which nitrogen atom may intervene;
$R^{13}$ to $R^{15}$ are each independently hydrogen, substituted or unsubstituted alkyl, substituted or unsubstituted acyl, substituted or unsubstituted aryl or substituted or unsubstituted heteroaryl.

The compounds represented by the formula (IV) encompass compounds shown on the basis of all possible combinations of all alternatives of respective substituents exemplified in the formula (IV-A) below.
In the formula (IV-A);

[Formula 33]

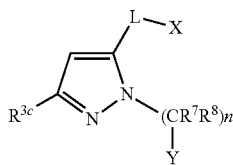

(IV-A)

1δ) $R^7$ is each independently hydrogen, halogen, or substituted or unsubstituted alkyl; $R^8$ is independently hydrogen, halogen, or substituted or unsubstituted alkyl; or $R^7$ and $R^8$ taken together form oxo,
2δ) $R^7$ is each independently hydrogen, halogen, or substituted or unsubstituted alkyl; or $R^8$ is each independently hydrogen, halogen, or substituted or unsubstituted alkyl,
3δ) $R^7$ and $R^8$ are hydrogen,
4δ) n is an integer from 1 to 3,
5δ) n is 2 or 3,
6δ) n is 3,
7δ) —Y is —N($R^9$)($R^{10}$), wherein $R^9$ and $R^{10}$ are each independently hydrogen, substituted or unsubstituted alkyl, substituted or unsubstituted acyl, substituted or unsubstituted alkyloxycarbonyl, substituted sulfonyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl; or $R^9$ and $R^{10}$ taken together with the adjacent nitrogen atom may form a ring in which oxygen atom, sulfur atom, or nitrogen atom may intervene,
8δ) —Y is —N($R^9$)($R^{10}$), wherein $R^9$ and $R^{10}$ are each independently hydrogen, unsubstituted alkyl, substituted alkyl (substituent is hydroxy, substituted or unsubstituted amino, substituted or unsubstituted non-aromatic heterocyclic group or substituted or unsubstituted cycloalkyl); or $R^9$ and $R^{10}$ taken together with the adjacent nitrogen atom may form a ring in which nitrogen atom may intervene,
9δ) —Y is a group represented by the following group,

[Formula 34]

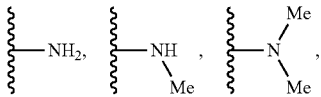

10δ) —Y is a group represented by the following group,

[Formula 35]

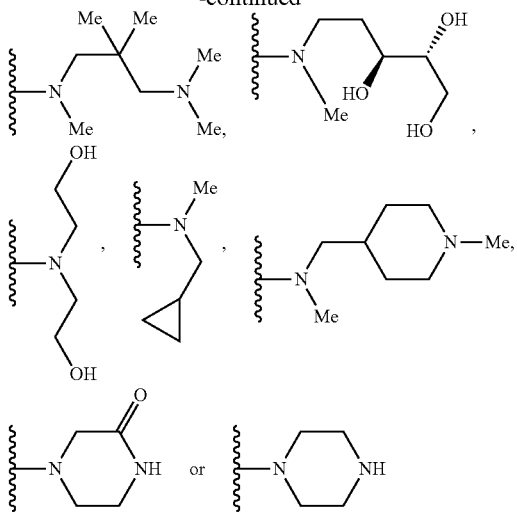

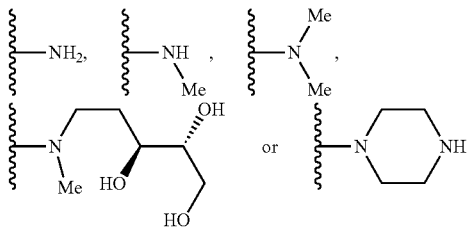

11δ) —Y is —N($R^9$)($R^{10}$), wherein $R^9$ and $R^{10}$ are each independently hydrogen, substituted or unsubstituted alkyl or substituted sulfonyl,
12δ) Y is a substituted or unsubstituted non-aromatic heterocyclic group,
13δ) $R^{4c}$ is substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl,
14δ) $R^{4c}$ is substituted or unsubstituted cycloalkyl,
15δ) $R^{4c}$ is substituted or unsubstituted heteroaryl or a substituted or unsubstituted non-aromatic heterocyclic group,
16δ) $R^{4c}$ is substituted or unsubstituted aryl,
17δ) -L- is —C(=O)—N($R^2$)—, —N($R^2$)—C(=O)—, or —N($R^2$)—SO$_2$—, wherein $R^2$ is hydrogen or substituted or unsubstituted alkyl,
18δ) -L- is —C(=O)—NH—,
19δ) -L- is —NH—C(=O)—,
20δ) -L- is —NH—SO$_2$—,
21δ) -L- is a single bond,
22δ) X is substituted or unsubstituted aryl, substituted or unsubstituted heteroaryl, substituted or unsubstituted cycloalkyl, substituted or unsubstituted cycloalkenyl, or a substituted or unsubstituted non-aromatic heterocyclic group,
23β) X is substituted or unsubstituted heteroaryl,
24δ) X is substituted or unsubstituted aryl, 25δ) —X is a group represented by the formula:

[Formula 36]

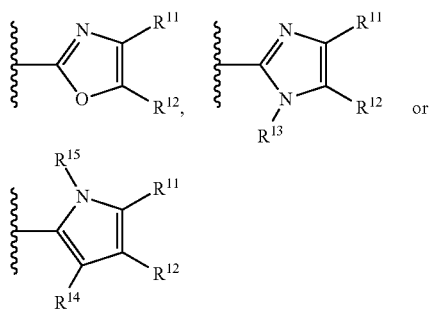

wherein $R^{11}$ and $R^{12}$ are each independently hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl; or $R^{11}$ and $R^{12}$ taken together with the adjacent carbon atoms may form a ring in which nitrogen atom may intervene;
$R^{13}$ to $R^{15}$ are each independently hydrogen, substituted or unsubstituted alkyl, substituted or unsubstituted acyl, substituted or unsubstituted aryl or substituted or unsubstituted heteroaryl.

The compounds represented by the formula (V) encompass compounds shown on the basis of all possible combinations of all alternatives of respective substituents exemplified in the formula (V-A) below.

In the formula (V-A);

[Formula 37]

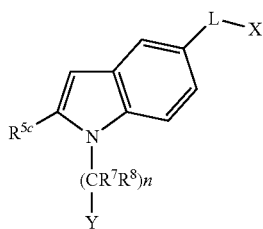

(V-A)

1ε) $R^7$ is each independently hydrogen, halogen, or substituted or unsubstituted alkyl; $R^8$ is each independently hydrogen, halogen, or substituted or unsubstituted alkyl; or $R^7$ and $R^8$ taken together form oxo,
2ε) $R^7$ is each independently hydrogen, halogen, or substituted or unsubstituted alkyl;
$R^8$ is each independently hydrogen, halogen, or substituted or unsubstituted alkyl,
3ε) $R^7$ and $R^8$ are hydrogen
4ε) n is an integer from 1 to 3,
5ε) n is 2 or 3,
6ε) n is 3,
7ε) —Y is —N($R^9$))($R^{10}$), wherein $R^9$ and $R^{10}$ are each independently hydrogen, substituted or unsubstituted alkyl, substituted or unsubstituted acyl, substituted or unsubstituted alkyloxycarbonyl, substituted sulfonyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl; or $R^9$ and ° taken together with the adjacent nitrogen atom may form a ring in which oxygen atom, sulfur atom, or nitrogen atom may intervene,
8ε) —Y is —N($R^9$)($R^{10}$), wherein $R^9$ and $R^{10}$ are each independently hydrogen, unsubstituted alkyl, substituted alkyl (substituents are hydroxy, substituted or unsubstituted amino, substituted or unsubstituted non-aromatic heterocyclic group or substituted or unsubstituted cycloalkyl); or $R^9$ and $R^{10}$ taken together with the adjacent nitrogen atom may form a ring in which nitrogen atom may intervene,
9ε) —Y is a group represented by the following group,

[Formula 38]

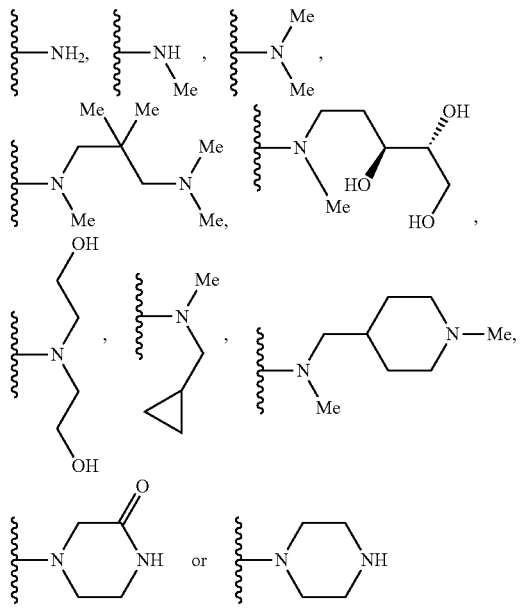

10ε) —Y is a group represented by the following group,

[Formula 39]

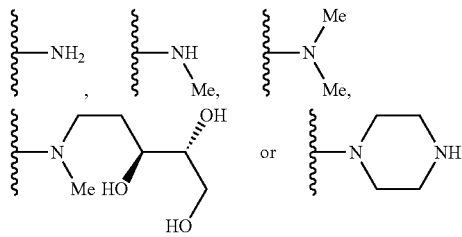

11ε) —Y is —N($R^9$)($R^{10}$), wherein $R^9$ and $R^{10}$ are each independently hydrogen, substituted or unsubstituted alkyl or substituted sulfonyl,
12ε) Y is a substituted or unsubstituted non-aromatic heterocyclic group,
13ε) $R^{5c}$ is substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl,
14ε) $R^{5c}$ is substituted or unsubstituted cycloalkyl,
15ε) $R^{5c}$ is substituted or unsubstituted heteroaryl or a substituted or unsubstituted non-aromatic heterocyclic group, 16ε) $R^{5c}$ is substituted or unsubstituted aryl,
17ε) -L- is —C(=O)—N($R^2$)—, —N($R^2$)—, or —N($R^2$)—$SO_2$—, wherein $R^2$ is hydrogen or substituted or unsubstituted alkyl,
18ε) -L- is —C(=O)—NH—,
19ε) -L- is —NH—,
20ε) -L- is —NH—$SO_2$—,
21ε) -L- is a single bond,
22ε) X is substituted or unsubstituted aryl, substituted or unsubstituted heteroaryl, substituted or unsubstituted cycloalkyl, substituted or unsubstituted cycloalkenyl, or a substituted or unsubstituted non-aromatic heterocyclic group,
23ε) X is substituted or unsubstituted heteroaryl,
24ε) X is substituted or unsubstituted aryl,
25ε) —X is a group represented by the formula:

[Formula 40]

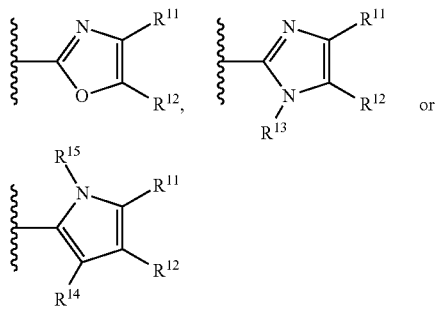

wherein $R^{11}$ and $R^{12}$ are each independently hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl; or $R^{11}$ and $R^{12}$ taken together with the adjacent carbon atoms may form a ring in which nitrogen atom may intervene;
$R^{13}$ to $R^{15}$ are each independently hydrogen, substituted or unsubstituted alkyl, substituted or unsubstituted acyl, substituted or unsubstituted aryl or substituted or unsubstituted heteroaryl.

The compounds represented by the formula (VI) encompass compounds shown on the basis of all possible combinations of all alternatives of respective substituents exemplified in the formula (VI-A) below.

In the formula (VI-A);

[Formula 41]

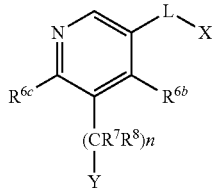
(VI)

1φ) $R^7$ is each independently hydrogen, halogen, or substituted or unsubstituted alkyl; $R^8$ is each independently hydrogen, halogen, or substituted or unsubstituted alkyl; or $R^7$ and $R^8$ taken together form oxo, 2φ) $R^7$ is each independently hydrogen, halogen, or substituted or unsubstituted alkyl; $R^8$ is each independently hydrogen, halogen, or substituted or unsubstituted alkyl,
3φ) $R^7$ and $R^8$ are hydrogen,
4φ) n is an integer from 1 to 3,
5φ) n is 2 or 3,
6φ) n is 3,
7φ) —Y is —N($R^9$)($R^{10}$), wherein $R^9$ and $R^{10}$ are each independently hydrogen, substituted or unsubstituted alkyl, substituted or unsubstituted acyl, substituted or unsubstituted alkyloxycarbonyl, substituted sulfonyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl; or $R^9$ and $R^{10}$ taken together with the adjacent nitrogen atom may form a ring in which oxygen atom, sulfur atom, or nitrogen atom may intervene,
8φ) —Y is —N($R^9$)($R^{10}$), wherein $R^9$ and $R^{10}$ are each independently hydrogen, unsubstituted alkyl, substituted alkyl (substituent is hydroxy, substituted or unsubstituted amino, substituted or unsubstituted non-aromatic heterocyclic group or substituted or unsubstituted cycloalkyl); or $R^9$ and $R^{10}$ taken together with the adjacent nitrogen-atom may form a ring in which nitrogen atom may intervene,
9φ) —Y is a group represented by the following group,

[Formula 42]

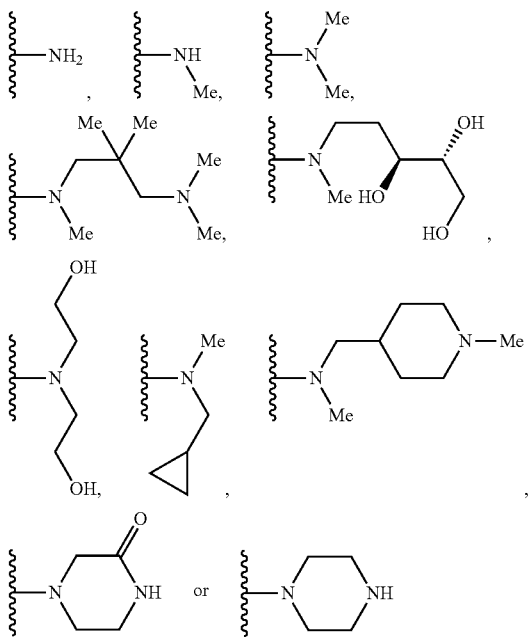

10φ) —Y is a group represented by the following group,

[Formula 43]

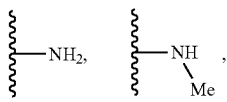

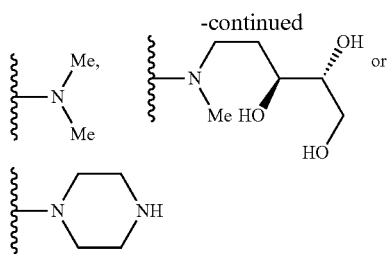

11φ) —Y is —N(R⁹)(R¹⁰) wherein R⁹ and R¹⁰ are each independently hydrogen, substituted or unsubstituted alkyl or substituted sulfonyl,
12φ) Y is a substituted or unsubstituted non-aromatic heterocyclic group,
13φ) $R^{6b}$ is hydrogen or substituted or unsubstituted alkyl,
14φ) $R^{6b}$ is substituted or unsubstituted alkyl,
15φ) $R^{6c}$ is substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group or substituted or unsubstituted heteroaryl,
16φ) $R^{6c}$ is substituted or unsubstituted cycloalkyl,
17φ) $R^{6c}$ is substituted or unsubstituted heteroaryl or a substituted or unsubstituted non-aromatic heterocyclic group,
18φ) $R^{6c}$ is substituted or unsubstituted aryl,
19φ) -L- is —C(=O)—N(R²)—, —N(R²)—C(=O)—, or —N(R²)—SO₂—, wherein R² is hydrogen or substituted or unsubstituted alkyl,
20φ) -L- is —C(=O)—NH—,
21φ) -L- is —NH—C(=O)—,
22φ) -L- is —NH—SO₂—,
23φ) -L- is a single bond,
24φ) X is substituted or unsubstituted aryl, substituted or unsubstituted heteroaryl, substituted or unsubstituted cycloalkyl, substituted or unsubstituted cycloalkenyl, or a substituted or unsubstituted non-aromatic heterocyclic group,
25φ) X is substituted or unsubstituted heteroaryl,
26φ) X is substituted or unsubstituted aryl,
27φ) —X is a group represented by the formula:

[Formula 44]

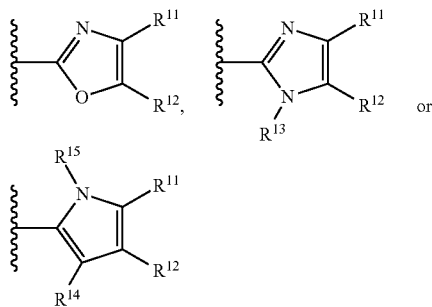

wherein R¹¹ and R¹² are each independently hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl; or R¹¹ and R¹² taken together with the adjacent carbon atoms may form a ring in which nitrogen atom may intervene;
R¹³ to R¹⁵ are each independently hydrogen, substituted or unsubstituted alkyl, substituted or unsubstituted acyl, substituted or unsubstituted aryl or substituted or unsubstituted heteroaryl.

It is considered that the following compounds have TRPV4 inhibitory activity.

[Formula 45]

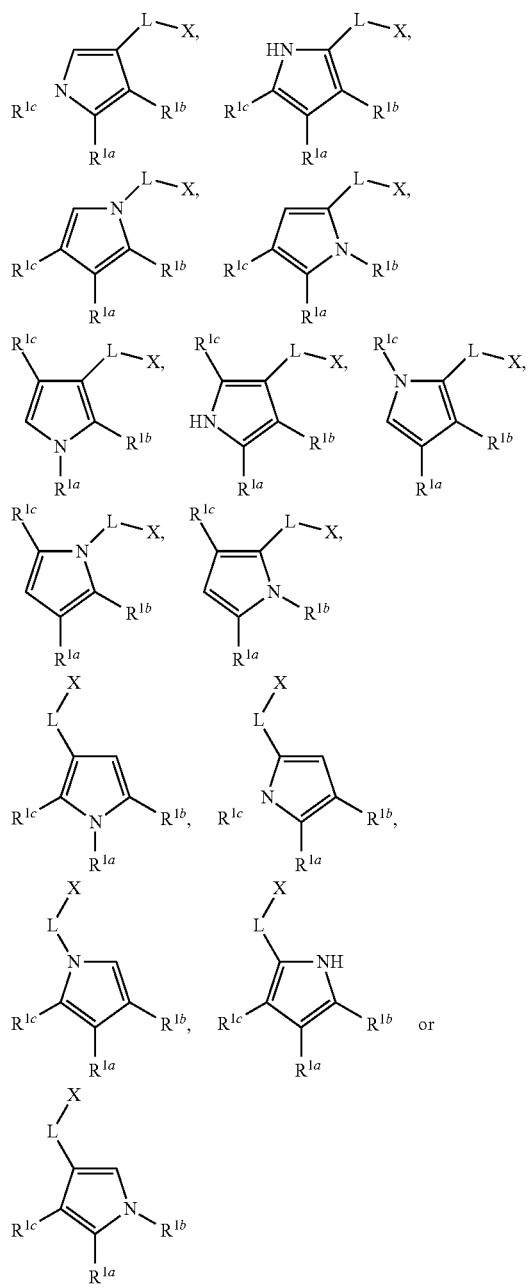

wherein $R^{1a}$, $R^{1b}$, $R^{1c}$, L and X are the same as the aforementioned (1).

Moreover, it is also considered that the following compounds have TRPV4 inihibitory activity.

[Formula 46]

wherein $R^{2a}$, $R^{2b}$, $R^{2c}$, L and X are the same as the aforementioned (7).

It is also considered that the following compounds have TRPV4 inihibitory activity.

[Formula 47]

wherein $R^{3a}$, $R^{3b}$, $R^{3c}$, L and X are the same as the aforementioned (10).

Moreover, it is also considered that the following compounds have TRPV4 inihibitory activity.

[Formula 48]

-continued
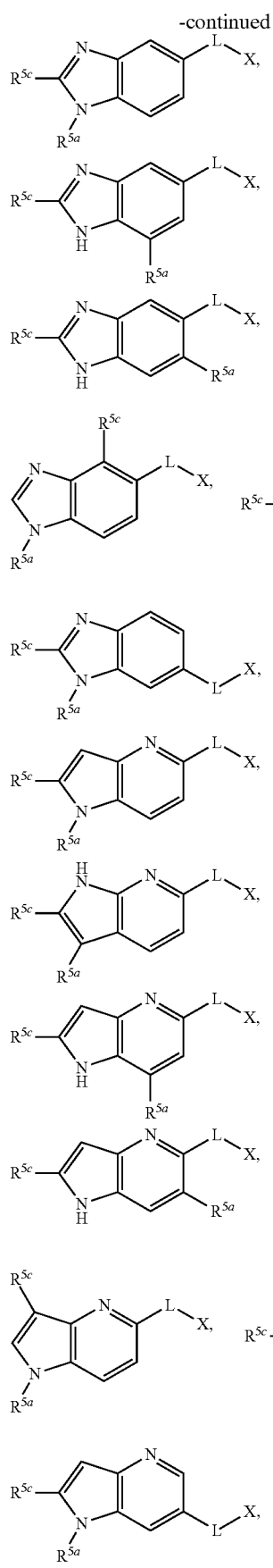
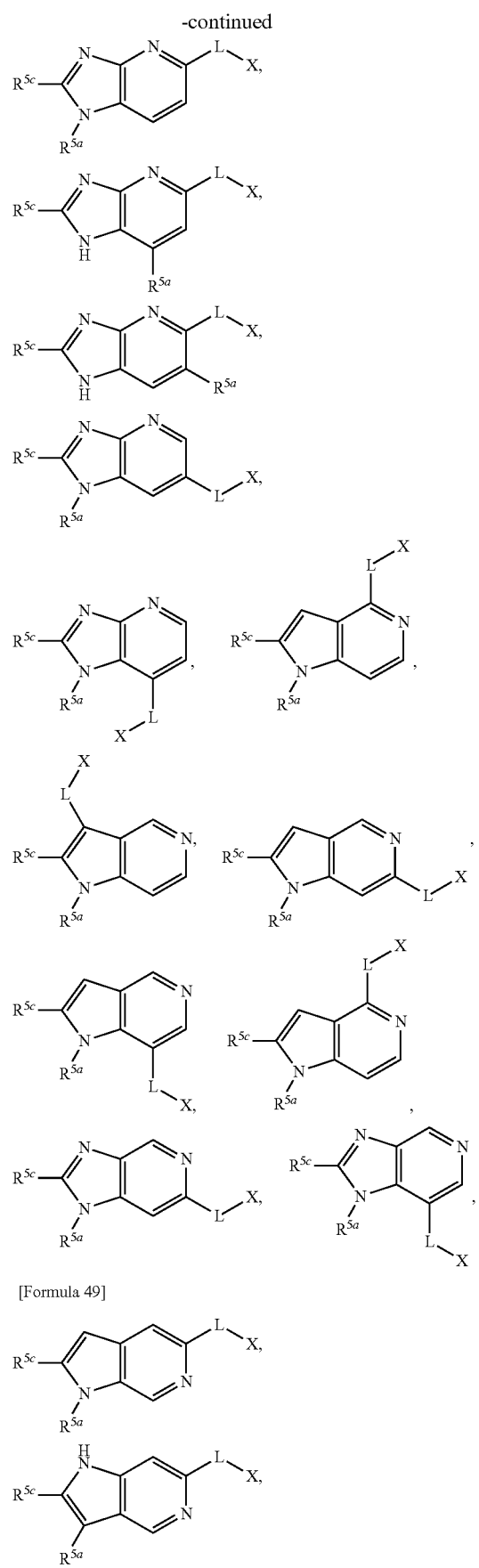
[Formula 49]

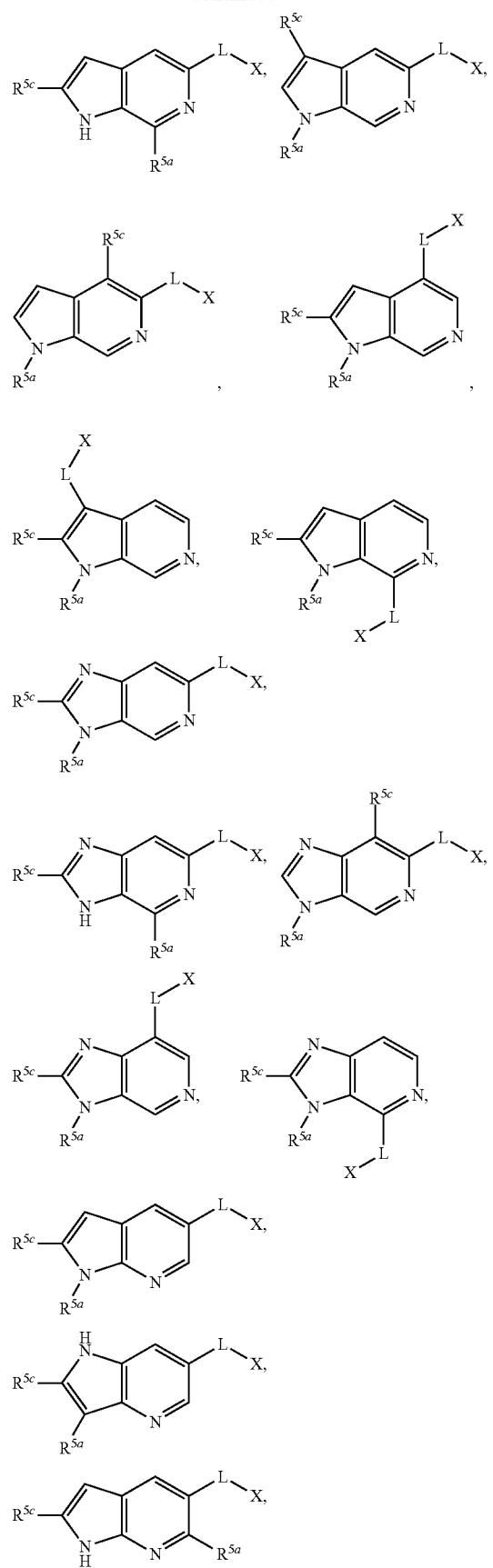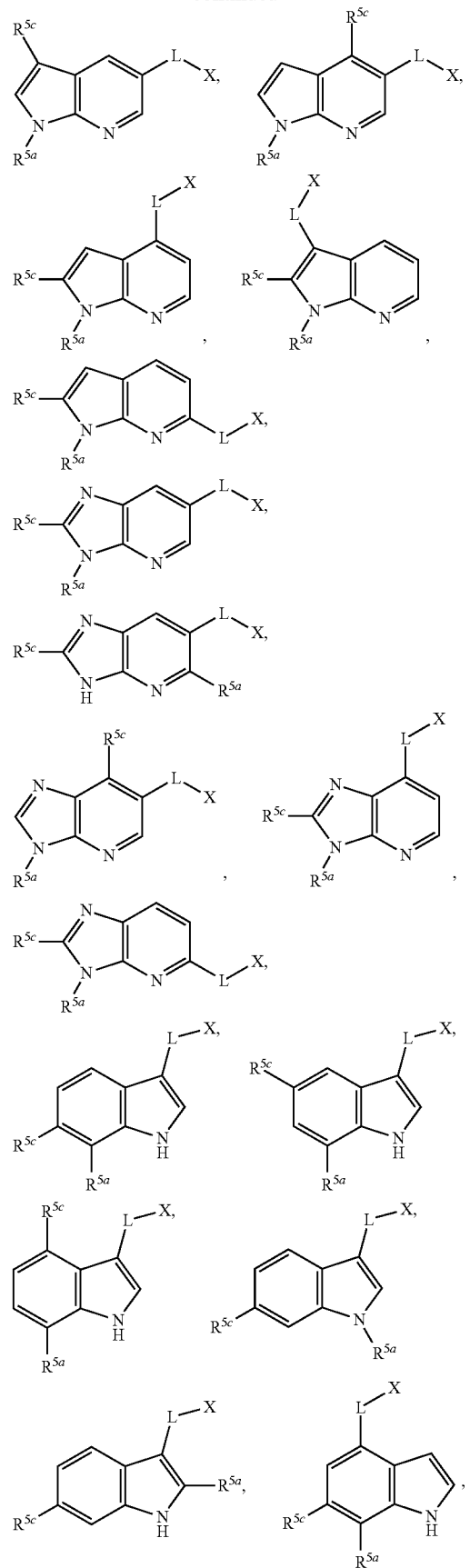

-continued
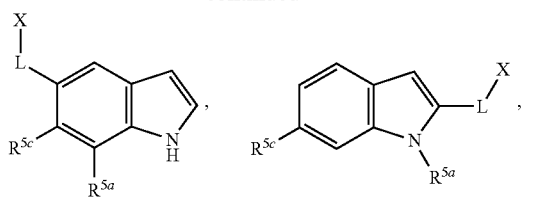
[Formula 50]
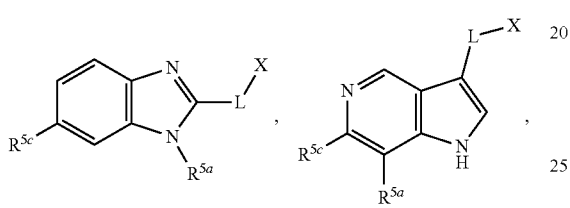
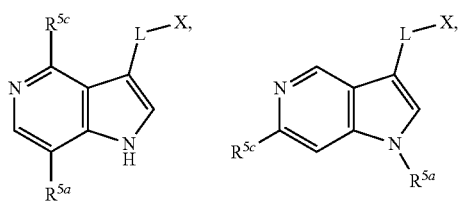
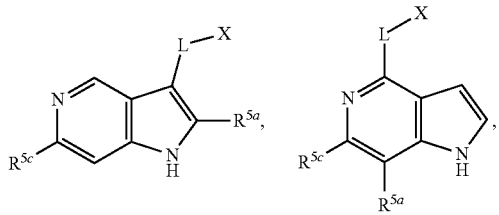
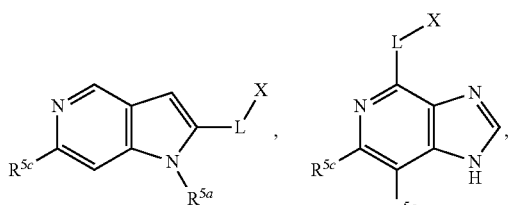
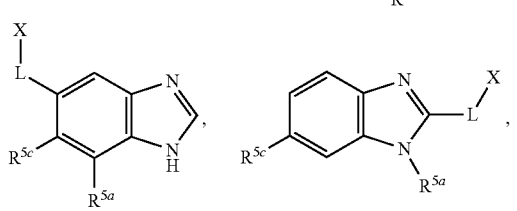
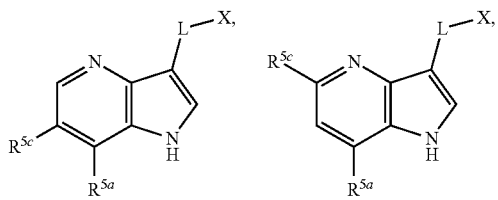
-continued
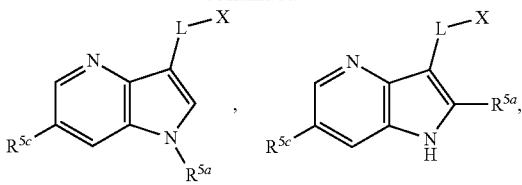
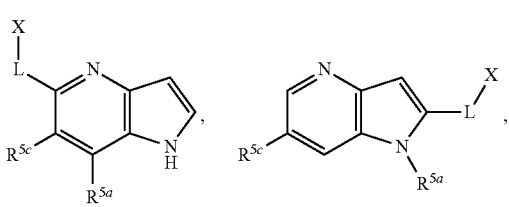
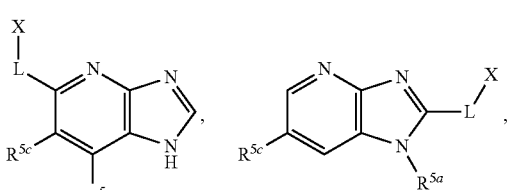
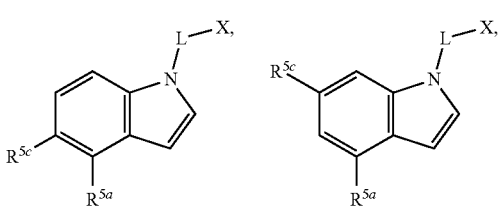
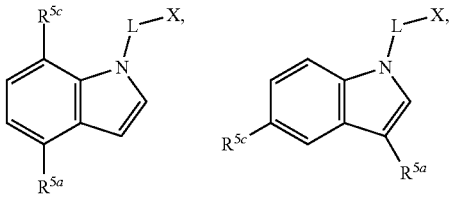
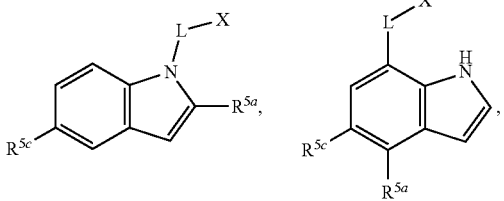
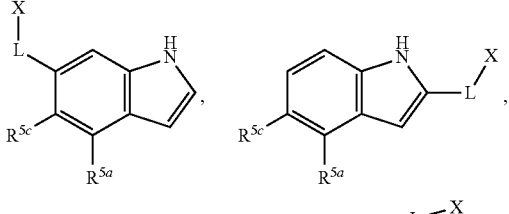
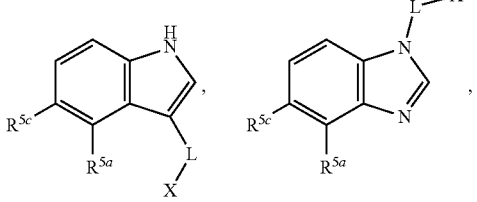

-continued
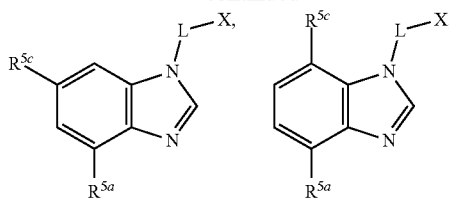
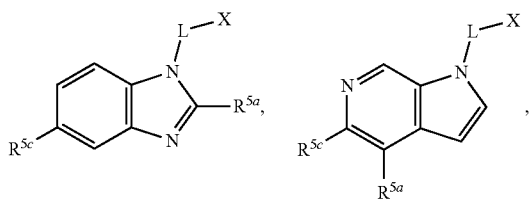
[Formula 51]
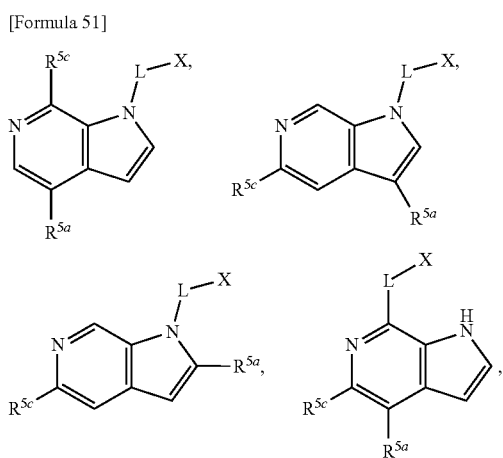
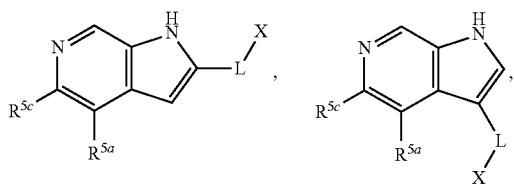
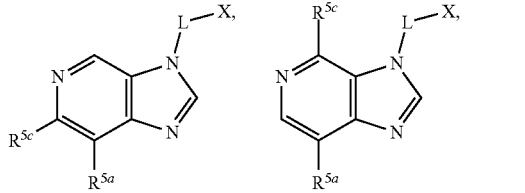
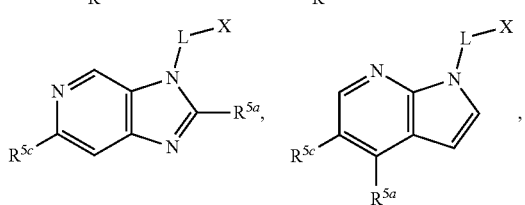
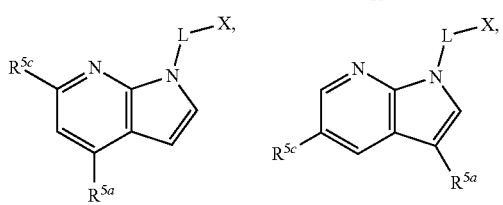
-continued
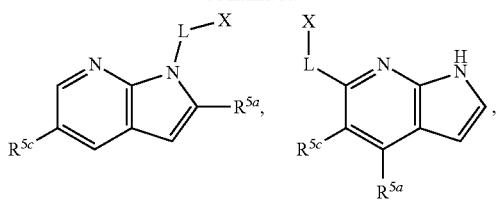
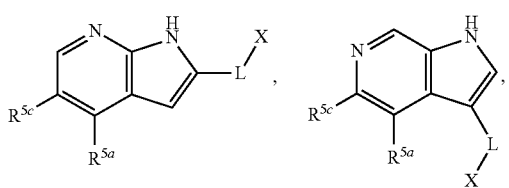
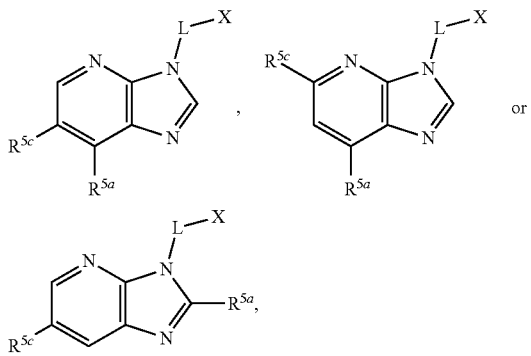
wherein $R^{5a}$, $R^{5b}$, $R^{5c}$, L and X are the same as the aforementioned (15).
Furthermore, it is considered that the following compounds have TRPV4 inhibitory activity.
[Formula 52]
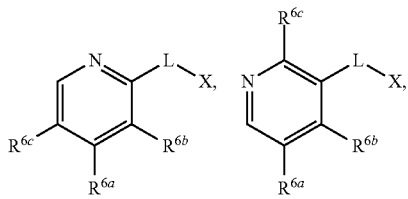
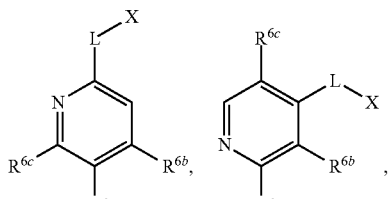
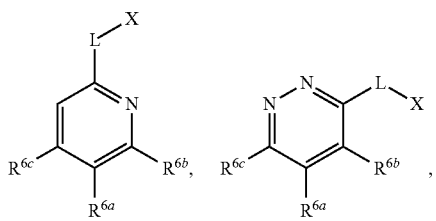

-continued

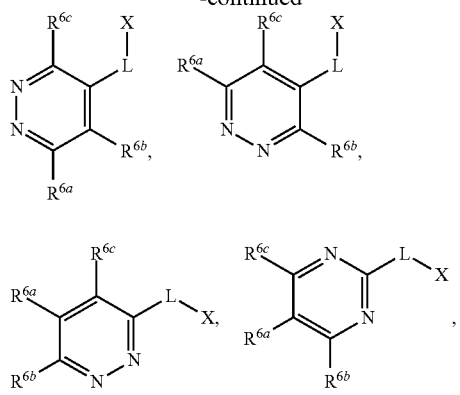

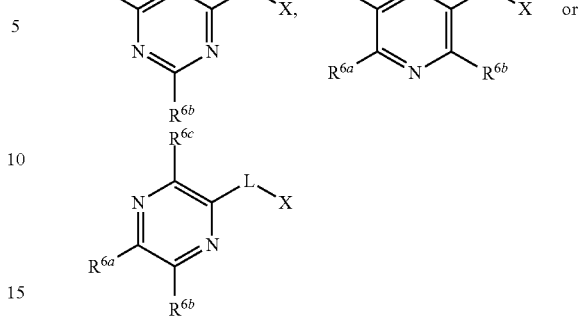

wherein $R^{6a}$, $R^{6b}$, $R^{6c}$, L and X are the same as the aforementioned (17).

General procedures for the synthesis of the compound of the invention are described bellow. Starting materials and reaction reagents used in such synthesis are commercially available or can be prepared according to methods well known in the art using compounds commercially available.

The compound of the present invention represented by the general formulas (I) to (VI) is able to be prepared in accordance with the synthetic methods as described bellow.

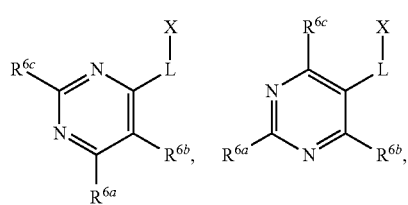

[Method A]

[Formula 53]

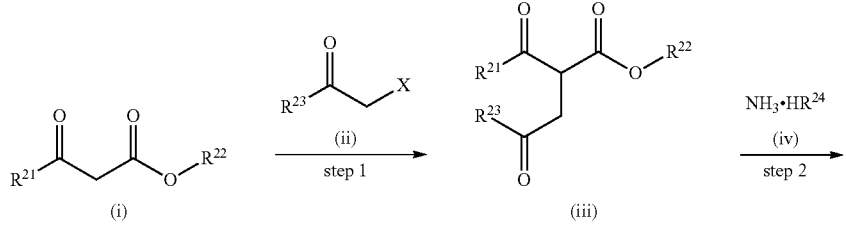

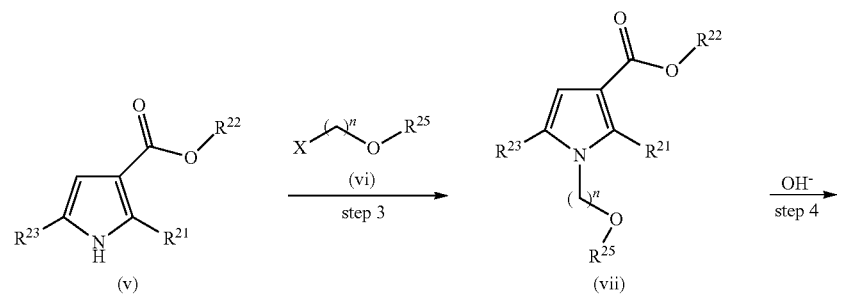

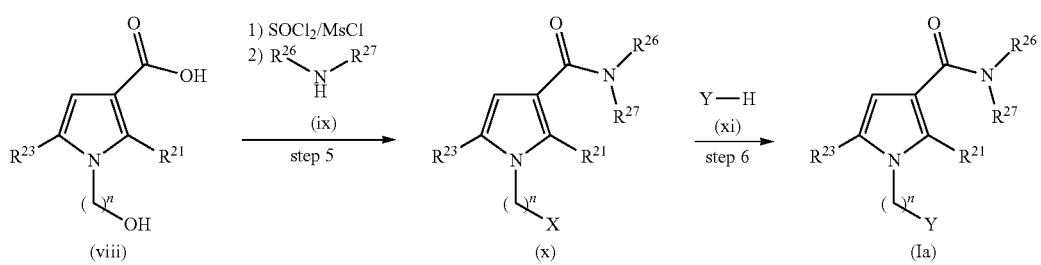

[Formula 54]

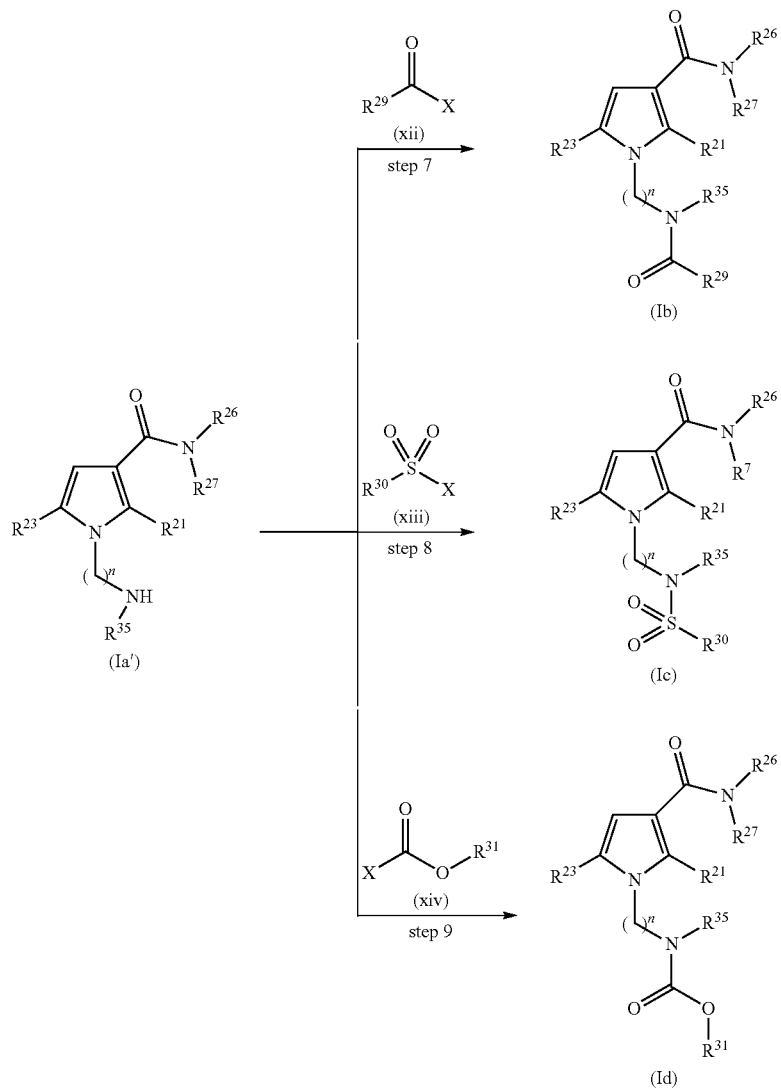

In cases where Y of (Ia) is $R^{35}$NH wherein $R^{21}$, $R^{23}$, $R^{26}$, $R^{27}$, $R^{29}$ and $R^{35}$ are each independently hydrogen, substituted or unsubstituted alkyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl; or $R^{26}$ and $R^{27}$ taken together with the adjacent nitrogen atom may form a ring in which oxygen atom, sulfur atom, or nitrogen atom may intervene; $R^{22}$, $R^{30}$ and $R^{31}$ are each independently substituted or unsubstituted alkyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl; $R^{24}$ is halide ion such as chloride ion, bromide ion and the like or acetate ion; $R^{25}$ is alkylsilyl such as TBS; X is a leaving group such as halogen, mesyloxy, tosyloxy and the like; Y is $OR^{32}$, $SR^{32}$ or $NR^{33}R^{34}$ (wherein $R^{32}$, $R^{33}$ and $R^{34}$ are each independently hydrogen, substituted or unsubstituted alkyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl); $R^{33}$ and $R^{34}$ taken together with the adjacent nitrogen atom may form a ring in which oxygen atom, sulfur atom, or nitrogen atom may intervene; n is an integer from 1 to 3.

(Step 1)

In the presence of a base, a compound (iii) can be synthesized by condensation of a ketoester (i) with a carbonyl compound (ii).

The carbonyl compound (ii) can be used at 1 to 2 mole equivalents relative to the ketoester (i).

Examples of the base include NaH, potassium tert-butoxide and the like, and the base can be used at 1 to 2 mole equivalents relative to the ketoester (i).

Examples of the reaction solvent include N,N-dimethylformamide, tetrahydrofuran and the like.

An example of a reaction temperature includes 0° C. to a refluxing temperature of a solvent.

An example of a reaction time includes 0.5 to 24 hours.

The resulting compound (iii) can be isolated and purified by the known means (e.g., chromatography, recrystallization and the like).

(Step 2)

A compound (v) can be synthesized by condensation of the compound (iii) and an amine (iv).

The amine (iv) can be used at 1 to 10 mole equivalents relative to the compound (iii).

Examples of the reaction solvent include acetic acid, formic acid and the like.

An example of a reaction temperature includes 0° C. to a refluxing temperature of a solvent.

An example of a reaction time includes 0.5 to 24 hours.

The resulting compound (v) can be isolated and purified by the known means (e.g., chromatography, recrystallization and the like).

(Step 3)

In the presence of a base, a compound (vii) can be synthesized by condensation of the compound (v) with the compound (vi).

The compound (vi) can be used at 1 to 4 mole equivalents relative to the compound (v).

Examples of the base include NaH, potassium tert-butoxide and the like, and the base can be used at 1 to 2 mole equivalents relative to the ketoester Examples of the reaction solvent include N,N-dimethylformamide, tetrahydrofuran and the like.

An example of a reaction temperature includes 0° C. to a refluxing temperature of a solvent.

An example of a reaction time includes 0.5 to 24 hours.

The resulting compound (vii) can be isolated and purified by the known means (e.g., chromatography, recrystallization and the like).

(Step 4)

Corboxylic acid (viii) can be synthesized by hydrolyzing a compound (vii).

Lithium hydroxide, sodium hydroxide, potassium hydroxide and the like can be used at 1 to 10 mole equivalents relative to the compound (vii)

Examples of a reaction solvent include methanol, ethanol, propanol, isopropanol, butanol, tetrahydrofuran, water and the like, and solvents can be used alone or by mixing them.

An example of a reaction temperature includes 0° C. to a refluxing temperature of a solvent.

An example of a reaction time includes 0.5 to 50 hours.

The resulting carboxylic acid (viii) can be isolated and purified by the known means (e.g., chromatography, recrystallization and the like).

(Step 5)

After mixing the carboxylic acid (viii) with thionyl chloride in the presence of N,N-dimethylformamide or mixing the carboxylic acid (viii) with methansulfonyl chloride in the presence of a base, a compound (x) can be synthesized by condensation of it with amine (ix).

Thionyl chloride or methansulfonyl chloride can be used at 1 to 4 mole equivalents relative to the carboxylic acid (viii).

Examples of the base include triethylamine, N,N-diisopropylethylamine and the like, and the base is used at 1 to 4 mole equivalents relative to the carboxylic acid (viii).

Amine (ix) is used at 1 to 15 mole equivalents relative to the compound (viii).

Examples of the reaction solvent include methylene chloride, tetrahydrofuran and the like.

An example of a reaction temperature includes 0° C. to a refluxing temperature of a solvent.

An example of a reaction time includes 0.5 to 24 hours.

The resulting compound (x) can be isolated and purified by the known means (e.g., chromatography, recrystallization and the like).

(Step 6)

In the presence of metallic iodide, a compound (Ia) can be synthesized by condensation of the compound (x) with the compound (xi).

The compound (xi) is used at 1 to 30 mole equivalents relative to the compound (x).

Examples of the reaction solvent include N,N-dimethylformamide, tetrahydrofuran, and the like.

Examples of the metallic iodide include sodium iodide, potassium iodide and the like, the metallic iodide is used at 0.1 to 2 mole equivalents.

An example of a reaction temperature includes 0° C. to a refluxing temperature of a solvent.

An example of a reaction time includes 0.5 to 24 hours.

The resulting compound (Ia) can be isolated and purified by the known means (e.g., chromatography, recrystallization and the like).

(Step 7)

In the presence of a base, amide (Ib) can be synthesized by condensation of the compound (Ia') with acid halide, acid anhydride or activated ester (xii) which is prepared by using the condensing agent.

The active ester (xii) which conditioned by the acid halide, the acid anhydride or the comdensing agent, can be used at 1 to 4 mole equivalents relative to the compound (Ia').

Examples of the condensing agent include dicyclohexylcarbodiimide, 1-(3-dimethylaminopropyl)-3-ethylcarbodiimide hydrochloride, N,N'-carbonyldiimidazole, HBTU (hexafluorophosphate 2-(1H-benzotriazole-1-yl)-1,1,3,3-tetramethyluronium), HATU (hexafluorophosphate 2-(7-azabenzotriazole-1-yl)-1,1,3,3-tetramethyluronium), ethyl chlorocarbonate, isobutyl chlorocarbonate, thionyl chloride, oxalyl chloride and the like, and the condensing agent can be used at 0.5 to 2 mole equivalents relative to the compound (Ia'). As a condensation aid, 1-hydroxybenzotriazole can be used at 0.5 to 2 mole equivalents.

Examples of the base include triethylamine, N,N-diisopropylethylamine, N-methylmorpholine, 4-dimethylaminopyridine and the like, and these can be used alone or by mixing them. Each of them can be used at 0.05 to 4 mole equivalents relative to the active ester (xii) conditioned by the acid halide, the acid anhydride or the comdensing agent Examples of the reaction solvent include methylene chloride, tetrahydrofuran, N,N-dimethylformamide and the like, these can be used alone or by mixing them.

An example of a reaction temperature includes 0° C. to a refluxing temperature of a solvent.

An example of a reaction time includes 0.5 to 72 hours.

The resulting compound represented by the formula (Ib) can be isolated and purified by the known means (e.g., chromatography, recrystallization and the like).

(Step 8)

In the presence of a base, sulfoneamide (Ic) can be synthesized by condensation of the compound (Ia') with sulfonyl chloride (xiii).

The sulfonyl chloride (xiii) can be used at 1 to 4 mole equivalents relative to the compound (Ia').

Examples of the base include triethylamine, N,N-diisopropylethylamine, N-methylmorpholine and the like, and each of them can be used at 1 to 4 mole equivalents relative to the compound (Ia').

Examples of the reaction solvent include methylene chloride, tetrahydrofuran and the like, and these can be used alone or by mixing them.

An example of a reaction temperature includes 0° C. to a refluxing temperature of a solvent.

An example of a reaction time includes 0.5 to 72 hours.

The resulting compound represented by the formula (Ic) can be isolated and purified by the known means (e.g., chromatography, recrystallization and the like).

(Step 9)

In the presence of a base, carbamate (Id) can be synthesized by condensation of the compound (Ia') with chlorocarbonic ester (xiv).

The chlorocarbonic ester (xiv) can be used at 1 to 4 mole equivalents relative to the compound (Ia').

Examples of the base include triethylamine, N,N-diisopropylethylamine, N-methylmorpholine and the like, and each of them can be used at 1 to 4 mole equivalents relative to the compound (Ia').

Examples of the reaction solvent include methylene chloride, tetrahydrofuran and the like, and these can be used alone or by mixing them.

An example of a reaction temperature includes 0° C. to a refluxing temperature of a solvent.

An example of a reaction time includes 0.5 to 72 hours.

The resulting compound represented by the formula (Id) can be isolated and purified by the known means (e.g., chromatography, recrystallization and the like).

[Method B]

[Formula 55]

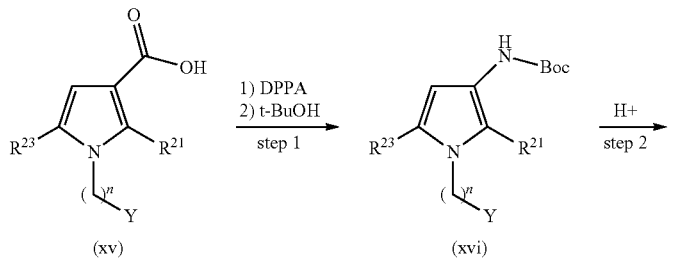

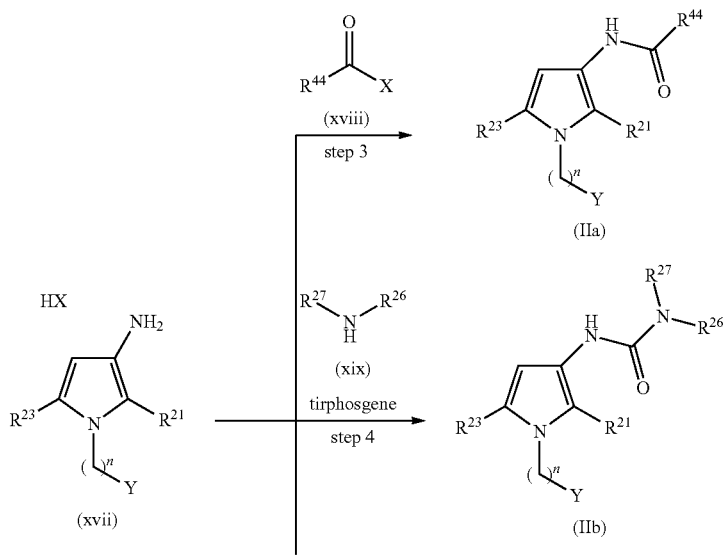

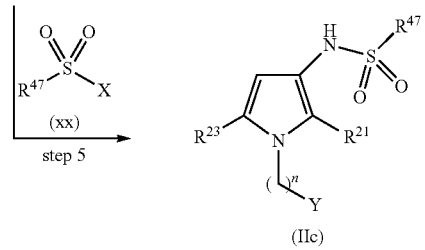

wherein $R^{21}$, $R^{23}$, $R^{26}$ and $R^{27}$ are defined above; $R^{44}$ and $R^{47}$ are each independently substituted or unsubstituted alkyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl; Y is $OR^{50}$, $SR^{50}$ or $NR^{51}R^{52}$ (wherein $R^{50}$, $R^{51}$ and $R^{52}$ are each independently substituted or unsubstituted alkyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl); $R^{51}$ and $R^{52}$ taken together with the adjacent nitrogen atom may form a ring in which oxygen atom, sulfur atom, or nitrogen atom may intervene; X and n are defined above.

(Step 1)

In the presence of a base, after mixing diphenylphosphoryl azide with carboxylic acids (xv), a carbamate (xvi) can be synthesized by mixing tert-butanol.

Diphenylphosphoryl azide can be used at 1 to 4 mole equivalents relative to the carboxylic acid (xv). tert-Butanol can be used at 1 mole equivalent relative to the compound (xv) to the solvent amount.

Examples of the base include triethylamine, N,N-diisopropylethylamine, N-methylmorpholine and the like, and each of them can be used at 1 to 4 mole equivalents relative to the carboxylic acid (xv).

Examples of the reaction solvent include toluene, xylene and the like, and these can be used alone or by mixing them.

An example of a reaction temperature includes 0° C. to a refluxing temperature of a solvent.

An example of a reaction time includes 0.5 to 72 hours.

The resulting carbamate (xvi) can be isolated and purified by the known means (e.g., chromatography, recrystallization and the like).

(Step 2)

In the presence of an acid, amine (xvii) can be synthesized by deprotecting the carbamate (xvi).

Examples of the acid include hydrogen chloride, trifluoroacetic acid and the like, and the acid can be used at 10 mole equivalents relative to the carbamate (xvi) to the solvent amount.

An example of a reaction temperature includes 0° C. to a refluxing temperature of a solvent.

An example of a reaction time includes 0.5 to 72 hours.

The resulting amine (xvii) can be isolated and purified by the known means (e.g., chromatography, recrystallization and the like).

(Step 3)

In the presence of a base, amide (IIa) can be synthesized by condensation of the amine (xvii) with acid halide, acid anhydride or activated ester (xviii) which is prepared by using the condensing agent.

The acid halide, acid anhydride or activated ester (xviii) which is prepared by using the condensing agent, can be used at 1 to 4 mole equivalents relative to the amine (xvii).

Examples of the condensing agent include dicyclohexylcarbodiimide, 1-(3-dimethylaminopropyl)-3-ethylcarbodiimide hydrochloride, N,N'-carbonyldiimidazole, HBTU (hexafluorophosphate 2-(1H-benzotriazole-1-yl)-1,1,3,3-tetramethyluronium), HATU (hexafluorophosphate 2-(7-azabenzotriazole-1-yl)-1,1,3,3-tetramethyluronium), ethyl chlorocarbonate, isobutyl chlorocarbonate, thionyl chloride, oxalyl chloride and the like, and the condensing agent can be used at 0.5 to 2 mole equivalents relative to the amine (xvii). As a condensation aid, 1-Hydroxybenzotriazole can be used at 0.5 to 2 mole equivalents.

Examples of the base include triethylamine, N,N-diisopropylethylamine, N-methylmorpholine, 4-dimethylaminopyridine and the like, and these can be used alone or by mixing them. Each of them can be used at 0.05 to 4 mole equivalents relative to acid halide, acid anhydride or activated ester (xviii) which is prepared by using the condensing agent.

Examples of the reaction solvent include methylene chloride, tetrahydrofuran, N,N-dimethylformamide and the like, and these can be used alone or by mixing them.

An example of a reaction temperature includes 0° C. to a refluxing temperature of a solvent.

An example of a reaction time includes 0.5 to 72 hours.

The resulting compound represented by the formula (IIa) can be isolated and purified by the known means (e.g., chromatography, recrystallization and the like).

(Step 4)

In the presence of a triphosgene, an urea (IIb) can be synthesized by condensation of the amine (xvii) with the amine (xix).

The triphosgene can be used at 0.3 to 2 mole equivalents relative to the amine (xvii).

The amine (xix) can be used at 1 to 4 mole equivalents relative to the amine (xvii).

Examples of the reaction solvent include methylene chloride, tetrahydrofuran and the like.

An example of a reaction temperature includes 0° C. to a refluxing temperature of a solvent.

An example of a reaction time includes 0.5 to 72 hours.

The resulting compound represented by the formula (IIb) can be isolated and purified by the known means (e.g., chromatography, recrystallization and the like).

(Step 5)

In the presence of a base, a sulfonamide (IIc) can be synthesized by condensation of the amine (xvii) with a sulfonylchloride (xx).

The sulfonylchloride (xx) can be used at 1 to 4 mole equivalents relative to the amine (xvii).

Examples of the base include triethylamine, N,N-diisopropylethylamine, N-methylmorpholine and the like, and these can be used at 1 to 4 mole equivalents relative to the amine (xvii).

Examples of the reaction solvent include methylene chloride, tetrahydrofuran and the like, these can be used alone or by mixing them.

An example of a reaction temperature includes 0° C. to a refluxing temperature of a solvent.

An example of a reaction time includes 0.5 to 72 hours.

The resulting compound represented by the formula (IIc) can be isolated and purified by the known means (e.g., chromatography, recrystallization and the like)

[Method C]

[Formula 56]

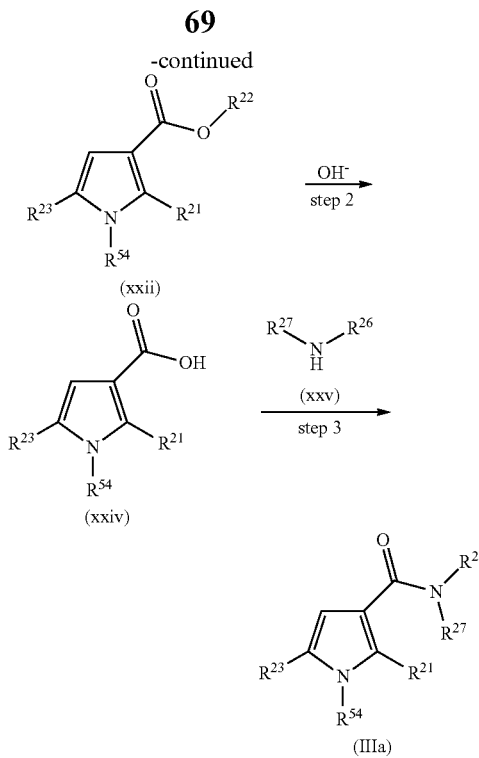

wherein $R^{21}$, $R^{22}$, $R^{23}$, $R^{26}$, $R^{27}$ and X are defined above; $R^{54}$ is substituted or unsubstituted alkyl, substituted or unsubstituted cycloalkyl, substituted or unsubstituted cycloalkenyl, a substituted or unsubstituted non-aromatic heterocyclic group.

(Step 1)

In the presence of a base, a compound (xxii) can be synthesized by condensation of the compound (v) with the compound (xxi).

The compound (xxi) can be used at 1 to 4 mole equivalents relative to the compound (v).

Examples of the base include NaH, potassium tert-butoxide and the like, and the base can be used at 1 to 2 mole equivalents relative to the compound (v).

Examples of the reaction solvent include N,N-dimethylformamide, tetrahydrofuran and the like.

An example of a reaction temperature includes 0° C. to a refluxing temperature of a solvent.

An example of a reaction time includes 0.5 to 24 hours.

The resulting compound (xxxii) can be isolated and purified by the known means (e.g., chromatography, recrystallization and the like).

(Step 2)

A carboxylic acid (xxiv) can be synthesized by hydrolyzing the compound (xxii).

Lithium hydroxide, sodium hydroxide, potassium hydroxide and the like can be used at 1 to 10 mole equivalents relative to the compound (xxii).

Examples of a reaction solvent include methanol, ethanol, propanol, isopropanol, butanol, tetrahydrofuran, water and the like, and solvents can be used alone or by mixing them.

An example of a reaction temperature includes 0° C. to a refluxing temperature of a solvent.

An example of a reaction time includes 0.5 to 50 hours.

The resulting carboxylic acid (xxiv) can be isolated and purified by the known means (e.g., chromatography, recrystallization and the like).

(Step 3)

In the presence of a condensing agent, an amide (IIIa) can be synthesized by condensation with the carboxylic acid (xxiv) with the amine (xxv).

The amine (xxv) can be used at 0.5 to 4 mole equivalents relative to the carboxylic acid (xxiv).

Examples of the condensing agent include dicyclohexylcarbodiimide, 1-(3-dimethylaminopropyl)-3-ethylcarbodiimide hydrochloride, N,N'-carbonyldiimidazole, HBTU (hexafluorophosphate 2-(1H-benzotriazole-1-yl)-1,1,3,3-tetramethyluronium), HATU (hexafluorophosphate 2-(7-azabenzotriazole-1-yl)-1,1,3,3-tetramethyluronium), ethyl chlorocarbonate, isobutyl chlorocarbonate, thionyl chloride, oxalyl chloride, methansulfonyl chloride and the like, and the condensing agent can be used at 0.5 to 2 mole equivalents relative to the carboxylic acid (xxiv). As a condensation aid, 1-hydroxybenzotriazole can be used at 0.5 to 2 mole equivalents.

Examples of the base include triethylamine, N,N-diisopropylethylamine, N-methylmorpholine, 4-dimethylaminopyridine and the like, and these can be used alone or by mixing them. Each of them can be used at 0.05 to 4 mole equivalents relative to the carboxylic aid (xxiv).

Examples of the reaction solvent include methylene chloride, tetrahydrofuran, N,N-dimethylformamide, pyridine and the like, and these can be used alone or by mixing them.

An example of a reaction temperature includes 0° C. to a refluxing temperature of a solvent.

An example of a reaction time includes 0.5 to 72 hours.

The resulting compound represented by the formula (IIIa) can be isolated and purified by the known means (e.g., chromatography, recrystallization and the like).

[Method D]

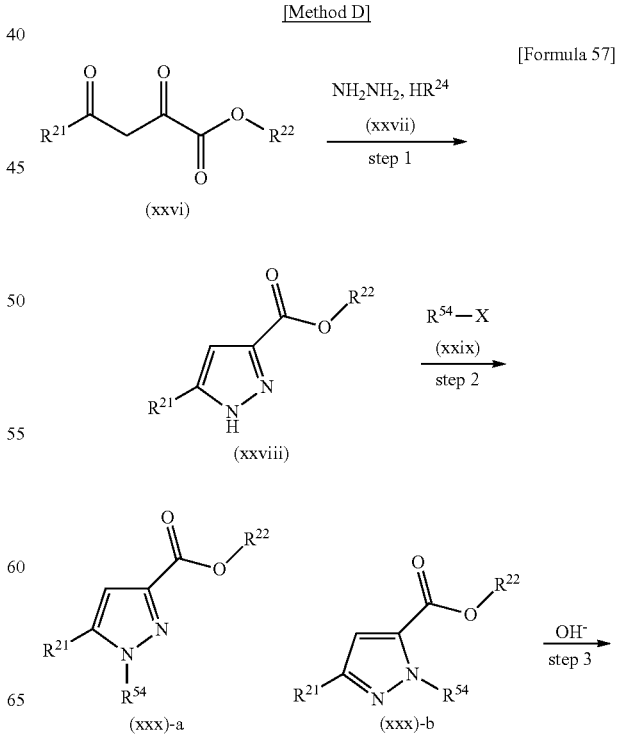

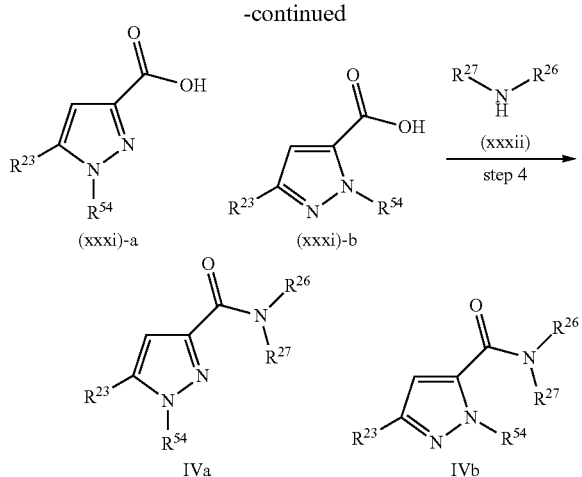

wherein $R^{21}$, $R^{22}$, $R^{24}$, $R^{26}$, $R^{27}$, $R^{54}$ and X are defined above.

(Step 1)

In the presence of an acid, a compound (xxviii) can be synthesized by condensation with the compound (xxvi) with a hydrazine (xxvii).

The hydrazine (xxvii) can be used at 1 to 10 mole equivalents relative to the compound (xxvi).

Examples of the acid include acetic acid, formic acid and the like, and the acid can be used at 1 to 3 mole equivalents relative to the compound (xxvi).

Examples of the reaction solvent include acetic acid, formic acid, ethanol, isopropanol and the like.

An example of a reaction temperature includes 0° C. to a refluxing temperature of a solvent.

An example of a reaction time includes 0.5 to 24 hours.

The resulting compound (xxviii) can be isolated and purified by the known means (e.g., chromatography, recrystallization and the like).

(step 2)

In the presence of a base, a compound (xxx) can be synthesized by condensation of the compound (xxviii) with the compound (xxix).

The compound (xxix) can be used at 1 to 4 mole equivalents relative to the compound (xxviii).

Examples of the base include NaH, potassium tert-butoxide, potassium carbonate and the like, and the base can be used at 1 to 3 mole equivalents relative the compound (xxviii).

Examples of the reaction solvent include N,N-dimethylformamide, tetrahydrofuran, acetonitrile and the like.

An example of a reaction temperature includes 0° C. to a refluxing temperature of a solvent.

An example of a reaction time includes 0.5 to 24 hours.

The resulting compound (xxx) can be isolated and purified by the known means (e.g., chromatography, recrystallization and the like).

(Step 3)

A carboxylic acid (xxxi) can be synthesized by hydrolyzing the compound (xxx).

Lithium hydroxide, sodium hydroxide, potassium hydroxide and the like can be used at 1 to 10 mole equivalents relative to the compound (xxx).

Examples of a reaction solvent include methanol, ethanol, propanol, isopropanol, butanol, tetrahydrofuran, water and the like, and solvents can be used alone or by mixing them.

An example of a reaction temperature includes 0° C. to a refluxing temperature of a solvent.

An example of a reaction time includes 0.5 to 50 hours.

The resulting carboxylic acid (xxxi) can be isolated and purified by the known means (e.g., chromatography, recrystallization and the like).

(Step 4)

In the presence of a condensing agent, an amide (IV) can be synthesized by condensation of the carboxylic acid (xxxi) with an amine (xxxii).

The amine (xxxii) can be used at 0.5 to 4 mole equivalents relative to the carboxylic acid (xxxi).

Examples of the condensing agent include dicyclohexylcarbodiimide, 1-(3-dimethylaminopropyl)-3-ethylcarbodiimide hydrochloride, N,N'-carbonyldiimidazole, HBTU (hexafluorophosphate 2-(1H-benzotriazole-1-yl)-1,1,3,3-tetramethyluronium), HATU (hexafluorophosphate 2-(7-azabenzotriazole-1-yl)-1,1,3,3-tetramethyluronium), ethyl chlorocarbonate, isobutyl chlorocarbonate, thionyl chloride, oxalyl chloride and the like, and the condensing agent can be used at 0.5 to 2 mole equivalents relative to the carboxylic acid (xxxi). As a condensation aid, 1-hydroxybenzotriazole can be used at 0.5 to 2 mole equivalents.

Examples of the base include triethylamine, N,N-diisopropylethylamine, N-methylmorpholine, 4-dimethylaminopyridine and the like, and these can be used alone or by mixing them. Each of them can be used at 0.05 to 4 mole equivalents relative to the carboxylic aid (xxxi).

Examples of the reaction solvent include methylene chloride, tetrahydrofuran, N,N-dimethylformamide, pyridine and the like, and these can be used alone or by mixing them.

An example of a reaction temperature includes 0° C. to a refluxing temperature of a solvent.

An example of a reaction time includes 0.5 to 72 hours.

The resulting compound represented by the formula (IV) can be isolated and purified by the known means (e.g., chromatography, recrystallization and the like).

[Method E]

[Formula 58]

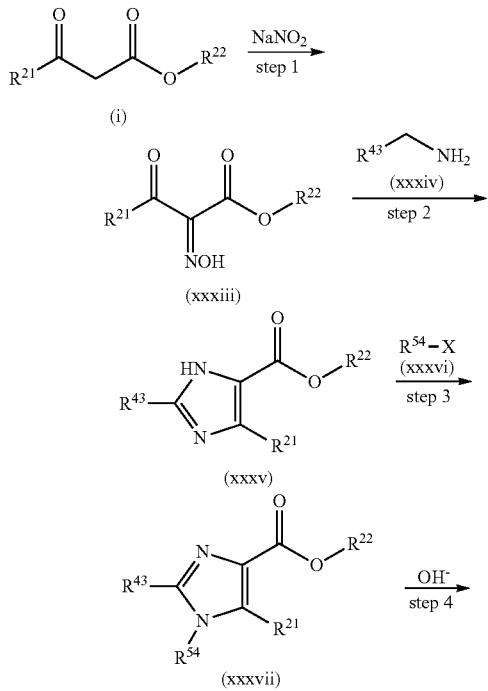

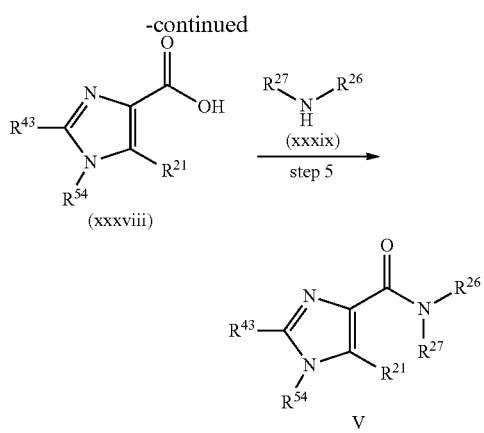

wherein $R^{21}$, $R^{22}$, $R^{26}$, $R^{27}$, $R^{54}$ and X are defined above; $R^{43}$ is substituted or unsubstituted aryl or substituted or unsubstituted heteroaryl.

(Step 1)

In the presence of an acid, a compound (xxxiii) can be synthesized by condensation of the compound (i) with sodium nitrite.

Sodium nitrite can be used at 1 to 5 mole equivalents relative to the compound (0.

Examples of the acid include acetic acid, formic acid and the like, and the acid can be used at 1 to 3 mole equivalents relative to the compound (i).

Examples of the reaction solvent include acetic acid, formic acid, water and the like.

An example of a reaction temperature includes 0° C. to a refluxing temperature of a solvent.

An example of a reaction time includes 0.5 to 24 hours.

The resulting compound (xxxiii) can be isolated and purified by the known means (e.g., chromatography, recrystallization and the like).

(Step 2)

A compound (xxxv) can be synthesized by condensation of the compound (xxxiii) with an amine (xxxiv).

The amine (xxxiv) can be used at 1 to 5 mole equivalents relative to the compound (xxviii).

Examples of the reaction solvent include N,N-dimethylformamide, tetrahydrofuran, acetonitrile and the like.

An example of a reaction temperature includes 0° C. to a refluxing temperature of a solvent.

An example of a reaction time includes 0.5 to 24 hours.

The resulting compound (xxxv) can be isolated and purified by the known means (e.g., chromatography, recrystallization and the like).

(Step 3)

In the presence of a base, a compound (xxxvii) can be synthesized by condensation of the compound (xxxv) with a compound (xxxvi).

The compound (xxxvi) can be used at 1 to 4 mole equivalents relative to the compound (xxxv).

Examples of the base include NaH, potassium tert-butoxide, potassium carbonate and the like, and the base can be used at 1 to 3 mole equivalents relative to the compound (xxxv).

Examples of the reaction solvent include N,N-dimethylformamide, tetrahydrofuran, acetonitrile and the like.

An example of a reaction temperature includes 0° C. to a refluxing temperature of a solvent.

An example of a reaction time includes 0.5 to 24 hours.

The resulting compound (xxxvii) can be isolated and purified by the known means (e.g., chromatography, recrystallization and the like).

(Step 4)

A carboxylic acid (xxxviii) can be synthesized by hydrolyzing the compound (xxxvii).

Lithium hydroxide, sodium hydroxide, potassium hydroxide and the like can be used at 1 to 10 mole equivalents relative to the compound (xxxvii).

Examples of a reaction solvent include methanol, ethanol, propanol, isopropanol, butanol, tetrahydrofuran, water and the like, and solvents can be used alone or by mixing them.

An example of a reaction temperature includes 0° C. to a refluxing temperature of a solvent.

An example of a reaction time includes 0.5 to 50 hours.

The resulting carboxylic acid (xxxviii) can be isolated and purified by the known means (e.g., chromatography, recrystallization and the like).

(Step 5)

In the presence of a condensing agent, an amide (V) can be synthesized by condensation of the carboxylic acid (xxxviii) with an amine (xxxix).

The amine (xxxix) can be used at 0.5 to 4 mole equivalents relative to the carboxylic acid (xxxviii).

Examples of the condensing agent include dicyclohexylcarbodiimide, 1-(3-dimethylaminopropyl)-3-ethylcarbodiimide hydrochloride, N,N'-carbonyldiimidazole, HBTU (hexafluorophosphate 2-(1H-benzotriazole-1-yl)-1,1,3,3-tetramethyluronium), HATU (hexafluorophosphate 2-(7-azabenzotriazole-1-yl)-1,1,3,3-tetramethyluronium), ethyl chlorocarbonate, isobutyl chlorocarbonate, thionyl chloride, oxalyl chloride and the like, and the condensing agent can be used at 0.5 to 2 mole equivalents relative to the carboxylic acid (xxxviii). As a condensation aid, 1-hydroxybenzotriazole can be used at 0.5 to 2 mole equivalents.

Examples of the base include triethylamine, N,N-diisopropylethylamine, N-methylmorpholine, 4-dimethylaminopyridine and the like, and these can be used alone or by mixing them. Each of them can be used at 0.05 to 4 mole equivalents relative to the carboxylic aid (xxxviii).

Examples of the reaction solvent include methylene chloride, tetrahydrofuran, N,N-dimethylformamide, pyridine and the like, and these can be used alone or by mixing them.

An example of a reaction temperature includes 0° C. to a refluxing temperature of a solvent.

An example of a reaction time includes 0.5 to 72 hours.

The resulting compound represented by the formula (V) can be isolated and purified by the known means (e.g., chromatography, recrystallization and the like).

[Method F]

[Formula 59]

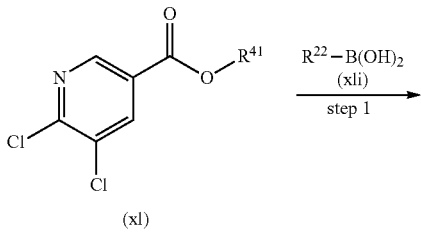

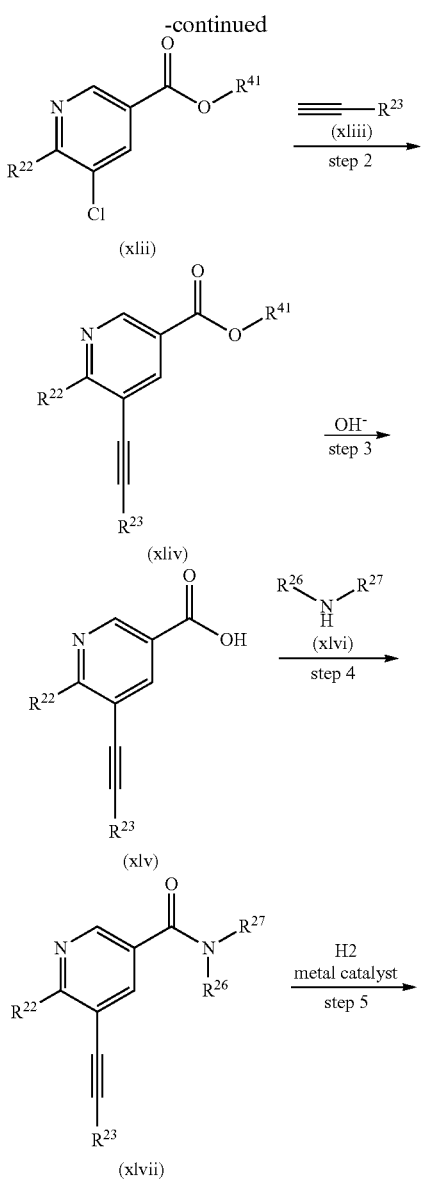

wherein $R^{22}$, $R^{23}$, $R^{26}$ and $R^{27}$ are defined above; $R^{41}$ is substituted or unsubstituted alkyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl.

(Step 1)

In the presence of a base and palladium catalyst, a compound (xlii) can be synthesized by the cross-coupling reaction of a compound (xl) with boronic acid (xli).

The boronic acid (xli) can be used at 1 to 5 mole equivalents relative to the compound (xl).

Examples of a base include potassium carbonate, cesium carbonate and the like and the base can be used at 1 to 4 mole equivalents relative to the compound (xl).

Examples of the palladium catalyst include tetrakis(triphenylphosphine)palladium(0), 1,1'-bis(diphenylphosphino)ferrocene-palladium(In dichloride and the like, and the palladium catalyst can be used at 0.01 to 0.1 mole equivalents relative to the compound (xl).

Examples of the reaction solvent include N,N-dimethylformamide, tetrahydrofuran, acetonitrile and the like.

An example of a reaction temperature includes 0° C. to a refluxing temperature of a solvent.

An example of a reaction time includes 0.5 to 24 hours.

The resulting compound (xlii) can be isolated and purified by the known means (e.g., chromatography, recrystallization and the like).

(Step 2)

In the presence of a base, a paradium catalyst and ligand or in the presence of a base, a paradium catalyst and copper iodide, a compound (xliv) can be synthesized by the cross-coupling reaction of the compound (xlii) with an alkyne (xliii).

The alkyne (xliii) can be used at 1 to 5 mole equivalents relative to the compound (xlii).

Examples of the base include triethylamine, diethylamine, cesium carbonate, and the like, and the base can be used at 1 to 4 mole equivalents relative to the compound (xlii).

Examples of the palladium catalyst include tetrakis(triphenylphosphine)palladium(0), palladium (II) acetate and the like, and the palladium catalyst can be used at 0.01 to 0.1 mole equivalents relative to the compound (xlii).

Examples of the ligand include 2-(dicyclohexylphosphino)-2',4',6'-triisopropylbiphenyl, 2-(dicyclohexylphosphino)-2',4',6'-diisopropoxybiphenyl and the like, and the ligand can be used at 0.01 to 0.2 mole equivalents relative to the compound (xlii).

The copper iodide can be used at 0.01 to 0.1 mole equivalents relative to the compound (xlii).

Examples of the reaction solvent include N,N-dimethylformamide, tetrahydrofuran, acetonitrile and the like.

An example of a reaction temperature includes 0° C. to a refluxing temperature of a solvent.

An example of a reaction time includes 0.5 to 24 hours.

The resulting compound (xliv) can be isolated and purified by the known means (e.g., chromatography, recrystallization and the like).

(Step 3)

A carboxylic acid (xlv) can be synthesized by hydrolyzing the compound (xliv).

Lithium hydroxide, sodium hydroxide, potassium hydroxide and the like can be used at 1 to 10 mole equivalents relative to the compound (xliv).

Examples of a reaction solvent include methanol, ethanol, propanol, isopropanol, butanol, tetrahydrofuran, water and the like, and solvents can be used alone or by mixing them.

An example of a reaction temperature includes 0° C. to a refluxing temperature of a solvent.

An example of a reaction time includes 0.5 to 50 hours.

The resulting carboxylic acid (xlv) can be isolated and purified by the known means (e.g., chromatography, recrystallization and the like).

(Step 4)

In the presence of a condensing agent, an amide (xlvii) can be synthesized by condensation of the carboxylic acid (xlv) with an amine (xlvi).

The amine (xlvi) can be used at 0.5 to 4 mole equivalents relative to the carboxylic acid (xlv).

Examples of the condensing agent include dicyclohexylcarbodiimide, 1-(3-dimethylaminopropyl)-3-ethylcarbodiimide hydrochloride, N,N'-carbonyldiimidazole, HBTU (hexafluorophosphate 2-(1H-benzotriazole-1-yl)-1,1,3,3-tetramethyluronium), HATU (hexafluorophosphate 2-(7-azabenzotriazole-1-yl)-1,1,3,3-tetramethyluronium), ethyl chlorocarbonate, isobutyl chlorocarbonate, thionyl chloride, oxalyl chloride and the like, and the condensing agent can be used at 0.5 to 2 mole equivalents relative to the carboxylic acid (xlv). As a condensation aid, 1-hydroxybenzotriazole can be used at 0.5 to 2 mole equivalents.

Examples of the base include triethylamine, N,N-diisopropylethylamine, N-methylmorpholine, 4-dimethylaminopyridine and the like, and these can be used alone or by mixing them. Each of them can be used at 0.05 to 4 mole equivalents relative to the carboxylic aid (xlv).

Examples of the reaction solvent include methylene chloride, tetrahydrofuran, N,N-dimethylformamide, pyridine and the like, and these can be used alone or by mixing them.

An example of a reaction temperature includes 0° C. to a refluxing temperature of a solvent.

An example of a reaction time includes 0.5 to 72 hours.

The resulting compound (xlvii) can be isolated and purified by the known means (e.g., chromatography, recrystallization and the like).

(Step 5)

In the presence of a metal catalyst, a compound (VI) can be synthesized by the hydrogenation of compound (xlvii).

Examples of the metal catalyst include palladium carbon, palladium hydroxide, platinum oxide and the like.

Examples of a reaction solvent include tetrahydrofuran, methanol and the like.

An example of a reaction temperature includes 0° C. to a refluxing temperature of a solvent.

An example of a reaction time includes 0.5 to 72 hours.

The resulting compound represented by the formula (VI) can be isolated and purified by the known means (e.g., chromatography, recrystallization and the like).

[Method G]

[Formula 60]

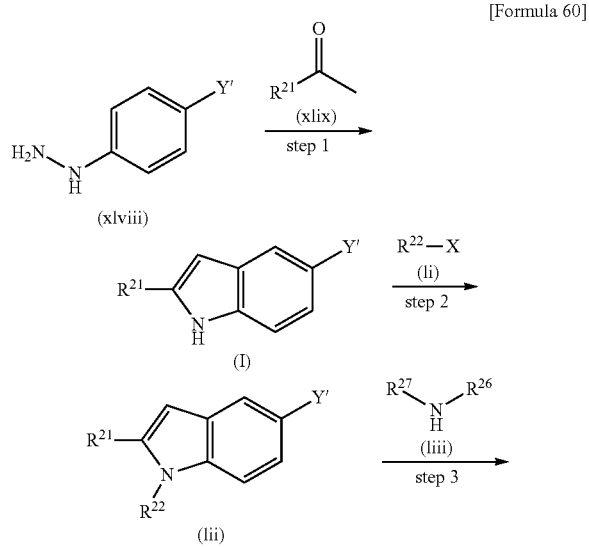

-continued

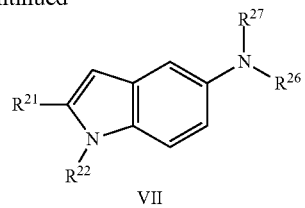

VII wherein $R^{21}$, $R^{26}$, $R^{27}$, $R^{54}$ and X are defined above; Y' is halogen or trifluoromethansulfonyloxy.

(Step 1)

In the presence of an acid, a compound (l) can be synthesized by condensation of the compound (xlviii) with a carbonyl compound (xlix).

The carbonyl compound (xlix) can be used at 1 to 5 mole equivalents relative to the compound (xlviii).

Examples of the acid include polyphosphoric acid, hydrochloric acid, sulfuric acid, acetic acid and the like, and the acid can be used at 1 mole equivalents relative to the compound (xlviii) to the solvent amount.

Examples of a reaction solvent include ethanol, propanol, isopropanol, butanol, water and the like, and these can be used alone or by mixing them.

An example of a reaction temperature includes 0° C. to a refluxing temperature of a solvent.

An example of a reaction time includes 0.5 to 24 hours.

The resulting compound (l) can be isolated and purified by the known means (e.g., chromatography, recrystallization and the like).

(Step 2)

In the preserve of a base, a compound (lii) can be synthesized by condensation of the compound (l) with a compound OD.

The compound (li) can be used at 1 to 4 mole equivalents relative to the compound (0.

Examples of the base include NaH, potassium tert-butoxide and the like, and the base can be used at 1 to 3 mole equivalents relative to the compound (l).

Examples of a reaction solvent include N,N-dimethylformamide, tetrahydrofuran, acetonitrile and the like.

An example of a reaction temperature includes 0° C. to a refluxing temperature of a solvent.

An example of a reaction time includes 0.5 to 24 hours.

The resulting compound (lii) can be isolated and purified by the known means (e.g., chromatography, recrystallization and the like).

(Step 3)

In the presence of a base, a palladium catalyst and a ligand, a compound (VII) can be synthesized by the cross-coupling reaction of the compound (lii) with an amine (liii).

The amine can be used at 1 to 5 mole equivalents relative to the compound (lii).

Examples of the base include sodium tert-butoxide, cesium carbonate and the like, and the base can be used at 1 to 4 mole equivalents relative to the compound (lii).

Examples of the palladium catalyst include tris(dibenzylideneacetone)dipalladium(0), palladium (II) acetate and the like, and the palladium catalyst can be used at 0.01 to 0.1 mole equivalents relative to the compound (lii).

Examples of the ligand include 2-(dicyclohexylphosphino)-2',4',6'-triisopropylbiphenyl, 2-(dicyclohexylphosphino)-2',4',6'-diisopropoxybiphenyl and the like, and the ligand can be used at 0.01 to 0.2 mole equivalents relative to the Compound (lii).

Examples of a reaction solvent include toluene, 1,4-dioxane and the like.

An example of a reaction temperature includes 0° C. to a refluxing temperature of a solvent.

An example of a reaction time includes 0.5 to 24 hours.

The resulting compound represented by the formula (VII) can be isolated and purified by the known means (e.g., chromatography, recrystallization and the like).

In another embodiment, the invention provides a pharmaceutical composition comprising an effective amount of the compound of the invention, in combination with a pharmaceutically acceptable carrier.

For use of the compound of the invention as a medicament, a pharmaceutical composition can be prepared according to conventional methods, using pharmaceutically acceptable carriers well known in the art, such as excipients, binders, disintegrants, lubricants, colourants, flavors, surfactants, etc.

For the pharmaceutical composition of the invention to be administered in the treatment of mammals including human, an appropriate unit dosage form may be selected depending on the purpose of the treatment and the route of administration. Specifically, such unit dosage form includes oral formulations such as tablet, coated tablet, powder, granule, capsule, liquid, pill, suspension, emulsion, etc., and parenteral formulations such as injectable solution, suppository, ointment, patch, aerosol, etc. Such unit dosage form can be formulated according to methods well known in the art.

The amount of the compound in a formulation can be varied depending on its dosage form, route for administration, dosing regimen, etc.

Means for administration of the pharmaceutical composition may be selected depending on dosage form, age, sex, body weight, severity of the disease, and other factors, etc., and route for administration can be selected from various routes such as oral, subcutaneous, transdermal, rectal, intranasal, buccal, etc.

Dose of the compound of the invention in a pharmaceutical composition of the invention can be determined depending on the choice of route for administration, age, sex, body weight, severity of the disease, the compound to be administered, and other factors, etc., and can be generally from 0.05 to 1000 mg/kg/day, preferably from 0.1 to 10 mg/kg/day, for oral administration to adults. For parenteral administration, dose can be varied widely depending on its route but generally from 0.005 to 100 mg/kg/day, preferably from 0.0-1 to 1 mg/kg/day. Such pharmaceutical composition of the invention may be administered once a day or in several times at a divided dosage in a day.

Following examples illustrate the present invention in more detail, however, the present invention is not limited to these examples. The meaning of each abbreviation is as follows.

Me: methyl
Et: ethyl
CF$_3$: trifluoromethyl
Ph: phenyl
Bn: benzyl
N$_3$: azide
TBS: tert-buthyldimethylsilyl
Ac: acetyl
Ms: methansulfonyl
DMSO: dimethyl sulfoxide
DMF: dimethylformamide
THF: tetrahydrofuran
MeOH: methanol
EtOH: ethanol
n-BuOH: normal butanol
t-BuOH: tert butanol
Boc: tert-butoxycarbonyl
Pd/C: palladium carbon
Pd(OAc)$_2$: palladium acetate
Pd$_2$(dba)$_3$: tris(dibenzylideneacetone)dipalladium(0)
XPhos: 2-dicyclohexylphosphino-2',4',6'-triisopropylbiphenyl
EDC: 1-ethyl-3-(3-dimethylaminopropyl)carbodiimide
HOBt: 1-hydroxybenzotriazole
Py: pyridine
NaHCO$_3$: sodium bicarbonate
KI: potassium iodide
K$_2$CO$_3$: potassium carbonate
Cs$_2$CO$_3$: Cesium carbonate
NaH: sodium hydride (ca.60% oil suspension)
NaOH: sodium hydroxide
NaI: sodium iodide
NaNO$_2$: sodium nitrite
Et$_3$N: triethylamine
NH$_2$NH$_2$: hydrazine
NH$_3$: ammonia
NH$_4$OAc: ammonium acetate
LiCl: lithium chloride
NH$_4$Cl: ammonium chloride
Na$_2$SO$_4$: sodium sulfate
CH$_3$COONa: sodium acetate
CH$_3$COONa.3H$_2$O: sodium acetate trihydrate
NaBH$_4$: sodium borohydride
TsOH: para toluenesulfonic acid
TFA: trifluoroacetic acid
PPA: polyphosphoric acid
HCl: hydrogen chloride
AcOH: acetic acid
AC$_2$O: acetic anhydride
SOCl: thionyl chloride
MSCl: methansulfonyl chloride
DPPA: diphenylphosphoryl azide
HPLC: High Performance Liquid Chromatography
p-HPLC: preparative high performance liquid chromatography
rt: room temperature
RT: retention time Example 1

Synthesis of Compound I-023 (Compound 9)

Step 1

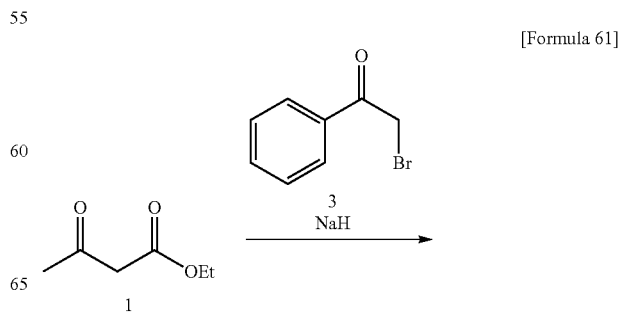

[Formula 61]

-continued

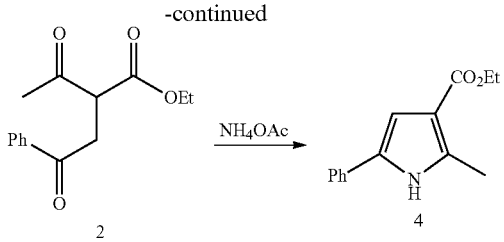

Step 3

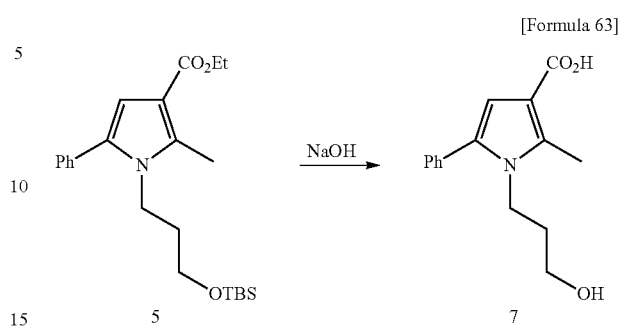

To a solution of compound 1 (9.76 g, 75.0 mmol) in 30 ml DMF was added NaH (3.60 g, 90.0 mmol) at 0° C. under N₂ atmosphere, and the mixture was stirred for 30 minutes at rt. After cooled to 0° C., to the reaction mixture was added a solution of compound 3 (16.4 g, 83.0 mmol) in 16 ml DMF, and the mixture was stirred for 45 minutes at rt. To the reaction mixture was added water at the temperature, and the mixture was extracted with ethyl acetate. The organic phase was washed by brine, dried by anhydrous MgSO₄, concentrated, purified by, column chromatography to afford compound 2. To a solution of compound 2 in 100 ml acetic acid was added ammonium acetate (7.32 g, 95.0 mmol), and the reaction mixture was stirred for 4 hours at 80° C., concentrated and the residue was purified by silica-gel column chromatography. The residue was solidified by hexane-ethy acetate, then filtered off and rinsed with hexane to afford compound 4 (9.42 g, 64.9% yield).

¹H-NMR (CDCl₃) δ: 1.37 (3H, t, J=7.1 Hz), 2.59 (3H, s), 4.29 (2H, q, J=7.1 Hz), 6.83 (1H, d, J=2.9 Hz), 7.18-7.26 (1H, m), 7.31-7.49 (4H, m), 8.36 (1H, br s).

Step 2

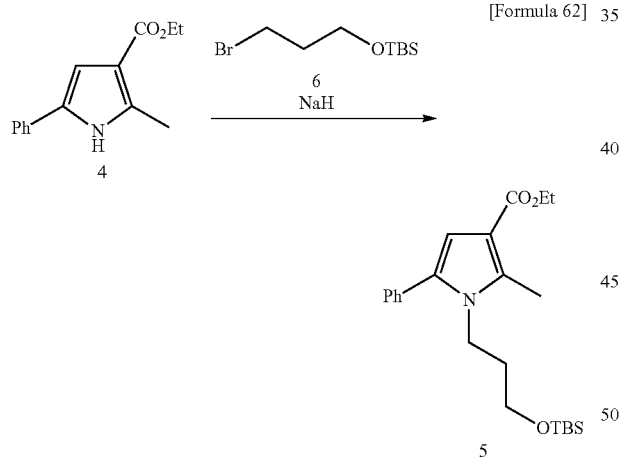

To a solution of compound 4 (4.00 g, 17.5 mmol) in 40 ml DMF was added NaH (837 mg, 20.9 mmol) at 0° C. under N₂ atmosphere, and the mixture was stirred for 30 minutes. To the reaction mixture was added compound 6 (4.85 ml, 20.9 mmol) at the temperature, and the mixture was stirred for 4.5 hours at rt. After cooled to 0° C., added water, and the mixture was extracted with ethyl acetate. The organic phase was washed by brine, dried by anhydrous MgSO₄, concentrated, purified by column chromatography to afford compound 5 (6.86 g, 98% yield).

¹H-NMR (CDCl₃) δ: −0.03 (6H, s), 0.83 (9H, s), 1.34 (3H, t, J=7.2 Hz), 1.62-1.75 (2H, m), 2.62 (3H, s), 3.46 (2H, t, J=5.8 Hz), 3.95-4.04 (2H, m), 4.27 (2H, q, J=7.1 Hz), 6.54 (1H, s), 7.28-7.42 (5H, m).

To a solution of a compound 5 (6.85 g, 17.1 mmol) in 20 ml THF-6 ml ethanol was added 2 mol/L sodium hydroxide (10.2 ml, 20.5 mmol), and the mixture was stirred for 1 hour at rt and for 3.5 hours at 80° C. Then to the reaction mixture was added 2 mol/L sodium hydroxide (10.2 ml, 20.5 mmol) at 80° C., and the mixture was stirred for 6.5 hours at the temperature. After leaved the reaction mixture at rt overnight, to the reaction mixture was added 2 mol/L sodium hydroxide (25.6 ml, 51.2 mmol) and 20 ml ethanol at 80° C., and the mixture was stirred for 13.5 hours at the temperature. After leaved the reaction mixture at rt overnight, to the reaction mixture was added 2 mol/L sodium hydroxide (10.2 ml, 20.5 mmol) at 80° C., and the mixture was stirred for 11 hours at the temperature. After leaved the reaction mixture at rt overnight, to the reaction mixture was added isopropylether, and extracted with water, then acidified by 2 mol/L HCl solution, filtered off and rinsed with water to afford compound 7 (3.41 g, 77% yield).

¹H-NMR (DMSO-d₆) δ: 1.53-1.65 (2H, m), 2.55 (3H, s), 3.25 (2H, dd, J=11.1, 5.9 Hz), 3.97 (2H, t, J=7.5 Hz), 4.53 (1H, t, J=5.0 Hz), 7.31-7.49 (5H, m), 11.69 (1H, s).

Step 4

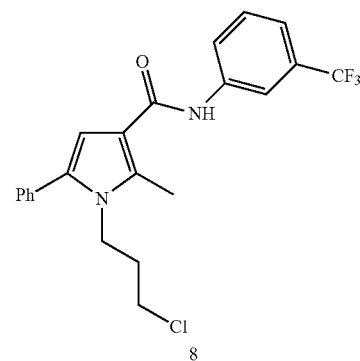

To a suspension of compound 7 (2.5 g, 9.64 mmol) in 25 ml methylene chloride was added thionyl chloride (1.55 ml, 21.2 mmol) and DMF (0.075 ml. 0.964 mmol), and the mixture was stirred for 3 hours under the reflux. After cooled to rt, the reaction mixture was added into a solution of 3-trifluoromethylaniline (12.0 ml, 21.2 mmol) in 25 ml methylene chloride at 0° C., and stirred for 1.5 hours at the temperature. To the reaction mixture was added water, and the mixture was extracted with ethyl acetate. The organic phase was washed by 2 mol/L HCl solution, brine, dried by anhydrous MgSO$_4$, concentrated, purified by column chromatography. The residue was solidified by hexane-isopropylether, then filtered off and rinsed with hexane to afford compound 8 (1.09 g, 27% yield).

$^1$H-NMR (CDCl$_3$) δ: 1.91-2.03 (2H, m), 2.70 (3H, s), 3.35 (2H, t, J=6.1 Hz), 4.12 (2H, t, J=7.4 Hz), 6.34 (1H, s), 7.29-7.49 (7H, m), 7.55 (1H, s), 7.77 (1H, d, J=7.6 Hz), 7.91 (1H, s).

Step 5

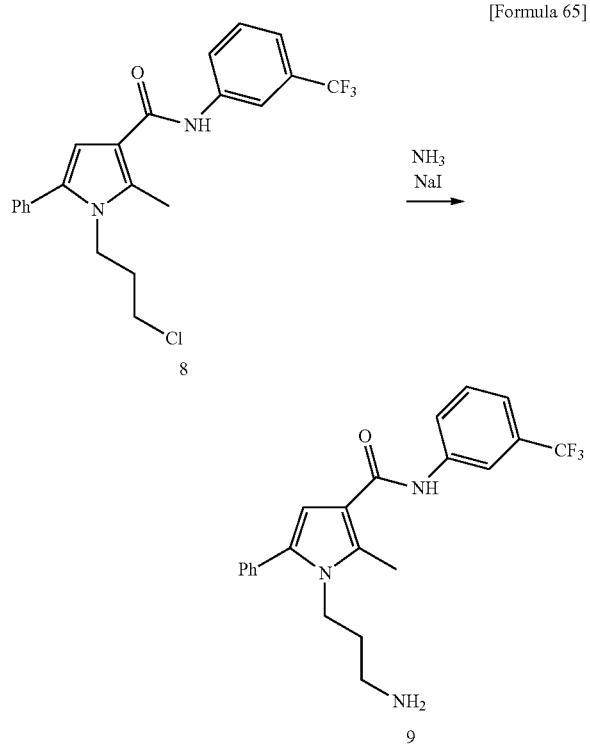

[Formula 65]

To a suspension of a compound 8 (500 mg, 1.19 mmol) and sodium iodide (178 mg, 1.19 mmol) in 5 ml DMSO was added 2 ml 28% w/w aqueous ammonia, and stirred for 7.5 hours at 80° C. Then 4 ml 28% w/w aqueous ammonia, 8 ml DMSO was, added at 80° C., and the mixture was stirred for 2 hours at the temperature. After leaved the reaction mixture at rt overnight, water was added to the mixture. The mixture was extracted with ethyl acetate. The organic phase was washed by brine, dried by anhydrous MgSO$_4$, concentrated, purified by column chromatography to afford compound 9 (I-023, 183 mg, 39% yield).

$^1$H-NMR (CDCl$_3$) δ: 1.67 (2H, quin, J=7.1 Hz), 2.54 (2H, t, J=6.8 Hz), 2.69 (3H, s), 4.02 (2H, t, J=7.5 Hz), 6.33 (1H, s), 7.29-7.48 (7H, m), 7.57 (1H, s), 7.77 (1H, d, J=8.2 Hz), 7.91 (1H, s).

Example 2

Synthesis of Compound I-025 (Compound 10)

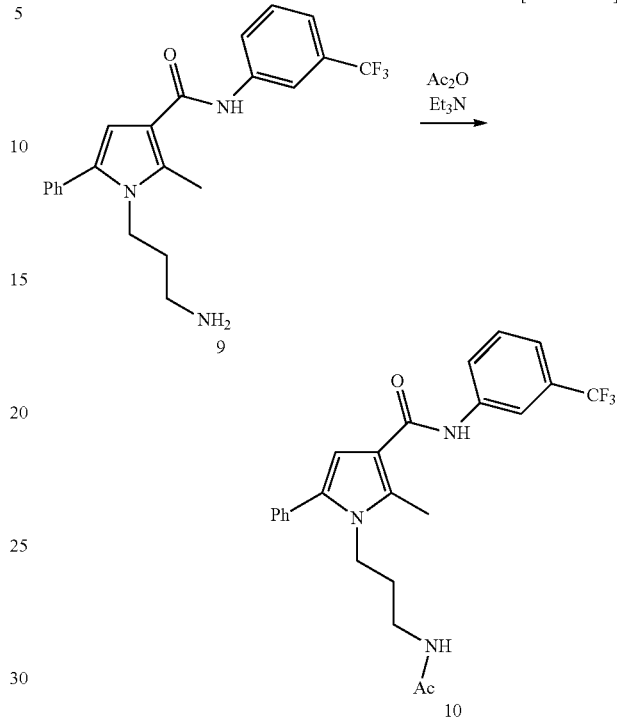

[Formula 66]

To a compound 9 (50 mg, 0.125 mmol) obtained in Example 1 in 1 mL methylene chloride was added triethylamine (0.0260 mL, 0.187 mmol), acetic anhydride (0.0180 mL, 0.187 mmol), and the mixture was stirred for 20 minutes at the temperature. Then to the reaction mixture was added 2 mol/L HCl solution, water, and the mixture was extracted with ethyl acetate. The organic phase was washed by saturated aqueous solution of Na$_2$CO$_3$, water, brine, dried by anhydrous MgSO$_4$, concentrated, purified by column chromatography. The residue was suspended with methylene chloride-hexane, filtered off, and rinsed with hexane to afford compound 10 (I-025, 32.6 mg, 59% yield).

$^1$H-NMR (CDCl$_3$) δ: 1.66-1.81 (2H, m), 1.75 (3H, s), 2.67 (3H, s), 2.99 (2H, q, J=6.3 Hz), 4.02 (2H, t, J=7.1 Hz), 4.69-4.88 (1H, m), 6.36 (1H, s), 7.30-7.51 (7H, m), 7.58 (1H, s), 7.78 (1H, d, J=8.4 Hz), 7.91 (1H, s).

Example 3

Synthesis of Compound I-026 (Compound 11)

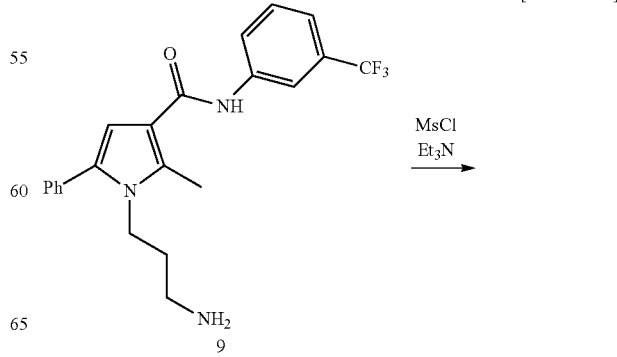

[Formula 67]

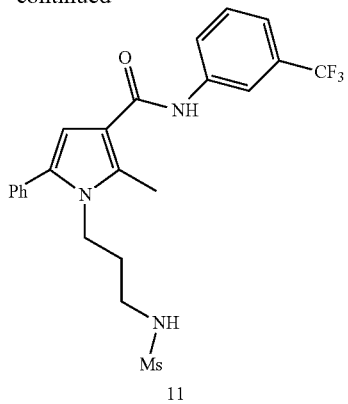

11

To a solution of the compound 9 (50 mg, 0.125 mmol) obtained in Example 1 in 1 mL methylene chloride was added triethylamine (0.0260 mL, 0.187 mmol), methansulfonyl chloride (0.0150 mL, 0.187 mmol) at 0° C., and the mixture was stirred for 20 minutes at the temperature. Then to the reaction mixture was added 2 mol/L HCl solution, water, and the mixture was extracted with ethyl acetate. The organic phase was washed by saturated aqueous solution of NaHCO$_3$, water, brine, dried by anhydrous MgSO$_4$, concentrated, purified by column chromatograph to afford compound 11 (I-026, 47.9 mg, 80% yield).

$^1$H-NMR (CDCl$_3$) δ: 1.77 (2H, quin, J=6.8 Hz), 2.68 (3H, s), 2.81 (3H, s), 2.91 (2H, q, J=6.4 Hz), 3.69 (1H, t, J=6.2 Hz), 4.09 (2H, t, J=7.1 Hz), 6.37 (1H, s), 7.30-7.52 (7H, m), 7.61 (1H, s), 7.77 (1H, d, J=7.9 Hz), 7.92 (1H, s).

Example 4

Synthesis of Compound I-027 (Compound 12)

[Formula 68]

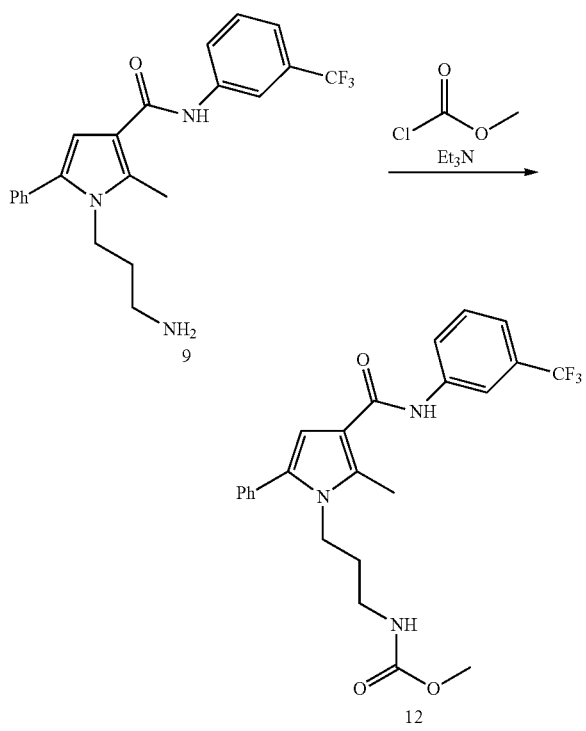

To a solution of the compound 9 (73 mg, 0.182 mmol) obtained in Example 1 in 1 mL methylene chloride was added triethylamine (0.0380 mL, 0.273 mmol), methyl chlorocarbonate (0.0210 mL, 0.273 mmol) at 0° C., and the mixture was stirred for 20 minutes at the temperature. Then to the reaction mixture was added 2 mol/L HCl solution, water, and the mixture was extracted with ethyl acetate. The organic phase was washed by saturated aqueous solution of NaHCO$_3$, water, brine, and dried by anhydrous MgSO$_4$, concentrated, purified by column chromatography to afford compound 12 (I-027, 56.0 mg, 67% yield).

$^1$H-NMR (CDCl$_3$) δ: 1.73 (2H, quin, J=6.9 Hz), 2.66 (3H, s), 2.97 (2H, q, J=6.2 Hz), 3.60 (3H, s), 4.00 (2H, t, J=7.3 Hz), 4.23 (1H, br s), 6.35 (1H, s), 7.30-7.49 (7H, m), 7.60 (1H, s), 7.78 (1H, d, J=8.6 Hz), 7.91 (1H, s).

Example 5

Synthesis of Compound I-082 (Compound 16)

Step 1

[Formula 69]

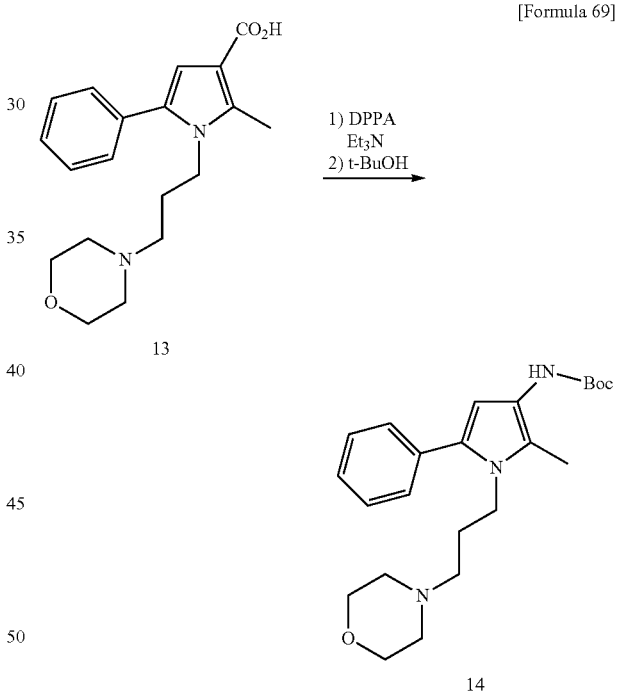

To a solution of a compound 13 (2 g, 6.09 mmol) in 30 ml toluene was added diphenylphosphoryl azide (3.67 mL, 17.1 mmol), triethylamine (3.38 mL, 24.36 mmol) at rt, and the mixture was stirred for 1.5 hours at reflux. To the reaction mixture was added 15 ml tert-buthanol, and the mixture was stirred for 7 hours at reflux. After leaved at rt overnight, the reaction mixture was stirred at reflux, and concentrated. The residue was purified by silica-gel column chromatography. The resulting solid was triturated with ethyl acetate and hexane. The solid was filtered off, and washed by hexane to afford compound 14 (857 mg, 35% yield).

$^1$H-NMR (CDCl$_3$) δ: 1.51 (9H, s), 1.56-1.69 (2H, m), 2.11-2.23 (9H, m), 3.58 (4H, t, J=4.7 Hz), 3.89-3.97 (2H, m), 5.85 (1H, br s), 6.18 (1H, s), 7.21-7.41 (5H, m).

Step 2

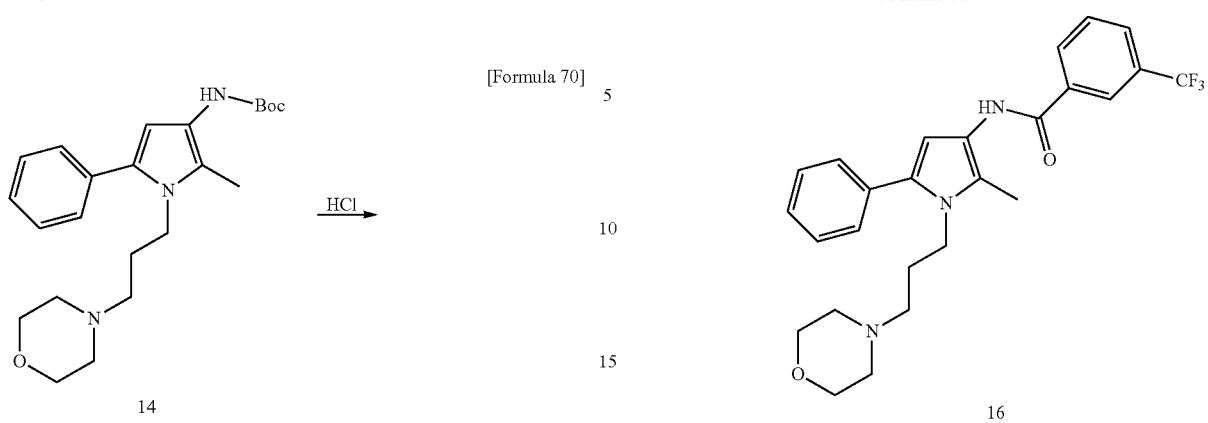

To a solution of the compound 14 (835 mg, 2.09 mmol) in 2 ml 1,4-dioxane was added 10 ml of 4 mol/L HCl-dioxane solution at rt, and the mixture was stirred for 3 hours at the temperature. After diluting the reaction mixture with diethylether, the obtained solid was filtered off, and washed by diethylether to afford compound 15 (8.48 mg, >100% yield).

$^1$H-NMR (DMSO-d$_6$) δ: 1.87-2.04 (2H, m), 2.32 (3H, s), 2.84-3.01 (4H, m), 3.23 (2H, d, J=12.4 Hz), 3.73 (2H, t, J=11.7 Hz), 3.81-3.99 (4H, m), 6.09 (1H, s), 7.33-7.49 (5H, m), 9.86 (3H, s), 11.21 (1H, br s).

Under N$_2$ atmosphere, to a suspension of the compound 15 (80 mg, 0.215 mmol) in 2 mL methylene chloride was added triethylamine (0.104 mL, 0.752 mmol), 3-trifluoromethyl-benzoyl chloride (0.0490 mL, 0.322 mmol), and the mixture was stirred for 30 minutes at the same temperature. Then to the reaction mixture was added water, saturated aqueous solution of NaHCO$_3$, the mixture was extracted with ethyl acetate. The organic phase was washed by water, brine, and dried by anhydrous MgSO$_4$, concentrated, purified by column chromatography. The obtained solid was suspended in diisopropylether, filtered off, and washed by diisopropylether to afford compound 16 (I-082, 69.8 mg, 69% yield).

$^1$H-NMR (CDCl$_3$) δ: 1.55-1.73 (2H, m), 2.12-2.25 (6H, m), 2.27 (3H, s), 3.58 (4H, t, J=4.5 Hz), 3.94-4.05 (2H, m), 6.29 (1H, s), 7.23-7.46 (6H, m), 7.61 (1H, t, J=7.7 Hz), 7.79 (1H, d, J=7.5 Hz), 8.05 (1H, d, J=7.3 Hz), 8.13 (1H, s).

Step 3

Example 6

Synthesis of Compound I-081 (Compound 17)

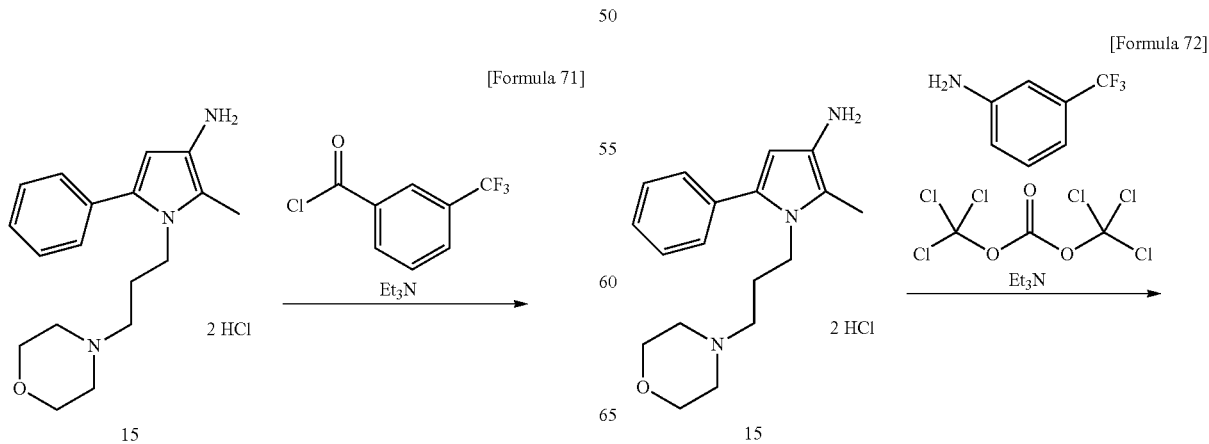

-continued

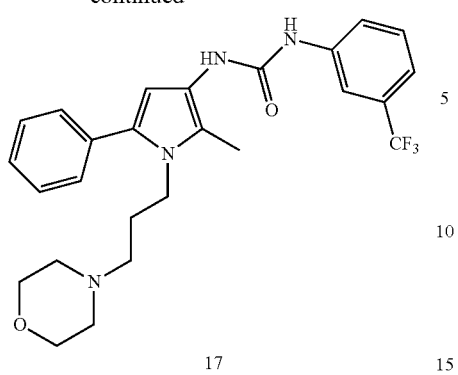

17

Under N₂ atmosphere, to a solution of triphosgene (38.3 mg, 0.129 mmol) in 2 mL methylene chloride was added 3 trifluoromethylaniline (0.0400 mL, 0.322 mmol), triethylamine (0.54 mL, 0.387 mmol) at 0° C., and stirred for 100 minutes at the same temperature (hereafter, the obtained reaction mixture being "the reaction mixture A").

Under N₂ atmosphere, to a suspension of the compound 15 (80 mg, 0.215 mmol) obtained at the step 2 in Example 5 in 2 mL methylene chloride was added triethylamine (0.104 mL, 0.752 mmol), the reaction mixture A at 0° C., and stirred for 10 minutes at the temperature. Then to the reaction mixture was added water, saturated aqueous solution of NaHCO₃, and the mixture was extracted with ethyl acetate. The organic phase was washed by water, brine, and dried by anhydrous MgSO₄, concentrated, purified by column chromatography to afford compound 17 (I-081, 24.3 mg, 23% yield).

¹H-NMR (CDCl₃) δ: 1.59-1.78 (2H, m), 2.13-2.40 (9H, m), 3.55-3.69 (4H, m), 4.02 (2H, t, J=7.5 Hz), 5.88 (1H, br s), 6.10 (1H, s), 6.94 (1H, br s), 7.21-7.46 (7H, m), 7.59 (1H, s), 7.65 (1H, d, J=8.1 Hz).

Example 7

Synthesis of Compound I-080 (Compound 18)

[Formula 73]

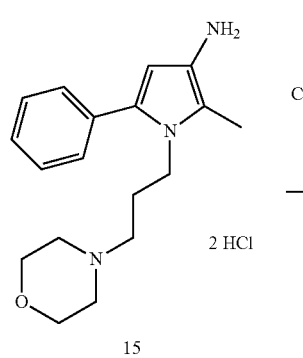

15

-continued

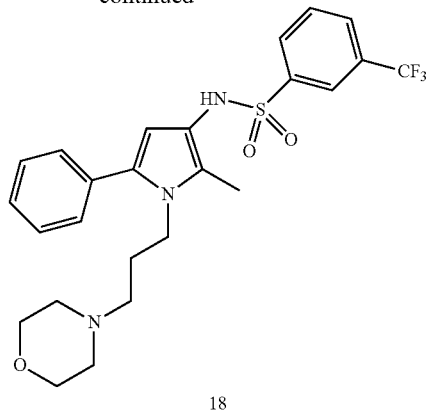

18

Under N₂ atmosphere, to a suspension of the compound 15 (80 mg, 0.215 mmol) obtained at the step 2 in Example 5 in 2 mL methylene chloride was added triethylamine (0.104 mL, 0.752 mmol), 3-trifluoromethylbenzenesulufonyl chloride (0.0520 mL, 0.322 mmol) at 0° C., and the mixture was stirred for 10 minutes at the temperature. Then to the reaction mixture was added water, saturated aqueous solution of NaHCO₃ at the temperature, and the mixture was extracted with ethyl acetate. The organic phase was washed by water, brine, and dried by anhydrous MgSO₄, concentrated, purified by column chromatography to afford compound 18 (I-080, 67.9 mg, 62% yield).

¹H-NMR (CDCl₃) δ: 1.55 (2H, quin, J=7.1 Hz), 2.03-2.27 (9H, m), 3.56 (4H, t, J=4.4 Hz), 3.90 (2H, t, J=7.5 Hz), 5.54 (1H, s), 5.99 (1H, s), 7.16-7.40 (5H, m), 7.61 (1H, t, J=7.7 Hz), 7.81 (1H, d, J=7.6 Hz), 7.93-8.04 (2H, m).

Example 8

Synthesis of Compound I-083 (Compound 21)

Step 1

[Formula 74]

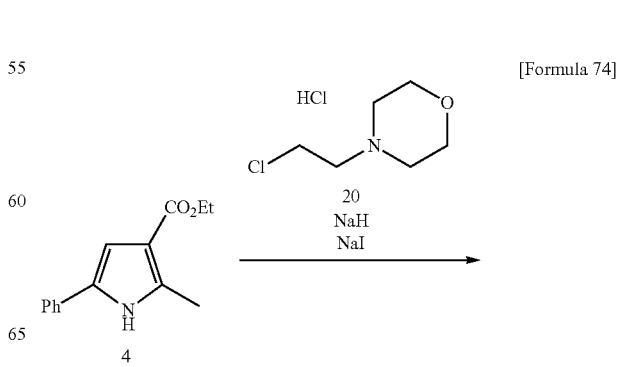

-continued

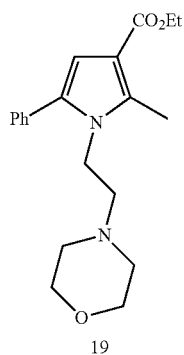

19

Under $N_2$ atmosphere, to a solution of the compound 4 (300 mg, 1.31 mmol) obtained at the step 1 in Example 1 in 3 mL DMF was added NaH (115 mg, 2.88 mmol) at 0° C., and the mixture was stirred for 30 minutes at the temperature. Then to the reaction mixture was added compound 20 (292 mg, 1.57 mmol), sodium iodide (196 mg, 1.31 mmol) at 0° C., and the mixture was stirred for 1 hour at rt, then stirred for 3 hours, at 80° C. After cooled to 0° C., to the reaction mixture was added water, and the mixture was extracted with ethylacetate. The organic phase was washed by water, brine, and dried by anhydrous $MgSO_4$, concentrated, purified by column chromatography. The obtained solid was suspended to hexane, filtered off, washed by hexane to afford compound 19 (236 mg, 53% yield).

$^1$H-NMR (CDCl$_3$) δ: 1.34 (3H, t, J=7.1 Hz), 2.25 (4H, t, J=4.6 Hz), 2.40 (2H, t, J=7.3 Hz), 2.63 (3H, s), 3.57 (4H, t, J=4.6 Hz), 4.01 (2H, t, J=7.3°Hz), 4.27 (2H, q, J=7.1 Hz), 6.53 (1H, s), 7.28-7.46 (5H, m).
Step 2

[Formula 75]

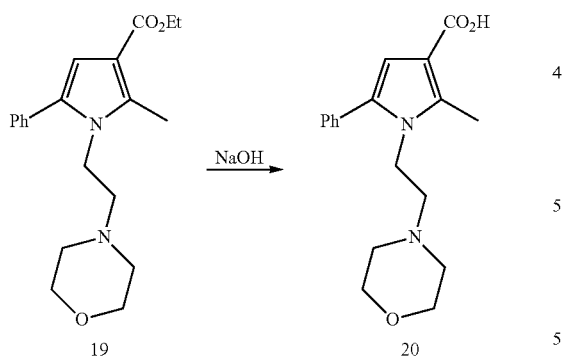

To a solution of the compound 19 (213 mg, 0.622 mmol) in 2 mL THF –2 mL ethanol was added 2 mol/L aqueous sodium hydroxide solution (0.373 ml, 0.746 mmol), and the mixture was stirred for 1 hour at rt, the stirred for 3.5 hours at 80° C. Then to the reaction mixture was added 2 mol/L aqueous sodium hydroxide solution (0.373 ml, 0.746 mmol) at 80° C., and the mixture was stirred for 6.5 hours at the temperature. After leaved at rt overnight, the reaction mixture was stirred for 15 hours at 80° C. After leaved at rt overnight, to the reaction mixture was added 2 mol/L aqueous sodium hydroxide solution (0.373 ml, 0.746 mmol) at 80° C., and the mixture was stirred for 11 hours at the temperature. After leaved at rt overnight, to the reaction mixture was added 2 mol/L aqueous sodium hydroxide solution (0.373 ml, 0.746 mmol) at 80° C., and the mixture was stirred for 14 hours at the temperature. After leaved at rt for 3 days, to the reaction mixture was added diethyl ether, and extracted with water. To the aqueous phase was added 2 mol/L HCl solution and the mixture was made into slightly acidic. The obtained solid wad filtered off, and washed by water to afford compound 20 (143.5 mg, 73% yield).

$^1$H-NMR (DMSO-d$_6$) δ: 2.12-2.24 (4H, m), 2.35 (2H, t, J=6.9 Hz), 2.56 (3H, s), 3.39-3.47 (4H, m), 4.01 (2H, t, J=7.0 Hz), 6.34 (1H, s), 7.32-7.49 (5H, m), 11.70 (1H, s).
Step 3

[Formula 76]

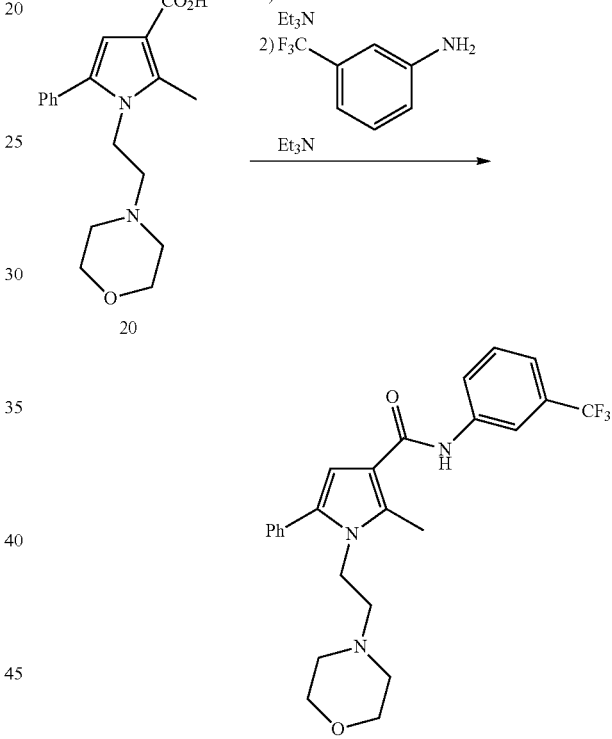

Under $N_2$ atmosphere, to a solution of the compound 20 (100 mg, 0.318 mmol) in 2 mL dimethylacetoamide was added triethylamine (0.0660 mL, 0.477 mmol), methansulfonyl chloride (0.0370 mL, 0.477 mmol) at 0° C., and the mixture was stirred for 15 minutes at the temperature. Then to the reaction mixture was added triethylamine (0.0660 mL, 0.477 mmol), 3-trifluoromethylaniline (0.0590 mL, 0.477 mmol) at 0° C., and the mixture was stirred for 50 minutes at the temperature. To the reaction mixture was added water, and the mixture was extracted with ethyl acetate. The organic phase was washed by water, brine, and dried by anhydrous $MgSO_4$, concentrated, purified by column chromatography to afford compound 21 (I-083, 102.6 mg, 71% yield).

$^1$H-NMR (CDCl$_3$) δ: 2.26 (4H, t, J=4.6 Hz), 2.44 (2H, t, J=7.2 Hz), 2.69 (3H, s), 3.58 (4H, t, J=4.6 Hz), 4.04 (2H, t, J=7.3 Hz), 6.33 (1H, s), 7.28-7.47 (7H, m), 7.57 (1H, s), 7.76 (1H, d, J=8.2 Hz), 7.91 (1H, s).

Example 9

Synthesis of Compound I-085 (Compound 26a) and Compound I-086 (Compound 26b)

Step 1

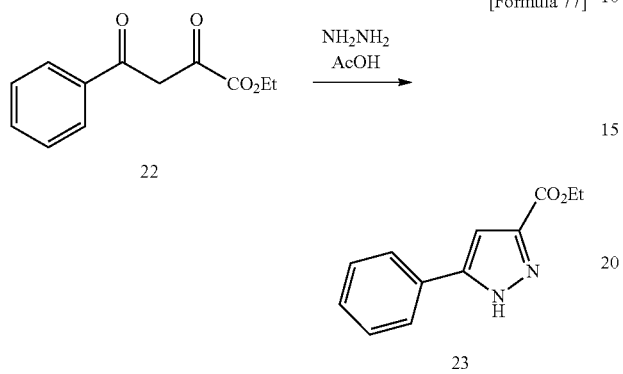

[Formula 77]

To a solution of compound 22 (1.1 g, 5 mmol) and AcOH (0.360 g, 5.00 mmol) in 20 ml EtOH was added 80% hydrazine hydrate (0.316 g, 5.05 mmol). After stirred at rt for 5 h, the mixture was diluted with water; then EtOH was removed under reduced pressure, and aqueous solution was made alkaline by saturated aqueous solution of NaHCO₃ then extracted with ethyl acetate, dried by anhydrous Na₂SO₄, concentrated to afford compound 23 (1.08 g, 99% yield).

LCMS m/z=217 [M+H]⁺

LC/MS information

Column: Xbridge C18 (3.5 μm 4.6×50 mm)

Flow rate: 1.8 mL/min

UV detection wavelength: 254 nm

Mobile phase: [A] is 0.05% TFA-containing aqueous solution, and [B] is 0.05% TFA-containing acetonitrile solution From 0 to 1.5 minutes, the percentage of [B] in the mobile phase was gradually increased from 5% to 100%. Thereafter a solution of 100% of [13] was used as the mobile phase.

retention time 1.21 minutes.

Step 2

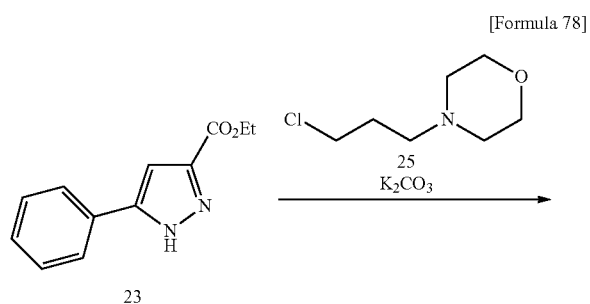

[Formula 78]

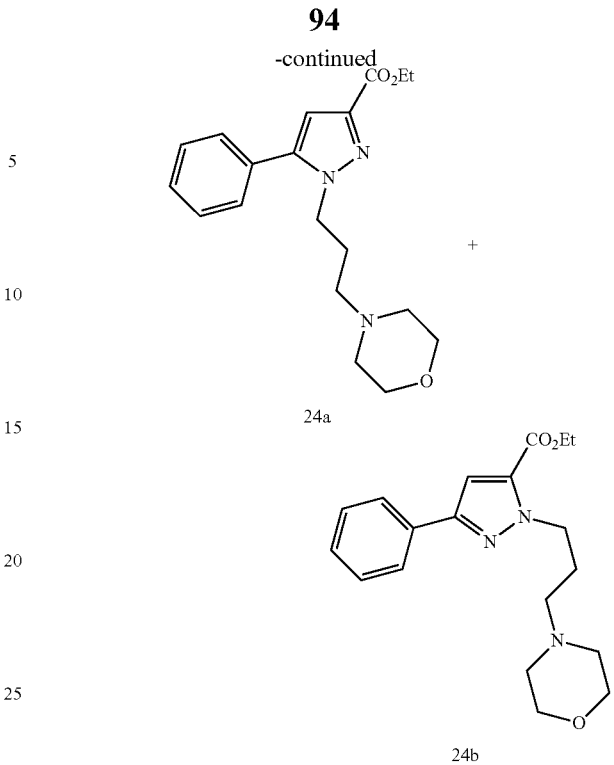

To a solution of compound 23 (1.08 g, 5.00 mmol) and compound 25 (981 mg, 6.00 mmol) in 50 ml acetonitrile was added K₂CO₃ (1.24 g, 9.00 mmol) and heated to reflux for 8 hours. After cooled to rt, filtered off, the filtrate was concentrated and the residue was purified by silica-gel column chromatography to afford compound 24a (950 mg, 55% yield) and compound 24b (150 mg, 8.7% yield).

(compound 24a)

LCMS m/z=344 [M+H]⁺

LC/MS information

Column: Xbridge C18 (3.5 μm 4.6×50 mm)

Flow rate: 1.8 mL/min

UV detection wavelength: 254 nm

Mobile phase: [A] is 0.05% TFA-containing aqueous solution, and [B] is 0.05% TFA-containing acetonitrile solution From 0 to 1.5 minutes, the percentage of [B] in the mobile phase was gradually increased from 5% to 100%. Thereafter a solution of 100% of [B] was used as the mobile phase.

retention time 1.41 minutes.

(compound 24b)

LCMS m/z=344 [M+H]⁺

LC/MS information

Column: Xbridge C18 (3.5 μm 4.6×50 mm)

Flow rate: 1.8 mL/min

UV detection wavelength: 254 nm

Mobile phase: [A] is 0.05% TFA-containing aqueous solution, and [B] is 0.05% TFA-containing acetonitrile solution From 0 to 1.5 minutes, the percentage of [B] in the mobile phase was gradually increased from 5% to 100%. Thereafter a solution of 100% of [B] was used as the mobile phase.

retention time 1.50 minutes.

Step 3

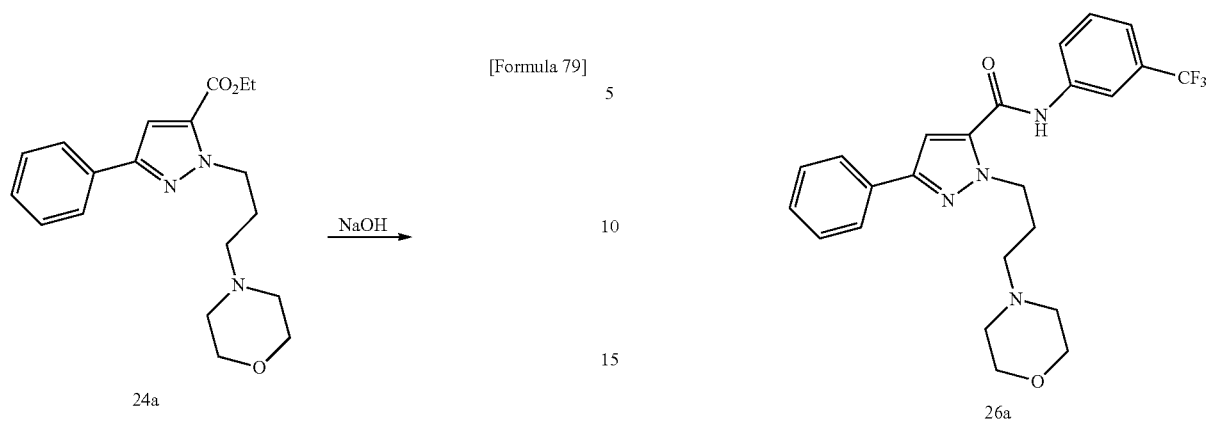

[Formula 79]

To a solution of compound 25a (300 mg, 0.950 mmol), 3-trifluoromethylaniline (227 mg, 2.00 mmol) and HOBt (200 mg, 1.48 mmol) in 5 ml pyridine was added EDC (385 mg, 2 mmol) then the mixture was stirred overnight at rt, then concentrated and the residue was purified by silica-gel column chromatography to afford compound 26a (I-085, 100 mg, 23% yield).

$^1$H-NMR (CDCl$_3$) δ: 2.08 (2H, t, J=6.9 Hz), 2.35-2.40 (6H, m), 3.59 (4H, t, J=4.5 Hz), 4.41 (2H, t, J=6.9 Hz), 6.87 (1H, s), 7.27-7.43 (5H, m), 7.71-7.75 (3H, m), 7.84 (1H, s), 8.10 (1H, s).

Step 5

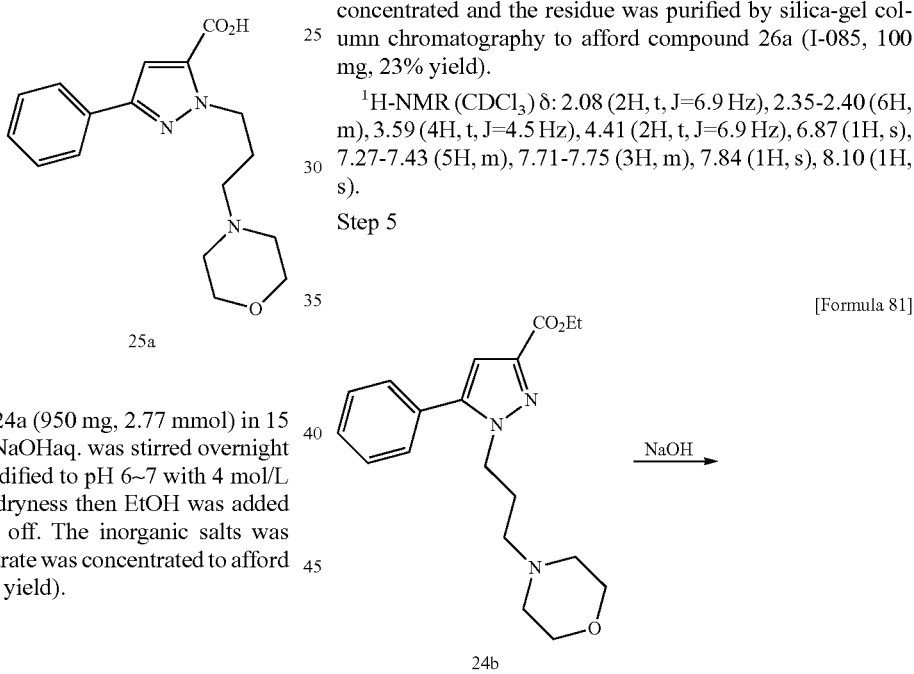

[Formula 81]

The mixture of compound 24a (950 mg, 2.77 mmol) in 15 ml EtOH and 14 ml 1 mol/L NaOHaq. was stirred overnight at rt, then the mixture was acidified to pH 6~7 with 4 mol/L aq. HCl and concentrated to dryness then EtOH was added and the mixture was filtered off. The inorganic salts was washed with EtOH, and the filtrate was concentrated to afford compound 25a (900 mg, 98% yield).

Step 4

[Formula 80]

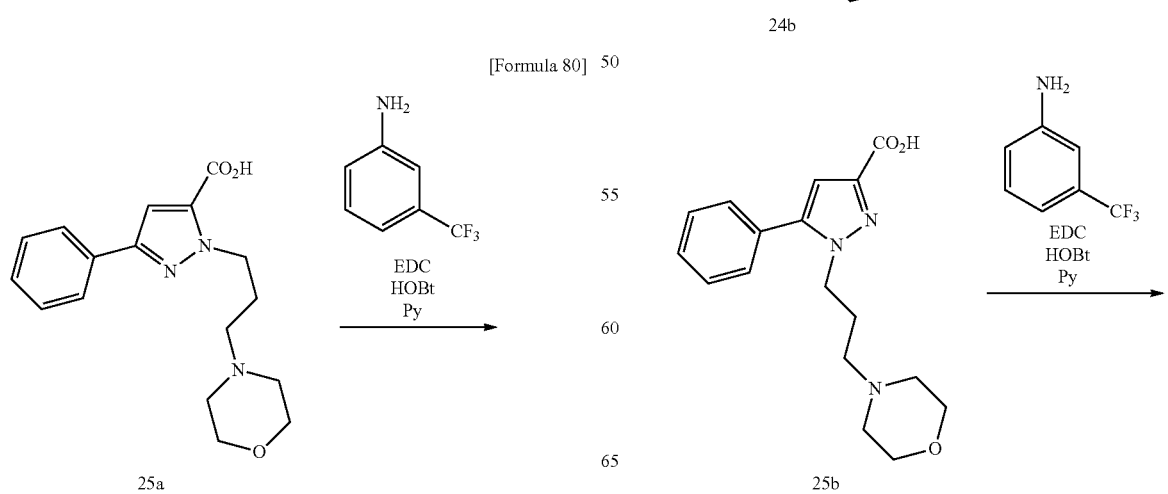

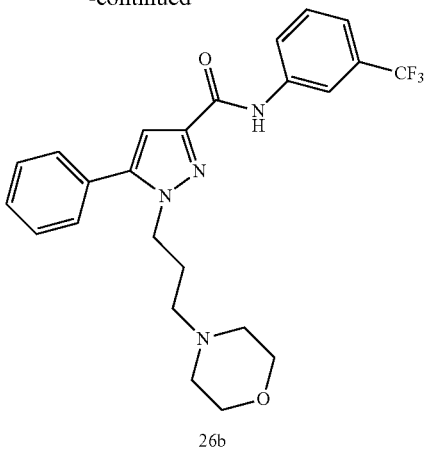

26b

Compound 26b (I-086, 70 mg, 67% yield, two processes) was obtained by using compound 24b as starting material and processing it like the step 3 and step 4.

$^1$H-NMR (CDCl$_3$) δ: 1.98 (2H, t, J=6.9 Hz), 2.18-2.23 (6H, m), 3.52-3.55 (4H, m), 4.19 (2H, t, J=6.9 Hz), 6.83 (s, 1H), 7.29-7.44 (7H, m), 7.88-7.91 (2H, m), 8.80 (1H, s).

Example 10

Synthesis of Compound I-087 (Compound 31)

Step 1

[Formula 82]

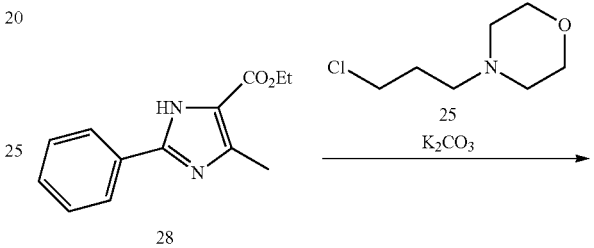

To a solution of compound 1 (5.20 g, 40.0 mmol) in 6 ml AcOH was added a solution of NaNO$_2$ (3.60 g, 52.0 mmol) in 6 ml water at 0° C. After stirred at 0° C. for overnight, saturated aqueous solution of NaHCO$_3$ was added to adjust pH to 7~8, then brine was added, and the mixture was extracted with ethyl acetate, dried by anhydrous Na$_2$SO$_4$, concentrated to afford compound 27 (6.35 g, 99% yield).

Step 2

[Formula 83]

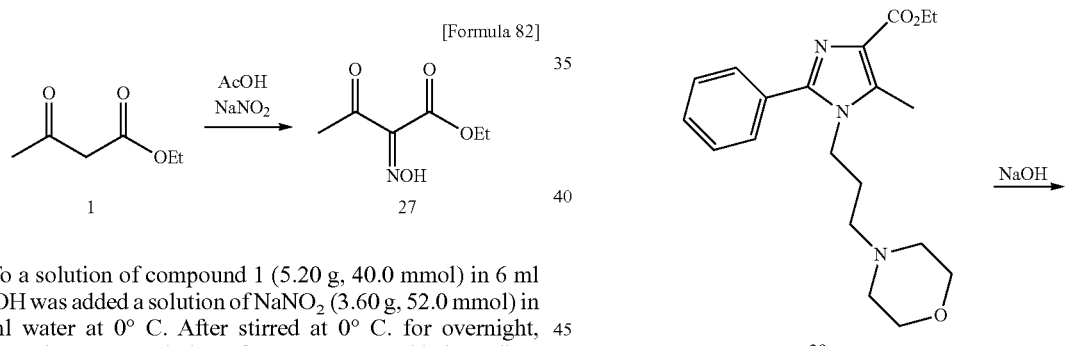

To a solution of compound 27 (5.20 g, 39.0 mmol) in 60 ml acetonitrile was added benzyl amine (3.85 g, 42.8 mmol) and heated to reflux for 5 hours. After cooled to rt, the precipitate was collected and washed with cold acetonitrile to afford compound 28 (3.2 g, 42% yield).

LCMS m/z=231 [M+H]$^+$

LC/MS information

Column: Xbridge C18 (3.5 μm 4.6×50 mm)

Flow rate: 1.8 mL/min

UV detection wavelength: 254 nm

Mobile phase: [A] is 0.05% TFA-containing aqueous solution, and [B] is 0.05% TFA-containing acetonitrile solution From 0 to 1.5 minutes, the percentage of [B] in the mobile phase was gradually increased from 5% to 100%. Thereafter a solution of 100% of [B] was used as the mobile phase.

retention time 1.31 minutes.

Step 3

[Formula 84]

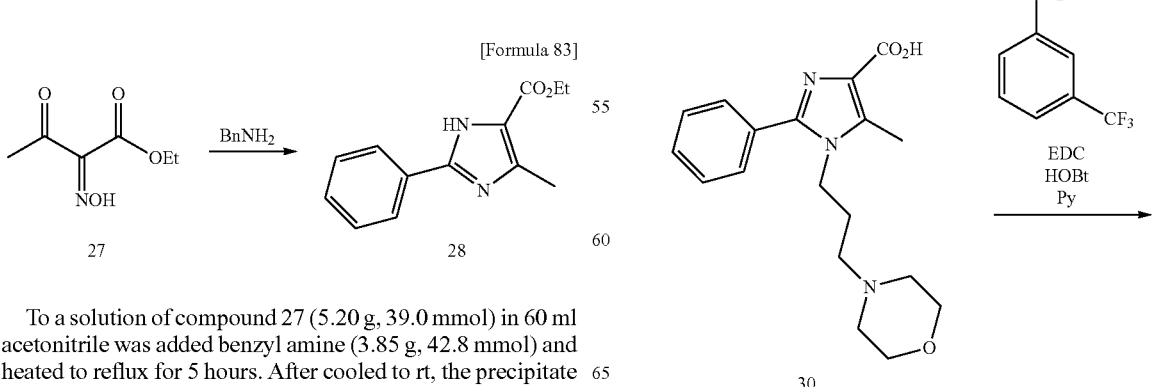

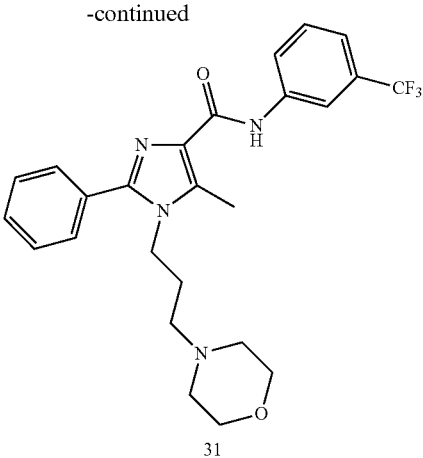

Compound 31 (I-087, 80 mg, 8.1% yield, three processes) was obtained by using compound 28 as starting material and processing it like the steps 2 to 4 in Example 9.

$^1$H-NMR (CDCl$_3$) δ: 1.73 (2H, t, J=7.2 Hz), 2.19-2.23 (6H, m), 2.73 (3H, s), 3.56 (4H, m), 4.07 (2H, t, J=7.2 Hz), 7.31-7.60 (7H, m), 7.83 (1H, d; J=9.1 Hz), 8.09 (1H, s), 9.23 (1H, s).

Example 11

Synthesis of Compound I-088 (Compound 37)

Step 1

[Formula 85]

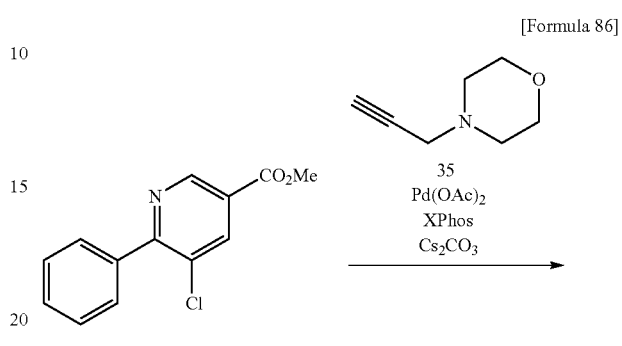

The mixture of compound 32 (618 mg, 3.00 mmol), phenyl boronic acid (366 mg, 3.00 mmol), potassium carbonate (621 mg, 4.5 mmol) and Pd(PPh$_3$)$_4$ (111 mg, 0.1 mmol) in 10 ml THF was heated to reflux under N$_2$ overnight. Then filtered off, and, the filtrate was concentrated and the residue was purified by silica-gel column chromatography to afford compound 33 (500 mg, 66% yield).

LCMS m/z=248 [M+H]$^+$
LC/MS information
Column: Xbridge C18 (3.5 μm 4.6×50 mm)
Flow rate: 1.8 mL/min
UV detection wavelength: 254 nm
Mobile phase: [A] is 0.05% TFA-containing aqueous solution, and [B] is 0.05% TFA-containing acetonitrile solution From 0 to 1.5 minutes, the percentage of [B] in the mobile phase was gradually increased from 5% to 100%. Thereafter a solution of 100% of [B] was used as the mobile phase.

retention time 2.05 minutes.

Step 2

[Formula 86]

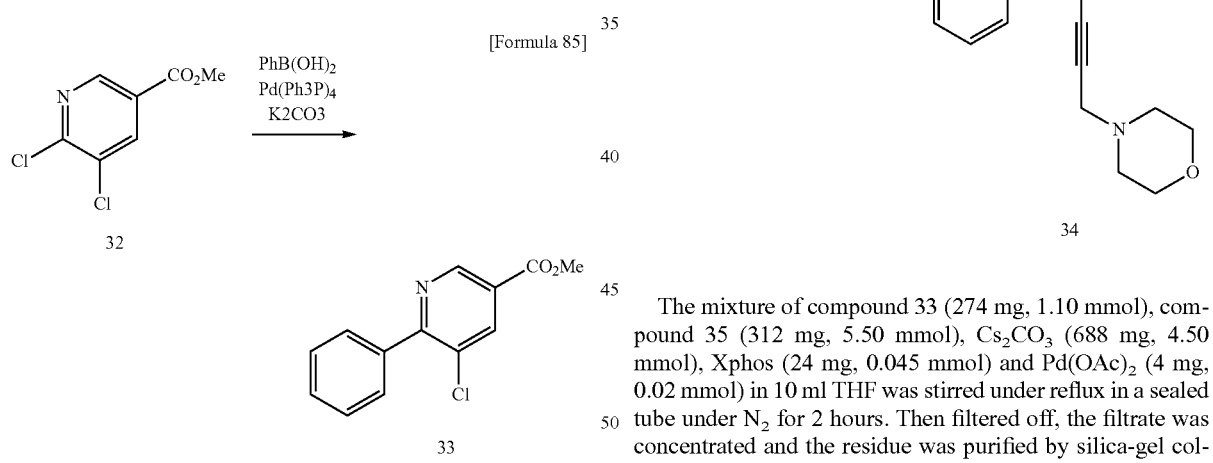

The mixture of compound 33 (274 mg, 1.10 mmol), compound 35 (312 mg, 5.50 mmol), Cs$_2$CO$_3$ (688 mg, 4.50 mmol), Xphos (24 mg, 0.045 mmol) and Pd(OAc)$_2$ (4 mg, 0.02 mmol) in 10 ml THF was stirred under reflux in a sealed tube under N$_2$ for 2 hours. Then filtered off, the filtrate was concentrated and the residue was purified by silica-gel column chromatography to afford compound 34 (350 mg, 90% yield).

LCMS m/z=337 [M+H]$^+$
LC/MS information
Column: Xbridge C18 (3.5 μm 4.6×50 mm)
Flow rate: 1.8 mL/min
UV detection wavelength: 254 nm
Mobile phase: [A] is 0.05% TFA-containing aqueous solution, and [B] is 0.05% TFA-containing acetonitrile solution From 0 to 1.5 minutes, the percentage of [B] in the mobile phase was gradually increased from 5% to 100%. Thereafter a solution of 100% of [B] was used as the mobile phase.

retention time 1.41 minutes.

Step 3

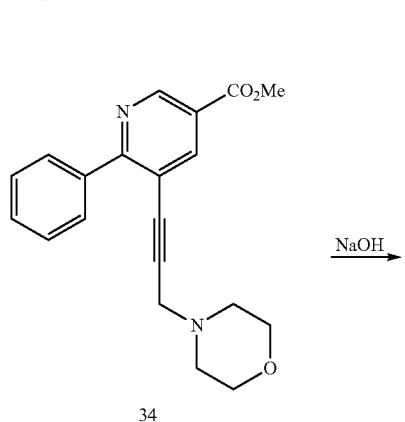

34

[Formula 87]

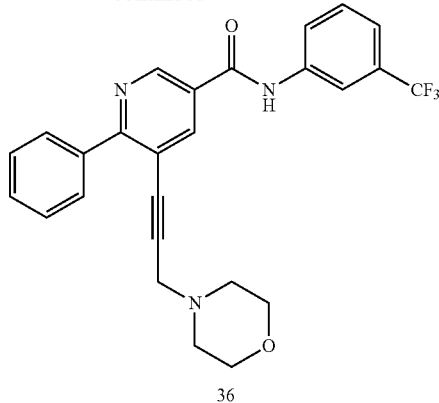

36

The mixture of compound 34 (350 mg, 2.52 mmol) in 5 ml 1 mol/L NaOHaq. and 5 ml methanol was heated to 60° C. for 5 hours, then methanol was removed, the residue was diluted with ether and extracted with water. The aqueous phase was acidified to pH 6~7 with 4 mol/L aqueous solution of HCl and concentrated to dryness. The solid was stirred with methanol/dichloromethane (=1/5) for 30 min then filtered off and rinsed with methanol/dichloromethane. The filtrate was concentrated to afford compound 35 (340 mg, 98% yield).

Step 4

[Formula 88]

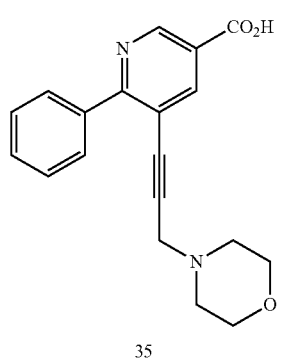

35

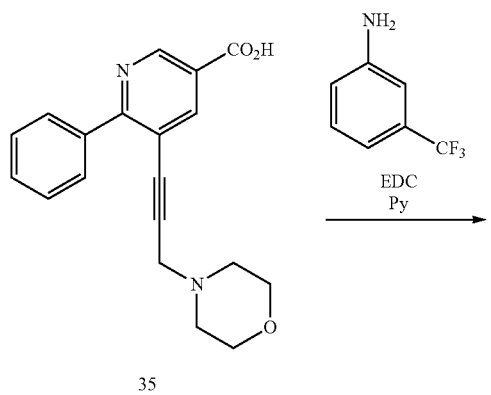

To a solution of compound 35 (335 mg, 1.04 mmol) and 3-trifluoromethylaniline (252 mg, 1.50 mmol) in 10 ml pyridine was added EDC (385 mg, 2.00 mmol). The mixture was heated to 50° C. for overnight then concentrated and the residue was diluted with ethyl acetate, washed with saturated aqueous solution of NaHCO$_3$, dried by anhydrous Na$_2$SO$_4$, concentrated and the residue was purified by silica-gel column chromatography to afford compound 36 (400 mg, 80% yield).

$^1$H-NMR (CDCl$_3$) δ: 2.49 (4H, t, J=4.5 Hz), 3.45 (2H, d, J=1.5 Hz), 3.70 (4H, t, J=4.5 Hz), 7.42-7.50 (5H, m), 7.85-7.94 (4H, m), 8.30-8.32 (2H, m), 9.05 (1H, d, J=3.6 Hz).

Step 5

[Formula 89]

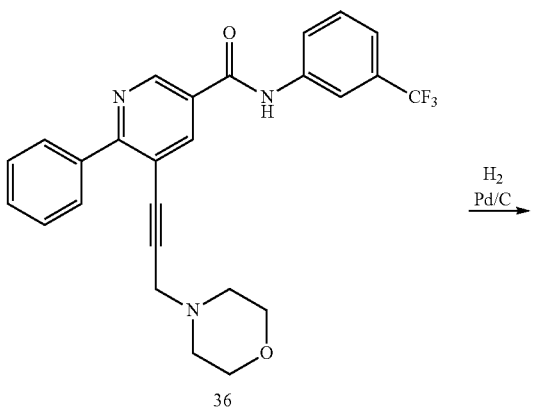

36

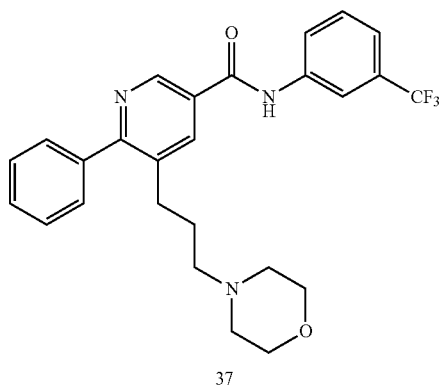

37

To a solution of compound 36 (160 mg, 0.334 mmol) in 10 ml methanol was added 70 mg 10% Pd/C (about 30% moisture); then the suspension was stirred for overnight at rt under H₂ atmosphere. Pd/C was filtered off, then the residue was purified by prep-HPLC to afford compound 37 (I-088, 110 mg, 68% yield).

¹H-NMR (CDCl₃) δ: 1.65-1.73 (2H, m), 2.20-2.28 (6H, m), 2.77 (2H, t, J=7.8 Hz), 3.61 (4H, t, J=4.5 Hz), 7.41-7.51 (7H, m), 7.86 (1H, d, J=8.1 Hz), 7.95 (1H, s), 8.18 (1H, d, J=2.1 Hz), 8.53 (1H, s), 8.96 (1H, d, J=2.1 Hz).

Example 12

Synthesis of Compound I-089 (Compound 41)

Step 1

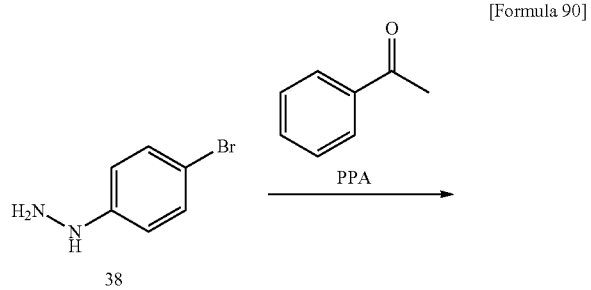

[Formula 90]

To a solution of acetophenone (8.80 g, 73.83 mmol) in PPA (200 mL) was added portion wisely compound 38 (15.0 g, 67.1 mmol) at 110° C. The reaction mixture was stirred at the temperature for 5 hours, cooled to room temperature, added into ice water, and extracted with ethyl acetate. The organic phase was washed by NaHCO₃ (aq, sat), brine, dried by anhydrous Na₂SO₄, concentrated, purified by column chromatography to afford compound 39 (5.5 g, 42% yield).

¹H-NMR (CDCl₃) δ: 6.76 (1H, s), 7.26-7.27 (2H, m), 7.35-7.37 (1H, m), 7.43-7.46 (2H, m), 7.64-7.67 (2H, m), 7.75 (1H, s), 8.36 (1H, s).

Step 2

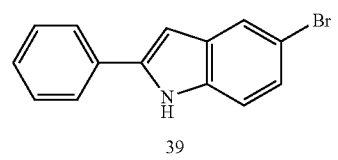

[Formula 91]

To a solution of compound 39 (0.500 g, 1.84 mmol) in DMF (20 ml) was added NaH (0.11 g, 2.76 mmol) at 0° C., and the mixture was stirred for 1 hours. Compound 25 (0.36 g, 2.2 mmol) was added to the mixture at 0° C., and the mixture was stirred for an additional 24 hours at rt. The reaction mixture was quenched by water, extracted with ethyl acetate. The organic phase was washed by brine, dried by anhydrous Na₂SO₄, concentrated, purified by column chromatography to afford compound 40 (0.450 g, 62% yield)

LCMS m/z=399 [M+H]⁺

LC/MS information

Column: Xbridge C18 (3.5 μm 4.6×50 mm)

Flow rate: 2 mL/min

UV detection wavelength: 254 nm

Mobile phase: [A] is 0.05% TFA-containing aqueous solution, and [B] is 0.05% TFA-containing acetonitrile solution From 0 to 1.5 minutes, the percentage of [B] in the mobile phase was gradually increased from 5% to 100%. Thereafter a solution of 100% of [B] was used as the mobile phase.

retention time=1.59 minutes.

Step 3

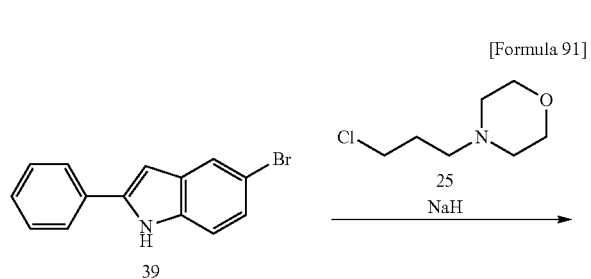

[Formula 92]

-continued

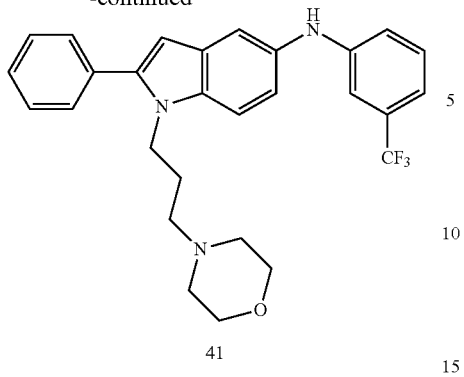

41

-continued

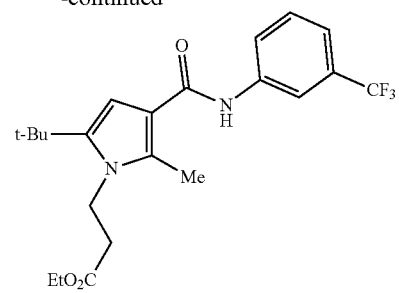

I-090

To a solution of compound 40 (0.470 g, 1.18 mmol) in toluene (10 ml) was added 3-trifluoromethylaniline (0.230 g, 1.41 mmol), Cs$_2$CO$_3$ (0.770 g, 2.35 mmol), Xphos (56.0 mg, 0.120 mmol), Pd$_2$(dba)$_3$ (11.0 mg, 0.0600 mmol). The reaction mixture was stirred at 90° C. overnight, concentrated, purified by column chromatography and HPLC to afford compound 41 (I-089, 0.118 g, 20% yield).

$^1$H-NMR (CDCl$_3$) δ: 1.77-1.82 (2H, m), 2.16-2.25 (6H, m), 3.60 (4H, t, J=4.5 Hz), 4.27 (2H, t, J=7.5 Hz), 5.79 (1H, s), 6.48 (1H, s), 7.00-7.08 (3H, m), 7.12 (1H, s), 7.25-7.30 (1H, m), 7.42-7.53 (7H, m).

Example 13

Synthesis of Compound I-090

[Formula 93]

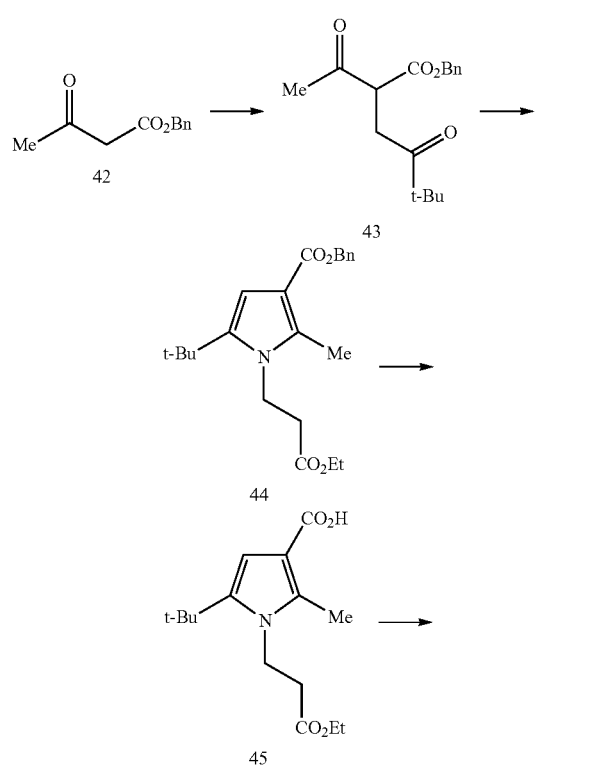

Step 1

To a suspension of NaH (16.2 g, 406 mmol) in THF (500 mL) was added a solution of compound 42 (60.0 g, 312 mmol) in THF (300 mL) at 0° C. dropwise. The reaction mixture was stirred at 0° C. for 1 hour, then a solution of 1-bromo-3,3-dimethylbutan-2-one (67.1 g, 375 mmol) in THF (200 mL) was added dropwise to the reaction mixture. The mixture was stirred at rt overnight, quenched by water and diluted with ethyl acetate. The organic phase was washed by water, brine, dried by anhydrous Na$_2$SO$_4$ and concentrated, and the residue was purified by silica gel column chromatography to afford compound 43 (100.0 g, crude).

LCMS m/z=291.0 [M+H]$^+$, RT: 1.96 minutes (Method 11).

Step 2

To a solution of compound 43 (35.0 g, 121 mmol) in EtOH (300 mL) were added ethyl 3-aminopropanoate (55.6 g, 362 mmol) and CH$_3$COONa (22.3 g, 271.22 mmol). The reaction mixture was stirred at 80° C. for 4 hours and concentrated to remove the solvent, and the residue was dissolved in dichloromethane (300 mL). The organic phase was washed by water, brine, dried by anhydrous Na$_2$SO$_4$ and concentrated, and the residue was purified by silica gel column chromatography to afford compound 44 (23.0 g, 51% yield).

LCMS m/z=372.0 [M+H]$^+$, RT: 2.20 minutes (Method 11).

Step 3

To a solution of compound 44 (21.0 g, 56.5 mmol) in MeOH (100 mL) and ethyl acetate (100 mL) was added Pd/C (5.0 g). The reaction mixture was stirred under H$_2$ at rt overnight, filtered through celite and concentrated to afford compound 45 (17.0 g, 98% yield).

LCMS m/z=282.0 [M+H]$^+$, RT: 1.86 minutes (Method 11).

Step 4

To a solution of compound 45 (12.0 g, 42.7 mmol) in Py (100 mL) were added 3-(trifluoromethyl)aniline (8.9 g, 55.5 mmol) and EDC (20.4 g, 107 mmol). The reaction mixture was stirred at rt overnight and concentrated, and the residue was purified by silica gel column chromatography to afford compound I-090 (13.5 g, 75% yield).

$^1$H-NMR (CDCl$_3$) δ: 1.32-1.44 (12H, m), 2.61-2.72 (5H, m), 4.22-4.36 (4H, m), 6.12 (1H, d, J=4.8 Hz), 7.30-7.56 (3H, m), 7.83-7.90 (2H, m).

Example 14

Synthesis of Compound I-091

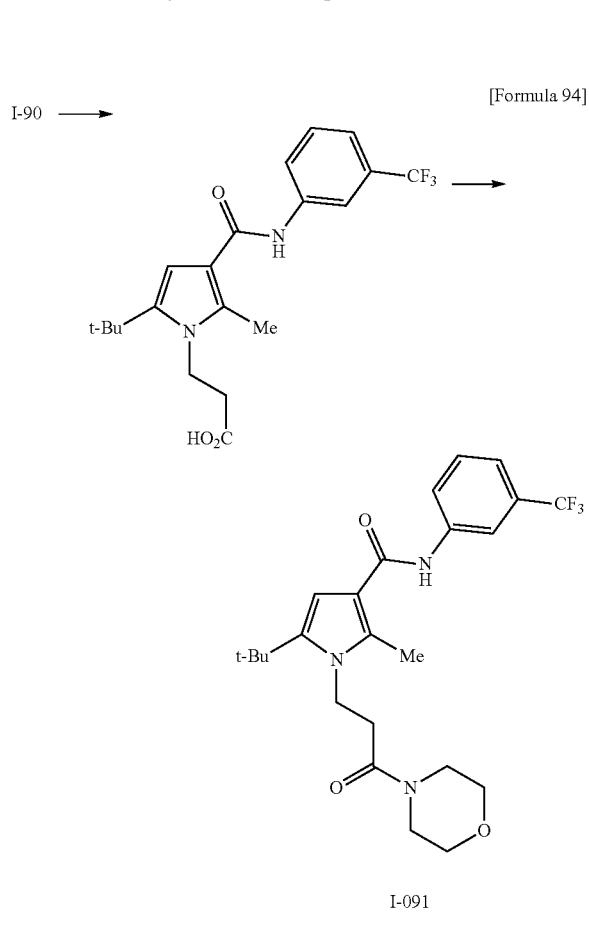

Step 1

To a solution of compound I-090 (0.5 g, 1.18 mmol) in THF (5 mL) and water (5 ml) was added lithium hydroxide (56 mg, 2.36 mmol). The reaction mixture was stirred at rt overnight and concentrated. A 1 mol/L HCl aqueous solution was added until pH=3-4 to the mixture, and then the mixture was filtered to afford compound 46 (0.35 g, 76% yield).

$^1$H-NMR (CDCl$_3$) δ: 1.33 (9H, s), 2.52 (3H, s), 2.70 (2H, t, J=8.4 Hz), 4.27 (2H, t, J=8.1 Hz), 6.03 (1H, s), 7.25 (1H, d, J=7.5 Hz), 7.36 (1H, t, J=7.8 Hz), 7.50 (1H, s), 7.72 (1H, d, J=8.4 Hz), 7.79 (1H, s).

Step 2

To a solution of compound 46 (0.15 g, 0.38 mmol) in Py (3 mL) were added morpholine (43 mg, 0.49 mmol) and EDC (0.18 mg, 0.95 mmol). The reaction mixture was stirred at rt overnight and concentrated, and the residue was purified by silica gel column chromatography to afford compound I-091 (35 mg, 9% yield).

$^1$H-NMR (CDCl$_3$) δ: 1.39 (9H, s), 2.58 (3H, s), 2.65 (2H, t, J=8.1 Hz), 3.39 (2H, t, J=4.5 Hz), 3.64-3.69 (6H, m), 4.38-4.43 (2H, m), 6.10 (1H, s), 7.32 (1H, d, J=8.1 Hz), 7.43 (1H, t, J=7.8 Hz), 7.55 (1H, s), 7.80 (1H, d, J=8.1 Hz), 7.88 (1H, s).

Example 15

Synthesis of Compound I-096

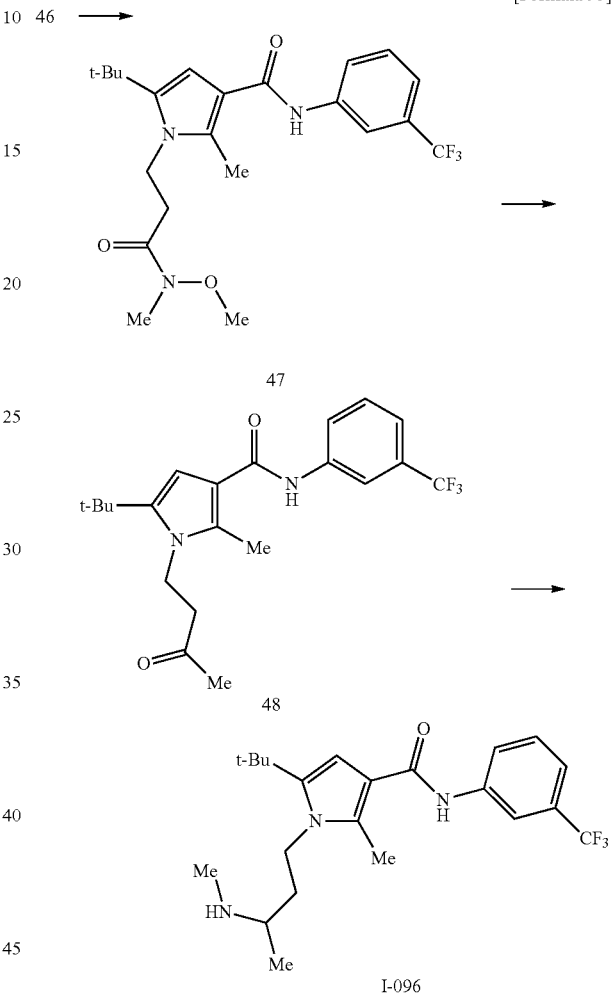

Step 1

To a solution of compound 46 (5.0 g, 12.6 mmol) in Py (60 mL) were added N, O-dimethylhydroxylamine hydrochloride (1.85 g, 18.92 mmol) and EDC (4.84 g, 25.23 mmol). The reaction mixture was stirred at rt overnight and concentrated, and the residue was dissolved in dichloromethane. The organic phase was washed by water, 1 mol/L HCl aqueous solution, brine, dried by anhydrous Na$_2$SO$_4$ and concentrated to afford compound 47 (5.2 g, 94% yield).

LCMS m/z=439.9 [M+H]$^+$, RT: 2.04 minutes (Method 11).

Step 2

To a solution of compound 47 (5.2 g, 11.8 mmol) in toluene (60 mL) was added methylmagnesiumbromide (3 mol/L in diethylether, 47.3 mmol, 16 mL) at 0° C. The reaction mixture was stirred at rt for 3 hours, and then the mixture was quenched by saturated aqueous solution of NH$_4$Cl and extracted with ethyl acetate. The organic phase was washed by water, brine, dried by anhydrous Na$_2$SO$_4$ and concentrated to afford compound 48 (1.8 g, crude).

LCMS m/z=394.9 [M+H]$^+$, RT: 2.07 minutes (Method 11).

Step 3

To a solution of compound 48 (0.25 g, 0.63 mmol) in dichloroethane (4 mL) were added methylamine (solution in water, 40%, 0.25 g, 3.17 mmol) and AcOH (0.4 mL). The reaction mixture was stirred at rt for 3 hours. To the reaction mixture was added Sodium cyanoborohydride (0.12 g, 1.90 mmol), and the mixture was stirred at rt overnight. The mixture was quenched by saturated aqueous solution of $NaHCO_3$ and extracted with dichloromethane. The organic phase was washed by brine, dried by anhydrous $Na_2SO_4$ and concentrated, and the residue was purified by p-HPLC to afford compound I-096 (41 mg, 16% yield).

$^1$H-NMR (CDCl$_3$) δ: 1.10 (3H, d, J=8.0 Hz), 1.33 (9H, s), 1.64-1.77 (2H, m), 2.38 (3H, s), 2.52 (3H, s), 2.62-2.68 (1H, m), 3.96-4.04 (2H, m), 6.01 (1H, s), 7.24 (1H, d, J=7.8 Hz), 7.35 (1H, t, J=7.8 Hz), 7.46 (1H, s), 7.72 (1H, d, J=8.1 Hz), 7.81 (1H, s).

Example 16

Synthesis of Compound I-095

[Formula 96]

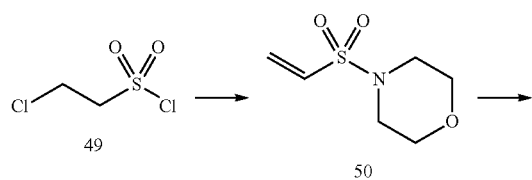

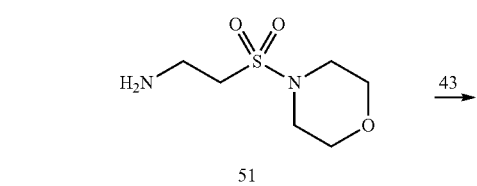

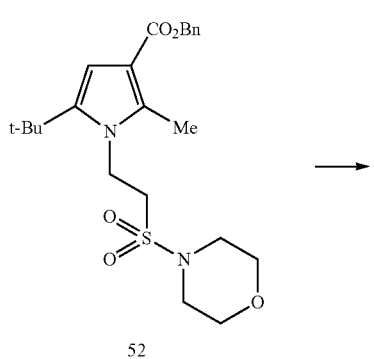

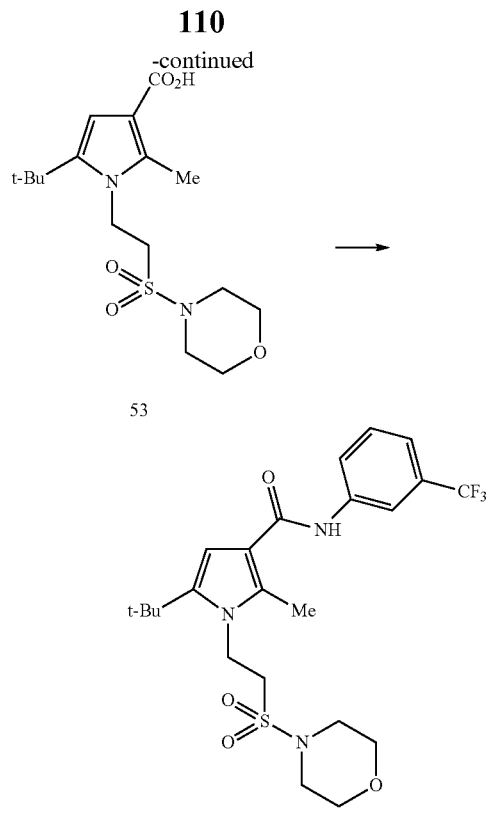

Step 1

To a solution of morpholine (3.53 g, 40.5 mmol) and Et$_3$N (4.1 g, 40.5 mmol) in dichloromethane (80 mL) was added compound 49 (6.0 g, 36.8 mmol) dropwise at 0° C. The reaction mixture was stirred, at rt overnight, the mixture was washed by water, brine, dried by anhydrous Na$_2$SO$_4$, and concentrated to afford compound 50 (5.0 g, crude).

LCMS m/z=178.1 [M+H]$^+$, RT: 1.21 minutes (Method 11).

Step 2

To a solution of compound 50 (5.0 g, 28.2 mmol) in MeOH (20 mL) was added NH$_4$OH (50 mL). The reaction mixture was stirred at rt overnight and concentrated to remove MeOH, and the residue was extracted with dichloromethane (100 mL). The organic phase was washed by water, brine, dried by anhydrous Na$_2$SO$_4$, and concentrated to afford compound 51 (2.4 g, crude).

LCMS m/z=195.1 [M+H]$^+$, RT: 0.50 minutes (Method 11).

Step 3

To a solution of compound 43 (1.5 g, 5.17 mmol) in EtOH (15 mL) were added compound 51 (1.2 g, 6.20 mmol) and AcOH (1.5 mL). The reaction mixture was stirred at 80° C. overnight, filtered and concentrated to afford compound 52 (0.8 g, yield=34%).

LCMS m/z=448.9 [M+H]$^+$, RT: 2.08 minutes (Method 11).

Step 4 to 5

Compound I-095 (36 mg, 8% yield in 2 steps) was obtained by using compound 28 as starting material and processing it like the step 3 and step 4 in Example 13.

$^1$H-NMR (CDCl$_3$) δ: 1.42 (9H, s), 2.61 (3H, s), 3.14-3.20 (2H, m), 3.29 (4H, t, J=4.5 Hz), 3.79 (4H, t, J=4.5 Hz), 4.49-4.55 (2H, m), 6.10 (1H, s), 7.33 (1H, d, J=7.8 Hz), 7.44 (1H, t, J=8.1 Hz), 7.50 (1H, s), 7.80 (1H, d, J=8.4 Hz), 7.87 (1H, s).

Example 17

Synthesis of Compound I-099

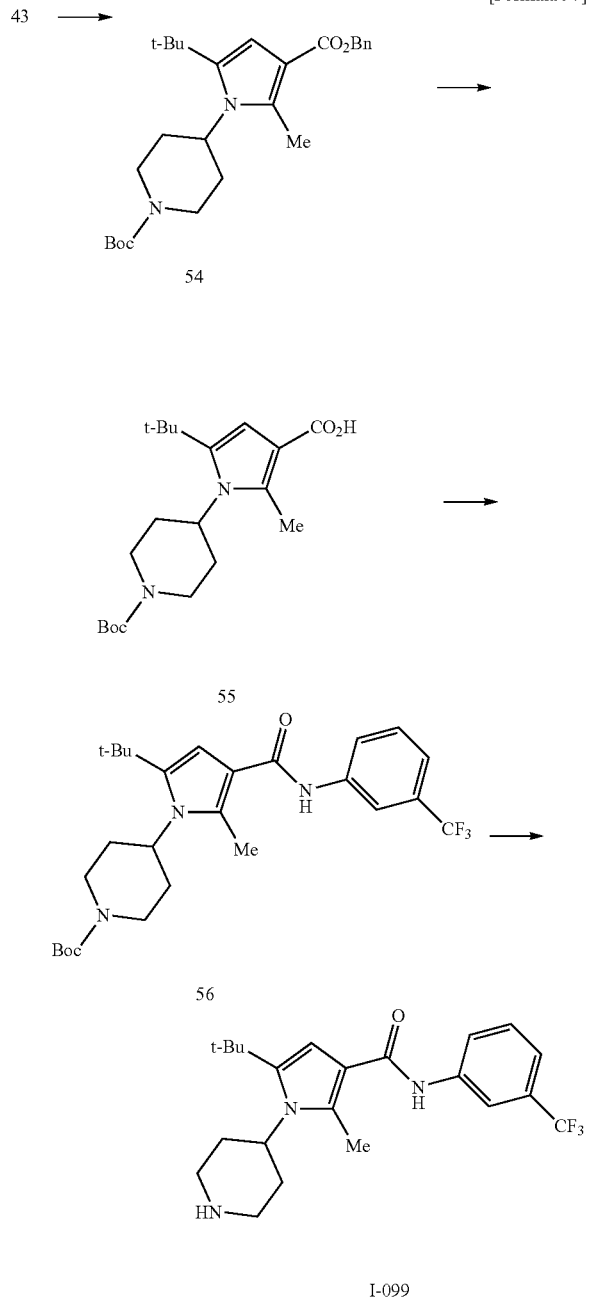

[Formula 97]

Step 1

To a solution of compound 43 (15.0 g, 51.7 mmol) in toluene (150 mL) were added tert-butyl 4-aminopiperidine-1-carboxylate (15.5 g, 77.5 mmol) and AcOH (15 mL). The reaction mixture was stirred at 100° C. overnight and then concentrated, and the residue was dissolved in dichloromethane. The organic phase was washed by water, saturated aqueous solution of NaHCO$_3$, brine, dried by anhydrous Na$_2$SO$_4$ and concentrated, and the residue was purified by silica gel column chromatography to afford compound 54 (7.0 g, 29% yield).

LCMS m/z=454.9[M+H]$^+$, RT: 2.32 minutes (Method 8).

Step 2 to 3

Compound 56 (3.32 g, 77% yield in 2 steps) was obtained by using compound 54 as starting material and processing it like the step 3 and step 4 in Example 13. LCMS m/z=507.9 [M+H]$^+$, RT: 2.14 minutes (Method 8).

Step 4

To a solution of compound 56 (6.0 g, 11.8 mmol) in dichloromethane (50 mL) was added TFA (10 mL). The reaction mixture was stirred at rt for 2 hours and concentrated, and the residue was dissolved in dichloromethane. The organic phase was washed by water, saturated aqueous solution of NaHCO$_3$, brine, dried by anhydrous Na$_2$SO$_4$, and concentrated to afford compound I-099 (4.0 g, 83% yield).

$^1$H-NMR (300 Mz) (CDCl$_3$): 1.33 (9H, s), 1.81 (2H, d, J=12.0 Hz), 2.26-2.32 (2H, m), 2.60-2.70 (5H, m), 3.23 (2H, d, J=12.0 Hz), 4.39-4.41 (1H, m), 6.00 (1H, s), 7.24 (1H, d, J=7.5 Hz), 7.35 (1H, t, J=7.8 Hz), 7.44 (1H, s), 7.72 (1H, d, J=8.1 Hz), 7.79 (1H, s).

Example 18

Synthesis of Compound I-107

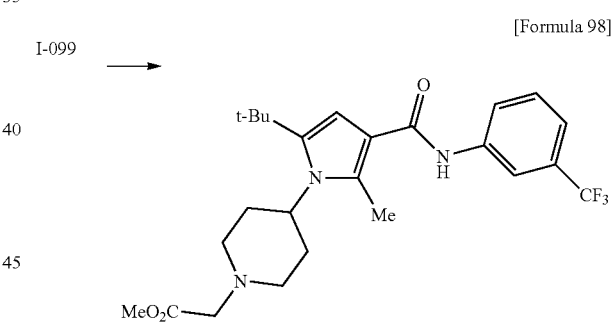

[Formula 98]

To a suspension of compound I-099 (1.5 g, 3.68 mmol) in acetonitrile (20 mL) were added methyl bromoacetate (0.85 g, 5.52 mmol) and K$_2$CO$_3$ (1.02 g, 7.36 mmol). The reaction mixture was stirred at rt overnight and concentrated to remove acetonitrile, and the residue was dissolved in dichloromethane. The organic phase was washed by water, brine, dried by anhydrous Na$_2$SO$_4$ and concentrated, and the residue was purified by silica gel column chromatography to afford compound I-107 (0.8 g, 45% yield).

$^1$H-NMR (300 Mz) (CDCl$_3$): 1.39 (9H, s), 1.84 (2H, d, J=12.6 Hz), 2.40-2.57 (4H, m), 2.76 (3H, s), 3.12 (2H, d, J=10.2 Hz), 3.33 (2H, s), 3.74 (3H, s), 4.35-4.43 (1H, m), 6.07 (1H, s), 7.30 (1H, d, J=7.5 Hz), 7.42 (1H, t, J=7.8 Hz), 7.51 (1H, s), 7.79 (1H, d, J=8.4 Hz), 7.85 (1H, s).

Example 19

Synthesis of Compound I-110

I-107 ⟶

[Formula 99]

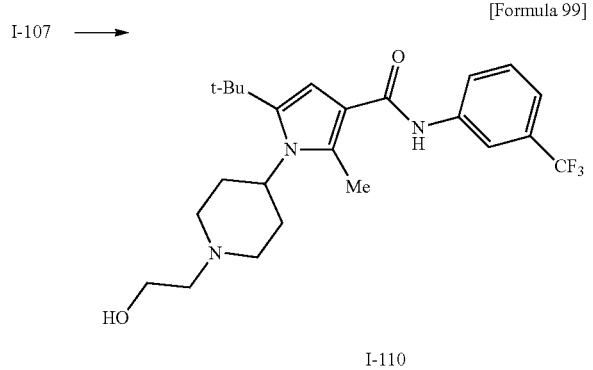

I-110

To a suspension of lithium aluminum hydride (33 mg, 0.84 mmol) in THF (4 mL) was added a solution of compound I-107 (0.2 g, 0.42 mmol) in THF (2 mL) at 0° C. The reaction mixture was stirred at 0° C. for 1 hour, quenched by water and extracted with dichloromethane. The organic phase was washed by brine, dried by anhydrous $Na_2SO_4$ and concentrated, and the residue was triturated with dichloromethane and petroleum ether to afford compound I-110 (50 mg, 27% yield).

$^1$H-NMR (300 Mz) ($CDCl_3$): 1.37 (9H, s), 1.85-1.89 (2H; in), 2.20 (2H, t, J=11.1 Hz), 2.41-2.54 (2H, m), 2.60 (2H, t, J=5.1 Hz), 2.75 (3H, s), 3.12 (2H, d, J=11.1 Hz), 3.65 (2H, t, J=5.1 Hz), 4.37-4.46 (1H, m), 6.07 (1H, s), 7.31 (1H, d, J=7.5 Hz), 7.42 (1H, t, J=7.8 Hz), 7.51 (1H, s), 7.80 (1H, d, J=7.8 Hz), 7.86 (1H, s).

Example 20

Synthesis of Compound I-117

[Formula 100]

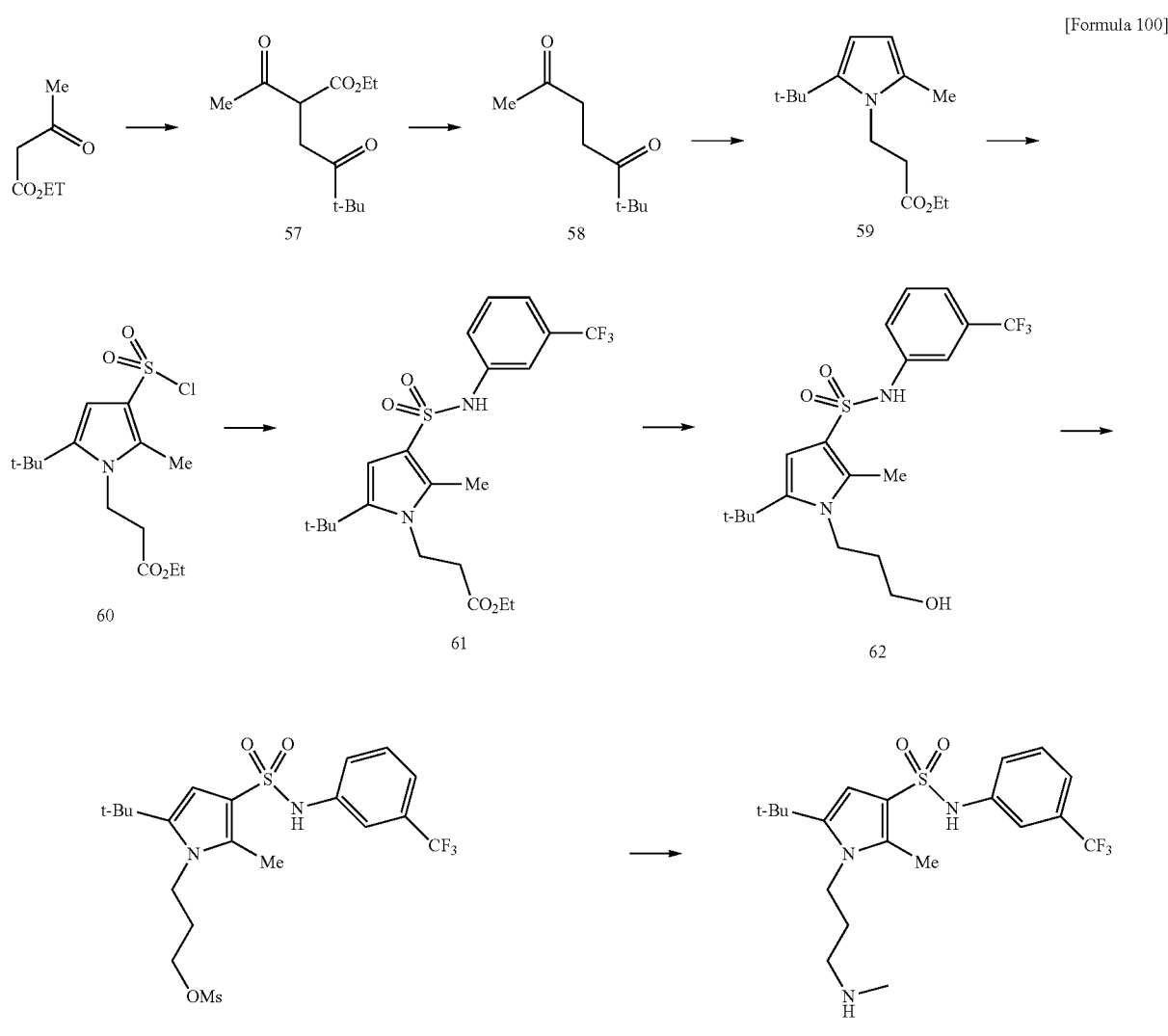

Step 1

To a solution of ethyl 3-oxobutanoate (40 g, 308 mmol) in THF (1000 mL) was added NaH (13.5 g, 339 mmol) at 0° C., and then the reaction mixture was stirred at 0° C. for 30 minutes. 1-bromo-3,3-dimethylbutan-2-one (60.5 g, 338 mmol) was added to the reaction mixture at 0° C. and the mixture was stirred at rt overnight. The reaction mixture was quenched by saturated aqueous solution of $NH_4Cl$ and extracted with ethyl acetate. The organic phase was washed by brine and dried by $Na_2SO_4$. The solvent was evaporated in vacuum to afford the crude product compound 57 (70 g, crude) which was used for the next step directly without further purification.

Step 2

To a solution of compound 57 (70 g, 307 mmol) in DMSO (400 mL) was added a solution of LiCl (14.2 g, 338 mmol) in water (24.9 g, 1.38 mol) at 0° C. The mixture was stirred at 160° C. for 50 hours. The reaction mixture was quenched by water and extracted with ethyl acetate. The organic phase was washed by brine and dried by $Na_2SO_4$. The solvent was evaporated in vacuum to afford the crude product compound 58 (43 g, 90% yield in 2 steps) which was used for the next step directly without further purification.

$^1$H-NMR ($CDCl_3$) δ: 1.15 (9H, s), 2.18 (3H, s), 2.67 (2H, t, J=6.3 Hz), 2.77 (2H, t, J=6.3 Hz).

Step 3

To a solution of compound 58 (20 g, 127 mmol) and ethyl 3-aminopropanoate hydrochloride (21.5 g, 140 mmol) in EtOH (400 mL) was added $CH_3COONa.3H_2O$ (19.6 g, 140 mmol) at 0° C. The mixture was stirred at reflux overnight. The mixture was filtered, the filtrate was concentrated and the residue was purified by silica gel column chromatography to afford compound 59 (9.4 g, 31% yield).

Step 4

To a solution of compound 59 (8.0 g, 33.8 mmol) in acetonitrile (40 mL) was added chlorosulfonic acid (19.6 g, 169 mmol) at 0° C. The mixture was stirred at rt overnight. The mixture was quenched by ice-water and extracted with ethyl acetate. The organic phase was washed by brine and dried by $Na_2SO_4$. The solvent was evaporated in vacuum to afford the crude product compound 60 (8.8 g, crude) which was used for the next step directly without further purification.

Step 5

To a mixture of 3-(trifluoromethyl)aniline (8.48 g, 52.6 mmol) and $Et_3N$ (15.9 g, 158 mmol) in dichloromethane (160 mL) was added compound 60 (17.6 g, 52.6 mmol) at 0° C. The mixture was stirred at rt overnight. The mixture was quenched by water and extracted with dichloromethane. The organic phase was washed by brine and dried by $Na_2SO_4$. The solvent was evaporated in vacuum and the residue was purified by silica gel column chromatography to afford compound 61 (3.36 g, 14% yield).

$^1$H-NMR ($CDCl_3$) δ: 1.18-1.27 (12H, m), 2.17 (3H, s), 2.45 (2H, t, J=8.4 Hz), 4.06-4.16 (4H, m), 7.00 (1H, s), 7.22-7.30 (4H, m).

Step 6

To a solution of compound 61 (3 g, 6.52 mmol) in MeOH (50 mL) was added $NaBH_4$ (0.74 g, 19.6 mmol) at 0° C. and the mixture was heated to reflux for 2 hours. The mixture was poured into saturated aqueous solution of $NH_4Cl$ and extracted with ethyl acetate. The organic phase was washed by brine and dried by $Na_2SO_4$. The solvent was evaporated in vacuum to afford compound 62 (1.8 g, 67% yield) which was used for the next step directly without further purification.

Step 7

To a solution of compound 62 (1.0 g, 2.39 mmol) in dichloromethane (30 mL) were added MsCl (0.3 g, 2.63 mmol) and $Et_3N$ (0.36 g, 2.63 mmol) at 0° C. The reaction mixture was stirred at rt for 2 hours and then diluted with dichloromethane. The organic phase was washed by saturated aqueous solution of $NaHCO_3$, brine, dried by anhydrous $Na_2SO_4$, and concentrated to afford compound 63 (0.75 g, crude).

Step 8

A sealed tube was charged with compound 63 (0.15 g, 0.30 mmol) and methylamine (solution in ethanol, 30%, 5 mL). The reaction mixture was stirred at 100° C. overnight and concentrated, and the residue was dissolved in dichloromethane. The organic phase was washed by water, brine, dried by anhydrous $Na_2SO_4$ and concentrated, and the residue was purified by p-HPLC to afford compound I-117 (32 mg, 13% yield).

$^1$H-NMR ($CDCl_3$) δ: 1.22 (9H, s), 1.58-1.66 (2H, m), 2.16 (3H, s), 2.36 (3H, s), 2.57 (2H, t, J=6.6 Hz), 3.84-3.90 (2H, m), 6.09 (1H, s), 7.15-7.21 (2H, m), 7.28-7.30 (2H, m).

Example 21

Synthesis of Compound I-121

[Formula 101]

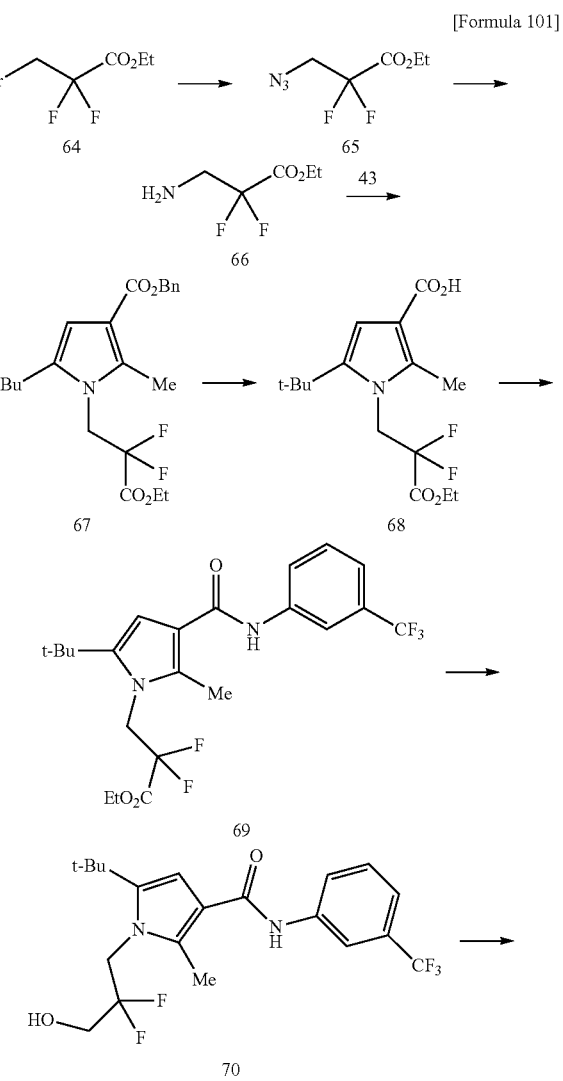

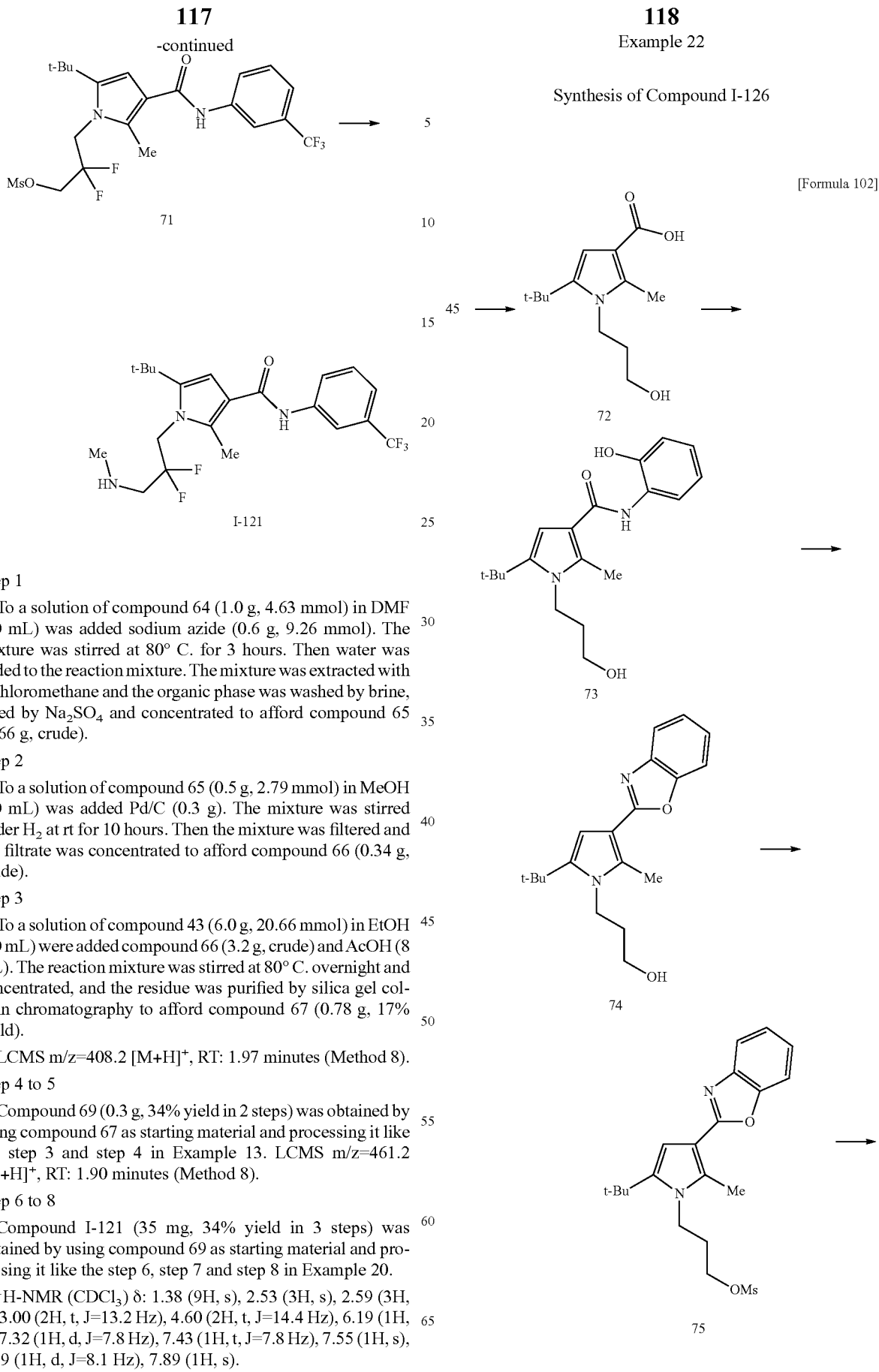

Example 22

Synthesis of Compound I-126

[Formula 102]

Step 1

To a solution of compound 64 (1.0 g, 4.63 mmol) in DMF (20 mL) was added sodium azide (0.6 g, 9.26 mmol). The mixture was stirred at 80° C. for 3 hours. Then water was added to the reaction mixture. The mixture was extracted with dichloromethane and the organic phase was washed by brine, dried by $Na_2SO_4$ and concentrated to afford compound 65 (0.66 g, crude).

Step 2

To a solution of compound 65 (0.5 g, 2.79 mmol) in MeOH (10 mL) was added Pd/C (0.3 g). The mixture was stirred under $H_2$ at rt for 10 hours. Then the mixture was filtered and the filtrate was concentrated to afford compound 66 (0.34 g, crude).

Step 3

To a solution of compound 43 (6.0 g, 20.66 mmol) in EtOH (80 mL) were added compound 66 (3.2 g, crude) and AcOH (8 mL). The reaction mixture was stirred at 80° C. overnight and concentrated, and the residue was purified by silica gel column chromatography to afford compound 67 (0.78 g, 17% yield).

LCMS m/z=408.2 [M+H]$^+$, RT: 1.97 minutes (Method 8).

Step 4 to 5

Compound 69 (0.3 g, 34% yield in 2 steps) was obtained by using compound 67 as starting material and processing it like the step 3 and step 4 in Example 13. LCMS m/z=461.2 [M+H]$^+$, RT: 1.90 minutes (Method 8).

Step 6 to 8

Compound I-121 (35 mg, 34% yield in 3 steps) was obtained by using compound 69 as starting material and processing it like the step 6, step 7 and step 8 in Example 20.

$^1$H-NMR (CDCl$_3$) δ: 1.38 (9H, s), 2.53 (3H, s), 2.59 (3H, s), 3.00 (2H, t, J=13.2 Hz), 4.60 (2H, t, J=14.4 Hz), 6.19 (1H, s), 7.32 (1H, d, J=7.8 Hz), 7.43 (1H, t, J=7.8 Hz), 7.55 (1H, s), 7.79 (1H, d, J=8.1 Hz), 7.89 (1H, s).

119
-continued

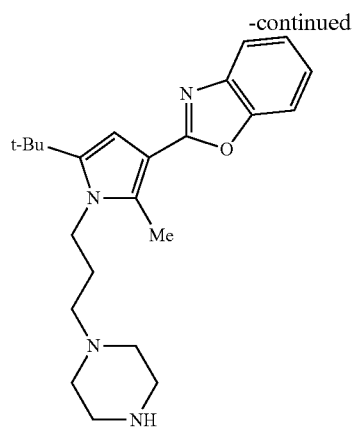

I-126

Step 1
To a solution of compound 45 (2.0 g, 7.1 mmol) in EtOH (10 mL) was added NaBH$_4$ (1.6 g, 42.6 mmol) at rt. The reaction mixture was stirred at 40° C. for 24 hours, quenched by water and concentrated to remove ethanol, and the residue was extracted with dichloromethane. The organic phase was washed by brine, dried by anhydrous Na$_2$SO$_4$ and concentrated to afford compound 72 (1.4 g, 82% yield).
Step 2
To a solution of compound 72 (1.4 g, 5.8 mmol) in Py (3 mL) were added EDC (2.8 g, 14.6 mmol) and 2-aminophenol (0.8 g, 7.6 mmol) at rt. The reaction mixture was stirred at rt overnight and concentrated to remove Py, and the residue was dissolved in dichloromethane. The organic phase was washed by water, brine, dried by anhydrous Na$_2$SO$_4$ and concentrated, and the residue was purified by silica gel column chromatography to afford compound 73 (1.5 g, 78% yield).
LCMS m/z=331.2 [M+H]$^+$, retention time=1.75 minutes (Method 8).
Step 3
To a solution of compound 73 (1.5 g, 4.5 mmol) in t-BuOH (10 mL) was added TsOH (2.35 g, 13.6 mmol) at rt. The reaction mixture was refluxed overnight and, concentrated to remove t-BuOH, and the residue was dissolved in dichloromethane. The organic phase was washed by water, brine and dried by anhydrous Na$_2$SO$_4$ and concentrated, and the residue was purified by silica gel column chromatography to afford compound 74 (0.9 g, 63% yield).
LCMS m/z=313.2 [M+H]$^+$, RT: 1.75 minutes (Method 8).
Step 4
To a solution of compound 74 (0.9 g, mmol) in dichloromethane (5 mL) were added Et$_3$N (0.2 g, 1.8 mmol) and MsCl (0.1 g, 0.9 mmol) at rt. The reaction mixture was stirred at rt for 3 hours and diluted with dichloromethane. The organic phase was washed by water, brine, dried by anhydrous Na$_2$SO$_4$ and concentrated to afford compound 75 (0.9 g, 80% yield), which was used directly in the next step.
LCMS m/z=391.2 [M+H]$^+$, RT: 1.81 minutes (Method 8).
Step 5
To a solution of compound 75 (0.2 g, 0.5 mmol) in n-BuOH (10 mL) was added piperazine (0.44 g, 5 mmol) at rt. The reaction mixture was stirred at 80° C. overnight and concentrated to remove n-BuOH, and the residue was dissolved in ethyl acetate. The organic phase was washed by water, brine, 120
dried by anhydrous Na$_2$SO$_4$ and concentrated, and the residue was purified by p-HPLC to afford compound I-126 (45 mg, 11% yield).
$^1$H-NMR (CDCl$_3$) δ: 1.42 (9H, s), 1.89-1.92 (2H, m), 2.41-2.45 (6H, m), 2.72 (3H, s), 2.91 (4H, t, J=9.6 Hz), 4.03-4.09 (2H, m), 6.54 (1H, s), 7.21-7.27 (2H, m), 7.47 (1H, d, J=8.4 Hz), 7.66 (1H, d, J=8.4 Hz).

Example 23

Synthesis of Compound I-129

[Formula 103]

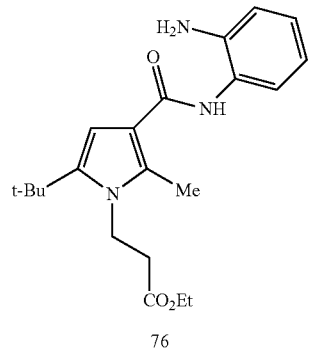

76

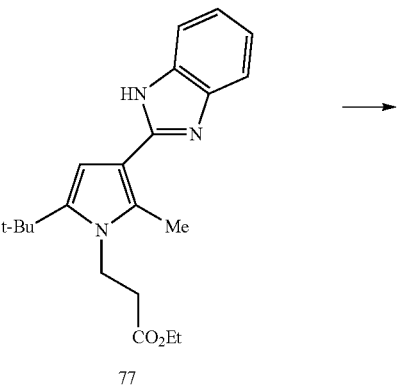

77

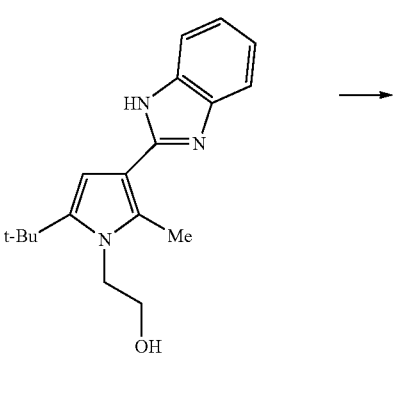

78

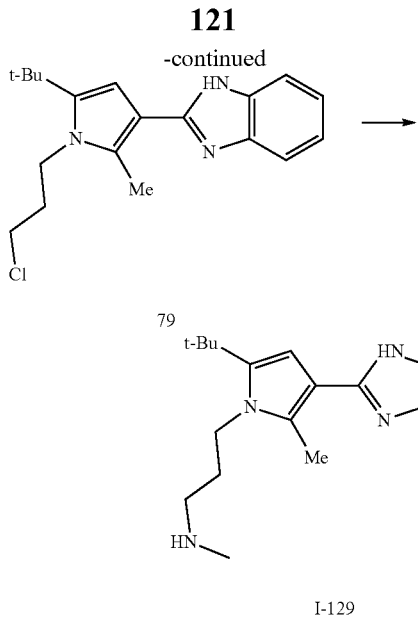

Step 1

To a solution of compound 45 (3 g, 10.7 mmol) in Py (10 mL) were added EDC (5.11 g, 26.7 mmol) and benzene-1,2-diamine (5.77 g, 53.3 mmol) at rt. The reaction mixture was stirred at rt overnight and concentrated to remove Py, and the residue was dissolved in dichloromethane. The organic phase was washed by water, brine, dried by anhydrous $Na_2SO_4$ and concentrated, and the residue was purified by silica gel column chromatography to afford compound 76 (2.1 g, 55% yield).

LCMS m/z=372.3 $[M+H]^+$, RT: 1.48 minutes (Method 8).

Step 2

A solution of compound 76 (2 g, 5.4 mmol) and AcOH (10 mL) was stirred at 80° C. overnight and concentrated to remove AcOH, and the residue was dissolved in dichloromethane. The organic phase was basified by saturated aqueous solution of $NaHCO_3$ to pH=8-9. The mixture was washed by brine, dried by anhydrous $Na_2SO_4$ and concentrated, and the residue was purified by silica gel column chromatography to afford compound 77 (1.38 g, 73% yield).

LCMS m/z=354.3 $[M+H]^+$, RT: 1.66 minutes (Method 8).

Step 3

To a solution of compound 77 (1.36 g, 3.85 mmol) in EtOH (10 mL) was added $NaBH_4$ (0.29 g, 7.7 mmol) at rt. The reaction mixture was stirred at 40° C. for 24 hours, quenched by water and concentrated to remove EtOH, and the residue was extracted with dichloromethane. The organic phase was washed by brine, dried by anhydrous $Na_2SO_4$ and concentrated to afford compound 78 (0.7 g, 53% yield).

LCMS m/z=312.3 $[M+H]^+$, RT: 1.49 minutes (Method 8).

Step 4

To a solution of compound 78 (0.7 g, 2.25 mmol) in dichloromethane (10 mL) were added $Et_3N$ (0.7 g, 6.7 mmol) and MsCl (0.4 g, 3.4 mmol) at rt. The reaction mixture was stirred at rt for 3 hours and diluted with dichloromethane (20 mL). The organic phase was washed by water, brine, dried by anhydrous $Na_2SO_4$ and concentrated to afford compound 79 (0.5 g, crude), which was used directly in next step.

LCMS m/z=330.2 $[M+H]^+$, RT: 1.74 minutes (Method 8).

Step 5

To a mixture of compound 79 (0.15 g, 0.5 mmol) in methylamine (solution in EtOH, 30%, 4 mL) were added $K_2CO_3$ (0.1 g, 0.6 mmol) and KI (0.1 g, 0.6 mmol) at rt. The reaction mixture was stirred at 80° C. overnight and concentrated to remove the solvent, and the residue was dissolved in dichloromethane. The organic phase was washed by water, brine, dried by anhydrous $Na_2SO_4$ and purified by p-HPLC to afford compound I-129 (25 mg, 17% yield).

$^1$H-NMR (DMSO-$d_6$) δ: 1.37 (9H, s), 1.77 (2H, brs), 2.30 (3H, brs), 2.58 (2H, brs), 2.70 (3H, s), 4.04-4.07 (2H, m), 6.42 (1H, s), 7.06-7.07 (2H, m), 7.36 (1H, brs), 7.49 (1H, brs), 12.01 (1H, s).

The following compounds were synthesized in a manner similar to those described in the general procedures and Examples. The chemical structure of the compounds and the physical properties of them are described below (LC/MS data and NMR spectrum).

(Method of Identification for the Compound)

LC/MS data of the compounds were measured under any one of the following 11 conditions (Method 1 to 11), and a retention time and $[M+H]^+$ are shown.

(Method 1)

Column: Shim-pack XR-ODS (2.2 μm, i.d. 50×3.0 mm) (Shimadzu)

Flow rate: 1.6 mL/min

UV detection wavelength: 254 nm

Mobile phase: [A] is 0.1% formic acid-containing aqueous solution, and [B] is 0.1% formic acid-containing acetonitrile solution Gradient: Linear gradient of 10% to 100% solvent [B] for 3 minutes was performed, and 100% solvent [B] was maintained for 1 minute.

(Method 2)

Column: ACQUITY UPLC™ BEH C18 (1.7 μm, i.d. 2.1× 50 mm) (Waters)

Flow rate: 0.8 mL/min

UV detection wavelength: 254 nm

Mobile phase: [A] is 0.1% formic acid-containing aqueous solution, and [B] is 0.1% formic acid-containing acetonitrile solution Gradient: Linear gradient of 10% to 100% solvent [B] for 3.5 minutes was performed, and 100% solvent [B] was maintained for 0.5 minute.

(Method 3)

Column: Gemini-NX (5 μm, i.d. 4.6×50 mm) (Phenomenex)

Flow rate: 3 mL/min

UV detection wavelength: 254 nm

Mobile phase: [A] is 0.1% formic acid-containing aqueous solution, and [B] is 0.1% formic acid-containing methanol solution Gradient: Linear gradient of 10% to 100% solvent [B] for 3.5 minutes was performed, and 100% solvent [B] was maintained for 0.5 minute.

(Method 4)

Column: Gemini-NX (5 μm, i.d. 4.6×50 mm) (Phenomenex)

Flow rate: 3 mL/min

UV detection wavelength: 254 nm

Mobile phase: [A] is 10 mmol/L ammonium carbonate-containing aqueous solution, and [B] is methanol Gradient: Linear gradient of 10% to 100% solvent [B] for 3.5 minutes was performed, and 100% solvent [B] was maintained for 0.5 minute.

(Method 5)

Column: Xbridge C18 (3.5 μm 4.6×50 mm)

Flow rate: 2 mL/min

UV detection wavelength: 254 nm

Mobile phase: [A] is 0.05% TFA-containing aqueous solution, and [B] is 0.05% TFA-containing acetonitrile solution Gradient: Linear gradient of 5% to 100% solvent [B] for 5 minutes was performed, and 100% solvent [B] was maintained for 0.8 minute.

(Method 6)
Column: Xbridge C18 (3.5 μm 4.6×50 mm)
Flow rate: 2 mL/min
UV detection wavelength: 254 nm
Mobile phase: [A] is 0.05% TFA-containing aqueous solution, and [B] is 0.05% TFA-containing acetonitrile solution
Gradient: Linear gradient of 5% to 100% solvent [B] for 3 minutes was performed, and 100% solvent [B] was maintained for 1 minute.

(Method 7)
Column: Xbridge C18 (3.5 μm 4.6×50 mm)
Flow rate: 2 mL/min
UV detection wavelength: 254 nm
Mobile phase: [A] is 0.01% $NH_4HCO_3$-containing aqueous solution, and [B] is acetonitrile solution
Gradient: Linear gradient of 0.05% to 100% solvent [B] for 5 minutes was performed, and 100% solvent [B] was maintained for 1 minute.

(Method 8)
Column: Xbridge C18 (3.5 μm 4.6×50 mm)
Flow rate 2 mL/min
UV detection wavelength: 254 nm
Mobile phase: [A] is 0.05% TFA-containing aqueous solution, and [B] is 0.05% TFA-containing acetonitrile solution
Gradient: Linear gradient of 5% to 100% solvent [B] for 1.6 minutes was performed, and 100% solvent [B] was maintained for 1.4 minute.

(Method 9)
Column: Xbridge C18 (3.5 μm 4.6×50 mm)
Flow rate: 2 mL/min
UV detection wavelength: 254 nm
Mobile phase: [A] is 0.01% $NH_4HCO_3$-containing aqueous solution, and [B] is acetonitrile solution
Gradient: Linear gradient of 5% to 100% solvent [B] for 3 minutes was performed, and 100% solvent [B] was maintained for 1 minute.

(Method 10)
Column: Xbridge C18 (3.5 μm 4.6×50 mm)
Flow rate: 2 mL/min
UV detection wavelength: 254 nm
Mobile phase: [A] is 0.05% TFA-containing aqueous solution, and [B] is 0.05% TFA-containing acetonitrile solution
Gradient: Linear gradient of 5% to 100% solvent [B] for 5 minutes was performed, and 100% solvent [B] was maintained for 1 minute.

(Method 11)
Column: Xbridge C18 (3.5 μm 4.6×50 mm)
Flow rate: 2 mL/min
UV detection wavelength: 254 nm
Mobile phase: [A] is 0.05% TFA-containing aqueous solution, and [B] is 0.05% TFA-containing acetonitrile solution
Gradient: Linear gradient of 5% to 100% solvent [B] for 1.6 minutes was performed, and 100% solvent [B] was maintained for 0.7 minute.

TABLE 1

| Compound No. | Structure | LC/MS retention time (mim) or NMR spectrum | MS[M + H]+ | LC method |
|---|---|---|---|---|
| I-001 | 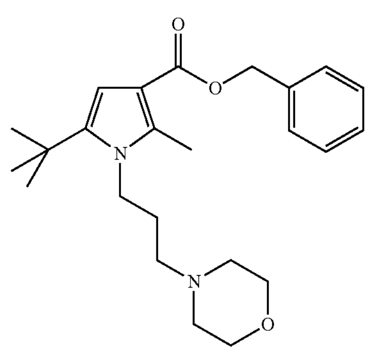 [SMILES: Cc1c(C(=O)OCc2ccccc2)cc(C(C)(C)C)n1CCCN1CCOCC1] | 1.71 | 399.3 | 2 |
| I-002 | 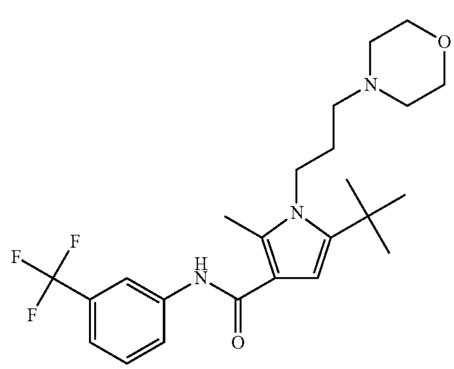 [SMILES: Cc1c(C(=O)Nc2cccc(C(F)(F)F)c2)cc(C(C)(C)C)n1CCCN1CCOCC1] | 1.72 | 452.4 | 2 |

TABLE 1-continued

| Compound No. | Structure | LC/MS retention time (min) or NMR spectrum | MS[M + H]+ | LC method |
|---|---|---|---|---|
| I-003 | 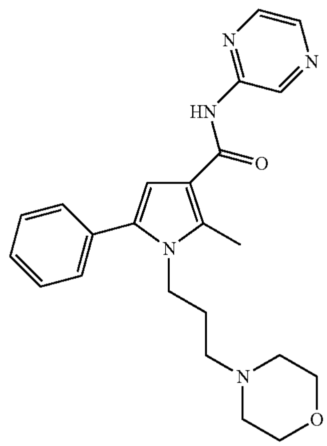 [SMILES: Cc1c(C(=O)Nc2cnccn2)cc(-c2ccccc2)n1CCCN1CCOCC1] | 1.06 | 406.2 | 1 |
| I-004 | 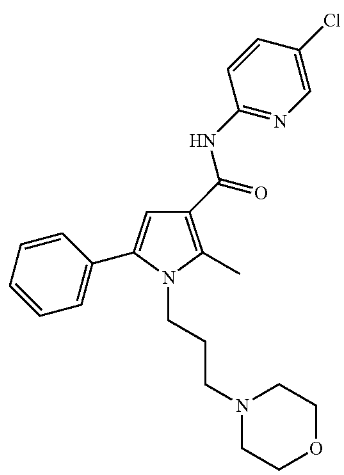 [SMILES: Cc1c(C(=O)Nc2ccc(Cl)cn2)cc(-c2ccccc2)n1CCCN1CCOCC1] | 1.42 | 439.2 | 1 |
| I-005 | 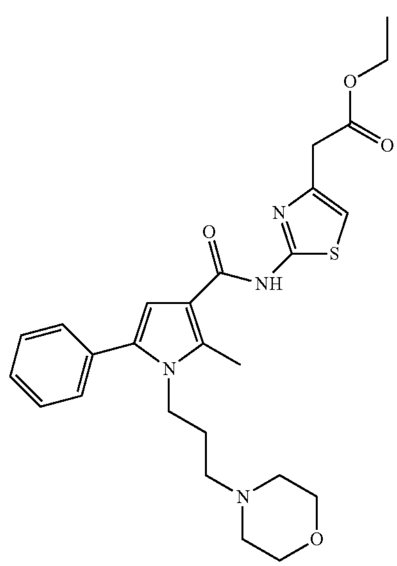 [SMILES: CCOC(=O)Cc1csc(NC(=O)c2cc(-c3ccccc3)n(CCCN3CCOCC3)c2C)n1] | 1.31 | 497.2 | 1 |

TABLE 2
| Compound No. | Structure | LC/MS retention time (min) or NMR spectrum | MS[M + H]+ | LC method |
|---|---|---|---|---|
| I-006 | 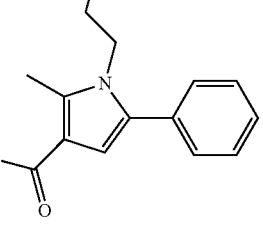 | 2.43 | 403.1 | 1 |
| I-007 | 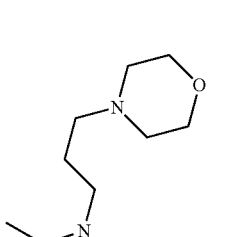 | 1.26 | 396.2 | 1 |
| I-008 | 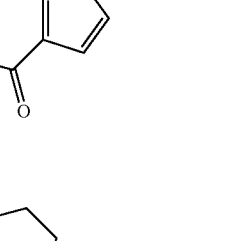 | 1.67 | 470.2 | 1 |
| I-009 | 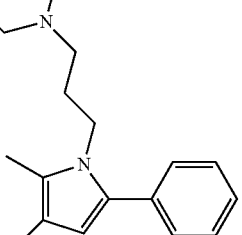 | 1.37 | 404.2 | 1 |

TABLE 2-continued

| Compound No. | Structure | LC/MS retention time (min) or NMR spectrum | MS[M + H]+ | LC method |
|---|---|---|---|---|
| I-010 | 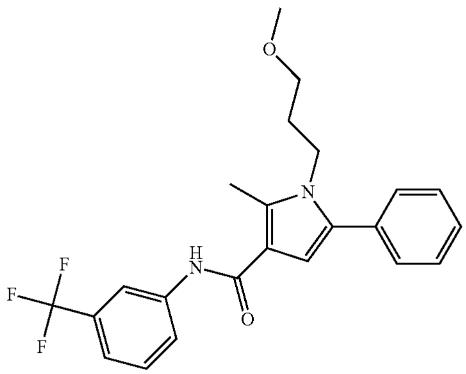 [SMILES: COCCCn1c(-c2ccccc2)cc(C(=O)Nc2cccc(C(F)(F)F)c2)c1C] | 2.77 | 417.1 | 1 |

TABLE 3

| Compound No. | Structure | LC/MS retention time (min) or NMR spectrum | MS[M + H]+ | LC method |
|---|---|---|---|---|
| I-011 | 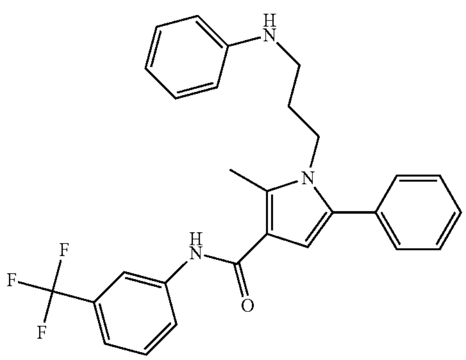 [SMILES: Cc1c(C(=O)Nc2cccc(C(F)(F)F)c2)cc(-c2ccccc2)n1CCCNc1ccccc1] | 2.92 | 478.2 | 1 |
| I-012 | 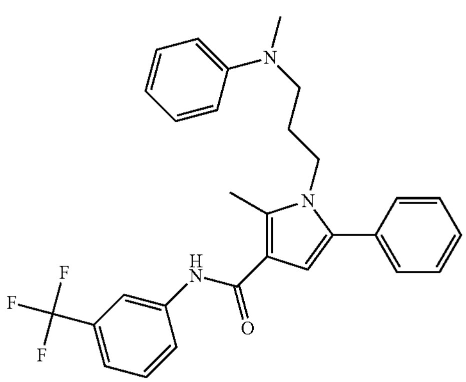 [SMILES: Cc1c(C(=O)Nc2cccc(C(F)(F)F)c2)cc(-c2ccccc2)n1CCCN(C)c1ccccc1] | 3.04 | 492.2 | 1 |

TABLE 3-continued

| Compound No. | Structure | LC/MS retention time (mim) or NMR spectrum | MS[M + H]+ | LC method |
|---|---|---|---|---|
| I-013 | 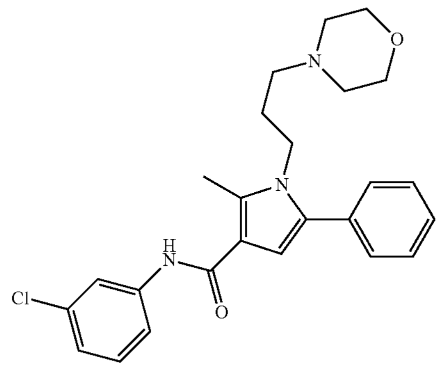 [SMILES: Cc1c(C(=O)Nc2cccc(Cl)c2)cc(-c2ccccc2)n1CCCN1CCOCC1] | 1.52 | 438.2 | 1 |
| I-014 | 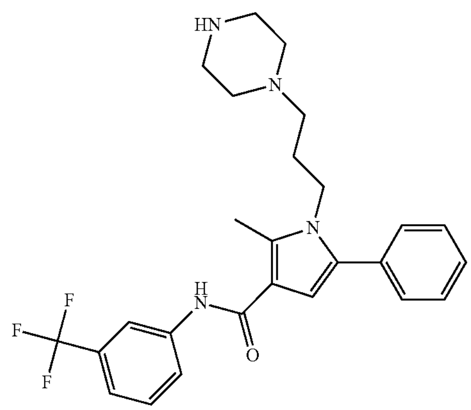 [SMILES: Cc1c(C(=O)Nc2cccc(C(F)(F)F)c2)cc(-c2ccccc2)n1CCCN1CCNCC1] | 1.56 | 471.3 | 1 |
| I-015 | 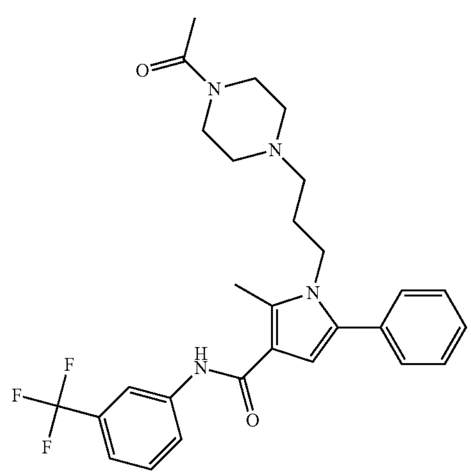 [SMILES: CC(=O)N1CCN(CCCn2c(-c3ccccc3)cc(C(=O)Nc3cccc(C(F)(F)F)c3)c2C)CC1] | 1.62 | 513.3 | 1 |

TABLE 4

| Compound No. | Structure | LC/MS retention time (min) or NMR spectrum | MS[M + H]+ | LC method |
|---|---|---|---|---|
| I-016 | 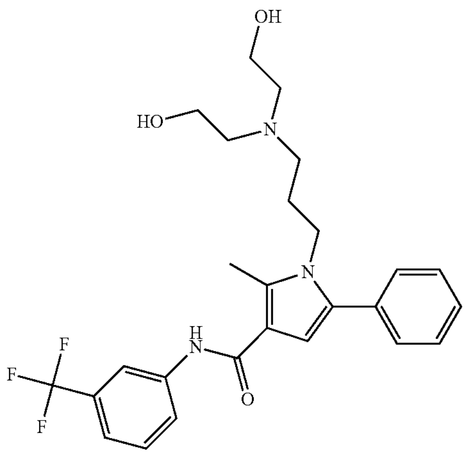 [SMILES: Cc1c(C(=O)Nc2cccc(C(F)(F)F)c2)cc(-c2ccccc2)n1CCCN(CCO)CCO] | 1.58 | 490.3 | 1 |
| I-017 | 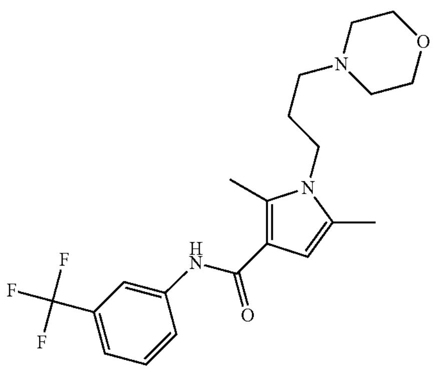 [SMILES: Cc1cc(C(=O)Nc2cccc(C(F)(F)F)c2)c(C)n1CCCN1CCOCC1] | 1.42 | 410.2 | 1 |
| I-018 | 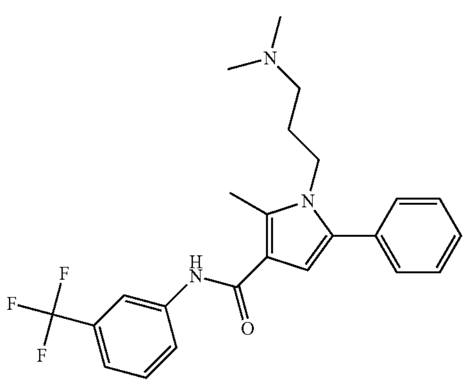 [SMILES: Cc1c(C(=O)Nc2cccc(C(F)(F)F)c2)cc(-c2ccccc2)n1CCCN(C)C] | 1.60 | 430.2 | 1 |

TABLE 4-continued
| Compound No. | Structure | LC/MS retention time (mim) or NMR spectrum | MS[M + H]+ | LC method |
|---|---|---|---|---|
| I-019 | 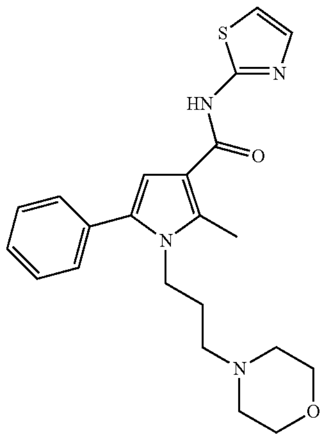 [SMILES: Cc1c(C(=O)Nc2nccs2)cc(-c2ccccc2)n1CCCN1CCOCC1] | 1.18 | 411.2 | 1 |
| I-020 | 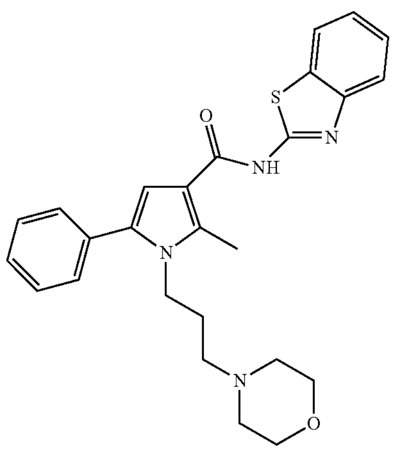 [SMILES: Cc1c(C(=O)Nc2nc3ccccc3s2)cc(-c2ccccc2)n1CCCN1CCOCC1] | 1.55 | 461.3 | 1 |
TABLE 5
| Compound No. | Structure | LC/MS retention time (mim) or NMR spectrum | MS[M + H]+ | LC method |
|---|---|---|---|---|
| I-021 | 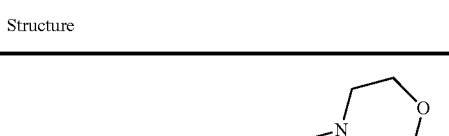 | 1.31 | 473.3 | 1 |

TABLE 5-continued

| Compound No. | Structure | LC/MS retention time (min) or NMR spectrum | MS[M + H]+ | LC method |
|---|---|---|---|---|
| I-022 | 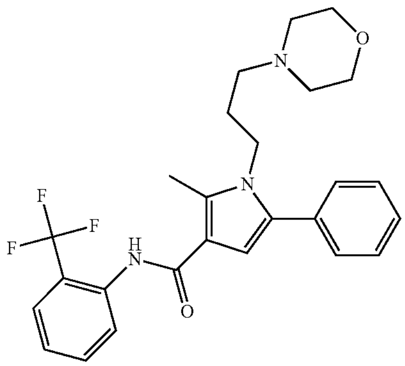 [SMILES: Cc1c(C(=O)Nc2ccccc2C(F)(F)F)cc(-c2ccccc2)n1CCCN1CCOCC1] | 1.52 | 472.3 | 1 |
| I-023 | 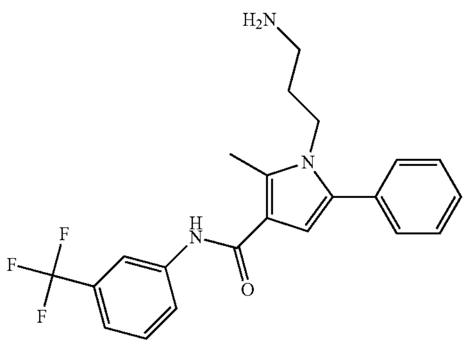 [SMILES: Cc1c(C(=O)Nc2cccc(C(F)(F)F)c2)cc(-c2ccccc2)n1CCCN] | 1.57 | 402.1 | 1 |
| I-024 | 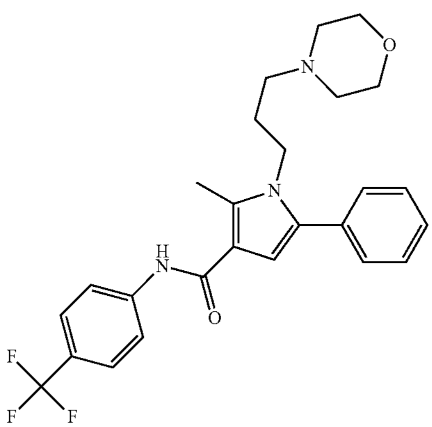 [SMILES: Cc1c(C(=O)Nc2ccc(C(F)(F)F)cc2)cc(-c2ccccc2)n1CCCN1CCOCC1] | 1.67 | 472.2 | 1 |
| I-025 | 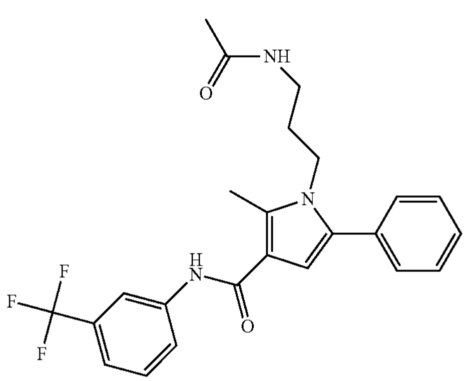 [SMILES: CC(=O)NCCCn1c(-c2ccccc2)cc(C(=O)Nc2cccc(C(F)(F)F)c2)c1C] | 2.30 | 444.2 | 1 |

TABLE 6

| Compound No. | Structure | LC/MS retention time (min) or NMR spectrum | MS[M + H]+ | LC method |
|---|---|---|---|---|
| I-026 | 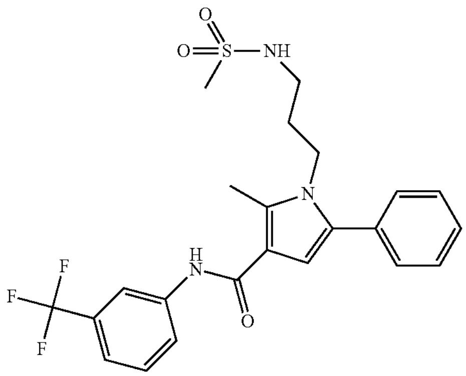 [SMILES: Cc1c(C(=O)Nc2cccc(C(F)(F)F)c2)cc(-c2ccccc2)n1CCCNS(C)(=O)=O] | 2.42 | 480.2 | 1 |
| I-027 | 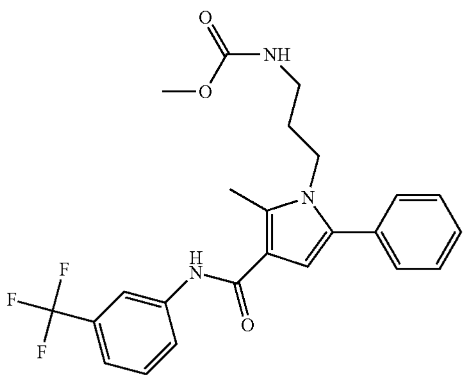 [SMILES: COC(=O)NCCCn1c(-c2ccccc2)cc(C(=O)Nc2cccc(C(F)(F)F)c2)c1C] | 2.52 | 460.2 | 1 |
| I-028 | 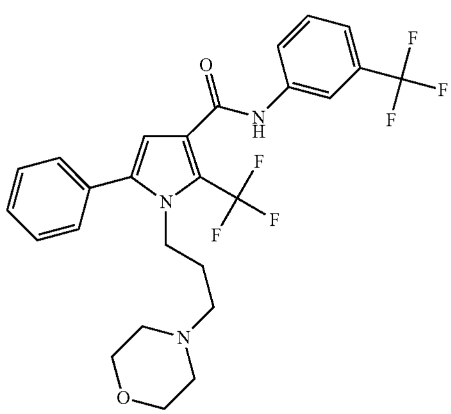 [SMILES: O=C(Nc1cccc(C(F)(F)F)c1)c1cc(-c2ccccc2)n(CCCN2CCOCC2)c1C(F)(F)F] | 1.70 | 526.3 | 1 |
| I-029 | 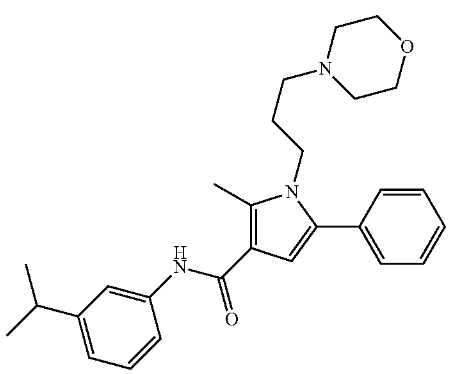 [SMILES: Cc1c(C(=O)Nc2cccc(C(C)C)c2)cc(-c2ccccc2)n1CCCN1CCOCC1] | 1.66 | 446.3 | 1 |

TABLE 6-continued

| Compound No. | Structure | LC/MS retention time (mim) or NMR spectrum | MS[M + H]+ | LC method |
|---|---|---|---|---|
| I-030 | 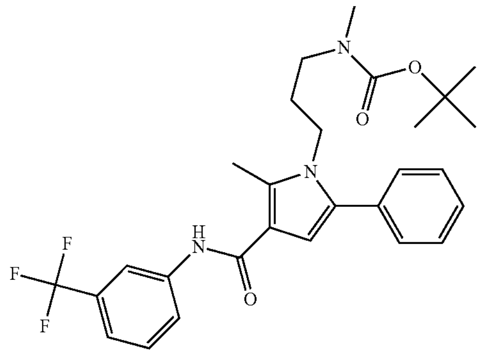 [SMILES: Cc1c(C(=O)Nc2cccc(C(F)(F)F)c2)cc(-c2ccccc2)n1CCCN(C)C(=O)OC(C)(C)C] | 2.97 | 516.3 | 1 |

TABLE 7

| Compound No. | Structure | LC/MS retention time (mim) or NMR spectrum | MS[M + H]+ | LC method |
|---|---|---|---|---|
| I-031 | 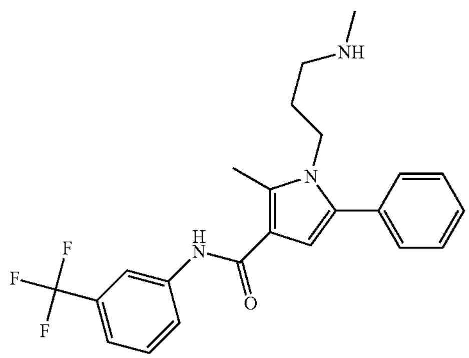 [SMILES: CNCCCn1c(-c2ccccc2)cc(C(=O)Nc2cccc(C(F)(F)F)c2)c1C] | 1.60 | 416.2 | 1 |
| I-032 | 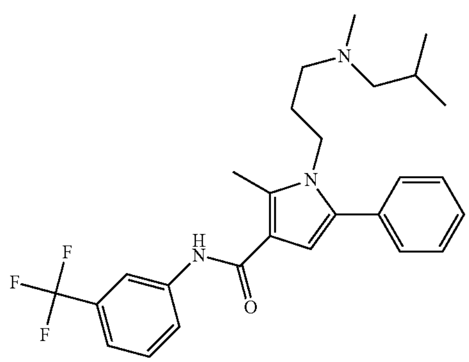 [SMILES: Cc1c(C(=O)Nc2cccc(C(F)(F)F)c2)cc(-c2ccccc2)n1CCCN(C)CC(C)C] | 2.25 | 472.1 | 3 |

TABLE 7-continued
| Compound No. | Structure | LC/MS retention time (min) or NMR spectrum | MS[M + H]+ | LC method |
|---|---|---|---|---|
| I-033 | 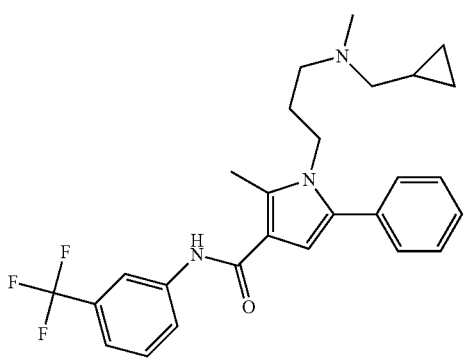 [SMILES: Cc1c(C(=O)Nc2cccc(C(F)(F)F)c2)cc(-c2ccccc2)n1CCCN(C)CC1CC1] | 2.24 | 470.1 | 3 |
| I-034 | 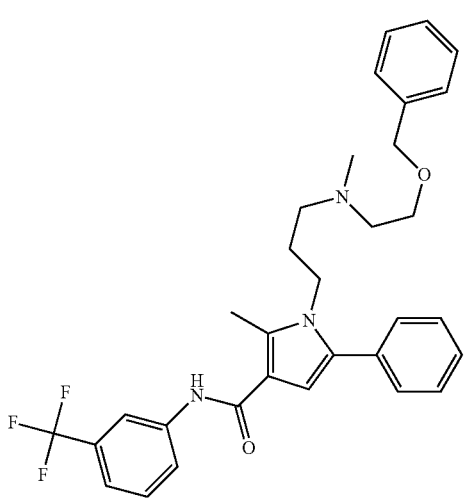 [SMILES: Cc1c(C(=O)Nc2cccc(C(F)(F)F)c2)cc(-c2ccccc2)n1CCCN(C)CCOCc1ccccc1] | 2.43 | 550.2 | 3 |
| I-035 | 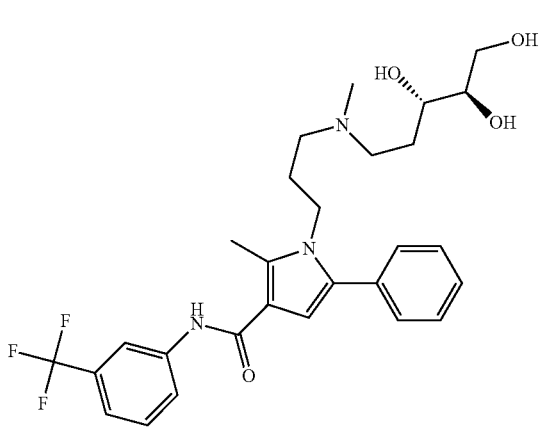 [SMILES: Cc1c(C(=O)Nc2cccc(C(F)(F)F)c2)cc(-c2ccccc2)n1CCCN(C)CC[C@H](O)[C@H](O)CO] | 2.18 | 534.1 | 3 |

TABLE 8
| Compound No. | Structure | LC/MS retention time (min) or NMR spectrum | MS[M + H]+ | LC method |
|---|---|---|---|---|
| I-036 | 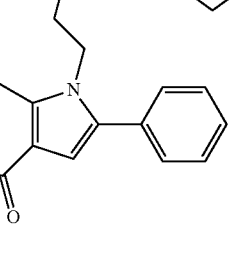 | 2.15 | 500.1 | 3 |
| I-037 | 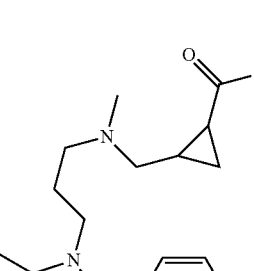 | 2.34 | 542.2 | 3 |
| I-038 | 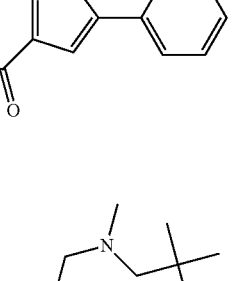 | 1.92 | 529.2 | 3 |
| I-039 | 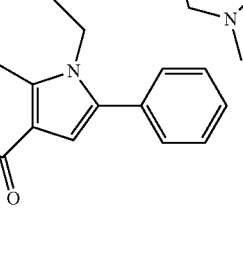 | 1.67 | 527.1 | 3 |

TABLE 8-continued
| Compound No. | Structure | LC/MS retention time (min) or NMR spectrum | MS[M + H]+ | LC method |
|---|---|---|---|---|
| I-040 | 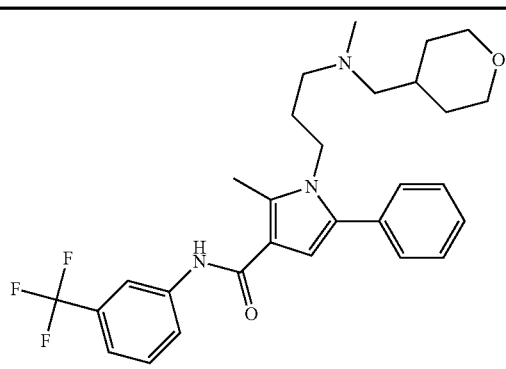 | 2.21 | 514.1 | 3 |
TABLE 9
| Compound No. | Structure | LC/MS retention time (min) or NMR spectrum | MS[M + H]+ | LC method |
|---|---|---|---|---|
| I-041 | 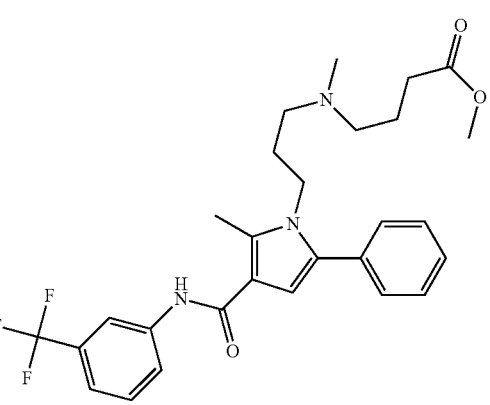 | 2.23 | 516.1 | 3 |
| I-042 | 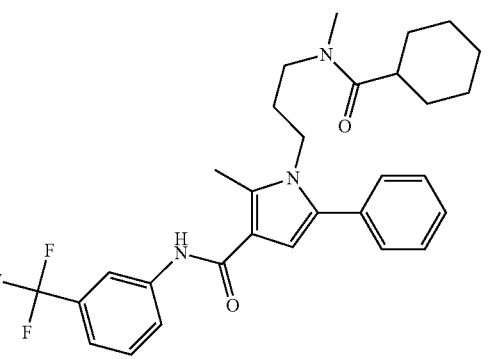 | 3.35 | 526.2 | 3 |

TABLE 9-continued
| Compound No. | Structure | LC/MS retention time (mim) or NMR spectrum | MS[M + H]+ | LC method |
|---|---|---|---|---|
| I-043 | 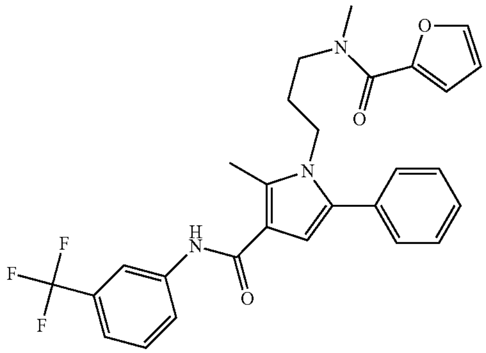 | 3.16 | 510.0 | 3 |
| I-044 | 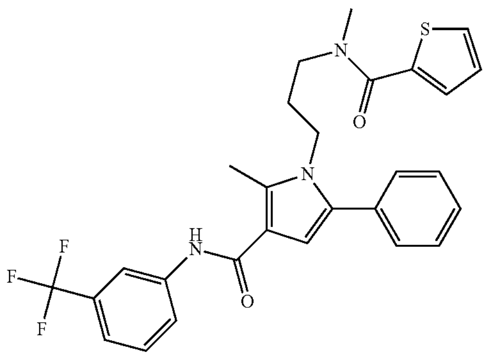 [SMILES: Cc1c(C(=O)Nc2cccc(C(F)(F)F)c2)cc(-c2ccccc2)n1CCCN(C)C(=O)c1cccs1] | 3.19 | 525.9 | 3 |
| I-045 | 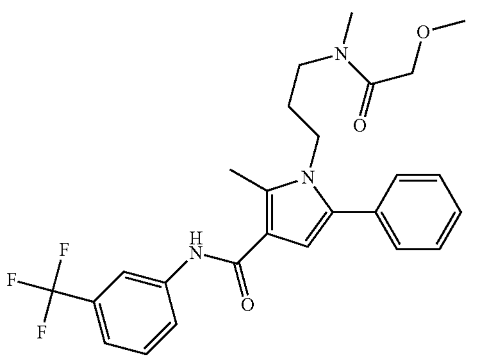 [SMILES: COCC(=O)N(C)CCCn1c(-c2ccccc2)cc(C(=O)Nc2cccc(C(F)(F)F)c2)c1C] | 3.04 | 488.0 | 3 |
TABLE 10
| Compound No. | Structure | LC/MS retention time (mim) or NMR spectrum | MS[M + H]+ | LC method |
|---|---|---|---|---|
| I-046 | 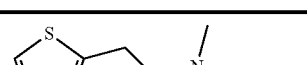 | 3.22 | 540.1 | 3 |

TABLE 10-continued
| Compound No. | Structure | LC/MS retention time (mim) or NMR spectrum | MS[M + H]+ | LC method |
|---|---|---|---|---|
| I-047 | 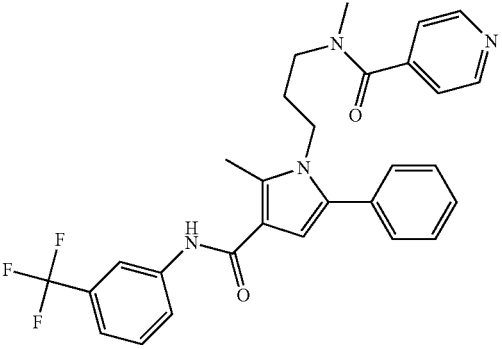 [SMILES: Cc1c(C(=O)Nc2cccc(C(F)(F)F)c2)cc(-c2ccccc2)n1CCCN(C)C(=O)c1ccncc1] | 3.01 | 521.1 | 3 |
| I-048 | 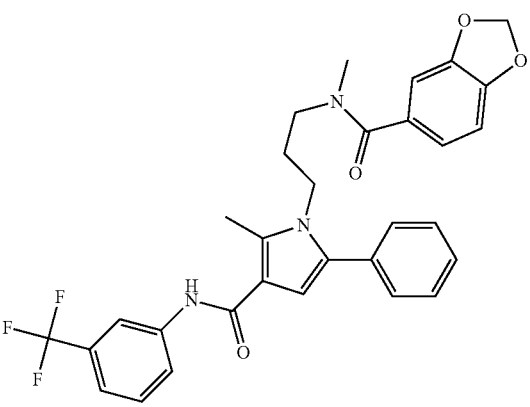 [SMILES: Cc1c(C(=O)Nc2cccc(C(F)(F)F)c2)cc(-c2ccccc2)n1CCCN(C)C(=O)c1ccc2c(c1)OCO2] | 3.17 | 564.1 | 3 |
| I-049 | 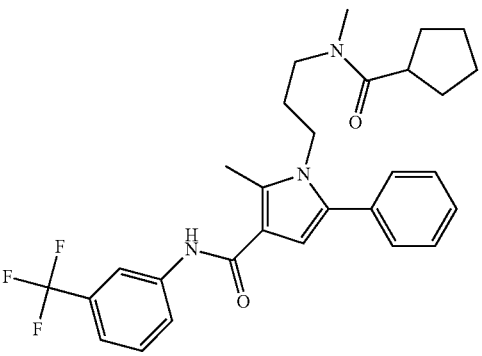 [SMILES: Cc1c(C(=O)Nc2cccc(C(F)(F)F)c2)cc(-c2ccccc2)n1CCCN(C)C(=O)C1CCCC1] | 3.32 | 512.1 | 3 |
| I-050 | 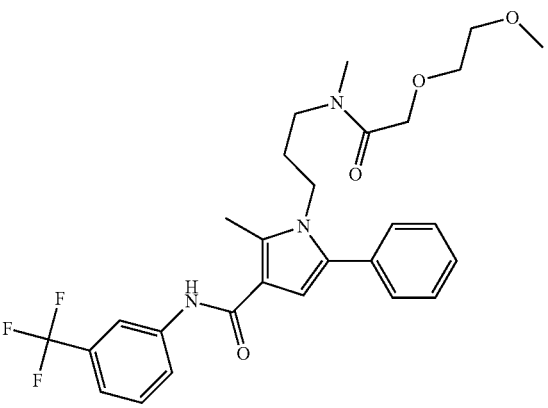 [SMILES: COCCOCC(=O)N(C)CCCn1c(-c2ccccc2)cc(C(=O)Nc2cccc(C(F)(F)F)c2)c1C] | 3.05 | 532.1 | 3 |

TABLE 11

| Compound No. | Structure | LC/MS retention time (mim) or NMR spectrum | MS[M + H]+ | LC method |
|---|---|---|---|---|
| I-051 | 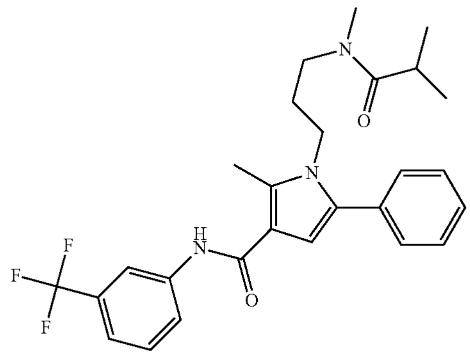 [SMILES: Cc1c(C(=O)Nc2cccc(C(F)(F)F)c2)cc(-c2ccccc2)n1CCCN(C)C(=O)C(C)C] | 3.22 | 486.1 | 3 |
| I-052 | 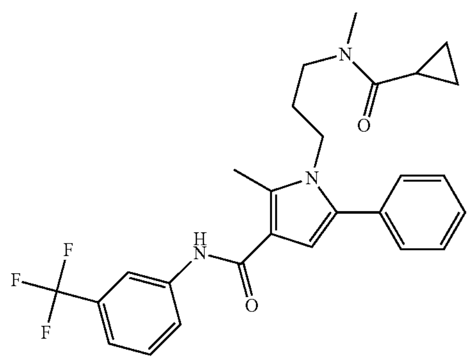 [SMILES: Cc1c(C(=O)Nc2cccc(C(F)(F)F)c2)cc(-c2ccccc2)n1CCCN(C)C(=O)C1CC1] | 3.16 | 484.1 | 3 |
| I-053 | 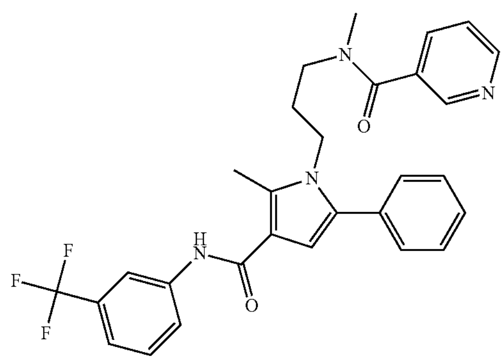 [SMILES: Cc1c(C(=O)Nc2cccc(C(F)(F)F)c2)cc(-c2ccccc2)n1CCCN(C)C(=O)c1cccnc1] | 3.02 | 521.1 | 3 |
| I-054 | 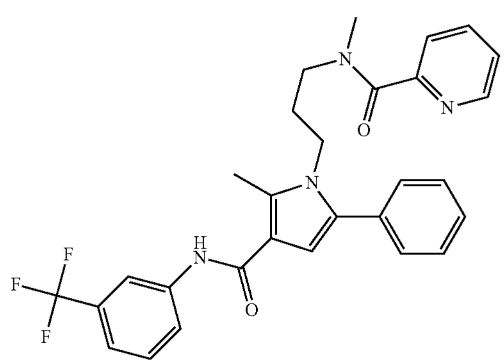 [SMILES: Cc1c(C(=O)Nc2cccc(C(F)(F)F)c2)cc(-c2ccccc2)n1CCCN(C)C(=O)c1ccccn1] | 3.06 | 521.1 | 3 |

TABLE 11-continued
| Compound No. | Structure | LC/MS retention time (mim) or NMR spectrum | MS[M + H]+ | LC method |
|---|---|---|---|---|
| I-055 | 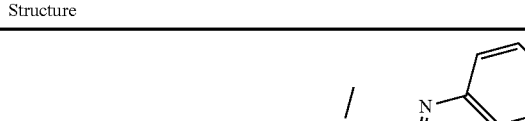 | 3.24 | 571.1 | 3 |
TABLE 12
| Compound No. | Structure | LC/MS retention time (mim) or NMR spectrum | MS [M + H]+ | LC method |
|---|---|---|---|---|
| I-056 | 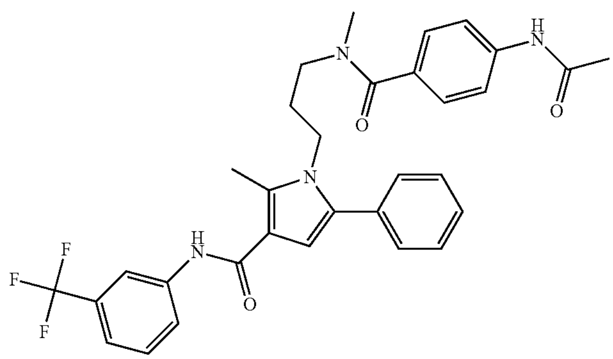 [SMILES: CC(=O)Nc1ccc(C(=O)N(C)CCCn2c(-c3ccccc3)cc(C(=O)Nc3cccc(C(F)(F)F)c3)c2C)cc1] | 3.07 | 577.1 | 3 |
| I-057 | 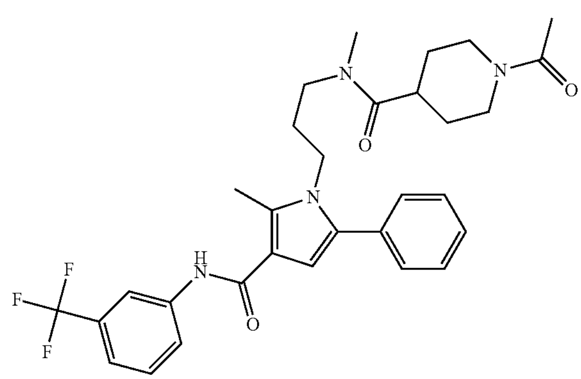 [SMILES: CC(=O)N1CCC(C(=O)N(C)CCCn2c(-c3ccccc3)cc(C(=O)Nc3cccc(C(F)(F)F)c3)c2C)CC1] | 3.00 | 569.2 | 3 |

TABLE 12-continued
| Compound No. | Structure | LC/MS retention time (min) or NMR spectrum | MS [M + H]+ | LC method |
|---|---|---|---|---|
| I-058 | 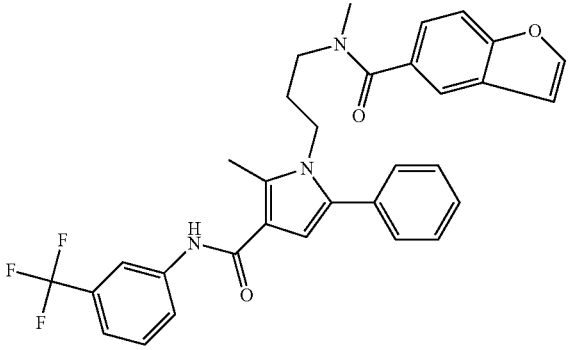 [SMILES: Cc1c(C(=O)Nc2cccc(C(F)(F)F)c2)cc(-c2ccccc2)n1CCCN(C)C(=O)c1ccc2occc2c1] | 3.24 | 560.1 | 3 |
| I-059 | 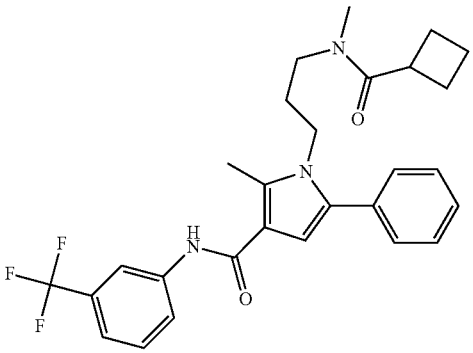 [SMILES: Cc1c(C(=O)Nc2cccc(C(F)(F)F)c2)cc(-c2ccccc2)n1CCCN(C)C(=O)C1CCC1] | 3.23 | 498.2 | 3 |
| I-060 | 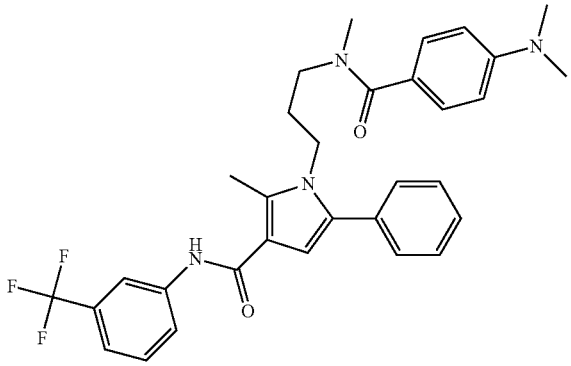 [SMILES: Cc1c(C(=O)Nc2cccc(C(F)(F)F)c2)cc(-c2ccccc2)n1CCCN(C)C(=O)c1ccc(N(C)C)cc1] | 3.30 | 563.2 | 3 |

TABLE 13

| Compound No. | Structure | LC/MS retention time (min) or NMR spectrum | MS [M + H]+ | LC method |
|---|---|---|---|---|
| I-061 | 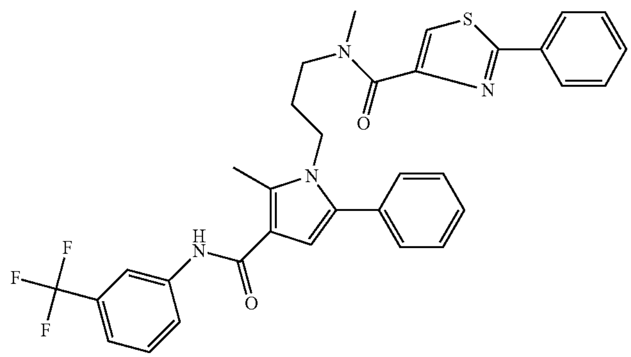 [SMILES: Cc1c(C(=O)Nc2cccc(C(F)(F)F)c2)cc(-c2ccccc2)n1CCCN(C)C(=O)c1csc(-c2ccccc2)n1] | 3.38 | 603.1 | 3 |
| I-062 | 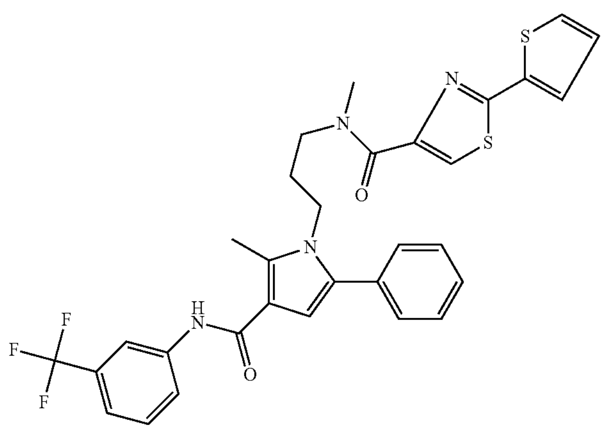 [SMILES: Cc1c(C(=O)Nc2cccc(C(F)(F)F)c2)cc(-c2ccccc2)n1CCCN(C)C(=O)c1csc(-c2cccs2)n1] | 3.36 | 609.1 | 3 |
| I-063 | 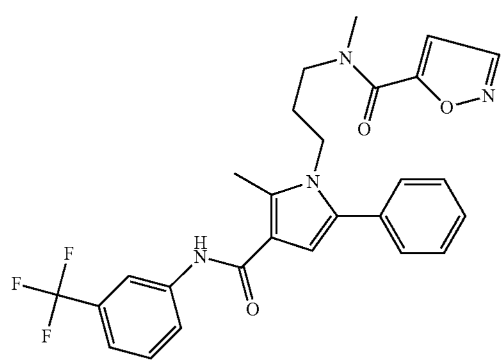 [SMILES: Cc1c(C(=O)Nc2cccc(C(F)(F)F)c2)cc(-c2ccccc2)n1CCCN(C)C(=O)c1ccno1] | 3.07 | 511.1 | 3 |
| I-064 | 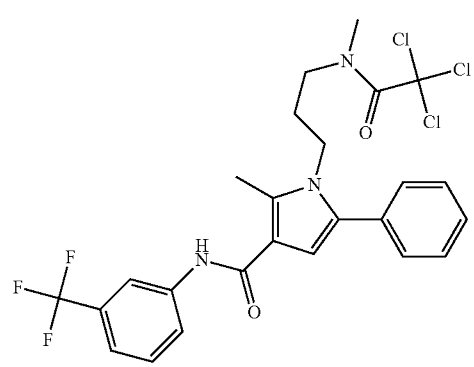 [SMILES: Cc1c(C(=O)Nc2cccc(C(F)(F)F)c2)cc(-c2ccccc2)n1CCCN(C)C(=O)C(Cl)(Cl)Cl] | 3.36 | 559.9 | 3 |

TABLE 13-continued
| Compound No. | Structure | LC/MS retention time (mim) or NMR spectrum | MS [M + H]+ | LC method |
|---|---|---|---|---|
| I-065 | 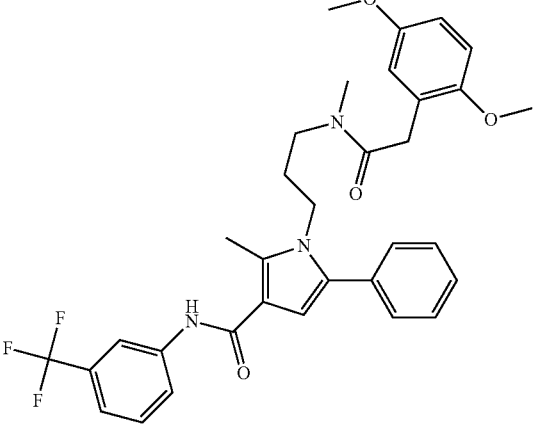 | 3.27 | 594.2 | 3 |
TABLE 14
| Compound No. | Structure | LC/MS retention time (mim) or NMR spectrum | MS [M + H]+ | LC method |
|---|---|---|---|---|
| I-066 | 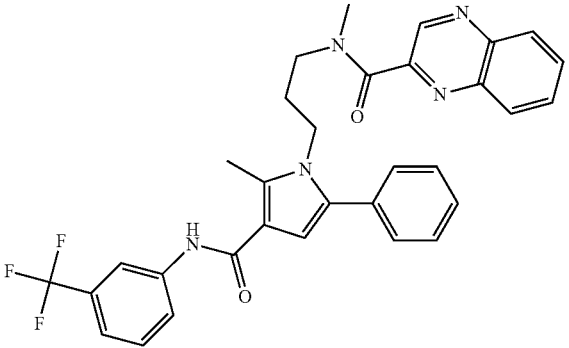 [SMILES: Cc1c(C(=O)Nc2cccc(C(F)(F)F)c2)cc(-c2ccccc2)n1CCCN(C)C(=O)c1cnc2ccccc2n1] | 3.25 | 572.2 | 3 |
| I-067 | 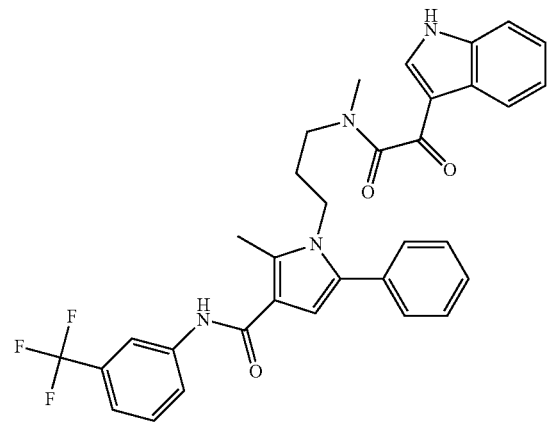 [SMILES: Cc1c(C(=O)Nc2cccc(C(F)(F)F)c2)cc(-c2ccccc2)n1CCCN(C)C(=O)C(=O)c1c[nH]c2ccccc12] | 3.16 | 587.2 | 3 |

TABLE 14-continued

| Compound No. | Structure | LC/MS retention time (mim) or NMR spectrum | MS [M + H]+ | LC method |
|---|---|---|---|---|
| I-068 | 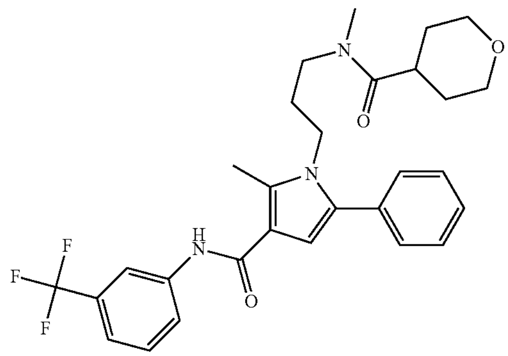 [SMILES: Cc1c(C(=O)Nc2cccc(C(F)(F)F)c2)cc(-c2ccccc2)n1CCCN(C)C(=O)C1CCOCC1] | 3.08 | 528.1 | 3 |
| I-069 | 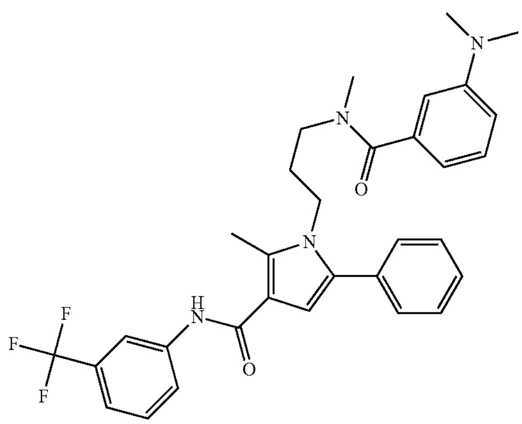 [SMILES: Cc1c(C(=O)Nc2cccc(C(F)(F)F)c2)cc(-c2ccccc2)n1CCCN(C)C(=O)c1cccc(N(C)C)c1] | 3.26 | 563.2 | 3 |
| I-070 | 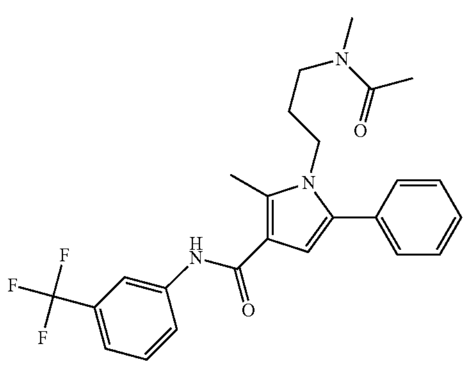 [SMILES: CC(=O)N(C)CCCn1c(-c2ccccc2)cc(C(=O)Nc2cccc(C(F)(F)F)c2)c1C] | 3.06 | 458.0 | 3 |

TABLE 15
| Compound No. | Structure | LC/MS retention time (mim) or NMR spectrum | MS [M + H]+ | LC method |
|---|---|---|---|---|
| I-071 | 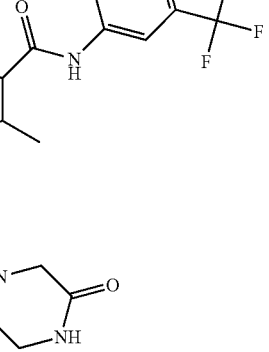 | 2.95 | 485.3 | 4 |
| I-072 | 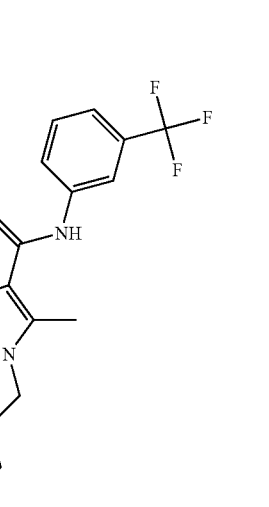 | 1.76 | 478.3 | 1 |
| I-073 | 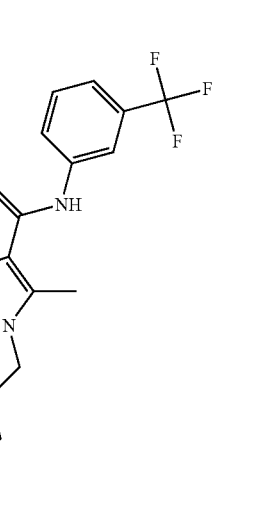 | 1.51 | 473.2 | 1 |

TABLE 15-continued
| Compound No. | Structure | LC/MS retention time (mim) or NMR spectrum | MS [M + H]+ | LC method |
|---|---|---|---|---|
| I-074 | 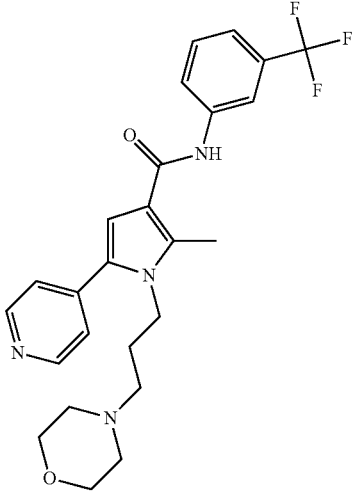 | 1.16 | 473.5 | 1 |
| I-075 | 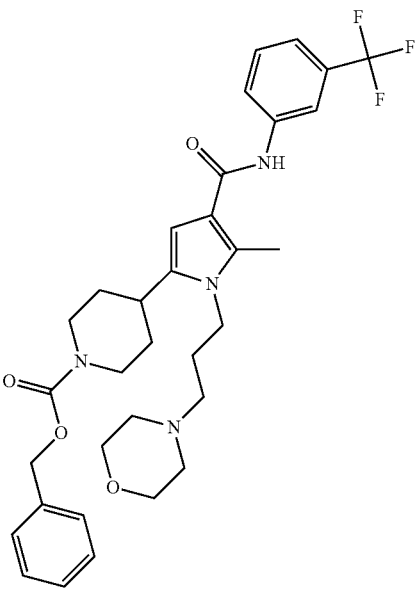 [SMILES: Cc1c(C(=O)Nc2cccc(C(F)(F)F)c2)cc(C2CCN(C(=O)OCc3ccccc3)CC2)n1CCCN1CCOCC1] | 1.81 | 613.3 | 1 |

TABLE 16

| Compound No. | Structure | LC/MS retention time (min) or NMR spectrum | MS [M + H]+ | LC method |
|---|---|---|---|---|
| I-076 | 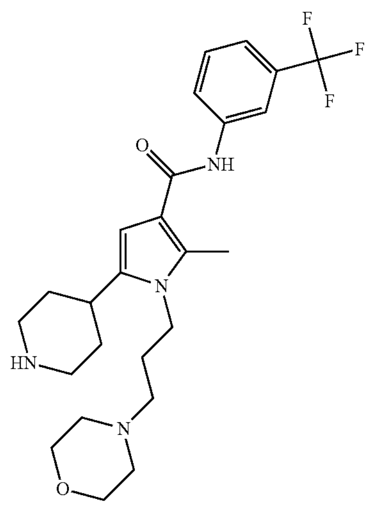 [SMILES: Cc1c(C(=O)Nc2cccc(C(F)(F)F)c2)cc(C2CCNCC2)n1CCCN1CCOCC1] | 1.10 | 479.3 | 1 |
| I-077 | 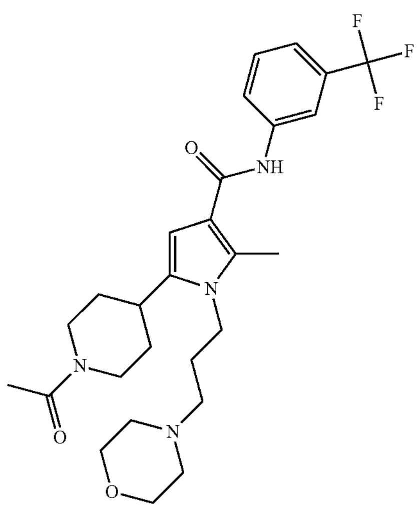 [SMILES: CC(=O)N1CCC(c2cc(C(=O)Nc3cccc(C(F)(F)F)c3)c(C)n2CCCN2CCOCC2)CC1] | 1.38 | 521.3 | 1 |
| I-078 | 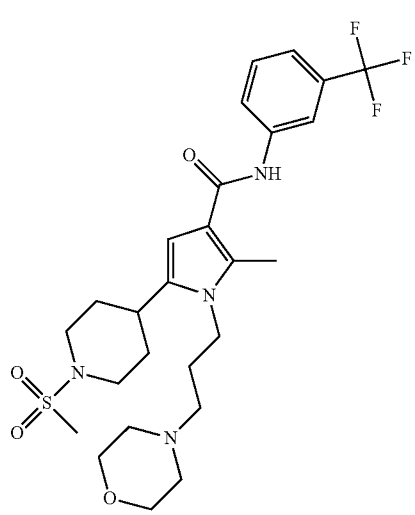 [SMILES: Cc1c(C(=O)Nc2cccc(C(F)(F)F)c2)cc(C2CCN(S(C)(=O)=O)CC2)n1CCCN1CCOCC1] | 1.50 | 557.3 | 1 |

//
TABLE 16-continued
| Compound No. | Structure | LC/MS retention time (mim) or NMR spectrum | MS [M + H]+ | LC method |
|---|---|---|---|---|
| I-079 | 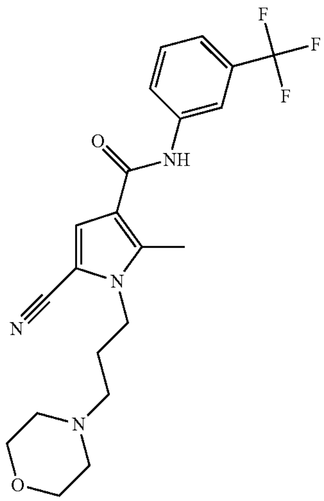 [SMILES: Cc1c(C(=O)Nc2cccc(C(F)(F)F)c2)cc(C#N)n1CCCN1CCOCC1] | 1.33 | 421.1 | 1 |
| I-080 | 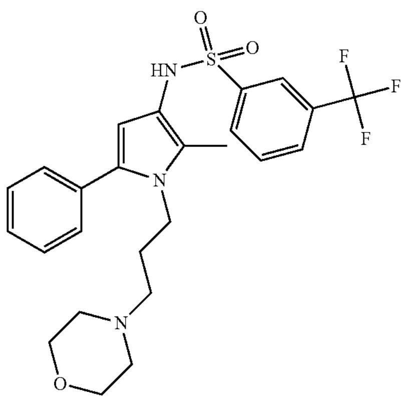 [SMILES: Cc1c(NS(=O)(=O)c2cccc(C(F)(F)F)c2)cc(-c2ccccc2)n1CCCN1CCOCC1] | 1H-NMR (CDCl3) δ: 1.55 (2H, quin, J = 7.1 Hz), 2.03-2.27 (9H, m), 3.56 (4H, t, J = 4.4 Hz), 3.90 (2H, t, J = 7.5 Hz), 5.54 (1H, s), 5.99 (1H, s), 7.16-7.40 (5H, m), 7.61 (1H, t, J = 7.7 Hz), 7.81 (1H, d, J = 7.6 Hz), 7.93-8.04 (2H, m). | | |
TABLE 17
| Compound No. | Structure | LC/MS retention time (mim) or NMR spectrum | MS [M + H]+ | LC method |
|---|---|---|---|---|
| I-081 | 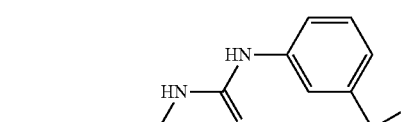 | 1H-NMR (CDCl3) δ: 1.59-1.78 (2H, m), 2.13-2.40 (9H, m), 3.55-3.69 (4H, m), 4.02 (2H, t, J = 7.5 Hz), 5.88 (1H, br s), 6.10 (1H, s), 6.94 (1H, br s), 7.21-7.46 (7H, m), 7.59 (1H, s), 7.65 (1H, d, J = 8.1 Hz). | | |

TABLE 17-continued

| Compound No. | Structure | LC/MS retention time (mim) or NMR spectrum | MS [M + H]+ | LC method |
|---|---|---|---|---|
| I-082 | 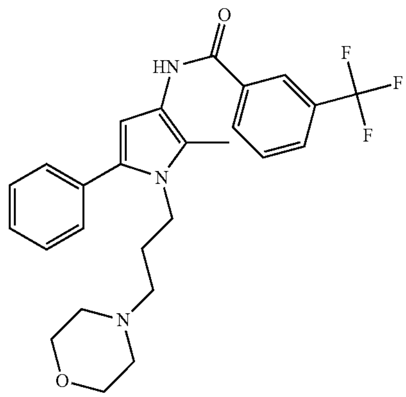 [SMILES: Cc1c(NC(=O)c2cccc(C(F)(F)F)c2)cc(-c2ccccc2)n1CCCN1CCOCC1] | 1H-NMR (CDCl₃) δ: 1.55-1.73 (2H, m), 2.12-2.25 (6H, m), 2.27 (3H, s), 3.58 (4H, t, J = 4.5 Hz), 3.94-4.05 (2H, m), 6.29 (1H, s), 7.23-7.46 (6H, m), 7.61 (1H, t, J = 7.7 Hz), 7.79 (1H, d, J = 7.5 Hz), 8.05 (1H, d, J = 7.3 Hz), 8.13 (1H, s). | | |
| I-083 | 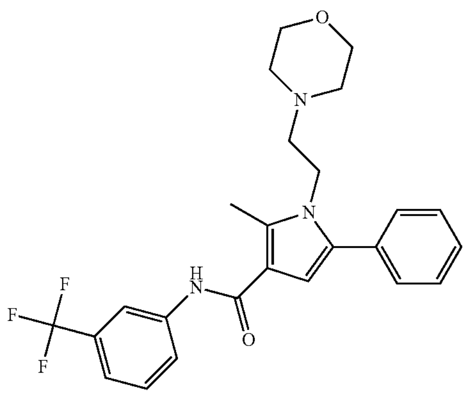 [SMILES: Cc1c(C(=O)Nc2cccc(C(F)(F)F)c2)cc(-c2ccccc2)n1CCN1CCOCC1] | 1H-NMR (CDCl₃) δ: 2.26 (4H, t, J = 4.6 Hz), 2.44 (2H, t, J = 7.2 Hz), 2.69 (3H, s), 3.58 (4H, t, J = 4.6 Hz), 4.04 (2H, t, J = 7.3 Hz), 6.33 (1H, s), 7.28-7.47 (7H, m), 7.57 (1H, s), 7.76 (1H, d, J = 8.2 Hz), 7.91 (1H, s). | | |
| I-084 | 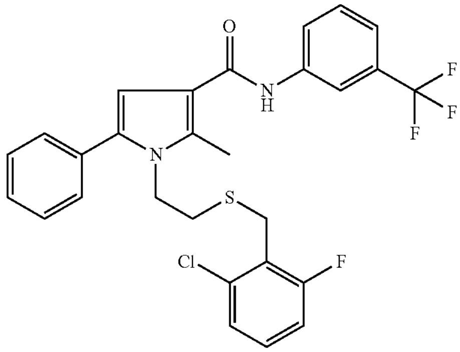 [SMILES: Cc1c(C(=O)Nc2cccc(C(F)(F)F)c2)cc(-c2ccccc2)n1CCSCc1c(F)cccc1Cl] | 3.11 | 547.1 | 2 |
| I-085 | 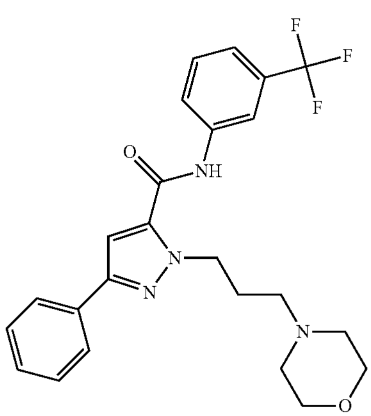 [SMILES: O=C(Nc1cccc(C(F)(F)F)c1)c1cc(-c2ccccc2)nn1CCCN1CCOCC1] | 1H-NMR (CDCl3) δ: 2.08 (2H, t, J = 6.9 Hz), 2.35-2.40 (6H, m), 3.59 (4H, t, J = 4.5 Hz), 4.41 (2H, t, J = 6.9 Hz), 6.87 (1H, s), 7.27-7.43 (5H, m), 7.71-7.75 (3H, m), 7.84 (1H, s), 8.10 (1H, s). | | |

TABLE 18
| Compound No. | Structure | LC/MS retention time (mim) or NMR spectrum | MS [M + H]+ | LC method |
|---|---|---|---|---|
| I-086 | 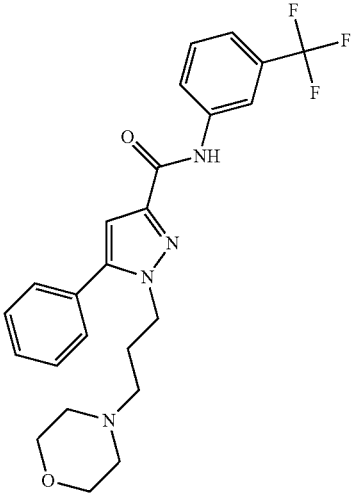 [SMILES: O=C(Nc1cccc(C(F)(F)F)c1)c1cc(-c2ccccc2)n(CCCN2CCOCC2)n1] | 1H-NMR (CDCl3) δ: 1.98 (2H, t, J = 6.9 Hz), 2.18-2.23 (6H, m), 3.52-3.55 (4H, m), 4.19 (2H, t, J = 6.9 Hz), 6.83 (s, 1H), 7.29-7.44 (7H, m), 7.88-7.91 (2H, m), 8.80 (1H, s). | | |
| I-087 | 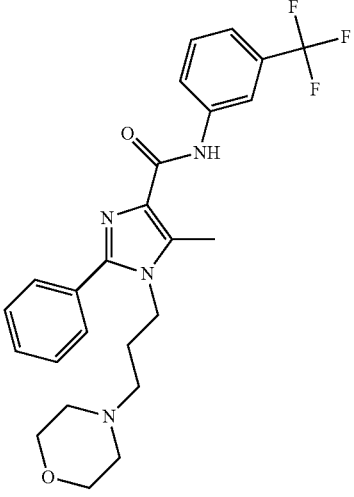 [SMILES: Cc1c(C(=O)Nc2cccc(C(F)(F)F)c2)nc(-c2ccccc2)n1CCCN1CCOCC1] | 1H-NMR (CDCl3) δ: 1.73 (2H, t, J = 7.2 Hz), 2.19-2.23 (6H, m), 2.73 (3H, s), 3.56 (4H, m), 4.07 (2H, t, J = 7.2 Hz), 7.31-7.60 (7H, m), 7.83 (1H, d, J = 9.1 Hz), 8.09 (1H, s), 9.23 (1H, s). | | |
| I-088 | 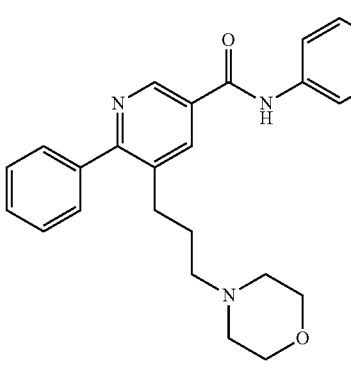 | 1H-NMR (CDCl3) δ: 1.65-1.73 (2H, m), 2.20-2.28 (6H, m), 2.77 (2H, t, J = 7.8 Hz), 3.61 (4H, t, J = 4.5 Hz), 7.41-7.51 (7H, m), 7.86 (1H, d, J = 8.1 Hz), 7.95 (1H, s), 8.18 (1H, d, J = 2.1 Hz), 8.53 (1H, s), 8.96 (1H, d, J = 2.1 Hz). | | |

TABLE 18-continued

| Compound No. | Structure | LC/MS retention time (mim) or NMR spectrum | MS [M + H]+ | LC method |
|---|---|---|---|---|
| I-089 | 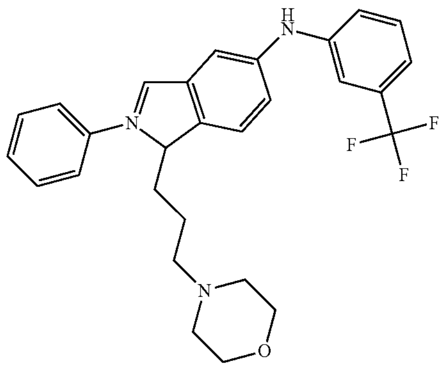 | 1H-NMR (CDCl3) δ: 1.77-1.82 (2H, m), 2.16-2.25 (6H, m), 3.60 (4H, t, J = 4.5 Hz), 4.27 (2H, t, J = 7.5 Hz), 5.79 (1H, s), 6.48 (1H, s), 7.00-7.08 (3H, m), 7.12 (1H, s), 7.25-7.30 (1H, m), 7.42-7.53 (7H, m). | | |

TABLE 19

| Compound No. | Structure | NMR | [M + H]+ | RT (min) | LC method |
|---|---|---|---|---|---|
| I-090 | 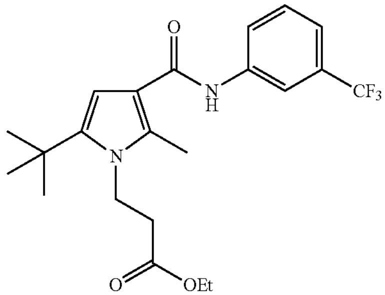 [SMILES: CCOC(=O)CCn1c(C(C)(C)C)cc(C(=O)Nc2cccc(C(F)(F)F)c2)c1C] | ¹H-NMR (CDCl₃) δ: 1.32-1.44 (12H, m), 2.61-2.72 (5H, m), 4.22-4.36 (4H, m), 6.12 (1H, d, J = 4.8 Hz), 7.30-7.56 (3H, m), 7.83-7.90 (2H, m). | 424.9 | 4.4 | 5 |
| I-091 | 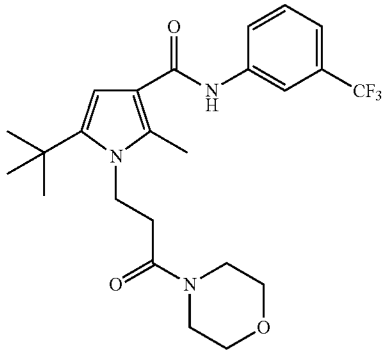 [SMILES: Cc1c(C(=O)Nc2cccc(C(F)(F)F)c2)cc(C(C)(C)C)n1CCC(=O)N1CCOCC1] | ¹H-NMR (CDCl₃) δ: 1.39 (9H, s), 2.58 (3H, s), 2.65 (2H, t, J = 8.1 Hz), 3.39 (2H, t, J = 4.5 Hz), 3.64-3.69 (6H, m), 4.38-4.43 (2H, m), 6.10 (1H, s), 7.32 (1H, d, J = 8.1 Hz), 7.43 (1H, t, J = 7.8 Hz), 7.55 (1H, s), 7.80 (1H, d, J = 8.1 Hz), 7.88 (1H, s). | 466.3 | 3.53 | 5 |
| I-092 | 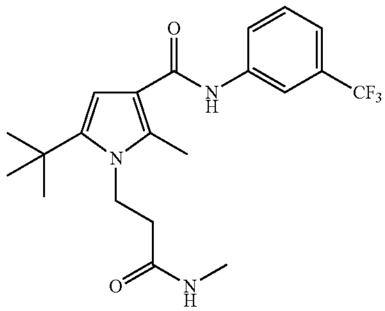 [SMILES: CNC(=O)CCn1c(C(C)(C)C)cc(C(=O)Nc2cccc(C(F)(F)F)c2)c1C] | | 410.3 | 3.36 | 5 |

TABLE 19-continued

| Compound No. | Structure | NMR | [M + H]⁺ | RT (min) | LC method |
|---|---|---|---|---|---|
| I-093 | 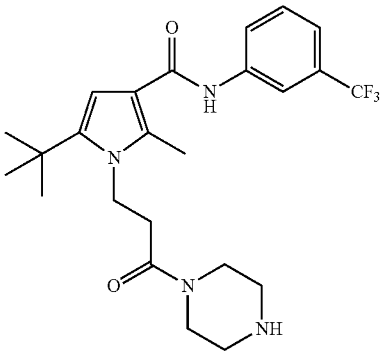 [SMILES: Cc1c(C(=O)Nc2cccc(C(F)(F)F)c2)cc(C(C)(C)C)n1CCC(=O)N1CCNCC1] | | 464.9 | 3.25 | 5 |
| I-094 | 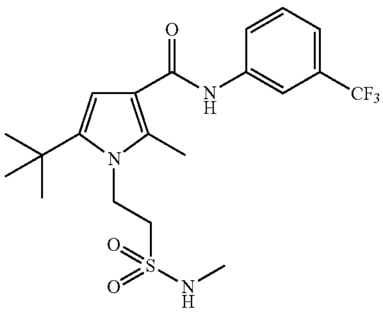 [SMILES: CNS(=O)(=O)CCn1c(C(C)(C)C)cc(C(=O)Nc2cccc(C(F)(F)F)c2)c1C] | | 445.9 | 3.88 | 5 |

TABLE 20

| Compound No. | Structure | NMR | [M + H]⁺ | RT (min) | LC method |
|---|---|---|---|---|---|
| I-095 | 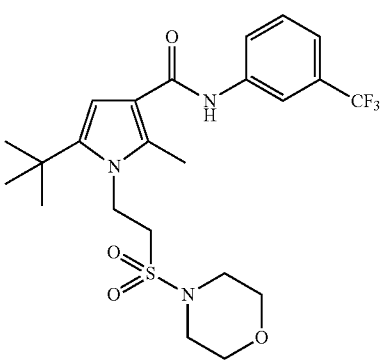 [SMILES: Cc1c(C(=O)Nc2cccc(C(F)(F)F)c2)cc(C(C)(C)C)n1CCS(=O)(=O)N1CCOCC1] | 1H-NMR (CDCl3) δ: 1.42 (9H, s), 2.61 (3H, s), 3.14-3.20 (2H, m), 3.29 (4H, t, J = 4.5 Hz), 3.79 (4H, t, J = 4.5 Hz), 4.49-4.55 (2H, m), 6.10 (1H, s), 7.33 (1H, d, J = 7.8 Hz), 7.44 (1H, t, J = 8.1 Hz), 7.50 (1H, s), 7.80 (1H, d, J = 8.4 Hz), 7.87 (1H, s). | 501.9 | 4.05 | 5 |
| I-096 | 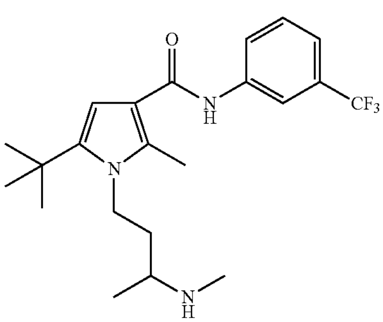 [SMILES: CNC(C)CCn1c(C(C)(C)C)cc(C(=O)Nc2cccc(C(F)(F)F)c2)c1C] | ¹H-NMR (CDCl₃) δ: 1.10 (3H, d, J = 8.0 Hz), 1.33 (9H, s), 1.64-1.77 (2H, m), 2.38 (3H, s), 2.52 (3H, s), 2.62-2.68 (1H, m), 3.96-4.04 (2H, m), 6.01 (1H, s), 7.24 (1H, d, J = 7.8 Hz), 7.35 (1H, t, J = 7.8 Hz), 7.46 (1H, s), 7.72 (1H, d, J = 8.1 Hz), 7.81 (1H, s). | 410 | 3.55 | 5 |

TABLE 20-continued

| Compound No. | Structure | NMR | [M + H]⁺ | RT (min) | LC method |
|---|---|---|---|---|---|
| I-097 | 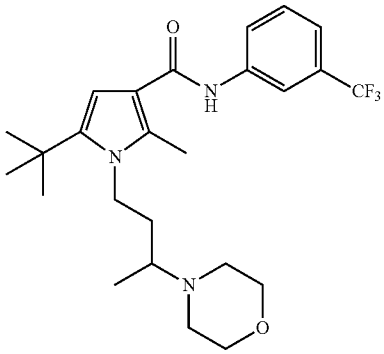 [SMILES: Cc1c(C(=O)Nc2cccc(C(F)(F)F)c2)cc(C(C)(C)C)n1CCC(C)N1CCOCC1] | | 465.9 | 3.45 | 5 |
| I-098 | 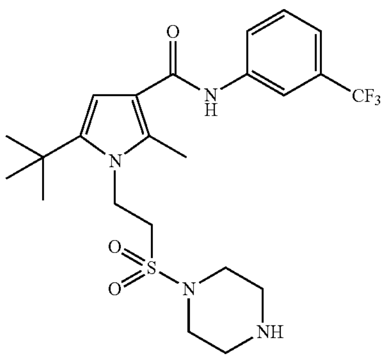 [SMILES: Cc1c(C(=O)Nc2cccc(C(F)(F)F)c2)cc(C(C)(C)C)n1CCS(=O)(=O)N1CCNCC1] | | 500.9 | 3.65 | 5 |
| I-099 | 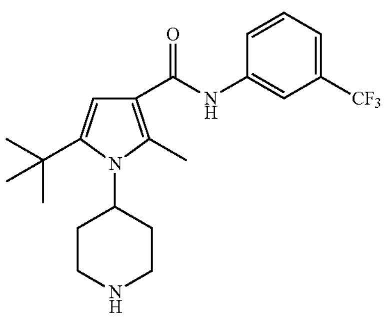 [SMILES: Cc1c(C(=O)Nc2cccc(C(F)(F)F)c2)cc(C(C)(C)C)n1C1CCNCC1] | 1H-NMR (300 Mz) (CDCl3): 1.33 (9H, s), 1.81 (2H, d, J = 12.0 Hz), 2.26-2.32 (2H, m), 2.60-2.70 (5H, m), 3.23 (2H, d, J = 12.0 Hz), 4.39-4.41 (1H, m), 6.00 (1H, s), 7.24 (1H, d, J = 7.5 Hz), 7.35 (1H, t, J = 7.8 Hz), 7.44 (1H, s), 7.72 (1H, d, J = 8.1 Hz), 7.79 (1H, s). | 407.9 | 3.24 | 5 |

TABLE 21

| Compound No. | Structure | NMR | [M + H]⁺ | RT (min) | LC method |
|---|---|---|---|---|---|
| I-100 | 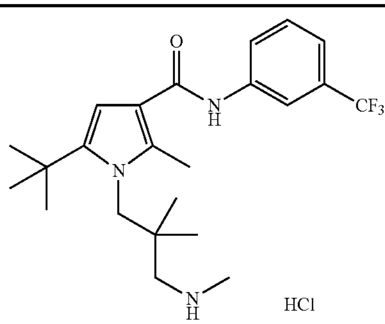 | | 424 | 2.15 | 6 |

TABLE 21-continued

| Compound No. | Structure | NMR | [M + H]+ | RT (min) | LC method |
|---|---|---|---|---|---|
| I-101 | 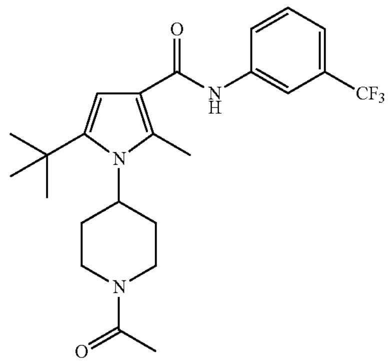 [SMILES: CC(=O)N1CCC(n2c(C(C)(C)C)cc(C(=O)Nc3cccc(C(F)(F)F)c3)c2C)CC1] | | 449.9 | 4.13 | 5 |
| I-102 | 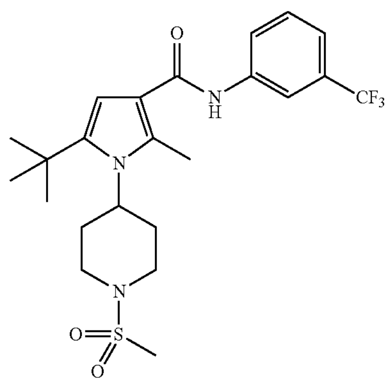 [SMILES: Cc1c(C(=O)Nc2cccc(C(F)(F)F)c2)cc(C(C)(C)C)n1C1CCN(S(C)(=O)=O)CC1] | | 485.8 | 4.2 | 5 |
| I-103 | 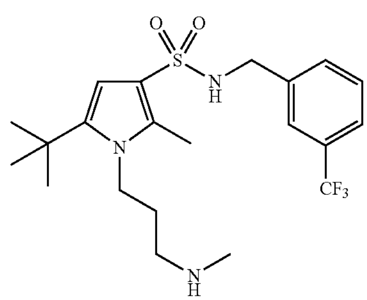 [SMILES: CNCCCn1c(C(C)(C)C)cc(S(=O)(=O)NCc2cccc(C(F)(F)F)c2)c1C] | | 445 | 3.55 | 7 |
| I-104 | 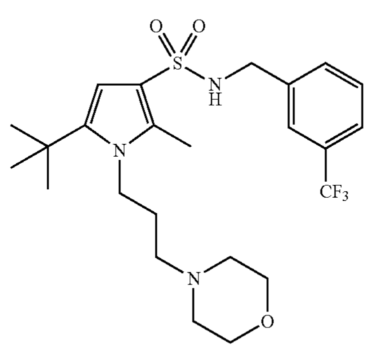 [SMILES: Cc1c(S(=O)(=O)NCc2cccc(C(F)(F)F)c2)cc(C(C)(C)C)n1CCCN1CCOCC1] | | 502 | 3.85 | 7 |

TABLE 22

| Compound No. | Structure | NMR | [M + H]⁺ | RT (min) | LC method |
|---|---|---|---|---|---|
| I-105 | 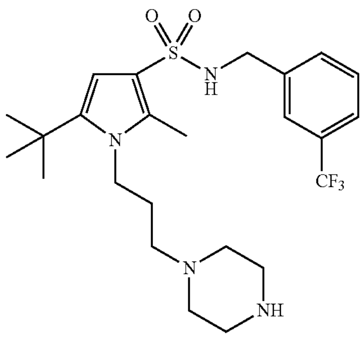 [SMILES: Cc1c(S(=O)(=O)NCc2cccc(C(F)(F)F)c2)cc(C(C)(C)C)n1CCCN1CCNCC1] | | 500 | 3.4 | 7 |
| I-106 | 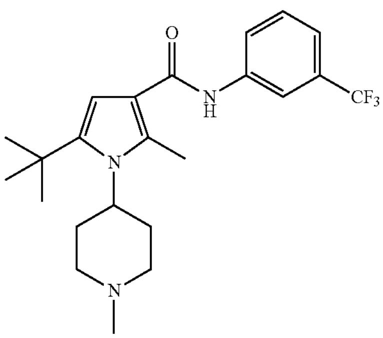 [SMILES: Cc1c(C(=O)Nc2cccc(C(F)(F)F)c2)cc(C(C)(C)C)n1C1CCN(C)CC1] | | 421.9 | 1.79 | 8 |
| I-107 | 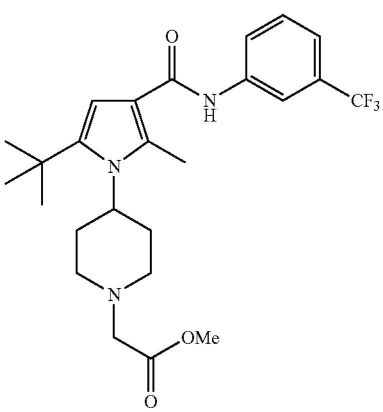 [SMILES: COC(=O)CN1CCC(n2c(C(C)(C)C)cc(C(=O)Nc3cccc(C(F)(F)F)c3)c2C)CC1] | 1H-NMR (300 Mz) (CDCl3): 1.39 (9H, s), 1.84 (2H, d, J = 12.6 Hz), 2.40-2.57 (4H, m), 2.76 (3H, s), 3.12 (2H, d, J = 10.2 Hz), 3.33 (2H, s), 3.74 (3H, s), 4.35-4.43 (1H, m), 6.07 (1H, s), 7.30 (1H, d, J = 7.5 Hz), 7.42 (1H, t, J = 7.8 Hz), 7.51 (1H, s), 7.79 (1H, d, J = 8.4 Hz), 7.85 (1H, s). | 479.9 | 3.4 | 5 |
| I-108 | 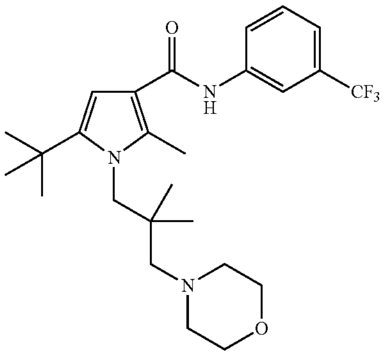 [SMILES: Cc1c(C(=O)Nc2cccc(C(F)(F)F)c2)cc(C(C)(C)C)n1CC(C)(C)CN1CCOCC1] | | 480 | 3.32 | 9 |

TABLE 22-continued
| Compound No. | Structure | NMR | [M + H]⁺ | RT (min) | LC method |
|---|---|---|---|---|---|
| I-109 | 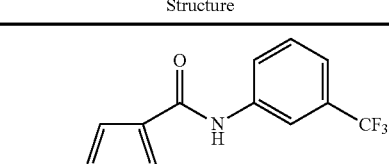 | | 491 | 3.2 | 5 |
TABLE 23
| Compound No. | Structure | NMR | [M + H]⁺ | RT (min) | LC method |
|---|---|---|---|---|---|
| I-110 | 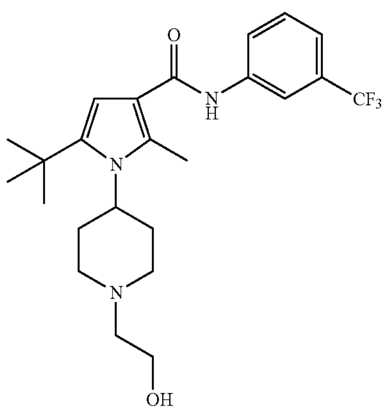 [SMILES: Cc1c(C(=O)Nc2cccc(C(F)(F)F)c2)cc(C(C)(C)C)n1C1CCN(CCO)CC1] | 1H-NMR (300 Mz) (CDCl3): 1.37 (9H, s), 1.85-1.89 (2H, m), 2.20 (2H, t, J = 11.1 Hz), 2.41-2.54 (2H, m), 2.60 (2H, t, J = 5.1 Hz), 2.75 (3H, s), 3.12 (2H, d, J = 11.1 Hz), 3.65 (2H, t, J = 5.1 Hz), 4.37-4.46 (1H, m), 6.07 (1H, s), 7.31 (1H, d, J = 7.5 Hz), 7.42 (1H, t, J = 7.8 Hz), 7.51 (1H, s), 7.80 (1H, d, J = 7.8 Hz), 7.88 (1H, s). | 451.9 | 3.49 | 5 |
| I-111 | 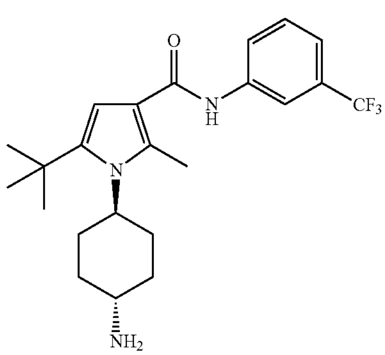 [SMILES: Cc1c(C(=O)Nc2cccc(C(F)(F)F)c2)cc(C(C)(C)C)n1[C@H]1CC[C@H](N)CC1] | | 422 | 3.39 | 5 |

TABLE 23-continued

| Compound No. | Structure | NMR | [M + H]+ | RT (min) | LC method |
|---|---|---|---|---|---|
| I-112 | 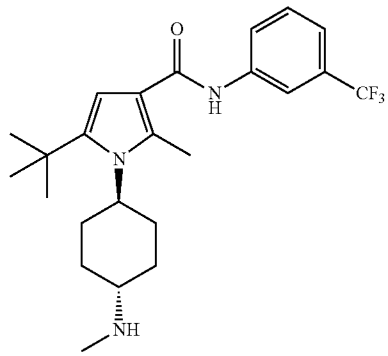 [SMILES: CN[C@H]1CC[C@H](n2c(C(C)(C)C)cc(C(=O)Nc3cccc(C(F)(F)F)c3)c2C)CC1] | | 435.9 | 3.35 | 5 |
| I-113 | 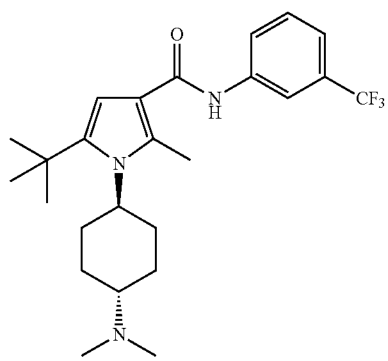 [SMILES: Cc1c(C(=O)Nc2cccc(C(F)(F)F)c2)cc(C(C)(C)C)n1[C@H]1CC[C@H](N(C)C)CC1] | | 449.9 | 3.41 | 5 |
| I-114 | 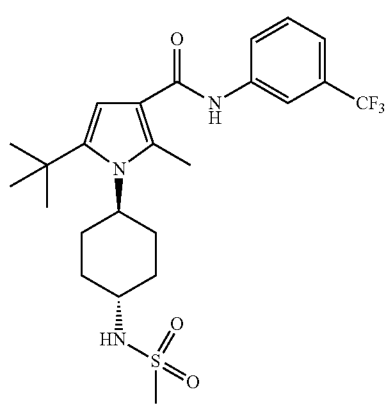 [SMILES: Cc1c(C(=O)Nc2cccc(C(F)(F)F)c2)cc(C(C)(C)C)n1[C@H]1CC[C@H](NS(C)(=O)=O)CC1] | | 500.2 | 3.98 | 5 |

TABLE 24

| Compound No. | Structure | NMR | [M + H]⁺ | RT (min) | LC method |
|---|---|---|---|---|---|
| I-115 | 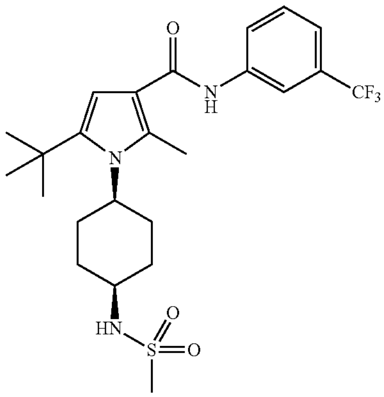 [SMILES: Cc1c(C(=O)Nc2cccc(C(F)(F)F)c2)cc(C(C)(C)C)n1[C@H]1CC[C@@H](NS(C)(=O)=O)CC1] | | 499.9 | 4.67 | 5 |
| I-116 | 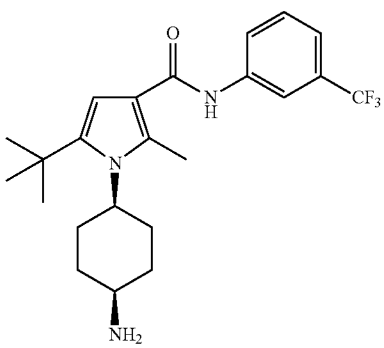 [SMILES: Cc1c(C(=O)Nc2cccc(C(F)(F)F)c2)cc(C(C)(C)C)n1[C@H]1CC[C@@H](N)CC1] | | 422 | 3.33 | 5 |
| I-117 | 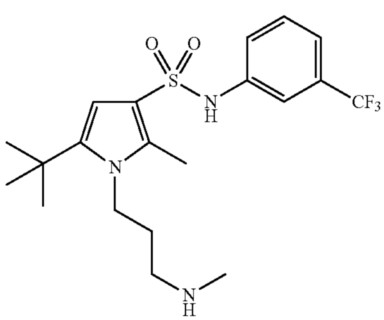 [SMILES: CNCCCn1c(C(C)(C)C)cc(S(=O)(=O)Nc2cccc(C(F)(F)F)c2)c1C] | 1H-NMR (CDCl3) δ: 1.22 (9H, s), 1.58-1.66 (2H, m), 2.16 (3H, 9), 2.36 (3H, s), 2.57 (2H, t, J = 6.6 Hz), 3.84-3.90 (2H, m), 6.09 (1H, s), 7.15-7.21 (2H, m), 7.28-7.30 (2H, m). | 431.9 | 3.78 | 10 |
| I-118 | 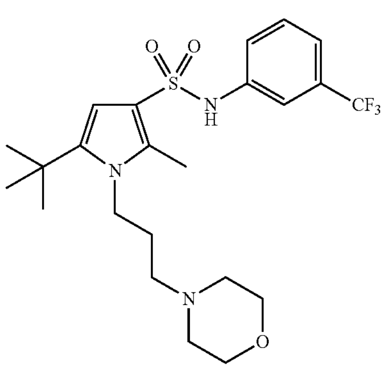 [SMILES: Cc1c(S(=O)(=O)Nc2cccc(C(F)(F)F)c2)cc(C(C)(C)C)n1CCCN1CCOCC1] | | 487.9 | 4.2 | 10 |

TABLE 24-continued

| Compound No. | Structure | NMR | [M + H]+ | RT (min) | LC method |
|---|---|---|---|---|---|
| I-119 | 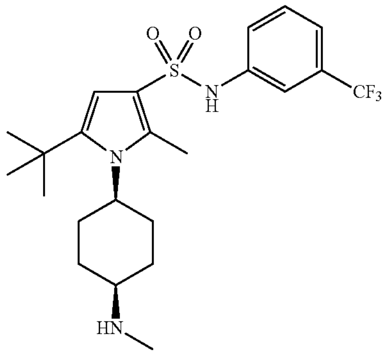 [SMILES: CN[C@H]1CC[C@@H](n2c(C(C)(C)C)cc(S(=O)(=O)Nc3cccc(C(F)(F)F)c3)c2C)CC1] | | 435.9 | 3.38 | 5 |

TABLE 25

| Compound No. | Structure | NMR | [M + H]+ | RT (min) | LC method |
|---|---|---|---|---|---|
| I-120 | 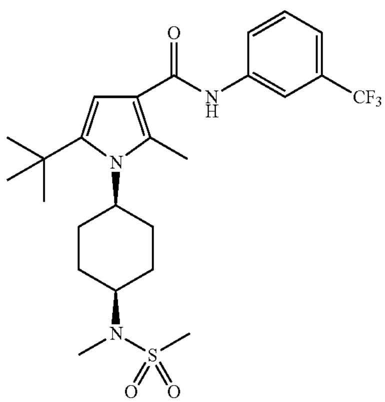 [SMILES: Cc1c(C(=O)Nc2cccc(C(F)(F)F)c2)cc(C(C)(C)C)n1[C@H]1CC[C@@H](N(C)S(C)(=O)=O)CC1] | | 514.3 | 4.24 | 5 |
| I-121 | 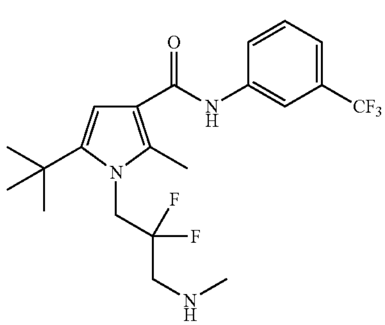 [SMILES: CNCC(F)(F)Cn1c(C(C)(C)C)cc(C(=O)Nc2cccc(C(F)(F)F)c2)c1C] | 1H-NMR (CDCl3) δ: 1.38 (9H, s), 2.53 (3H, s), 2.59 (3H, s), 3.00 (2H, t, J = 13.2 Hz), 4.60 (2H, t, J = 14.4 Hz), 6.19 (1H, s), 7.32 (1H, d, J = 7.8 Hz), 7.43 (1H, t, J = 7.8 Hz), 7.55 (1H, s), 7.79 (1H, d, J = 8.1 Hz), 7.89 (1H, s). | 432.3 | 3.21 | 5 |

TABLE 25-continued

| Compound No. | Structure | NMR | [M + H]+ | RT (min) | LC method |
|---|---|---|---|---|---|
| I-122 | 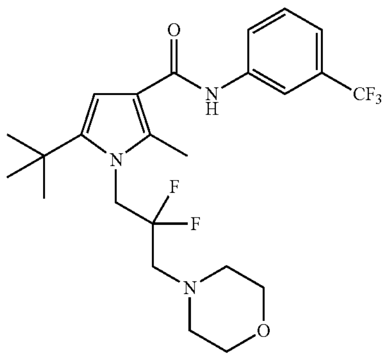 [SMILES: Cc1c(C(=O)Nc2cccc(C(F)(F)F)c2)cc(C(C)(C)C)n1CC(F)(F)CN1CCOCC1] | | 488.3 | 3.82 | 5 |
| I-123 | 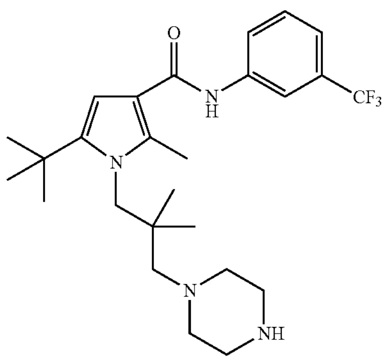 | | 479 | 2.62 | 6 |
| I-124 | 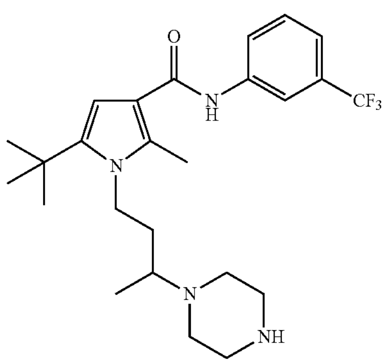 [SMILES: Cc1c(C(=O)Nc2cccc(C(F)(F)F)c2)cc(C(C)(C)C)n1CCC(C)N1CCNCC1] | | 465 | 3 | 5 |

TABLE 26

| Compound No. | Structure | NMR | [M + H]+ | RT (min) | LC method |
|---|---|---|---|---|---|
| I-125 | 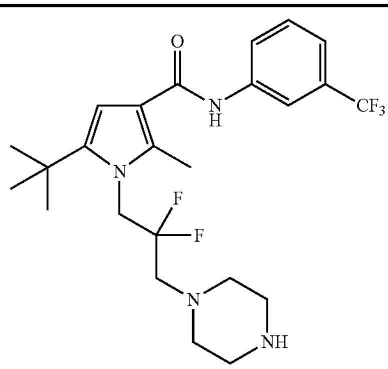 | | 487.3 | 3.41 | 5 |

TABLE 26-continued

| Compound No. | Structure | NMR | [M + H]⁺ | RT (min) | LC method |
|---|---|---|---|---|---|
| I-126 | 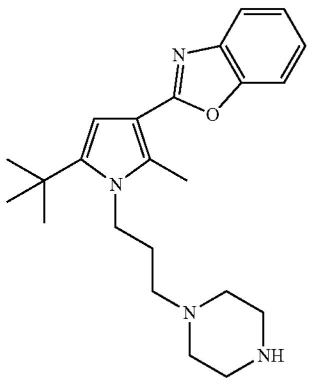 [SMILES: Cc1c(-c2nc3ccccc3o2)cc(C(C)(C)C)n1CCCN1CCNCC1] | 1H-NMR (CDCl3) δ: 1.42 (9H, s), 1.89-1.92 (2H, m), 2.41-2.45 (6H, m), 2.72 (3H, s), 2.91 (4H, t, J = 9.6 Hz), 4.03-4.09 (2H, m), 6.54 (1H, s), 7.21-7.27 (2H, m), 7.47 (1H, d, J = 8.4 Hz), 7.66 (1H, d, J = 8.4 Hz). | 381.4 | 3.9 | 10 |
| I-127 | 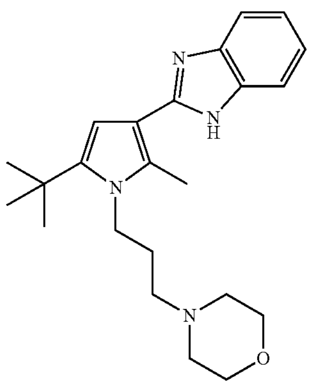 [SMILES: Cc1c(-c2nc3ccccc3[nH]2)cc(C(C)(C)C)n1CCCN1CCOCC1] | | 381.4 | 3.23 | 7 |
| I-128 | 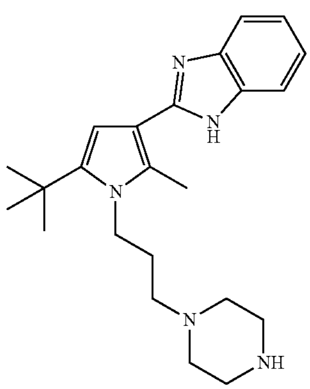 [SMILES: Cc1c(-c2nc3ccccc3[nH]2)cc(C(C)(C)C)n1CCCN1CCNCC1] | | 380.4 | 2.04 | 10 |
| I-129 | 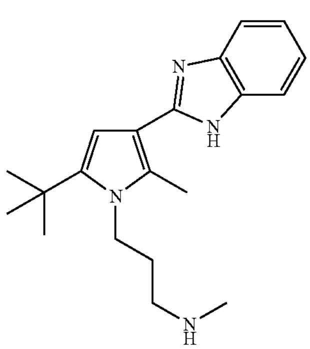 [SMILES: CNCCCn1c(C(C)(C)C)cc(-c2nc3ccccc3[nH]2)c1C] | 1H-NMR (DMSO-d6) δ: 1.37 (9H, s), 1.77 (2H, brs), 2.30 (3H, brs), 2.58 (2H, brs), 2.70 (3H, s), 4.04-4.07 (2H, m), 6.42 (1H, s), 7.06-7.07 (2H, m), 7.36 (1H, brs), 7.49 (1H, brs), 12.01 (1H, s). | 325.7 | 2.24 | 10 |

By carrying out the same reactions as in the above-described methods, the following compounds can be synthesized.
[Formula 104]
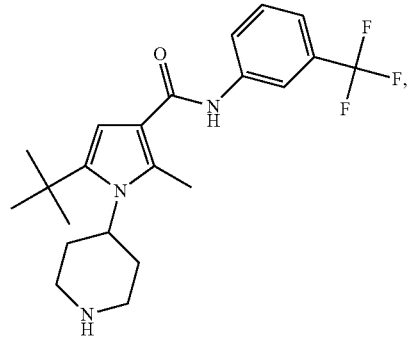
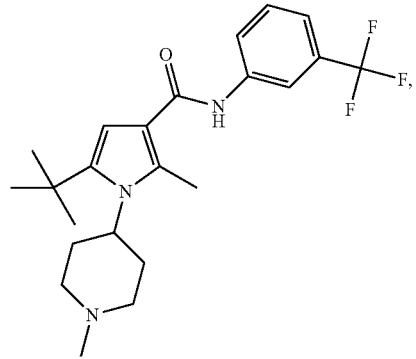
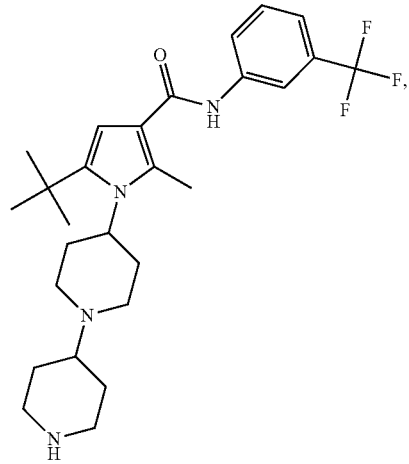
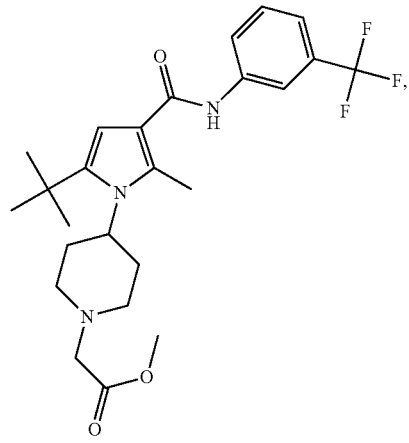
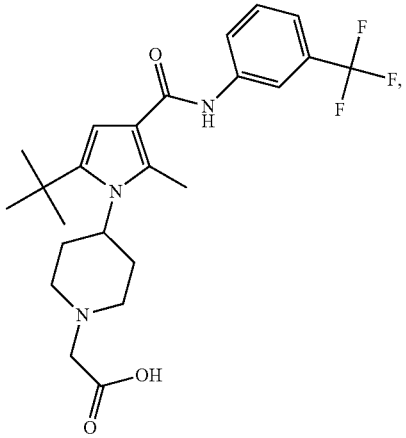
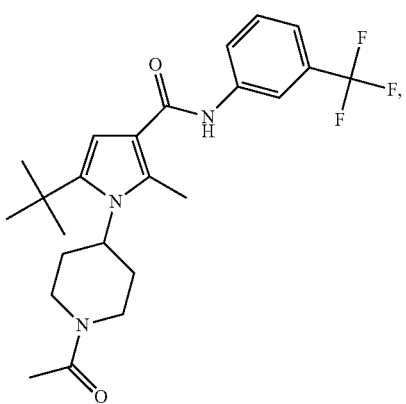
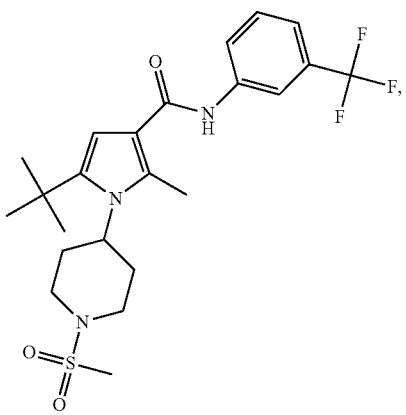
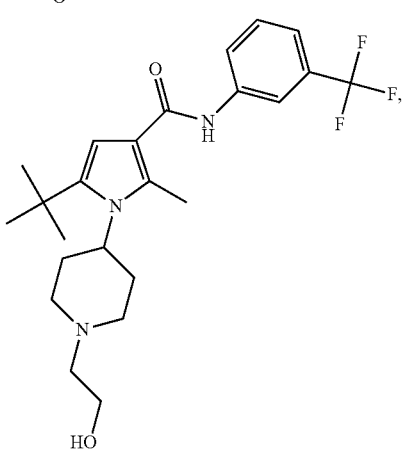

201
-continued
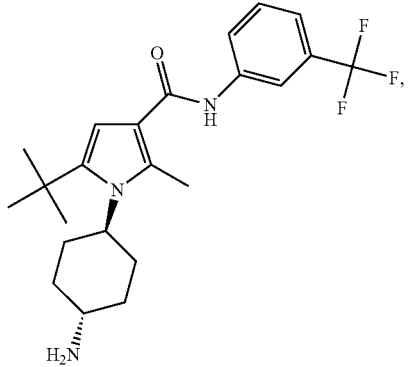
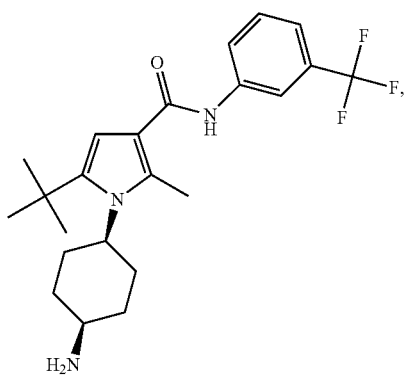
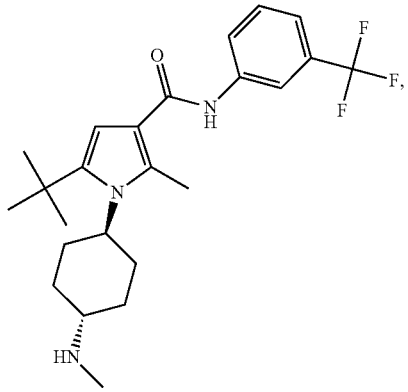
202
-continued
[Formula 105]
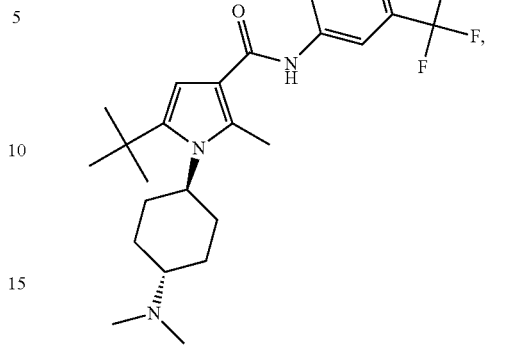
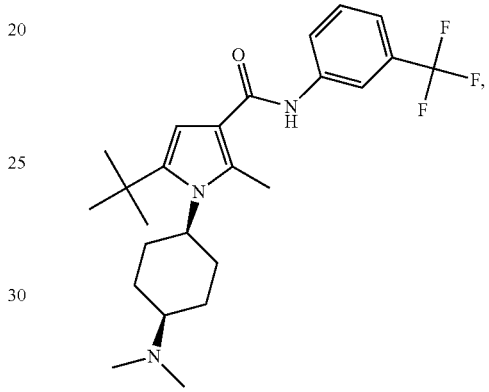
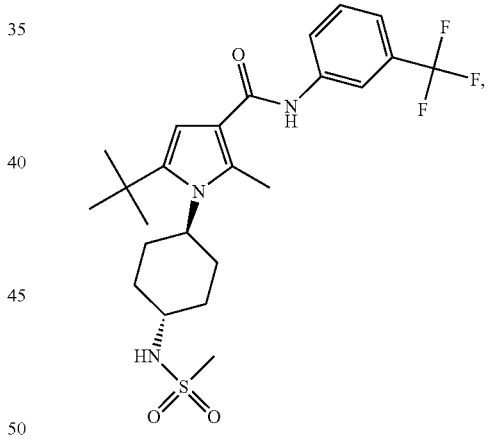
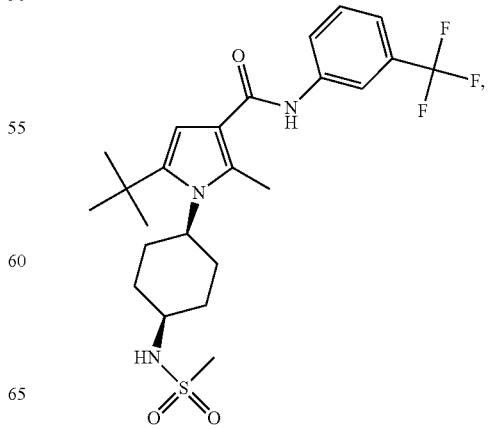

203
-continued
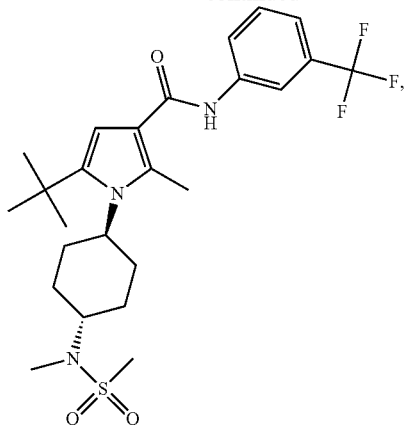
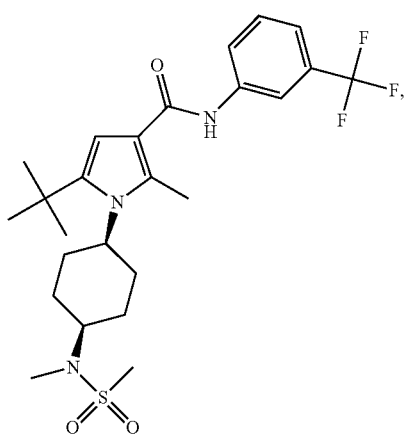
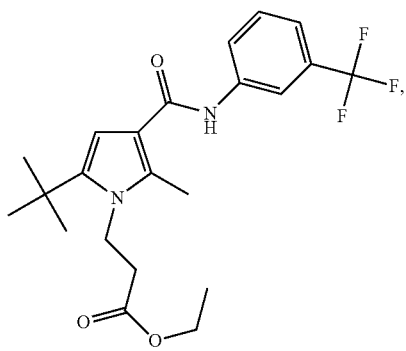
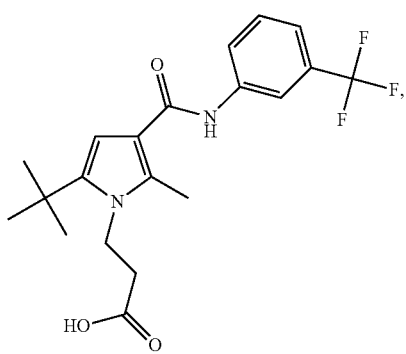
204
-continued
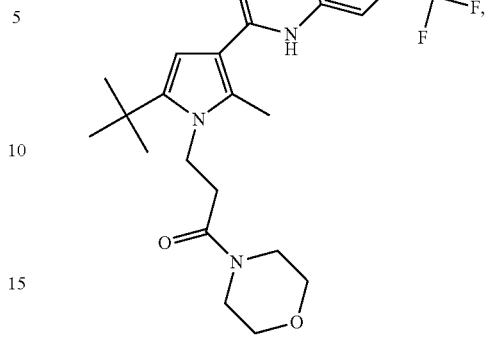
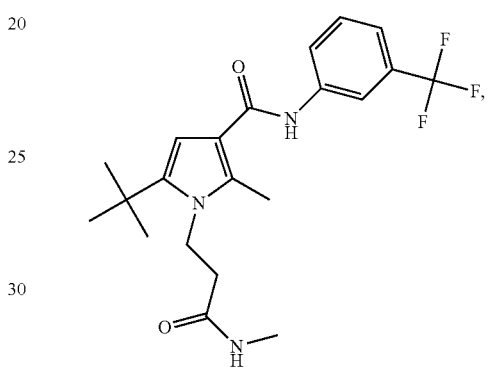
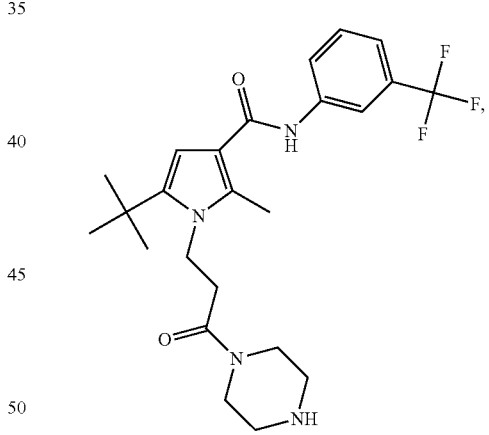
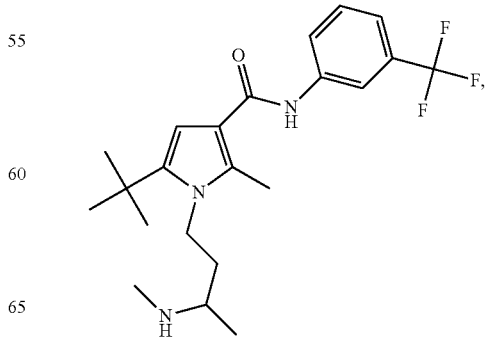

[Formula 106]
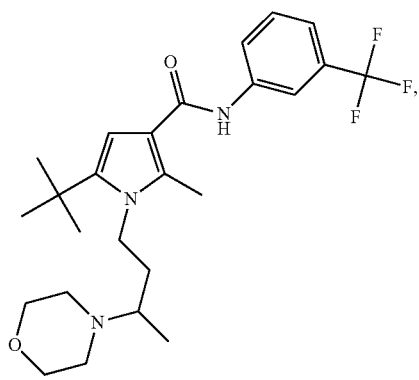
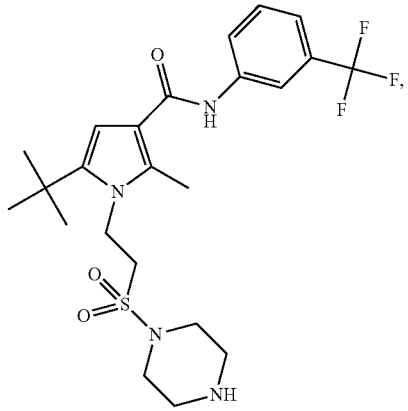
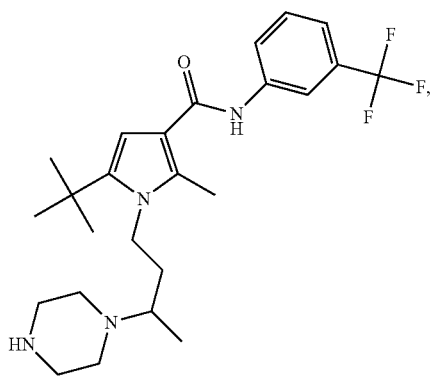
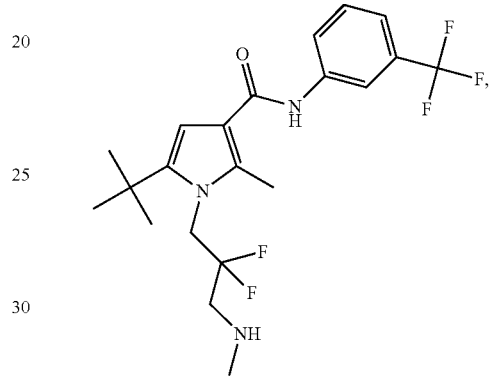
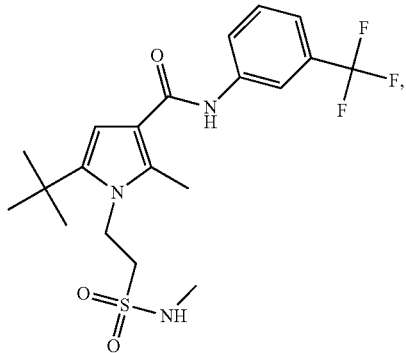
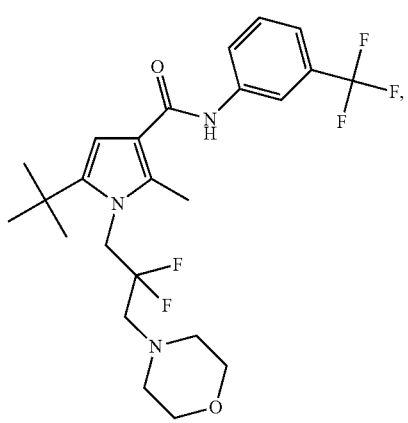
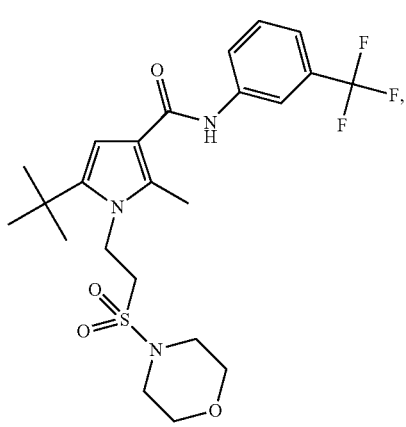
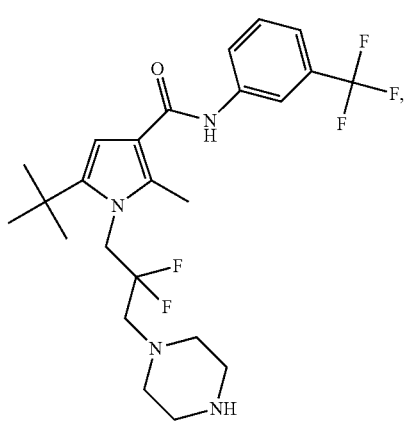

207
-continued
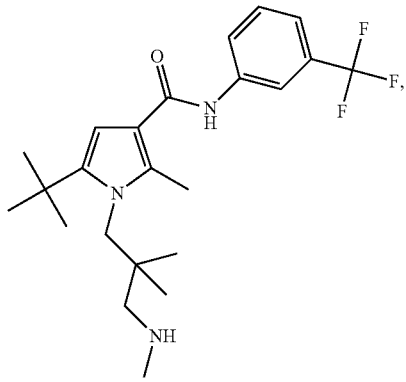
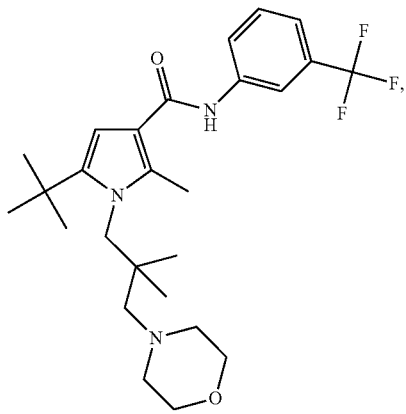
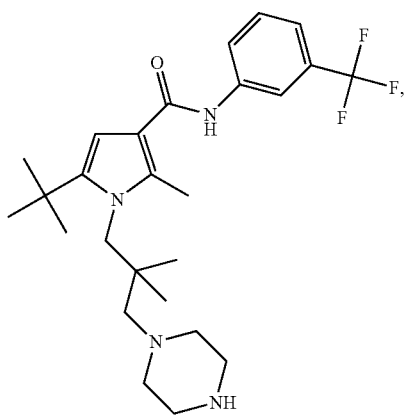
[Formula 107]
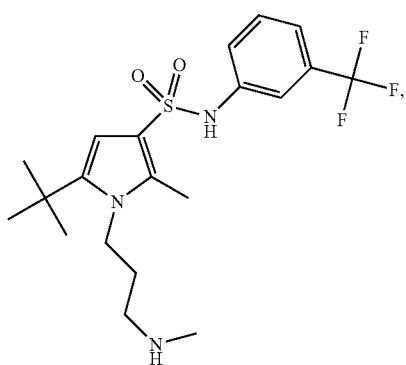
208
-continued
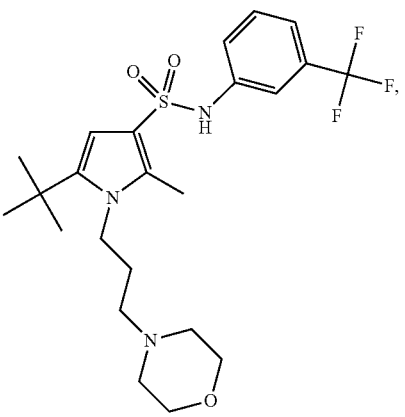
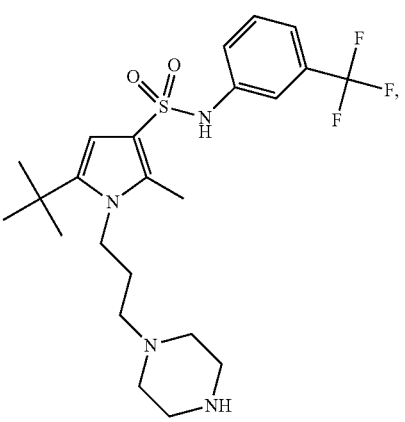
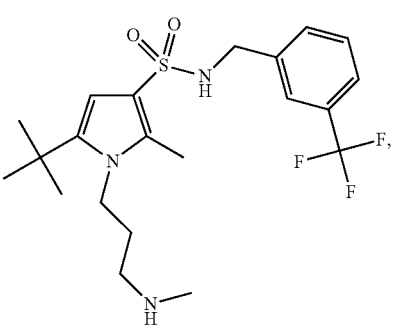
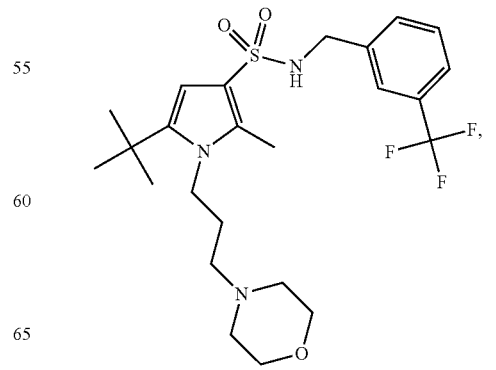

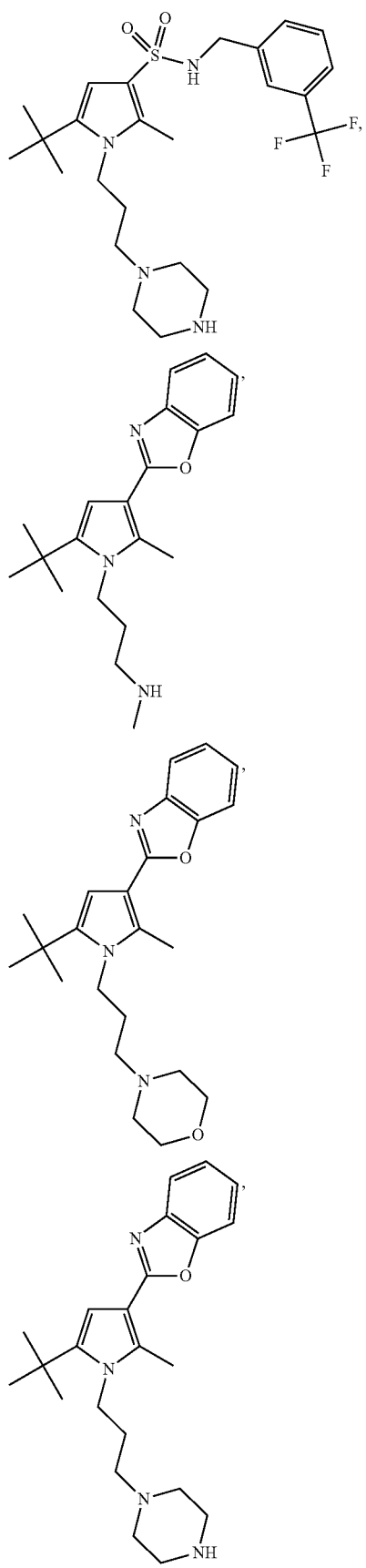
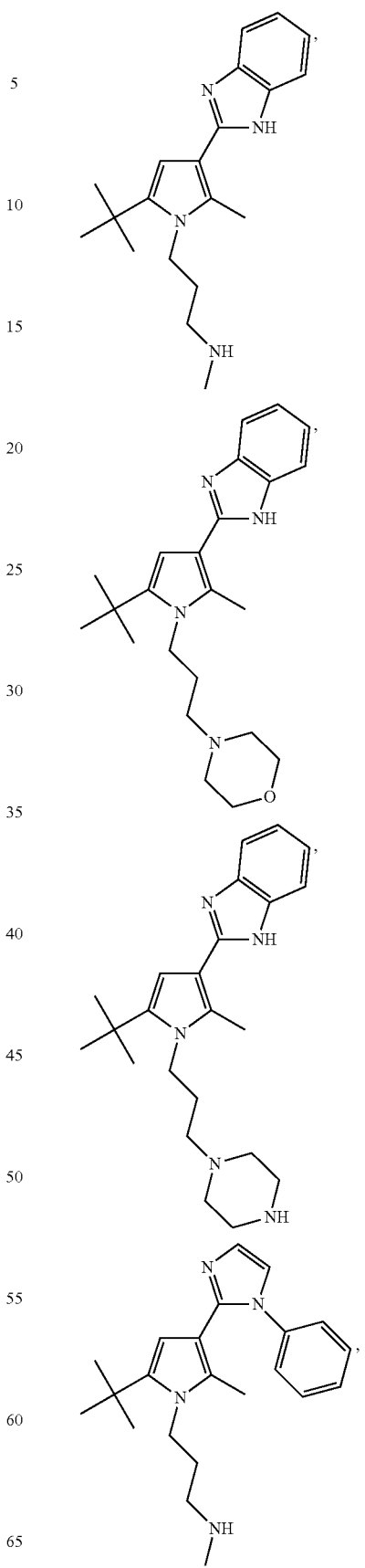

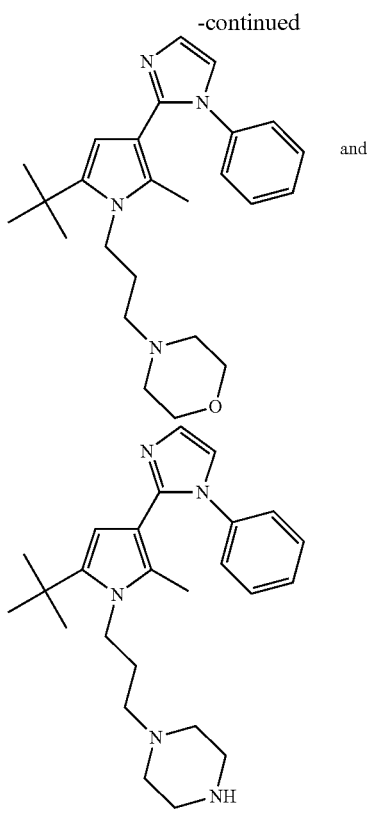

and

Test Example 1

Measurement of TRPV4 Inhibitory Activity

For each compound, TRPV4 inhibitory activity was measured using cells.
(1) The TRPV4 inhibitory activity was measured using CHO-K1 cells stably expressing human TRPV4 (hTRPV4/CHO cells).
(2) In the day before the experimental day, frozen cell were thawed and washed with the culture medium (MEM-α, 10% FBS, 2 mmol/L GlutaMax, 50 unit Penicillin, 50 μg/mL Streptomycin). Then cells were suspended in the culture medium.
(3) The 384-well plates which hTRPV4/CHO cells were seeded at densities of 4000 cells/well in the culture medium and cultured in a $CO_2$ incubator in the presence of 5% $CO_2$ at 37° C. for overnight was used as assay plates.
(4) The assay plate was washed with assay buffer (Hanks, 20 mmol/L HEPES, 2.5 mmol/L probenecid, pH7.4), and the buffer were remained at 20 μL/well.
(5) 10 μl of dye loading buffer (9 μmol/L Fluo 4-AM, 0.09% Pluronic F-127/assay buffer) was added to each well, then the assay plate was incubated in a $CO_2$ incubator in the presence of 5% $CO_2$ at 37° C. for one hour. (final 3 μmol/L Fluo4-AM).
(6) The assay plate was washed with the assay buffer, and the buffers were remained at 20 μL/well. Then the assay plate was incubated for 10 min at room temperature.
(7) Diluted compound solution was dispensed to each well in the compound plate, and mixed with built-in Pipette and Mixer of the Fluorescence analysis system FLIPR TETRA (Molecular devices).
(8) After incubation for 5 min, 20 μL of 4α-PDD solution were applied to each well of assay plate and mixed with the FLIPR TETRA. (final 1 μmol/L 4α-PDD)
(9) The fluorescent intensity was measured with FLIPR TETRA system for 10 min from the point of time addition the compound solution, at Ex 470-495 nm, Em 515-575 nm wavelength.

TRPV4 inhibitory activity ($IC_{50}$ value and Ki value) of a compound was evaluated according to the following procedure.
(10) In the presence of the compound, the difference between maximal and minimal of fluorescent intensity value for 5 min from just before addition of 4α-PDD solution was calculated, and it was referred as Max-Min value. Max-Min value of the Ruthenium Red at 20 μM was defined as 100% inhibitory activity, Max-Min value in the absence of the compound was defined as 0% inhibitory activity. The TRPV4 inhibitory activity of the compound was calculated by the following formula.

(1−(Max-Min value of the compound−100% inhibitory activity)/(0% inhibitory activity−100% inhibitory activity))×100

(11) Inhibitory activity was calculated at 10 points with three fold serial dilution, in the final concentration of the compound from 10 μmmol/L to 0.5 nmol/L, the $IC_{50}$ value was calculated by logistic approximation method.
(12) In the absence of the compound, the fluorescent intensity was measured as the same method with 10, 1, 0.5, 0.2, and 0 μmol/L as final concentration of 4α-PDD. The difference of minimal and maximal fluorescent intensity value for 5 min from just before addition of 4α-PDD solution was calculated, and it was referred as Max-Min value. Max-Min value of the 4α-PDD at 10 μmol/L was defined as 100% activity, Max-Min value in the absence of 4α-PDD was defined as 0% activity. The TRPV4 activity of each concentration of 4α-PDD was calculated by the following formula.

(Max-Min value of the each 4α-PDD concentration−0% activity)/(100% activity−0% activity))×100

(13) Effective activity was calculated in 5 concentrations of 4α-PDD the above. The $EC_{50}$ value was calculated by logistic approximation method. The Ki value of a compound was calculated by the following formula.

Ki (nmol/L)=$IC_{50}$ value (nmol/L)/(1+1000 (test 4α-PDD concentration (nmol/L)/EC50 value (nmol/L))

Test Example 2

Measurement of TRPV4 Inhibitory Activity

For each compound, TRPV4 inhibitory activity was measured using cells.
(1) The TRPV4 inhibitory activity was measured using CHO-K1 cells stably expressing human TRPV4 (hTRPV4/CHO cells).
(2) In the day before the experimental day, frozen cell were thawed and washed with the culture medium (MEM-α, 10% FBS, 4 mmol/L L-Glutamine, 50 unit Penicillin, 50 μg/mL Streptomycin). Then cells were suspended in the culture medium.
(3) The 384-well plates which hTRPV4/CHO cells were seeded at densities of 4000 cells/well in the culture medium and cultured in a $CO_2$ incubator in the presence of 5% $CO_2$ at 37° C. for overnight was used as assay plates.
(4) The assay plate was washed with assay buffer (Hanks, 20 mmol/L HEPES, 2.5 mmol/L probenecid, pH7.4), and the buffer were remained at 20 μL/well.

(5) 10 μl of dye loading buffer (9 μmol/L Fluo 3-AM, 0.09% Pluronic F-127, 1% BSA/assay buffer), was added to each well, then the assay plate was incubated in a $CO_2$ incubator in the presence of 5% $CO_2$ at 37° C. for one hour. (final 3 μmol/L Fluo3-AM).
(6) The assay plate was washed with the assay buffer, and the buffers were remained at 20 μL/well. Then the assay plate was incubated for 10 min at room temperature.
(7) Diluted compound solution was dispensed to each well in the compound plate, and mixed with built-in Pipette and Mixer of the Fluorescence analysis system FLIPR 384 (Molecular devices).
(8) After incubation for 4 min, 25 μL of 4α-PDD solution were applied to each well of assay plate and mixed with the FLIPR TETRA. (final 600 nmol/L 4α-PDD)
(9) The fluorescent intensity was measured with FLIPR TETRA system for 7 min from the point of time addition the compound solution, at Ex 488 nm, Em 510-570 nm wavelength.

TRPV4 inhibitory activity ($IC_{50}$ value) of a compound was evaluated according to the following procedure.
(10) In the presence of the compound, the difference between maximal and minimal of fluorescent intensity value for 3 min from just before addition of 4α-PDD solution was calculated, and it was referred as Max-Min value. Max-Min value of the Ruthenium Red at 20 μM was defined as 100% inhibitory activity, Max-Min value in the absence of the compound was defined as 0% inhibitory activity. The TRPV4 inhibitory activity of the compound was calculated by the following formula.

(1−(Max-Min value of the compound−100% inhibitory activity)/(0% inhibitory activity−100% inhibitory activity))×100

(11) Inhibitory activity was calculated at 10 points with twice serial dilution, in the final concentration of the compound from 3.85 μg/mL to 7.5 ng/mL, the $IC_{50}$ value was calculated by logistic approximation method.

Test Example 3

Measurement of TRPV4 Inhibitory Activity

For each compound, TRPV4 inhibitory activity was measured using cells.
(1) The TRPV4 inhibitory activity was measured using CHO-K1 cells stably expressing human TRPV4 (hTRPV4/CHO cells).
(2) Frozen cells were thawed and subcultured with the medium (MEM-α, 10% FBS, 200 mmol/L Glutamine, 50 unit/mL penicillin, 50 μg/mL streptomycin, 1 mg/mL G418).
(3) The 96-well plates which hTRPV4/CHO cells were seeded at densities of $2 \times 10^4$ cells/well in the culture medium and cultured in a $CO_2$ incubator in the presence of 5% $CO_2$ at 37° C. for 24 h was used as assay plates.
(4) The assay plate was washed with assay buffer (Hanks, 1 mol/L HEPES, 250 mmol/L probenecid, pH7.4).
(5) Fluo-3, fluorescent dye for Ca influx assay was added to each well, then the assay plate was incubated in a $CO_2$ incubator in the presence of 5% $CO_2$ at 37° C. for one hour (final conc.; 5 μmmol/L Fluo-3).
(6) The assay plate was washed with the assay buffer, and the buffer was remained at 30 μL/well. Then the assay plate was incubated for 10 min at 37° C.
(7) Diluted compound solution was dispensed to each well in the compound plate, and mixed with built-in Pipette and Mixer of the fluorescence analysis system FDSS 3000 (Hamamatsu Photonics).
(8) 50 μL of 4α-PDD solution (concluding 0.1% Pluronic F-127) was applied to each well of assay plate and mixed.
(9) The fluorescent intensity was measured by FDSS 3000 for 8 min from the point of time addition the compound solution, at Ex 480 nm, Em 540 nm wavelength.

TRPV4 inhibitory activity (Ki value) of a compound was evaluated according to the following procedure.
(10) In the presence of the compound, the difference between maximal and minimal of fluorescent intensity value for 8 min from just before addition of 4α-PDD solution was calculated, and it was referred as Max-Min value. Max-Min value of the Ruthenium Red at 10 μM was defined as 100% inhibitory activity, Max-Min value in the absence of the compound was defined as 0% inhibitory activity. The TRPV4 inhibitory activity of the compound was calculated by the following formula.

(1−(Max-Min value of the compound−100% inhibitory activity)/(0% inhibitory activity−100% inhibitory activity))×100

(11) By the following formula, inhibitory activity was calculated at 10 points with three fold serial dilution, in the final concentration of the compound from 10 μmmol/L to 0.5 nmol/L. The IC50 value was calculated by dose-response curve.

100−[(fluorescent intensity in the presence of the compound−fluorescent intensity of back ground)/(total fluorescent intensity−fluorescent intensity of back ground)]×100

(12) In the presence of the compound, activity of 4α-PDD was measured at 9 points with three fold serial dilution from 20 μmol/L. Activity of 4α-PDD was calculated by the following formula.

(Max-Min value of the each 4α-PDD concentration−0% activity)/(100% activity−0% activity))×100

(13) Effective activity was calculated in 4α-PDD the above. The $EC_{50}$ value was calculated by dose-response curve.
(14) The Ki value of a compound was calculated by the following formula.

Ki (nmol/L)=$IC_{50}$ value (nmol/L)/([A]/$EC_{50}$ value (nmol/L))

[A]; Concentration of agonist (nmol/L)
The results of the compounds of the invention are shown in the following table.

TABLE 27

| Compound No. | Test 1 IC50 (nmol/L) | Test 1 Ki (nmol/L) | Test 2 IC50 (nmol/L) | Test 3 Ki (nmol/L) |
|---|---|---|---|---|
| I-001 | | | | 3955 |
| I-002 | 360 | | | 197 |
| I-003 | | | | 3066 |
| I-004 | | | | 1569 |
| I-005 | | | | 1700 |
| I-006 | 2300 | | | 1059 |
| I-007 | 8900 | | | 1454 |
| I-008 | 82 | | | 327 |
| I-009 | 1500 | | | 678 |
| I-010 | 800 | | | 714 |
| I-011 | | | | 1696 |
| I-012 | | | | 1143 |
| I-013 | | | | 453 |
| I-014 | | | | 355 |
| I-015 | 2600 | | | 1436 |
| I-016 | 130 | | | 191 |
| I-017 | | | | 1557 |
| I-018 | 330 | | | 169 |

TABLE 27-continued

| | Test 1 | | Test 2 | Test 3 |
|---|---|---|---|---|
| Compound No. | IC50 (nmol/L) | Ki (nmol/L) | IC50 (nmol/L) | Ki (nmol/L) |
| I-019 | | | | 1495 |
| I-020 | | | | 992 |
| I-021 | 610 | | | 379 |
| I-022 | 2400 | | | 2484 |
| I-023 | | | | 605 |
| I-024 | 340 | | | 755 |
| I-025 | 3200 | | | 1134 |
| I-026 | 860 | | | 427 |
| I-027 | 1800 | | | 936 |
| I-028 | 3800 | | | 1707 |
| I-029 | | | | 519 |
| I-030 | | | | 701 |
| I-031 | | | | 160 |
| I-032 | 640 | | | 1612 |
| I-033 | | | | 655 |
| I-034 | | | | 2619 |
| I-035 | | | | 771 |
| I-036 | | | | 1003 |
| I-037 | | | | 1802 |
| I-038 | | | | 352 |
| I-039 | | | | 282 |
| I-040 | | | | 1137 |
| I-041 | | | | 988 |
| I-042 | | | | 1118 |
| I-043 | | | | 1375 |
| I-044 | | | | 844 |
| I-045 | | | | 1722 |
| I-046 | | | | 1676 |
| I-047 | | | | 320 |
| I-048 | | | | 1312 |
| I-049 | 240 | | | 418 |
| I-050 | | | | 1140 |
| I-051 | | | | 590 |
| I-052 | | | | 707 |
| I-053 | | | | 978 |
| I-054 | | | | 1165 |
| I-055 | | | | 984 |
| I-056 | | | | 560 |
| I-057 | | | | 1793 |
| I-058 | | | | 1648 |
| I-059 | | | | 472 |
| I-060 | | | | 1352 |
| I-061 | | | | 1699 |
| I-062 | | | | 1392 |
| I-063 | 510 | | | 251 |
| I-064 | | | | 713 |
| I-065 | | | | 850 |
| I-066 | | | | 662 |
| I-067 | | | | 2366 |
| I-068 | | | | 1013 |
| I-069 | | | | 816 |
| I-070 | 590 | | | 1682 |
| I-071 | 260 | | | 196 |
| I-072 | 45 | | 21 | |
| I-073 | 340 | | 160 | |
| I-074 | 1700 | | 780 | |
| I-075 | 270 | | 130 | |
| I-076 | 9700 | | 4700 | |
| I-077 | 4700 | | 2000 | |
| I-078 | 4900 | | 2100 | |
| I-079 | 7800 | | 3200 | |
| I-080 | 7400 | | | 1801 |
| I-081 | 3900 | | | 1611 |
| I-082 | | | | 1437 |
| I-083 | 400 | | | 443 |
| I-084 | 1200 | | 1600 | |
| I-085 | 1300 | 590 | | |
| I-086 | 3400 | 1600 | | |
| I-087 | 710 | 320 | | |
| I-088 | 5800 | 2800 | | |
| I-089 | 8000 | 3900 | | |

TABLE 28

| | Test 1 | |
|---|---|---|
| Compound No. | IC50 (nmol/L) | Ki (nmol/L) |
| I-090 | 1100 | 380 |
| I-091 | 1500 | 560 |
| I-092 | 6400 | 2400 |
| I-093 | 1400 | 530 |
| I-094 | 6100 | 2200 |
| I-095 | 970 | 380 |
| I-096 | 420 | 130 |
| I-097 | 430 | 130 |
| I-098 | 1900 | 590 |
| I-099 | 5900 | 2100 |
| I-100 | 830 | 290 |
| I-101 | 7400 | 2600 |
| I-102 | 4200 | 1500 |
| I-103 | 7000 | 2400 |
| I-104 | 7700 | 2700 |
| I-105 | 8900 | 3100 |
| I-106 | 3900 | 1200 |
| I-107 | 6600 | 2100 |
| I-108 | 540 | 170 |
| I-109 | 6300 | 2300 |
| I-110 | 6600 | 2400 |
| I-111 | 4100 | 1500 |
| I-112 | 5600 | 1500 |
| I-113 | 5800 | 1500 |
| I-114 | 8700 | 2300 |
| I-115 | 6000 | 1600 |
| I-116 | 5300 | 1500 |
| I-117 | 9200 | 2500 |
| I-118 | 9200 | 2500 |
| I-119 | 5700 | 1800 |
| I-120 | 3500 | 1100 |
| I-121 | 1400 | 450 |
| I-122 | 780 | 240 |
| I-123 | 1400 | 450 |
| I-124 | 260 | |
| I-125 | 1500 | |
| I-126 | 4500 | |
| I-127 | 3100 | |
| I-128 | 5400 | |
| I-129 | 6400 | |

[CYP3A4 Fluorescent MBI Test]

The CYP3A4 fluorescent MBI test is a test of investigating enhancement of CYP3A4 inhibition of a compound by a metabolism reaction, and the test was performed using, as CYP3A4 enzyme expressed in *Escherichia coli* and employing, as an index, a reaction in which 7-benzyloxytrifluoromethylchmarin (7-BFC) is debenzylated by the CYP3A4 enzyme to produce a metabolite, 7-hydroxytrifluoromethylchmarin (HFC) emitting fluorescent light.

The reaction conditions were as follows: substrate, 5.6 μmol/L 7-BFC; pre-reaction time, 0 or 30 minutes; reaction time, 15 minutes; reaction temperature, 25° C. (room temperature); CYP3A4 content (expressed in *Escherichia coli*), at pre-reaction 62.5 μmol/mL, at reaction 6.25 μmol/mL (at 10-fold dilution); test drug concentration, 0.625, 1.25, 2.5, 5, 10, 20 μmol/L (six points).

An enzyme in a K-Pi buffer (pH 7.4) and a test drug solution as a pre-reaction mixture were added to a 96-well plate at the composition of the pre-reaction, a part of it was transferred to another 96-well plate so that it was 1/10 diluted by a substrate in a K-Pi buffer, NADPH as a co-factor was added to initiate a reaction as an index (without preincubation) and, after a predetermined time of a reaction, acetonitrile/0.5 mol/L Tris (trishydroxyaminomethane)=4/1 was added to stop the reaction. In addition, NADPH was added to a remaining preincubation solution to initiate a preincubation (with preincubation) and, after a predetermined time of a preincubation, a part was transferred to another plate so that it was 1/10 diluted with a substrate and a K-Pi buffer to initiate a reaction as an index. After a predetermined time of a reaction, acetonitrile/0.5 mol/L Tris (trishydroxyaminomethane)=4/1 was added to stop the reaction. For the plate on which each index reaction had been performed, a fluorescent value of 7-HFC which is a metabolite was measured with a fluorescent plate reader. (Ex=420 nm, Em=535 nm).

Addition of only DMSO which is a solvent dissolving a drug to a reaction system was adopted as a control (100%), remaining activity (%) was calculated at each concentration of a test drug added as the solution, and 1050 was calculated by reverse-presumption by a logistic model using a concentration and an inhibition rate. When a difference between IC50 values is 5 µM or more, this was defined as (+) and, when the difference is 3 µM or less, this was defined as (−).

[CYP Inhibition Test]

Using commercially available pooled human hepatic microsome, and employing, as markers, 7-ethoxyresorufin O-deethylation (CYP1A2), tolbutamide methyl-hydroxylation (CYP2C9), mephenyloin 4'-hydroxylation (CYP2C19), dextromethorphan O-demethylation (CYP2D6), and terfenedine hydroxylation as typical substrate metabolism reactions of human main five CYP enzyme forms (CYP1A2, 2C9, 2C19, 2D6, 3A4), an inhibitory degree of each metabolite production amount by a test compound was assessed.

The reaction conditions were as follows: substrate, 0.5 µmol/L ethoxyresorufin (CYP1A2), 100 µmol/L tolbutamide (CYP2C9), 50 µmol/L S-mephenitoin (CYP2C19), 5 µmol/L dextromethorphan (CYP2D6), 1 µmol/L terfenedine (CYP3A4); reaction time, 15 minutes; reaction temperature, 37° C.; enzyme, pooled human hepatic microsome 0.2 mg protein/mL; test drug concentration, 1, 5, 10, 20 µmol/L (four points).

Each five kinds of substrates, human hepatic microsome, or a test drug in 50 mM Hepes buffer as a reaction mixture was added to a 96-well plate at the composition as described above, NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and tributamide hydroxide (CYP2CP metabolite), mephenyloin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%), remaining activity (%) was calculated at each concentration of a test drug added as the solution and $IC_{50}$ was calculated by reverse presumption by a logistic model using a concentration and an inhibition rate.

[FAT Test]

20 µL of freezing-stored rat typhoid bacillus (Salmonella typhimurium TA98 strain, TA100 strain) was inoculated on 10 mL of a liquid nutrient medium (2.5% Oxoid nutrient broth No. 2), and this was cultured before shaking at 37° C. for 10 hours. 9 mL of a bacterial solution of the TA98 strain was centrifuged (2000×g, 10 minutes) to remove a culturing solution, the bacteria was suspended in 9 mL of a Micro F buffer ($K_2HPO_4$: 3.5 g/L, $KH_2PO_4$: 1 g/L, $(NH_4)_2SO_4$: 1 g/L, trisodium citrate dehydrate: 0.25 g/L, $MgSO_4.7H_2O$: 0.1 g/L), the suspension was added to 110 mL of an Exposure medium (Micro F buffer containing Biotin: 8 µg/mL, histidine: 0.2 µg/mL, glucose: 8 mg/mL), and the TA100 strain was added to 120 mL of the Exposure medium relative to 3.16 mL of the bacterial solution to prepare a test bacterial solution. Each 12 µL of a test substance DMSO solution (8 stage dilution from maximum dose 50 mg/mL at 2-fold ratio), DMSO as a negative control, 50 µg/mL of 4-nitroquinoline-1-oxide DMSO solution for the TA98 strain, 0.25 µg/mL of 2-(furyl)-3-(5-nitro-2-furyl)acrylamide DMSO solution for the TA100 strain under the non-metabolism activating condition, 40 µg/mL of 2-aminoanthracene DMSO solution for the TA98 strain, 20 µg/mL of 2-aminoanthracene DMSO solution for the TA100 strain under, the metabolism activating condition as a positive control, and 588 µL of the test bacterial solution (a mixed solution of 498 µl of the test bacterial solution and 90 µL of S9 mix under the metabolism activating condition) were mixed, and this was shaking-cultured at 37° C. for 90 minutes. 460 µL of the bacterial solution exposed to the test substance was mixed with 2300 µL of an Indicator medium (Micro F buffer containing biotin: 8 µg/mL, histidine: 0.2 µg/mL, glucose: 8 mg/mL, Bromo Cresol Purple: 37.5 µg/mL), each 50 µl was dispensed into microplate 48 wells/dose, and this was subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turned to yellow in 48 wells per dose is counted, and was assessed by comparing with a negative control group. (−) means that mutagenicity is negative and (+) is positive.

[Solubility Test]

The solubility of each compound is determined under 1% DMSO addition conditions. A 10 mmol/L solution of the compound is prepared with DMSO, and 6 µL of the compound solution is added to 594 µL of an artificial intestinal juice (water and 118 mL of 0.2 mol/L NaOH reagent are added to 250 mL of 0.2 mol/L potassium dihydrogen phosphate reagent to reach 1000 mL) with a pH of 6.8. The mixture is left standing for 16 hours at 25° C., and the mixture is vacuum-filtered. The filtrate is two-fold diluted with methanol/water=1/1, and the compound concentration in the filtrate is measured with HPLC or LC/MS/MS by the absolute calibration method.

(Result)
I-002:19.3 µmol/L
I-003:>50 µmol/L
I-004:39.2 µmol/L
I-005:>50 µmol/L
I-007:>50 µmol/L
I-009:>50 µmol/L
I-014:>50 µmol/L
I-016:>50 µmol/L
I-017:>50 µmol/L
I-018:>50 µmol/L
I-019:>50 µmol/L
I-021:>50 µmol/L
I-022:>50 µmol/L
I-022:>50 µmol/L
I-026:10.1 µmol/L
I-031:>50 µmol/L
I-033:26.8 µmol/L
I-035:>50 µmol/L
I-038:>50 µmol/L
I-039:>50 µmol/L
I-071:18.5 µmol/L
I-073:28.9 µmol/L
I-074:>50 µmol/L
I-076:>50 µmol/L
I-077:>50 µmol/L
I-078:20.1 µmol/L I-079:40.2 µmol/L
I-080:24.3 µmol/L
I-082:>50 µmol/L
I-085:14.5 µmol/L
I-086:8.3 µmol/L
I-087:5.2 µmol/L
I-088:35.1 µmol/L

[Metabolism Stability Test]

Using a commercially available pooled human hepatic microsomes, a test compound was reacted for a constant time, a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 µL of the reaction mixture was added to 100 µL of a methanol/acetonitrile=1/1 (v/v), mixed and centrifuged at 3000 rpm for 15 minutes. The test compound in the supernatant was quantified by LC/MS/MS, and a remaining amount of the test compound after the reaction was calculated, letting a compound amount at 0 minute reaction time to be 100%. Hydrolysis reaction was performed in the absence of NADPH and glucuronidation reaction was in the presence of 5 mM UDP-glucuronic acid in place of NADPH, followed by similar operations.

(Result)
Compound concentration: 2 µmol/L
I-003:71.4%
I-007:85%
I-014:66.3%
I-018:70.6%
I-019:89.1%
Compound concentration: 0.5 µmol/L
I-023:96.9%
I-031:92.2%
I-035:82.2%
I-076:92.7%

[hERG Test]

For the purpose of assessing risk of an electrocardiogram QT interval prolongation, effects on delayed rectifier K$^+$ current ($I_{Kr}$), which plays an important role in the ventricular repolarization process, was studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.), $I_{Kr}$ induced by depolarization pulse stimulation at +40 mV for 2 seconds and, further, repolarization pulse stimulation at −50 mV for 2 seconds was recorded. After the generated current was stabilized, extracellular solution (NaCl: 135 mmol/L, KCl: 5.4 mmol/L, $CaCl_2.2H_2O$: 1.8 mmol/L, $MgCl_2.6H_2O$: 1 mmol/L, glucose: 10 mmol/L, HEPES (4-(2-hydroxyethyl)-1-piperazineethanesulfonic acid): 10 mmol/L, pH=7.4) in which the test compound had been dissolved at an objective concentration was applied to the cell under the room temperature condition for 10 minutes. From the recording $I_{Kr}$, an absolute value of the tail peak current was measured based on the current value at the resting membrane potential using an analysis software (DataXpress ver. 1, Molecular Devices Corporation). Further, the % inhibition relative to the tail peak current before application of the test substance was calculated, and compared with the vehicle-applied group (0.1% dimethyl sulfoxide solution) to assess influence of the test substance on $I_{Kr}$.

(Result) % inhibition was shown at 1 µmol/L of test compound.
I-026:11.7%
I-082:13.5%

[BA Test]

An experimental material and a method for examining oral absorbability
(1) Animals used rats or mice were used.
(2) Breeding condition: chow and sterilized tap water were allowed to be taken in freely.
(3) Setting of a dosage and grouping: a predetermined dosage was administered orally or intravenously. Groups were formed as shown below. (A dosage varied depending on each compound)

Oral administration 1-30 mg/kg (n=2 to 3)

Intravenous administration 0.5-10 mg/kg (n=2 to 3)

(4) Preparation of administered liquid: In oral administration, a solution or suspension was administered. In intravenous administration, after solubilization, the administration was performed.
(5) Method of Administration: In oral administration, compulsory administration to the stomach was conducted using an oral probe.

In intravenous administration, administration from the caudal vein was conducted using a syringe with an injection needle.
(6) Evaluation item: Blood was chronologically collected, and then the drug concentration in blood plasma was measured using a LC/MS/MS.
(7) Statistical analysis: With regard to a shift in plasma concentration, the plasma concentration-time area under the curve (AUC) was calculated using a nonlinear least-squares program WinNonlin®. Bioavailability (BA) was calculated from the AUCs of the oral administration group and the intravenous administration group, respectively.

(Result) Mouse, Oral administration 1 mg/kg
I-014:15.2%
I-031:24.4%

Formulation Example 1

A granule containing the following ingredient is prepared.

| Ingredient | |
|---|---|
| Compound represented by any of the formula (I) to (VI) | 10 mg |
| Lactose | 700 mg |
| Corn starch | 274 mg |
| HPC-L | 16 mg |

The compound represented by any of the formula (I) to (VI) and lactose are passed through a 60 mesh sieve. Corn starch is passed through a 120 mesh sieve. These are mixed with a V-type mixing machine. An aqueous solution of HPC-L (low viscosity hydroxypropylcellulose) is added to a mixture powder, and this is kneaded, granulated (extrusion granulation, pore diameter 0.5 to 1 mm), and dried. The resulting dry granule is sieved with a vibration sieve (12/60 mesh) to obtain a granule.

Formulation Example 2

A powder for filling into a capsule containing the following ingredients is prepared.

| Ingredient | |
|---|---|
| Compound represented by any of the formula (I) to (VI) | 15 mg |
| Lactose | 90 mg |
| Corn starch | 42 mg |
| HPC-L | 3 mg |

The compound represented by any of the formula (I) to (VI), and lactose are passed through a 60 mesh sieve. Corn starch is passed through a 120 mesh sieve. These and HPC-L are mixed, kneaded, granulated, and dried. The resulting dry granule is granulate, then 150 mg of them is filled into a No. 4 hard gelatin capsule.

Formulation Example 3

A tablet containing the following ingredients is prepared.

| Ingredient | |
|---|---|
| Compound represented by any of the formula (I) to (VI) | 10 mg |
| Lactose | 90 mg |
| Microcrystaline cellulose | 30 mg |
| CMC-Na | 15 mg |
| Magnesium stearate | 5 mg |

The compound represented by any of the formula (I) to (VI), lactose, microcrystalline cellulose, CMC-Na (carboxymethylcellulose sodium salt) are passed through a 60 mesh sieve, and mixed. Magnesium stearate is mixed into a mixture powder to obtain a mixture powder for tabletting. The present mixed powder is directly compressed to obtain a 150 mg tablet.

Formulation Example 4

The following ingredients are warmed, mixed, and sterilized to obtain an injectable.

| Ingredient | |
|---|---|
| Compound represented by any of the formula (I) to (VI) | 3 mg |
| Nonionic surfactant | 15 mg |
| Purified water for injection | 1 ml |

Formulation Example 5

A cataplasm containing the following ingredients is prepared.

| Ingredient | |
|---|---|
| Compound represented by any of the formula (I) to (VI) | 50 mg |
| aqueous-based (5% ethanol/5% butylene glycol/90% purified water) | 950 mg |
| glycerin | |
| kaoline | |
| aqueous polyvinyl alcohol | |

The compound represented by any of the formula (I) to (VI) is added to aqueous-based. The mixture is irradiated by ultrasonic for 15 minutes and then is sufficiently stirred to obtain a solution. 5 part of glycerin, 1 part of kaoline and 5 part of aqueous polyvinyl alcohol are homogeneously mixed and 1 part of the resulting solution is added to the above solution including the compound represented by any of the formula (I) to (VI). The obtained solution is mixed and to give a paste form and the resulting paste is applied to an onwoven fabric. The resulting composition is covered by polyester film to give a cataplasm.

INDUSTRIAL APPLICABILITY

The compound of the invention has TRPV4 inhibitory activity and is useful in the treatment and/or prevention of a TRPV4 receptor-mediated disorder such as inflammatory pain (bladder inflammatory pain, pain after tooth extraction, postoperative pain, pain in the low back, periarthritis scapulohumeralis, cervico-omo-brachial syndrome, inflammation of a tendon or a tendon sheath, osteoarthritis, chronic articular rheumatism), neuropathic pain (sciatica, postherpetic neuralgia, diabetic neuropathy), pain related to cancer (cancer pain, bone metastasis pain, pain with the administration of anticancer agent), IBS, inflammatory bowel disease, osteoporosis, articular cartilage degeneration, cerebral stroke, incontinence, overactive bladder, urinary disturbance by bladder inflammation, asthma, dry skin, atopic dermatitis, metastasis and invasion of cancer, corneal ulcer, obesity, insulin resistance, diabetes, or the like.

The invention claimed is:
1. A compound of formula (I-A),

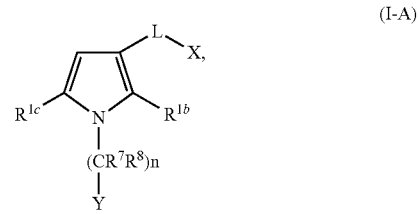

wherein:
$R^{1b}$ is hydrogen or substituted or unsubstituted alkyl;
$R^{1c}$ is substituted or unsubstituted alkyl wherein the carbon number is 2 or more, substituted or unsubstituted cycloalkyl, a substituted or unsubstituted non-aromatic heterocyclic group, or substituted or unsubstituted heteroaryl;
-L is —C(=O)—NH—;
X is substituted or unsubstituted aryl, substituted or unsubstituted heteroaryl, substituted or unsubstituted cycloalkyl, substituted or unsubstituted cycloalkenyl, or a substituted or unsubstituted non-aromatic heterocyclic group;
$R^7$ is each independently hydrogen, halogen, or substituted or unsubstituted alkyl;
$R^8$ is each independently hydrogen, halogen, or substituted or unsubstituted alkyl;
n is an integer from 1 to 3;
—Y is —N($R^9$)($R^{10}$), wherein $R^9$ and $R^{10}$ are each independently hydrogen, unsubstituted alkyl, substituted alkyl (wherein the substituent is hydroxy, substituted or unsubstituted amino, a substituted or unsubstituted non-aromatic heterocyclic group or substituted or unsubstituted cycloalkyl), or substituted or unsubstituted acyl, or $R^9$ and $R^{10}$ taken together with the adjacent nitrogen atom may form a ring in which a nitrogen atom or an oxygen atom may intervene;
or a pharmaceutically acceptable salt thereof.

2. The compound according to claim 1, wherein
n is 2 or 3;
or a pharmaceutically acceptable salt thereof.

3. The compound according to claim 1, wherein
—Y is —N($R^9$)($R^{10}$), wherein $R^9$ and $R^{10}$ are each independently hydrogen, unsubstituted alkyl, substituted alkyl (wherein the substituent is hydroxy, substituted or unsubstituted amino, a substituted or unsubstituted non-aromatic heterocyclic group or substituted or unsubstituted cycloalkyl); or $R^9$ and $R^{10}$ taken together with the adjacent nitrogen atom may form a ring in which a nitrogen atom or an oxygen atom may intervene;
or a pharmaceutically acceptable salt thereof.

4. The compound according to claim 1, wherein
$R^{1b}$ is hydrogen or unsubstituted alkyl;
or a pharmaceutically acceptable salt thereof.

5. The compound according to claim 1, wherein
X is substituted or unsubstituted aryl, or substituted or unsubstituted heteroaryl;
or a pharmaceutically acceptable salt thereof.

6. The compound according to claim 1, wherein
$R^{1b}$ is hydrogen or substituted or unsubstituted alkyl;
$R^{1c}$ substituted or unsubstituted alkyl wherein the carbon number is 2 or more, a substituted or unsubstituted non-aromatic heterocyclic group, or substituted or unsubstituted heteroaryl;
X is substituted or unsubstituted aryl;
$R^7$ is each independently hydrogen or substituted or unsubstituted alkyl;
$R^8$ is each independently hydrogen or substituted or unsubstituted alkyl;
n is an integer from 1 to 3;
—Y is —N($R^9$)($R^{10}$), wherein $R^9$ and $R^{10}$ are each independently hydrogen, unsubstituted alkyl, substituted alkyl (wherein the substituent is hydroxy, substituted or unsubstituted amino, a substituted or unsubstituted non-aromatic heterocyclic group or substituted or unsubstituted cycloalkyl), or $R^9$ and $R^{10}$ taken together with the adjacent nitrogen atom may form a substituted or unsubstituted ring in which a nitrogen atom or an oxygen atom may intervene;
or a pharmaceutically acceptable salt thereof.

7. A pharmaceutical composition comprising the compound according to claim 1, 2, 3, 4, 5 or 6, or a pharmaceutically acceptable salt thereof, and a pharmaceutically acceptable carrier.

8. The pharmaceutical composition according to claim 7, which is a TRPV4 receptor inhibitor.

9. A method for treating a TRPV4 receptor-mediated disorder, which comprises administering to a subject in need of such treatment a therapeutically effective amount of the compound or pharmaceutically acceptable salt thereof according to claim 1, 2, 3, 4, 5 or 6.

\* \* \* \* \*